US011920125B2

(12) United States Patent
Guan et al.

(10) Patent No.: US 11,920,125 B2
(45) Date of Patent: Mar. 5, 2024

(54) METHODS AND AGRICULTURAL COMPOSITIONS FOR PREVENTING OR CONTROLLING PLANT DISEASES

(71) Applicant: Tenfold Technologies, LLC, Pilot Point, TX (US)

(72) Inventors: Shaohua Guan, Frisco, TX (US); Shashi Shankar Rajbanshi, Frisco, TX (US); Curtis Brian Hill, Little Elm, TX (US)

(73) Assignee: Tenfold Technologies, LLC, Pilot Point, TX (US)

( * ) Notice: Subject to any disclaimer, the term of this patent is extended or adjusted under 35 U.S.C. 154(b) by 830 days.

(21) Appl. No.: 16/498,937

(22) PCT Filed: Mar. 27, 2018

(86) PCT No.: PCT/US2018/024638
§ 371 (c)(1),
(2) Date: Sep. 27, 2019

(87) PCT Pub. No.: WO2018/183381
PCT Pub. Date: Oct. 4, 2018

(65) Prior Publication Data

US 2021/0106011 A1 Apr. 15, 2021

Related U.S. Application Data

(60) Provisional application No. 62/477,297, filed on Mar. 27, 2017, provisional application No. 62/597,796, filed on Dec. 12, 2017.

(51) Int. Cl.

| | |
|---|---|
| ***C12N 1/20*** | (2006.01) |
| ***A01H 5/10*** | (2018.01) |
| ***A01N 63/22*** | (2020.01) |
| ***A01N 63/25*** | (2020.01) |
| ***C12R 1/07*** | (2006.01) |
| ***C12R 1/12*** | (2006.01) |

(52) U.S. Cl.
CPC ............... *C12N 1/205* (2021.05); *A01H 5/10* (2013.01); *A01N 63/22* (2020.01); *A01N 63/25* (2020.01); *C12R 2001/07* (2021.05); *C12R 2001/12* (2021.05)

(58) Field of Classification Search
CPC ........ C12N 1/205; A01N 63/25; A01N 63/22; A01H 5/10; C12R 2001/07; C12R 2001/12
USPC ...................................................... 435/252.5
See application file for complete search history.

(56) References Cited

U.S. PATENT DOCUMENTS

| | | | |
|---|---|---|---|
| 5,075,109 A | 12/1991 | Tice et al. | |
| 6,602,500 B1 | 8/2003 | Kharbanda et al. | |
| 6,878,179 B2 | 4/2005 | Porubcan | |
| 7,935,335 B2 | 5/2011 | Kochi et al. | |
| 2003/0045428 A1 | 3/2003 | Porubcan | |
| 2007/0248583 A1 | 10/2007 | Kochi et al. | |
| 2014/0179521 A1* | 6/2014 | Fuller .................... | A01N 43/16 504/101 |
| 2016/0278388 A1 | 9/2016 | Beau et al. | |
| 2021/0085752 A1 | 3/2021 | Guan et al. | |

FOREIGN PATENT DOCUMENTS

| | | |
|---|---|---|
| CN | 1095892 A | 12/1994 |
| CN | 1899047 A | 1/2007 |
| CN | 105646015 A | 6/2016 |
| EP | 0705807 A1 | 4/1996 |
| JP | 62-273998 A | 11/1987 |
| JP | 62-273999 A | 11/1987 |
| JP | 2006-304684 A | 11/2006 |
| JP | 2011-519824 A | 7/2011 |
| JP | 2015-181423 A | 10/2015 |
| WO | WO-9639840 A2 | 12/1996 |
| WO | 2004/049778 A1 | 6/2004 |
| WO | 2012/161160 A1 | 11/2012 |
| WO | WO-2013050867 A2 | 4/2013 |
| WO | 2014/085576 A1 | 6/2014 |
| WO | 2015/156274 A1 | 10/2015 |
| WO | 2015/169919 A1 | 11/2015 |
| WO | 2016/020371 A1 | 2/2016 |

OTHER PUBLICATIONS

Beatty et al., "Paenibacillus polymyxa produces fusaricidin-type antifungal antibiotics active against Leptosphaeria maculans, the causative agent of blackleg disease of canola", Canadian Journal of Microbiology, vol. 48, Mar. 3, 2002, pp. 159-169.
Broders, K. (2007). Characterization of *Pythium* spp. Associated with Corn and Soybean Seed and Seedling Disease in Ohio. Plant Disease, 91(6):727-735.
Brown, G. D., et al. (2012). Tackling Human Fungal Infections. Science Translational Medicine, Editorial, 4(165):647.
De Farias Neto, A. L., et al. (Nov.-Dec. 2006). Irrigation and Inoculation Treatments that Increase the Severity of Soybean Sudden Death Syndrome in the Field. Crop Science, 46:2547-2554.
Fu et al., "Identification of a plant growth promoting bacterium", NCBI, Sep. 2015 (PDF not available).
George-Okafor et al., "Screening and Optimal Protease Production by *Bacillus* sp. Sw-2 Using Low Cost Substrate Medium," Research Journal of Microbiology, 7(7): 327-336 (2012).
Goris, J., et al. (2007). DNA-DNA hybridization values and their relationship to whole-genome sequence similarities. International Journal of Systematic and Evolutionary Microbiology, 57:81-91.
Hamilton-Miller, J. M. T. (Jun. 1973). Chemistry and Biology of the Polyene Macrolide Antibiotics. American Society for Microbiology, Bacteriological Reviews, 37(2):166-196.

(Continued)

*Primary Examiner* — Jennifer M. H. Tichy
(74) *Attorney, Agent, or Firm* — Wilson Sonsini Goodrich & Rosati

(57) ABSTRACT

The disclosure provides a method of treating, preventing, and/or controlling plant diseases by applying the agricultural composition comprising a bacterial isolate belonging to *Paenibacillus* or *Bacillus*. Also, the disclosure provides a method of enhancing disease resistance of a plant seed by applying the agricultural composition to the plant seed, and an agricultural composition comprising the bacterial isolate.

11 Claims, 23 Drawing Sheets

Specification includes a Sequence Listing.

(56) References Cited

OTHER PUBLICATIONS

Haron et al., "Quantitative determination and pharmacokinetic study of fusaricidin A in mice plasma and tissues using ultra-high performance liquid chromatography-tandem mass spectrometry", Journal of Pharmaceutical and Biomedical Analysis, vol. 170, 2019, pp. 187-192.
International Preliminary Report on Patentability received for PCT Patent Application No. PCT/US2018/024638, dated Oct. 10, 2019, 8 pages.
International Preliminary Report on Patentability received for PCT Patent Application No. PCT/US2018/024642, dated Oct. 10, 2019, 11 pages.
International Search Report and Written Opinion received for PCT Patent Application No. PCT/US2018/024638, dated Jul. 20, 2018, 10 pages.
International Search Report and Written Opinion received for PCT Patent Application No. PCT/US2018/024642, dated May 15, 2018, 12 pages.
Kajimura et al., "Fusaricidin A, a new depsipeptide antibiotic produced by Bacillus polymyxa KT-8.Taxonomy, fermentation, isolation, structure elucidation and biological activity", The Journal of Antibiotics, vol. 49, No. 2, Feb. 1, 1996, pp. 129-135.
Klevens, R. M., et al. (Mar.-Apr. 2007). Estimating Health Care-Associated Infections and Deaths in U.S. Hospitals, 2002. Public Health Records, 122:160-166.
Lee et al., "An antibiotic fusaricidin: a cyclic depsipeptide from Paenibacillus polymyxa E681 induces systemic resistance against Phytophthora blight of red-pepper," Phytoparasitica, 41:49-58 (2013).
Lee et al., "Mannheimia succiniciproducens Phosphotransferase System for Sucrose Utilization", Applied and Environmental Microbiology, vol. 76, No. 5, Mar. 2010, pp. 1699-1703.
Mamun et al., "Optimization of fermenting medium by statistical method for production of alkaline protease by Bacillus licheniformis MZK05M9", Journal of Applied Biology & Biotechnology, 5(6):24-28 (Nov.-Dec. 2017).
Mukhtar et al., "Comparative Evaluation of Agroindustrial Byproducts for the Production of Alkaline Protease by Wild and Mutant Strains of Bacillus subtilis in Submerged and Solid State Fermentation," Hindawi Publishing Corporation The Scientific World Journal, vol. 2013, Article ID 538067, 6 pages.
Qiu et al., "Identification of fusaricidins from the antifungal microbial strain *Paenibacillus* sp. MS2379 using ultra-high performance liquid chromatography coupled to quadrupole time-of-flight mass spectrometry", Journal of Chromatography A, vol. 1586, Dec. 5, 2018, pp. 91-100.
Silva et al., "Production of Bio-inseticide *Bacillus thuringiensis* var. israelensis in Semicontinuous Processes Combined with Batch Processes for Sporulation," Braz. Arch. Biol. Technol., 54(1):45-52, (Jan./Feb. 2011).
Smith, K. D. (Dec. 2015). Increased Antifungal Drug Resistance in Clinical Isolates of Cryptococcus neoformans in Uganda. Antimicrobial Agents and Chemotherapy, 59(12):7197-7204.
Song, J. L., et al. (Apr. 2004). The Candida albicans Lanosterol 14-alpha-Demethylase (ERG11) Gene Promoter Is Maximally Induced after Prolonged Growth with Antifungal Drugs. Antimicrobial Agents and Chemotherapy, 48:1136-1144.
Vater et al., "Characterization of Novel Fusaricidins Produced by Paenibacillus polymyxa-M1 Using MALDI-TOF Mass Spectrometry", Journal of American Society of Mass Spectrometry, vol. 26, Jun. 23, 2015, pp. 1548-1558.
Infectious Diseases—A to Z List, Rhode Island Department of Health (https://health.ri.gov/diseases/infectious/accessed Mar. 11, 2022).
Methicillin-Resistant *Staphylococcus aureus* (MRSA), New York State Department of Health (https://www.health.ny.gov/diseases/communicable/staphylococcus_aureus/methicillin_resistant/ available online Nov. 2, 2007).
Non-Final Office Action received for U.S. Appl. No. 16/498,901, dated Apr. 5, 2022, 30 pages.
Extended European Search Report and Written Opinion received for EP Patent Application No. 18775154, dated May 3, 2021, 11 pages.
Extended European Search Report and Written Opinion received for EP Patent Application No. 18777897, dated Dec. 16, 2020, 10 pages.
Notice of Reasons for Refusal received for Japanese Application No. 2019-553033, dated Nov. 9, 2021, 4 pages (2 pages of English Translation and 2 pages of Original Document).
Brazilian Patent Office, Official Action with machine English translation; BR Application No. BR112019020151-3, dated May 17, 2022.
Cochrane, Stephen A. et al., "Lipopeptides from *Bacillus* and *Paenibacillus* spp.: a Gold Mine of Antibiotic Candidates," Medicinal Research Reviews, 36, No. 1, 4-31, 2016.
De Souza, Rocheli et al., "Plant growth-promoting bacteria as inoculants in agricultural soils," Genetics and Molecular Biology, 38, 4. 401-419, 2015.
Kuroda, Jun et al., Li-F Antibiotics, a Family of Antifungal Cyclic Depsipeptides Produced by Bacillus Polymyxa L-1129; 2000.
Yang, Anming et al., "Characterization and antifungal activity against Pestalotiopsis of a fusaricidin-type compound produced by Paenibacillus polymyxa Y-1," Pesticide Biochemistry and Physiology, 147, 67-74, 2018.
Yu, Wen-Bang et al., "Prediction of the Mechanism of Action of Fusaricidin on Bacillus subtilis," Plos One, 7, 11, 2012.

* cited by examiner

*Macrophomina phaseolina* *Rhizoctonia solani*

*Boytrytis cinerea*

| Sample | Microbial Strain | Medium |
|---|---|---|
| **SF1** | MS1479 | TSB |
| **SF2** | | BS3 |
| **SF3** | | BS3-M2 |
| **SF4** | | GB6-M3 |
| **SF5** | MS2379 | TSB |
| **SF6** | | BS3 |
| **SF7** | | BS3-M2 |
| **SF8** | | GB6-M3 |
| **SF9** | MS2414 | TSB |
| **SF10** | | BS3 |
| **SF11** | | BS3-M2 |
| **SF12** | | GB6-M3 |
| **SF13** | MS2820 | TSB |
| **SF14** | | BS3 |
| **SF15** | | BS3-M2 |
| **SF16** | | GB6-M3 |

SEQUENCE LISTING

<160> NUMBER OF SEQ ID NOS: 32

<210> SEQ ID NO 1
<211> LENGTH: 1147
<212> TYPE: DNA
<213> ORGANISM: Paenibacillus sp.

<400> SEQUENCE: 1
gagtttgatc ctggctcagg acgaacgctg gcggcgtgcc taatacatgc aagtcgagcg 60
gggttatgta gaagcttgct tctaaataac ctagcggcgg acgggtgagt aacacgtagg 120
caacctgccc acaagacagg gataactacc ggaaacggta gctaataccc gatacatcct 180
tttcctgcat gggagaggga ggaaagacgg agcaatctgt cacttgtgga tgggcctgcg 240
gcgcattagc tagttggtgg ggtaaaggcc taccaaggcg acgatgcgta gccgacctga 300
gagggtgatc ggccacactg ggactgagac acggcccaga ctcctacggg aggcagcagt 360
agggaatctt ccgcaatggg cgaaagcctg acggagcaac gccgcgtgag tgatgaaggt 420
tttcggatcg taaagctctg ttgccaggga agaacgtctt gtagagtaac tgctacaaga 480
gtgacggtac ctgagaagaa agccccggct aactacgtgc cagcagccgc ggtaatacgt 540
agggggcaag cgttgtccgg aattattggg cgtaaagcgc gcgcaggcgg ctctttaagt 600
ctggtgttta atcccgaggc tcaacttcgg gtcgcactgg aaactgggga gcttgagtgc 660
agaagaggag agtggaattc cacgtgtagc ggtgaaatgc gtagagatgt ggaggaacac 720
cagtggcgaa ggcgactctc tgggctgtaa ctgacgctga ggcgcgaaag cgtggggagc 780
aaacaggatt agataccctg gtagtccacg ccgtaaacga tgaatgctag gtgttagggg 840
tttcgatacc cttggtgccg aagttaacac attaagcatt ccgcctgggg agtacggtcg 900
caagactgaa actcaaagga attgacgggg acccgcacaa gcagtggagt atgtggttta 960
attcgaagca acgcgaagaa ccttaccagg tcttgacatc cctctgaccg ctgtagagat 1020
atggctttcc ttcgggacag aggagacagg tggtgcatgg ttgtcgtcag ctcgtgtcgt 1080
gagatgttgg gttaagtccc gcaacgagcg caacccttat gcttagttgc cagcaggtca 1140
agctggg 1147

<210> SEQ ID NO 2
<211> LENGTH: 1025
<212> TYPE: DNA
<213> ORGANISM: Bacillus sp.

<400> SEQUENCE: 2
agtcgagcgg acagatggga gcttgctccc tgatgttagc ggcggacggg tgagtaacac 60
gtgggtaacc tgcctgtaag actgggataa ctccgggaaa ccggggctaa taccggatgg 120
ttgtctgaac cgcatggttc agacataaaa ggtggcttcg gctaccactt acagatggac 180
ccgcggcgca ttagctagtt ggtgaggtaa cggctcacca aggcgacgat gcgtagccga 240
cctgagaggg tgatcggcca cactgggact gagacacggc ccagactcct acgggaggca 300
gcagtaggga atcttccgca atggacgaaa gtctgacgga gcaacgccgc gtgagtgatg 360
aaggttttcg gatcgtaaag ctctgttgtt agggaagaac aagtgccgtt caaatagggc 420
ggcaccttga cggtacctaa ccagaaagcc acggctaact acgtgccagc agccgcggta 480
atacgtaggt ggcaagcgtt gtccggaatt attgggcgta aagggctcgc aggcggtttc 540
ttaagtctga tgtgaaagcc cccggctcaa ccggggaggg tcattggaaa ctggggaact 600
tgagtgcaga agaggagagt ggaattccac gtgtagcggt gaaatgcgta gagatgtgga 660
ggaacaccag tggcgaaggc gactctctgg tctgtaactg acgctgagga gcgaaagcgt 720
ggggagcgaa caggattaga taccctggta gtccacgccg taaacgatga gtgctaagtg 780
ttagggggtt tccgcccctt agtgctgcag ctaacgcatt aagcactccg cctggggagt 840
acggtcgcaa gactgaaact caaaggaatt gacgggggcc cgcacaagcg gtggagcatg 900
tggtttaatt cgaagcaacg cgaagaacct taccaggtct tgacatcctc tgacaatcct 960
agagatagga cgtccccttc gggggcagag tgacaggtgg tgcatggttg tcgtcagctc 1020
gtgtc 1025

<210> SEQ ID NO 3
<211> LENGTH: 1544
<212> TYPE: DNA
<213> ORGANISM: Bacillus sp.

<400> SEQUENCE: 3
ttatcggaga gtttgatcct ggctcaggac gaacgctggc ggcgtgccta atacatgcaa 60
gtcgagcgga cagatgggag cttgctccct gatgttagcg gcggacgggt gagtaacacg 120
tgggtaacct gcctgtaaga ctgggataac tcgggaaacc gggctaatga tggttgtctg 180

```
aaccgcatgg ttcagacata aaaggtggct tcggctacca cttacagatg gacccgcggc    240
gcattagcta gttggtgagg taacggctca ccaaggcgac gatgcgtagc cgacctgaga    300
gggtgatcgg ccacactggg actgagacac ggcccagact cctacgggag gcagcagtag    360
ggaatcttcc gcaatggacg aaagtctgac ggagcaacgc cgcgtgagtg atgaaggttt    420
tcggatcgta aagctctgtt gttagggaag aacaagtgcc gttcaaatag ggcggcacct    480
tgacggtacc taaccagaaa gccacggcta actacgtgcc agcagccgcg gtaatacgta    540
ggtggcaagc gttgtccgga attattgggc gtaaagggct cgcaggcggt ttcttaagtc    600
tgatgtgaaa gcccccggct caaccgggga gggtcattgg aaactgggga acttgagtgc    660
agaagaggag agtggaattc cacgtgtagc ggtgaaatgc gtagagatgt ggaggaacac    720
cagtggcgaa ggcgactctc tggtctgtaa ctgacgctga ggagcgaaag cgtggggagc    780
gaacaggatt agataccctg gtagtccacg ccgtaaacga tgagtgctaa gtgttagggg    840
gtttccgccc cttagtgctg cagctaacgc attaagcact ccgcctgggg agtacggtcg    900
caagactgaa actcaaagga attgacgggg gcccgcacaa gcggtggagc atgtggttta    960
attcgaagca acgcgaagaa ccttaccagg tcttgacatc ctctgacaat cctagagata   1020
ggacgtcccc ttcgggggca gagtgacagg tggtgcatgg ttgtcgtcag ctcgtgtcgt   1080
gagatgttgg gttaagtccc gcaacgagcg caacccttga tcttagttgc cagcattcag   1140
ttgggcactc taaggtgact gccggtgaca aaccggagga aggtggggat gacgtcaaat   1200
catcatgccc cttatgacct gggctacaca cgtgctacaa tggacagaac aaagggcagc   1260
gaaaccgcga ggttaagcca atcccacaaa tctgttctca gttcggatcg cagtctgcaa   1320
ctcgactgcg tgaagctgga atcgctagta atcgcggatc agcatgccgc ggtgaatacg   1380
ttcccgggcc ttgtacacac cgcccgtcac accacgagag tttgtaacac ccgaagtcgg   1440
tgaggtaacc tttatggagc cagccgccga aggtgggaca gatgattggg gtgaagtcgt   1500
aacaaggtag ccgtatcgga aggtgcggct ggatcacctc cttt                    1544
```

```
<210> SEQ ID NO 4
<211> LENGTH: 1015
<212> TYPE: DNA
<213> ORGANISM: Bacillus sp.

<400> SEQUENCE: 4

agtcgagcgg acagatggga gcttgctccc tgatgttagc ggcggacggg tgagtaacac     60
gtgggtaacc tgcctgtaag actgggataa ctccgggaaa ccggggctaa taccggatgg    120
ttgtctgaac cgcatggttc agacataaaa ggtggcttcg gctaccactt acagatggac    180
ccgcggcgca ttagctagtt ggtgaggtaa cggctcacca aggcgacgat gcgtagccga    240
cctgagaggg tgatcggcca cactgggact gagacacggc ccagactcct acgggaggca    300
gcagtaggga atcttccgca atggacgaaa gtctgacgga gcaacgccgc gtgagtgatg    360
aaggttttcg gatcgtaaag ctctgttgtt agggaagaac aagtgccgtt caaatagggc    420
ggcaccttga cggtacctaa ccagaaagcc acggctaact acgtgccagc agccgcggta    480
atacgtaggt ggcaagcgtt gtccggaatt attgggcgta aagggctcgc aggcggtttc    540
ttaagtctga tgtgaaagcc cccggctcaa ccggggaggg tcattggaaa ctggggaact    600
tgagtgcaga agaggagagt ggaattccac gtgtagcggt gaaatgcgta gagatgtgga    660
ggaacaccag tggcgaaggc gactctctgg tctgtaactg acgctgagga gcgaaagcgt    720
```

```
ggggagcgaa caggattaga taccctggta gtccacgccg taaacgatga gtgctaagtg    780

ttagggggtt tccgcccctt agtgctgcag ctaacgcatt aagcactccg cctggggagt    840

acggtcgcaa gactgaaact caaaggaatt gacgggggcc cgcacaagcg gtggagcatg    900

tggtttaatt cgaagcaacg cgaagaacct taccaggtct tgacatcctc tgacaatcct    960

agagatagga cgtccccttc gggggcagag tgacaggtgg tgcatggttg tcgtc        1015


<210> SEQ ID NO 5
<211> LENGTH: 989
<212> TYPE: DNA
<213> ORGANISM: Bacillus sp.

<400> SEQUENCE: 5

agtcgagcgg acagatggga gcttgctccc tgatgttagc ggcggacggg tgagtaacac     60

gtgggtaacc tgcctgtaag actgggataa ctccgggaaa ccggggctaa taccggatgg    120

ttgtctgaac cgcatggttc agacataaaa ggtggcttcg gctaccactt acagatggac    180

ccgcggcgca ttagctagtt ggtgaggtaa cggctcacca aggcgacgat gcgtagccga    240

cctgagaggg tgatcggcca cactgggact gagacacggc ccagactcct acgggaggca    300

gcagtaggga atcttccgca atggacgaaa gtctgacgga gcaacgccgc gtgagtgatg    360

aaggttttcg gatcgtaaag ctctgttgtt agggaagaac aagtgccgtt caaatagggc    420

ggcaccttga cggtacctaa ccagaaagcc acggctaact acgtgccagc agccgcggta    480

atacgtaggt ggcaagcgtt gtccggaatt attgggcgta aagggctcgc aggcggtttc    540

ttaagtctga tgtgaaagcc cccggctcaa ccggggaggg tcattggaaa ctggggaact    600

tgagtgcaga agaggagagt ggaattccac gtgtagcggt gaaatgcgta gagatgtgga    660

ggaacaccag tggcgaaggc gactctctgg tctgtaactg acgctgagga gcgaaagcgt    720

ggggagcgaa caggattaga taccctggta gtccacgccg taaacgatga gtgctaagtg    780

ttagggggtt tccgcccctt agtgctgcag ctaacgcatt aagcactccg cctggggagt    840

acggtcgcaa gactgaaact caaaggaatt gacgggggcc cgcacaagcg gtggagcatg    900

tggtttaatt cgaagcaacg cgaagaacct taccaggtct tgacatcctc tgacaatcct    960

agagatagga cgtccccttc gggggcaga                                     989


<210> SEQ ID NO 6
<211> LENGTH: 1025
<212> TYPE: DNA
<213> ORGANISM: Bacillus sp.

<400> SEQUENCE: 6

agtcgagcgg acagatggga gcttgctccc tgatgttagc ggcggacggg tgagtaacac     60

gtgggtaacc tgcctgtaag actgggataa ctccgggaaa ccggggctaa taccggatgg    120

ttgtctgaac cgcatggttc agacataaaa ggtggcttcg gctaccactt acagatggac    180

ccgcggcgca ttagctagtt ggtgaggtaa cggctcacca aggcgacgat gcgtagccga    240

cctgagaggg tgatcggcca cactgggact gagacacggc ccagactcct acgggaggca    300

gcagtaggga atcttccgca atggacgaaa gtctgacgga gcaacgccgc gtgagtgatg    360

aaggttttcg gatcgtaaag ctctgttgtt agggaagaac aagtgccgtt caaatagggc    420

ggcaccttga cggtacctaa ccagaaagcc acggctaact acgtgccagc agccgcggta    480

atacgtaggt ggcaagcgtt gtccggaatt attgggcgta aagggctcgc aggcggtttc    540

ttaagtctga tgtgaaagcc cccggctcaa ccggggaggg tcattggaaa ctggggaact    600
```

```
tgagtgcaga agaggagagt ggaattccac gtgtagcggt gaaatgcgta gagatgtgga    660

ggaacaccag tggcgaaggc gactctctgg tctgtaactg acgctgagga gcgaaagcgt    720

ggggagcgaa caggattaga taccctggta gtccacgccg taaacgatga gtgctaagtg    780

ttagggggtt tccgcccctt agtgctgcag ctaacgcatt aagcactccg cctggggagt    840

acggtcgcaa gactgaaact caaaggaatt gacgggggcc cgcacaagcg gtggagcatg    900

tggtttaatt cgaagcaacg cgaagaacct taccaggtct tgacatcctc tgacaatcct    960

agagatagga cgtccccttc gggggcagag tgacaggtgg tgcatggttg tcgtcagctc   1020

gtgtc                                                               1025
```

```
<210> SEQ ID NO 7
<211> LENGTH: 1374
<212> TYPE: DNA
<213> ORGANISM: Paenibacillus sp.

<400> SEQUENCE: 7

atccttttcc tgcatgggag aaggaggaaa gacggagcaa tctgtcactt gtggatgggc     60

ctgcggcgca ttagctagtt ggtggggtaa aggcctacca aggcgacgat gcgtagccga    120

cctgagaggg tgatcggcca cactgggact gagacacggc ccagactcct acgggaggca    180

gcagtaggga atcttccgca atgggcgaaa gcctgacgga gcaacgccgc gtgagtgatg    240

aaggttttcg gatcgtaaag ctctgttgcc agggaagaac gtcttgtaga gtaactgcta    300

caagagtgac ggtacctgag aagaaagccc cggctaacta cgtgccagca gccgcggtaa    360

tacgtagggg gcaagcgttg tccggaatta ttgggcgtaa agcgcgcgca ggcggctctt    420

taagtctggt gtttaatccc gaggctcaac ttcgggtcgc actggaaact ggggagcttg    480

agtgcagaag aggagagtgg aattccacgt gtagcggtga aatgcgtaga gatgtggagg    540

aacaccagtg gcgaaggcga ctctctgggc tgtaactgac gctgaggcgc gaaagcgtgg    600

ggagcaaaca ggattagata ccctggtagt ccacgccgta aacgatgaat gctaggtgtt    660

aggggtttcg atacccttgg tgccgaagtt aacacattaa gcattccgcc tggggagtac    720

ggtcgcaaga ctgaaactca aaggaattga cggggacccg cacaagcagt ggagtatgtg    780

gtttaattcg aagcaacgcg aagaacctta ccaggtcttg acatccctct gaccggtcta    840

gagatagacc tttccttcgg gacagaggag acaggtggtg catggttgtc gtcagctcgt    900

gtcgtgagat gttgggttaa gtcccgcaac gagcgcaacc cttatgctta gttgccagca    960

ggtcaagctg ggcactctaa gcagactgcc ggtgacaaac cggaggaagg tggggatgac   1020

gtcaaatcat catgcccctt atgacctggg ctacacacgt actacaatgg ccggtacaac   1080

gggaagcgaa atcgcgaggt ggagccaatc ctagaaaagc cggtctcagt tcggattgta   1140

ggctgcaact cgcctacatg aagtcggaat tgctagtaat cgcggatcag catgccgcgg   1200

tgaatacgtt cccgggtctt gtacacaccg cccgtcacac cacgagagtt tacaacaccc   1260

gaagtcggtg gggtaacccg caagggagcc agccgccgaa ggtggggtag atgattgggg   1320

tgaagtcgta acaaggtagc cgtatcggaa ggtgcggctg gatcacctcc tttc         1374
```

```
<210> SEQ ID NO 8
<211> LENGTH: 1547
<212> TYPE: DNA
<213> ORGANISM: Paenibacillus sp.

<400> SEQUENCE: 8
```

```
gagtttgatc ctggctcagg acgaacgctg gcggcgtgcc taatacatgc aagtcgagcg     60
gggttattta gaagcttgct tctaaataac ctagcggcgg acgggtgagt aacacgtagg    120
caacctgccc acaagacagg gataactacc ggaaacggta gctaataccc gatacatcct    180
tttcctgcat gggagaagga ggaaagacgg agcaatctgt cacttgtgga tgggcctgcg    240
gcgcattagc tagttggtgg ggtaaaggcc taccaaggcg acgatgcgta gccgacctga    300
gagggtgatc ggccacactg ggactgagac acggcccaga ctcctacggg aggcagcagt    360
agggaatctt ccgcaatggg cgaaagcctg acggagcaac gccgcgtgag tgatgaaggt    420
tttcggatcg taaagctctg ttgccaggga agaacgtctt atagagtaac tgctataaga    480
gtgacggtac ctgagaagaa agccccggct aactacgtgc cagcagccgc ggtaatacgt    540
agggggcaag cgttgtccgg aattattggg cgtaaagcgc gcgcaggcgg ctctttaagt    600
ctggtgttta atcccgaggc tcaacttcgg gtcgcactgg aaactgggga gcttgagtgc    660
agaagaggag agtggaattc cacgtgtagc ggtgaaatgc gtagagatgt ggaggaacac    720
cagtggcgaa ggcgactctc tgggctgtaa ctgacgctga ggcgcgaaag cgtggggagc    780
aaacaggatt agataccctg gtagtccacg ccgtaaacga tgaatgctag gtgttagggg    840
tttcgatacc cttggtgccg aagttaacac attaagcatt ccgcctgggg agtacggtcg    900
caagactgaa actcaaagga attgacgggg acccgcacaa gcagtggagt atgtggttta    960
attcgaagca acgcgaagaa ccttaccagg tcttgacatc cctctgaccg ctgtagagat   1020
atggctttcc ttcgggacag aggagacagg tggtgcatgg ttgtcgtcag ctcgtgtcgt   1080
gagatgttgg gttaagtccc gcaacgagcg caacccttat gcttagttgc cagcaggtca   1140
agctgggcac tctaagcaga ctgccggtga caaaccggag gaaggtgggg atgacgtcaa   1200
atcatcatgc cccttatgac ctgggctaca cacgtactac aatggccggt acaacgggaa   1260
gcgaagccgc gaggtggagc caatcctaga aaagccggtc tcagttcgga ttgcaggctg   1320
caactcgcct gcatgaagtc ggaattgcta gtaatcgcgg atcagcatgc cgcggtgaat   1380
acgttcccgg gtcttgtaca caccgcccgt cacaccacga gagtttacaa cacccgaagt   1440
cggtgaggta accgcaaggg gccagccgcc gaaggtgggg tagatgattg gggtgaagtc   1500
gtaacaaggt agccgtatcg gaaggtgcgg ctggatcacc tcctttc                 1547
```

<210> SEQ ID NO 9
<211> LENGTH: 986
<212> TYPE: DNA
<213> ORGANISM: Bacillus sp.

<400> SEQUENCE: 9

```
agtcgagcgg acagatggga gcttgctccc tgatgttagc ggcggacggg tgagtaacac     60
gtgggtaacc tgcctgtaag actgggataa ctccgggaaa ccggggctaa taccggatgg    120
ttgtctgaac cgcatggttc agacataaaa ggtggcttcg gctaccactt acagatggac    180
ccgcggcgca ttagctagtt ggtgaggtaa cggctcacca aggcgacgat gcgtagccga    240
cctgagaggg tgatcggcca cactgggact gagacacggc ccagactcct acgggaggca    300
gcagtaggga atcttccgca atggacgaaa gtctgacgga gcaacgccgc gtgagtgatg    360
aaggttttcg gatcgtaaag ctctgttgtt agggaagaac aagtgccgtt caaatagggc    420
ggcaccttga cggtacctaa ccagaaagcc acggctaact acgtgccagc agccgcggta    480
atacgtaggt ggcaagcgtt gtccggaatt attgggcgta aagggctcgc aggcggtttc    540
ttaagtctga tgtgaaagcc cccggctcaa ccggggaggg tcattggaaa ctggggaact    600
```

```
tgagtgcaga agaggagagt ggaattccac gtgtagcggt gaaatgcgta gagatgtgga    660

ggaacaccag tggcgaaggc gactctctgg tctgtaactg acgctgagga gcgaaagcgt    720

ggggagcgaa caggattaga taccctggta gtccacgccg taaacgatga gtgctaagtg    780

ttagggggtt tccgcccctt agtgctgcag ctaacgcatt aagcactccg cctggggagt    840

acggtcgcaa gactgaaact caaaggaatt gacgggggcc cgcacaagcg gtggagcatg    900

tggtttaatt cgaagcaacg cgaagaacct taccaggtct tgacatcctc tgacaatcct    960

agagatagga cgtccccttc gggggc                                          986


<210> SEQ ID NO 10
<211> LENGTH: 1549
<212> TYPE: DNA
<213> ORGANISM: Paenibacillus sp.

<400> SEQUENCE: 10

gagtttgatc ctggctcagg acgaacgctg gcggcgtgcc taatacatgc aagtcgagcg     60

ggattgttta gaagcttgct tctaaacaat ctagcggcgg acgggtgagt aacacgtagg    120

caacctgccc acaagacagg gataactacc ggaaacggta gctaataccc gatacatcct    180

tttcctgcat gggagaagga ggaaagacgg agcaatctgt cacttgtgga tgggcctgcg    240

gcgcattagc tagttggtgg ggtaaaggcc taccaaggcg acgatgcgta gccgacctga    300

gagggtgatc ggccacactg ggactgagac acggcccaga ctcctacggg aggcagcagt    360

agggaatctt ccgcaatggg cgaaagcctg acggagcaac gccgcgtgag tgatgaaggt    420

tttcggatcg taaagctctg ttgccaggga agaacgtctt gtagagtaac tgctacaaga    480

gtgacggtac ctgagaagaa agccccggct aactacgtgc cagcagccgc ggtaatacgt    540

agggggcaag cgttgtccgg aattattggg cgtaaagcgc gcgcaggcgg ctctttaagt    600

ctggtgttta atcccgaggc tcaacttcgg gtcgcactgg aaactgggga gcttgagtgc    660

agaagaggag agtggaattc cacgtgtagc ggtgaaatgc gtagagatgt ggaggaacac    720

cagtggcgaa ggcgactctc tgggctgtaa ctgacgctga ggcgcgaaag cgtggggagc    780

aaacaggatt agataccctg gtagtccacg ccgtaaacga tgaatgctag gtgttagggg    840

tttcgatacc cttggtgccg aagttaacac attaagcatt ccgcctgggg agtacggtcg    900

caagactgaa actcaaagga attgacgggg acccgcacaa gcagtggagt atgtggttta    960

attcgaagca acgcgaagaa ccttaccagg tcttgacatc cctctgaccg gtctagagat   1020

agacctttcc ttcgggacag aggagacagg tggtgcatgg ttgtcgtcag ctcgtgtcgt   1080

gagatgttgg gttaagtccc gcaacgagcg caacccttat gcttagttgc cagcaggtca   1140

agctgggcac tctaagcaga ctgccggtga caaaccggag gaaggtgggg atgacgtcaa   1200

atcatcatgc cccttatgac ctgggctaca cacgtactac aatggccggt acaacgggaa   1260

gcgaaatcgc gaggtggagc caatcctaga aaagccggtc tcagttcgga ttgtaggctg   1320

caactcgcct acatgaagtc ggaattgcta gtaatcgcgg atcagcatgc cgcggtgaat   1380

acgttcccgg gtcttgtaca caccgcccgt cacaccacga gagtttacaa cacccgaagt   1440

cggtggggta acccgcaagg gagccagccg ccgaaggtgg ggtagatgat tggggtgaag   1500

tcgtaacaag gtagccgtat cggaaggtgc ggctggatca cctcctttc               1549


<210> SEQ ID NO 11
<211> LENGTH: 1005
<212> TYPE: DNA
```

<213> ORGANISM: Bacillus sp.

<400> SEQUENCE: 11

```
agtcgagcgg acagatggga gcttgctccc tgatgttagc ggcggacggg tgagtaacac     60
gtgggtaacc tgcctgtaag actgggataa ctccgggaaa ccggggctaa taccggatgg    120
ttgtttgaac cgcatggttc agacataaaa ggtggcttcg gctaccactt acagatggac    180
ccgcggcgca ttagctagtt ggtgaggtaa cggctcacca aggcgacgat gcgtagccga    240
cctgagaggg tgatcggcca cactgggact gagacacggc ccagactcct acgggaggca    300
gcagtaggga atcttccgca atggacgaaa gtctgacgga gcaacgccgc gtgagtgatg    360
aaggttttcg gatcgtaaag ctctgttgtt agggaagaac aagtgccgtt caaatagggc    420
ggcaccttga cggtacctaa ccagaaagcc acggctaact acgtgccagc agccgcggta    480
atacgtaggt ggcaagcgtt gtccggaatt attgggcgta aagggctcgc aggcggtttc    540
ttaagtctga tgtgaaagcc cccggctcaa ccggggaggg tcattggaaa ctggggaact    600
tgagtgcaga agaggagagt ggaattccac gtgtagcggt gaaatgcgta gagatgtgga    660
ggaacaccag tggcgaaggc gactctctgg tctgtaactg acgctgagga gcgaaagcgt    720
ggggagcgaa caggattaga taccctggta gtccacgccg taaacgatga gtgctaagtg    780
ttagggggtt tccgcccctt agtgctgcag ctaacgcatt aagcactccg cctggggagt    840
acggtcgcaa gactgaaact caaaggaatt gacgggggcc cgcacaagcg gtggagcatg    900
tggtttaatt cgaagcaacg cgaagaacct taccaggtct tgacatcctc tgacaatcct    960
agagatagga cgtccccttc gggggcagag tgacaggtgg tgcat                   1005
```

<210> SEQ ID NO 12
<211> LENGTH: 1980
<212> TYPE: DNA
<213> ORGANISM: Paenibacillus sp.

<400> SEQUENCE: 12

```
ctactctacg tattccgtga aatctacgtt ttccacgatc cagcgtttgc gcggatccac     60
cttatcaccc atcaaagtgg acaccctacg ttcagccttg gctgcatcct ctatctgaac    120
gcgtaacaag gtgcgtgaat cgggattcat cgttgtttcc cataactgat cagggttcat    180
ttccccaagt cctttatagc gctgaagctc aaaattccgt ccaaattctt ttaaataatt    240
atcaagctgc tcgtcagtcc aagcataacg caccgtttcg agcttacccg actttcgagt    300
tattttatac aatggcggtt gagcaataaa tatgcgtcct gcatcaataa gctctttcat    360
gtaccgataa aagaacgtca acaacagcac ttgaatgtgc gcaccatctg tgtctgcatc    420
ggtcataatg atgattttgg aataattgct gtcttccagc gaaaactctg ttcctacccc    480
cgcaccaata gctgctgtaa tagcacggta ctcatcattc ttcataatat ccgccagttt    540
ggatttctcc ggattcatcg gcttaccctt tagcggtaag atggcctgaa ttttggaatc    600
ccgtccctgc ttggctgatc ctccagccga atcgccttcc acaataaaca actcattacg    660
tgtaaaatcc ttggactgcg caggcgacag tttaccattc aaattggaac tttcactgcg    720
ctttttaccg gaacgcatct catcccgagc tttacgtgca gcttcacgcg ctctggatgc    780
ttgaactgcc ttcttgatca aagtttgtgc tatctgcgga ttttcttcca aaaaacgctg    840
catctgctca gatacgatgg catccactgt actccgtgcc gaagcgctac ccagttgatc    900
ctttgtctga ccgacaaatt caacctcagc catcttgaca ctgattacaa ccatcatgcc    960
ctcacgtaga tcgttgccct ccaagttttt atccttttct ttcaacatca ccgttttccg   1020
```

```
ggcatagtcg ttcatgacac gagtgtaagc ggttttgaat cccgtttcat gcgtacctcc   1080

gccacgtgtc ggaatggagt taacgaacga agcaatcgtc tctgtataac ccgcattgta   1140

ctggatggca atctctactt caatgtcttc tttctcggca ttaaagtgaa taacgtcatg   1200

cagcacatcc ttgccctcat tcagaaaagc aacaaactga cttgcgccac cctcataaaa   1260

atactcatct gactttccgc tgcgttcgtc tttaagttga atacgaaggc ccgaatttag   1320

aaaagcaatt tcctgaaggc gctcagccaa cgtatcgtag ttaaaatgaa tgcctgcttg   1380

aaaaacacga atatccggtt taaatgtaat tttcgagccc gtcttgttag tattgcccag   1440

cacttcaagg cctgtggtcg gttccccgac atgctccacg cccttcttgt cctgccaata   1500

ttcaaaccgc tgacggtgaa tcttgccgtc ccggtaaatt tctacttcaa gccattccga   1560

aagagcgttc gttacagatg cacctacacc gtgcagaccc ccggactttt tatatcccga   1620

accgccaaac ttgcctccgg cgtgcaaaat ggtgaataca acctgaggcg taggaatccc   1680

cgttttgtgc attcctgtag gaataccgcg cccgttgtct gataccgtaa tggaaccgtc   1740

cttatgcatt gtaatatcaa tgcgagagca aaacttggcg agatgttcat ccaccgcgtt   1800

gtctacaatt tcccatacca aatgatgcag ccccgaagaa ctggtgctcc cgatgtacat   1860

gcccggccgt ttgcgaactg ccacaagccc ttcgagcact tgaatgtcgt ccgcgccata   1920

ttctgaagct ccgctttgtg tgccggacgc tcccgcagac aagtcgattt tgtcgaccat   1980
```

<210> SEQ ID NO 13
<211> LENGTH: 350
<212> TYPE: DNA
<213> ORGANISM: Bacillus sp.

<400> SEQUENCE: 13

```
gaccggaacg attacgcact tcgttccgga tccggaaatc ttcaaagaaa caaccgtata     60

cgactatgat ctgctttcaa accgtgtccg ggaattggcc ttcctgacaa aaggcgtaaa    120

catcacgatt gaagacaaac gtgaaggaca agaacggaaa aacgagtacc actacgaagg    180

cggaatcaaa agctatgttg agtacttaaa ccgttccaaa gaagtcgttc atgaagagcc    240

gatttatatc gaaggcgaga aagacggcat aacggttgaa gttgcattgc aatacaacga    300

cagctataca agcaatattt attctttcac gaataatatc aacacatacg               350
```

<210> SEQ ID NO 14
<211> LENGTH: 1917
<212> TYPE: DNA
<213> ORGANISM: Bacillus sp.

<400> SEQUENCE: 14

```
atggaacagc agcaaaatag ttatgatgag aatcagatac aggtattaga aggtttggaa     60

gctgttcgaa agagaccggg gatgtacatc ggatcaacta acagcaaagg ccttcaccac    120

ttggtgtggg aaatcgtcga caacagtatt gacgaagccc tggccggtta ttgtacagat    180

attaacatcg agattgaaaa agataacagc attaccgtta aggacaacgg gcgcggcatt    240

ccggtcggta tccaggagaa gatgggccgc cctgcggttg aagtcatcat gaccgttctc    300

cacgccggcg gtaaatttga cggaagcgga tataaagtat ccggcggtct tcacggtgta    360

ggggcgtctg tcgtaaacgc cttgtcgacc actcttgacg ttacggttca tcgtgacgga    420

aaaatccact atcaggcgta cgagcgcggt gtacctgtgg ccgatcttga agtgatcggt    480

gatactgata agaccggaac gattacgcac ttcgttccgg atccggaaat tttcaaagaa    540
```

```
acaaccgtat acgactatga tctgctttca aaccgtgtcc gggaattggc cttcctgaca    600

aaaggcgtaa acatcacgat tgaagacaaa cgtgaaggac aagaacggaa aaacgagtac    660

cactacgaag gcggaatcaa aagctatgtt gagtacttaa accgttccaa agaagtcgtt    720

catgaagagc cgatttatat cgaaggcgag aaagacggca taacggttga agttgcattg    780

caatacaacg acagctatac aagcaatatt tattctttca cgaataatat caacacatac    840

gaaggcggca cgcacgaggc cggatttaaa accggtctga cccgtgtcat aaacgactat    900

gcaagaagaa aagggatttt caaagaaaat gatccgaatt taagcgggga tgatgtgaga    960

gaagggctga ctgccattat ttcaattaag caccctgatc cgcaattcga aggtcagacg   1020

aaaacgaagc tcggcaactc cgaagcgaga acgatcactg atacgctgtt ttcttctgcg   1080

ctggaaacat tccttcttga aaatccggac tcagcccgca aaatcgttga aaaaggttta   1140

atggccgcaa gagcgcggat ggcagcgaaa aaagcgcggg aattgacccg ccgcaaaagt   1200

gcgcttgaga tttccaatct gccgggcaaa ctggcggact gttcttctaa agatccgagc   1260

atttccgagc tgtatatcgt agagggtgac tctgcgggcg gatcagcgaa acagggacgg   1320

gaccgtcatt tccaagccat tctgccgctg cgcggtaaga ttctgaacgt tgagaaagcc   1380

agacttgata agattctctc aaacaatgag gtcagatcaa tgatcacggc cctcggaaca   1440

ggaatcggag aagattttaa tcttgaaaaa gcgcgttatc ataaagtggt catcatgacg   1500

gatgccgatg ttgacggcgc ccacatcaga acgcttttat taacgttctt ctacagatac   1560

atgcgggaaa tcatcgaaaa cggctatgtc tacattgccc agccgccgct ttataaagtg   1620

cagcagggaa aacgggtgga atacgcttat aacgataagc agcttgatga gctgttaaaa   1680

gagcttccgc aatcacctaa gcccggcctc cagcgttata aaggtcttgg agaaatgaac   1740

gcgactcagc tttgggaaac gacaatggac cctgcgacca gaacgcttct gcaagtcaat   1800

cttgaagatg caatggacgc tgacgagact tttgaaatgc tgatgggtga caaagtagaa   1860

ccgcggagaa acttcataga agcaaacgcc agatacgtga aaaatcttga tatttaa      1917
```

<210> SEQ ID NO 15
<211> LENGTH: 255
<212> TYPE: DNA
<213> ORGANISM: Bacillus sp.

<400> SEQUENCE: 15

```
tcctgacaaa aggcgtaaac atcacgattg aagacaaacg tgaaggacaa gaacggaaaa     60

acgagtacca ctacgaaggc ggaatcaaaa gctatgttga gtacttaaac cgttccaaag    120

aagtcgttca tgaagagccg atttatatcg aaggcgagaa agacggcata acggttgaag    180

ttgcattgca atacaacgac agctatacaa gcaatattta ttctttcacg aataatatca    240

acacatacga aggcg                                                      255
```

<210> SEQ ID NO 16
<211> LENGTH: 495
<212> TYPE: DNA
<213> ORGANISM: Bacillus sp.

<400> SEQUENCE: 16

```
cacggtgtag gggcatctgt cgtaaacgcc ttgtcgacca ctcttgacgt tacggttcat     60

cgtgacggaa aaatccacta tcaggcgtac gagcgcggtg tacctgtggc cgatcttgaa    120

gtgatcggtg atactgataa gaccggaacg attacgcact tcgttccgga tccggaaatc    180

ttcaaagaaa caatcgtata cgactatgat ctgctttcaa accgtgtccg ggaattggcc    240
```

```
ttcctgacaa aaggcgtaaa catcacgatt gaagacaaac gtgaaggaca agaacggaaa    300

aacgagtacc actacgaagg cggaatcaaa agctatgttg agtacttaaa ccgttccaaa    360

gaagtcgttc atgaagagcc gatttatatc gaaggcgaga aagacggcat aacggttgaa    420

gttgcattgc aatacaacga cagctataca agcaatattt attctttcac gaataatatc    480

aacacatacg aaggc                                                     495
```

```
<210> SEQ ID NO 17
<211> LENGTH: 1980
<212> TYPE: DNA
<213> ORGANISM: Paenibacillus sp.

<400> SEQUENCE: 17

ctactctacg tattccgtga aatctacgtt ttccacgatc cagcgcttgc gcggatccac     60

cttatcaccc atcaaagtgg acaccctgcg ttcagccttg gctgcatcct ctatctgaac    120

gcgtaacaag gtgcgtgaat cgggattcat cgttgtttcc cataactgat cagggttcat    180

ttccccaagt cctttatagc gctgaagctc aaaatttcgt ccaaattctt ttaaataatt    240

atcaagctgc tcgtcagtcc aagcataacg caccgtttcg agcttacccg actttcgagt    300

tattttatac aatggcggtt gagcaataaa tatgcgtcct gcatcaataa gctctttcat    360

gtaccgataa aagaacgtca acaacagcac ttgaatgtgc gcaccatctg tatctgcatc    420

ggtcataatg atgattttgg aataattgct gtcttccagc gaaaactctg ttcctactcc    480

cgcaccaata gctgctgtaa tagcacggta ctcatcattc ttcataatat ccgccagttt    540

ggatttttcc ggattcatcg gcttgccctt tagcggcaat atggcctgaa ttttggaatc    600

ccgtccctgc ttggctgaac ctccagccga atcgccttcc acaataaaca actcattacg    660

tgtaaaatcc ttggactgcg caggcgacag tttaccattc aaattggaac tttcactgcg    720

ctttttaccg gaacgcatct catctcgagc tttacgtgca gcttcacgcg ctctggatgc    780

ttgaactgcc ttcttgatca aagtttgtgc tatctgcgga ttttcttcca aaaaacgctg    840

catctgctca gatacgatgg catccactgt actccgtgcc gaagcgctac ccagctgatc    900

ctttgtctgg ccgacaaatt caacttcagc cattttgaca ctgattacag ccatcatgcc    960

ctcacgtaga tcgttgccct ccaagttttt atccttttct ttcaacatca ccgttttgcg   1020

cgcatagtcg ttcatgacac gagtgtaagc ggttttgaat cccgtttcat gcgtacctcc   1080

gccacgtgtc ggaatggagt taacgaacga agcaatcgtc tctgtataac cagcattgta   1140

ctggatggca atctctactt caatgtcttc tttctcggca ttaaagtgaa taacgtcatg   1200

tagcacatcc ttgccctcat tcagaaaagc aacaaactga cttgcgccac cctcataaaa   1260

atactcatct gactttccgc tgcgttcgtc tttaagttga atacgaaggc ccgaatttag   1320

aaaagcaatt tcctgaaggc gctcagccaa cgtatcgtag ttaaaatgaa tgcctgcctg   1380

aaaaacacga atatccggtt taaatgtaat tttcgagccc gtcttgttag tattgcccag   1440

cacttcaagg cctgtggtcg gttctccgac atgctccacg cccttcttgt cctgccaata   1500

ttcaaaccgc tgacggtgaa tcttgccgtc ccggtaaatt tctacttcaa gccattccga   1560

aagagcgttc gttacagacg cacctacacc gtgcagaccc ccggactttt tatatcccga   1620

accgccaaac ttacctccgg cgtgcaaaat ggtgaataca acctgaggcg taggaattcc   1680

cgttttgtgc attcctgtag gaataccgcg cccgttgtct gatactgtaa cggaaccgtc   1740

cttatgcatt gtaatatcaa tgcgagagca aaacttggcg agatgttcat ccaccgcgtt   1800
```

```
gtctacaatt tcccatacca aatgatgcag tcccgaagaa ctggtgctcc cgatgtacat   1860

gcccggccgt ttgcgaactg ccacaagccc ttcgagcact tgaatgtcgt ccgcgccata   1920

ttctgaagct ccgctttgtg tgccggatac tcccgcagac aagtcgattt tgtcgaccat   1980


<210> SEQ ID NO 18
<211> LENGTH: 1980
<212> TYPE: DNA
<213> ORGANISM: Paenibacillus sp.

<400> SEQUENCE: 18

ctactctacg tattccgtga aatccacgtt ttccacgatc cagcgcttac gtggatctac     60

cttgtcaccc atcaatgtgg acacacggcg ttcagctttg gcagcatcct caatttgaac    120

gcgcaacagg gtgcgtgatt cgggattcat tgtcgtttcc cataactgat caggattcat    180

ctccccgagt cctttataac gttgaagctc aaaattccgt ccaaattctt ttaggtaatt    240

atcaagctgc tcgtcagtcc aggcataacg aaccgtttcg agcttacccg acttgcgggt    300

tattttatac aatggcggct gagcaataaa tatgcgtcct gcatcaatga gttctttcat    360

gtaccgataa aagaacgtca acaacagtac ttgaatgtgc gcgccgtccg tatctgcgtc    420

ggtcataatg atgattttgg aataattgct gtcttccagc gagaactctg ttcctacccc    480

cgcgccaatc gctgccgtaa tagcacggta ctcatcattt ttcataatat cggcaagctt    540

tgacttttcc ggattcatcg gcttgccctt taacggtaaa atagcctgga tcttggaatc    600

tcgaccctgt ttggccgatc ctcccgccga atcgccttcc acgataaata attcattacg    660

tgtaaaatct ttagattgcg caggcgacag cttaccattc aaattagaac tttcactgcg    720

cttcttgcca gaacgcattt cgtcccgagc cttacgcgca gcttcacgtg ctttggacgc    780

ttgaactgcc tttttaatca aagtttgcgc aatctgtgga ttttcttcca agaaacgctg    840

catctgttca gatacgatgg catccactgt acttcgtgcc gaagcactcc ccagctgatc    900

ttttgtctga ccgacaaatt caacctcagc catcttgaca ctgattacag ccatcatgcc    960

ctcacgtaga tcgttaccct ccaggttttt atccttttcc ttcaacagcg ctgttttgcg   1020

tgcatagtca ttcatcacac gagtgtaagc ggttttgaag cctgtttcat gcgttccccc   1080

gccacgtgtt ggaatggagt taacgaacga agcaatcgtc tctgtgtaac cagcattgta   1140

ttggatggca atctctactt caatgtcctc tttctcagca ttaaagtgaa taacatcatg   1200

cagtacatcc ttgccctcat tcaaaaaagc aacaaactga ctcgctccac cctcataata   1260

atattcatct gactttccac tgcgttcgtc tttaagctga atacgaaggc cggaattcag   1320

aaaggcaatt tcctgaaggc gctcagccag tgtatcatag ttaaaatgga tgcctgactg   1380

aaaaacgcga atatccggtt taaatgtaac ttttgagccc gtcttgttag tattgcccag   1440

cacttcaagg cctgtggtcg gttcaccgac atgctccacg cccttcttgt cctgccaata   1500

ttcgaaccgc tgacggtgaa tcttgccgtc ccggtagatt tccacttcaa gccattccga   1560

aagagcgttc gttacagacg cacctacccc atgcagaccc ccggactttt tatatcccga   1620

accgccaaac ttacctccgg cgtgcaaaat ggtgaataca acttgaggcg taggaattcc   1680

cattttatgc attcccgtag gaataccgcg cccgttgtct gatactgtaa tagagccgtc   1740

cttatgcatt gtgatatcaa tgcgagagca aaacttggca agatgttcat ccaccgcgtt   1800

gtctacaatt tcccatacca aatgatgcag tcccgaagaa ctggtgctcc cgatgtacat   1860

gcccggccgt ttgcgaactg ccacaagccc ttcgagcact tgaatgtcgt ccgcgccata   1920

ttctgaagct ccgttctgtg taccggaagc tcccgcagac aagtcgattt tgtcgaccat   1980
```

<210> SEQ ID NO 19
<211> LENGTH: 312
<212> TYPE: DNA
<213> ORGANISM: Bacillus sp.

<400> SEQUENCE: 19

```
tcttcaaaga aacaatcgta tacgactatg atctgctttc aaaccgtgtc cgggaattgg      60
ccttcctgac aaaaggcgta aacatcacga ttgaagacaa acgtgaagga caagaacgga     120
aaaacgagta ccactacgaa ggcggaatca aaagctatgt tgagtactta aaccgttcca     180
aagaagtcgt tcatgaagag ccgatttata tcgaaggcga gaaagacggc ataacggttg     240
aagttgcatt gcaatacaac gacagctata caagcaatat ttattctttc acgaataata     300
tcaacacata cg                                                         312
```

<210> SEQ ID NO 20
<211> LENGTH: 1980
<212> TYPE: DNA
<213> ORGANISM: Paenibacillus sp.

<400> SEQUENCE: 20

```
ctactctacg tattccgtga aatctacgtt ttccacgatc cagcgcttgc gcggatccac      60
cttatcaccc atcaaagtgg acaccctgcg ttcagccttg gctgcatcct ctatctgaac     120
gcgtaacaag gtgcgtgaat cgggattcat cgttgtttcc cataactgat cagggttcat     180
ttccccaagt cctttatagc gctgaagctc aaaatttcgt ccaaattctt ttaaataatt     240
atcaagctgc tcgtcagtcc aagcataacg caccgtttcg agcttacccg actttcgagt     300
tattttatac aatggcggtt gagcaataaa tatgcgtcct gcatcaataa gctctttcat     360
gtaccgataa aagaacgtca acaacagcac ttgaatgtgc gcaccatctg tatctgcatc     420
ggtcataatg atgattttgg aataattgct gtcttccagc gaaaactctg ttcctactcc     480
cgcaccaata gctgctgtaa tagcacggta ctcatcattc ttcataatat ccgccagttt     540
ggatttttcc ggattcatcg gcttgccctt tagcggcaat atggcctgaa ttttggaatc     600
ccgtccctgc ttggctgaac ctccagccga atcgccttcc acaataaaca actcattacg     660
tgtaaaatcc ttggactgcg caggcgacag tttaccattc aaattggaac tttcactgcg     720
ctttttaccg gaacgcatct catctcgagc tttacgtgca gcttcacgcg ctctggatgc     780
ttgaactgcc ttcttgatca aagtttgtgc tatctgcgga ttttcttcca aaaaacgctg     840
catctgctca gatacgatgg catccactgt actccgtgcc gaagcgctac ccagctgatc     900
ctttgtctgg ccgacaaatt caacttcagc cattttgaca ctgattacag ccatcatgcc     960
ctcacgtaga tcgttgccct ccaagttttt atccttttct ttcaacatca ccgttttgcg    1020
cgcatagtcg ttcatgacac gagtgtaagc ggttttgaat cccgtttcat gcgtacctcc    1080
gccacgtgtc ggaatggagt taacgaacga agcaatcgtc tctgtataac cagcattgta    1140
ctggatggca atctctactt caatgtcttc tttctcggca ttaaagtgaa taacgtcatg    1200
tagcacatcc ttgccctcat tcagaaaagc aacaaactga cttgcgccac cctcataaaa    1260
atactcatct gactttccgc tgcgttcgtc tttaagttga atacgaaggc ccgaatttag    1320
aaaagcaatt tcctgaaggc gctcagccaa cgtatcgtag ttaaaatgaa tgcctgcctg    1380
aaaaacacga atatccggtt taaatgtaat tttcgagccc gtcttgttag tattgcccag    1440
cacttcaagg cctgtggtcg gttctccgac atgctccacg cccttcttgt cctgccaata    1500
```

```
ttcaaaccgc tgacggtgaa tcttgccgtc ccggtaaatt tctacttcaa gccattccga   1560

aagagcgttc gttacagacg cacctacacc gtgcagaccc ccggactttt tatatcccga   1620

accgccaaac ttacctccgg cgtgcaaaat ggtgaataca acctgaggcg taggaattcc   1680

cgttttgtgc attcctgtag gaataccgcg cccgttgtct gatactgtaa cggaaccgtc   1740

cttatgcatt gtaatatcaa tgcgagagca aaacttggcg agatgttcat ccaccgcgtt   1800

gtctacaatt tcccatacca aatgatgcag tcccgaagaa ctggtgctcc cgatgtacat   1860

gcccggccgt ttgcgaactg ccacaagccc ttcgagcact tgaatgtcgt ccgcgccata   1920

ttctgaagct ccgctttgtg tgccggatac tcccgcagac aagtcgattt tgtcgaccat   1980
```

<210> SEQ ID NO 21
<211> LENGTH: 321
<212> TYPE: DNA
<213> ORGANISM: Bacillus sp.

<400> SEQUENCE: 21

```
gaaatcttca aagaaacaat cgtatacgac tatgatctgc tttcaaaccg tgtccgggaa     60

ttggccttcc tgacaaaagg cgtaaacatc acgattgaag acaaacgtga aggacaagaa    120

cggaaaaacg agtaccacta cgaaggcgga atcaaaagct atgttgagta cttaaaccgt    180

tccaaagaag tcgttcatga agagccgatt tatatcgaag gcgagaaaga cggcataacg    240

gttgaagttg cgttgcaata caacgacagc tatacaagca acatttattc tttcacaaat    300

aacatcaaca catacgaagg c                                              321
```

<210> SEQ ID NO 22
<211> LENGTH: 3564
<212> TYPE: DNA
<213> ORGANISM: Paenibacillus sp.

<400> SEQUENCE: 22

```
atgaggggtg agtttaagtt ggcaggacat cttgttcaat atggtcgacg cactcggcgc     60

agttatgcac gtattaatga ggtactcgag gttccgaacc tgattgagat ccaacaaaaa    120

tcctatgatt ggtttttgga ggaaggatta cgggaaatgt ttcgggatat ttcaccaatt    180

caagatttca ctggaaatct gattttggag tttatcgact attctctcgg agaacccaaa    240

tataccgttg acgacgcaaa ggaacgcgac gttacgtatg cagcaccgct tcgggtaaaa    300

gtccggctta ttaataaaga gaccggggaa gtgaaagagc aggaagtatt catgggagac    360

ttcccgctga tgactgaaac gggtacgttt attattaacg gtgcggaacg ggttattgtc    420

agccagttgg ttcgctctcc cagcgtctat ttcagcacaa aagtcgacaa gaatgcgaaa    480

acaacataca ccgcaacggt aattcctaac cggggggctt ggctcgaact ggagatggat    540

gcgaaggata ttatctatgt ccggattgac cgtacccgta aaattccggt tacggtgttg    600

ctgcgtgcac ttggctttgg cactgatgct gagattctgg atttgctcgg caatgacgaa    660

tatatccgca acacacttga taaagacaat acggattcca cggagaaagc gctgattgaa    720

atttatgagc gtcttcgccc gggtgagcca cctacactgg ataacgcaaa gagcttgctt    780

gttgcacgct tctttgatcc aaaacgttat gatctggcca acgtaggccg ttacaaaatc    840

aataaaaagc ttcacatcaa aaaccgtctg ttcaatcaac gtcttgctga gacattgatt    900

gatacaacaa ctggtgaaat tatcgctgaa gcaggacaaa tggtggatcg tcgcctgttg    960

gacgagattc tggcccaact ggaggaatca gtaggacacc gcacgtatca tgttgctagc   1020

ggcgtgctgg aaagcaatga tattccactt caaacgattg atgtgttctc gccaatcgag   1080
```

```
gacggtaaag tagtaaaact gattgctaac ggaaatattg ataaatcggt taagaatatt   1140
acgcctgccg atattatttc ctccatcagt tattttatta acttgcttca cggtatcgga   1200
agtacggacg atattgacca tttgggtaac cgtcgtttac gttctgtagg tgagttgctc   1260
caaaaccagt tccgtatcgg tttatcccgt atggaacgcg tggtgcgtga aagaatgtcg   1320
attcaggatg ctaatgtaat tacgccacaa gcgttgatta acatacgtcc agtaattgct   1380
tcgattaaag agttctttgg tagctcgcag ctgtcacagt ttatggatca gacaaacccg   1440
cttgctgaat taacgcacaa acgtcgtctg tccgcactcg gacccggcgg tttgacgcgt   1500
gaacgcgcag gcatggaagt gcgtgacgtc catccaagtc actacggccg tatgtgtcct   1560
atcgagacac cagagggacc aaacattggt ttgatcaact ctttgtccac atttgcacgt   1620
atcaacgagt acggatttat cgaagctcct tatcgttggg tagatccgaa aaccggaaaa   1680
gttacagacc agattgatta cctgactgct gatgaagaag ataactacat cgtagctcag   1740
gcgaacgcgg aattgacgga ggaaaacacc tttaaggatg aggtcgtcat tgtccgttat   1800
aacaaacagt ctgataacat tattccaatg gctagtagcc gtgttgatta catggacgta   1860
tcacctaaac aggtcgtatc agttgcgaca gcactgattc cgtttctgga gaatgatgac   1920
tctaaccgcg cattgatggg ttccaatatg caacgtcagg ctgtcccact attgattccg   1980
aagtctccat tggtcggaac aggaatggag cacaagtctg caaaagattc tggtgtttgc   2040
attgtatcca aatacaacgg agttatcgaa cgctcttcgg ctaacgaaat ttggttgcgt   2100
cgtatcgaaa ctgtagatgg tgctgaagtg aagggcgaca ttgttaagta taaattacac   2160
aaatttatgc gatctaacca aggaacttgc attaaccaac gtccgattgt gaacagagga   2220
gatattgtca aagttggcga tattcttgca gatggtccat ctacggagat gggtgagttg   2280
gcgttgggac gtaacgttgt cgttgccttc atgacttggg aaggttacaa ctacgaggat   2340
gcgatcctgc tgagtgagaa actggtcaag gaggatgtat acacctcgat ccatattgag   2400
gaatacgaat ccgaggctcg tgacacgaaa cttggacctg aagaaatcac tcgtgacatt   2460
ccaaatgtcg gtgaagaggc gcttcgcaac ttggatgagc gtggaatcat tcgtattggt   2520
gccgaaatcg gtgcaggtga cattcttgtt ggtaaagtta cacctaaagg tgtgactgaa   2580
ttgacagctg aggaacgtct cttacacgca atctttggtg agaaggcacg cgaggttcgc   2640
gatacttctt tgagagttcc tcacggaaca gatgggattg ttgtagatgt aaaggtgttt   2700
acacgtgaaa atggtgatga actgccacca ggtgtaaatc agttggttcg tgtatatatt   2760
gctcaaaaac gtaaaatctc cgaaggcgat aaaatggctg gacgtcacgg taacaagggt   2820
gtcgttgccc gtattttgcc tgaagaagat atgccgttcc tgccggatgg cacaccagta   2880
caggtcgttc tgaacccgct gggggtacct tcacggatga acatcggaca ggtgcttgaa   2940
gtccatctgg gtatggctgc aatgcgtctt ggtattcatg tggcaactcc agtattcgat   3000
ggtgccaagg agtatgacgt gttcgataca atggaagagg caggcatgca gcgtaatggt   3060
aagactgtgt tgtatgacgg acgtacgggt gatcgttttg aacgtgaagt tactgtcggt   3120
gtcatgcaca tgatcaaact ggcgcacatg gtcgatgata aaatccatgc tcgttctaca   3180
ggtccttact ctctcgttac gcagcaacca ttgggtggta aagctcaatt cggtggacag   3240
cgcttcgggg agatggaagt atgggcattg gaagcctacg gcgcggcgta cacgcttcag   3300
gaaattttga ctgtgaaatc cgatgatgtg gttggacgtg ttaaaactta cgaatccatt   3360
gtcaaaggtg aaaatgtacc tgaaccgggt gttccagaat catttaaggt cttgatcaaa   3420
```

gagctgcaaa gcttgggtat ggacgtgaag attctgtctg aagacgaaca agagattgaa 3480
atgagagagc ttgatgatga ggatgacaca agcggcgata agctgagttt gaatctggaa 3540
ggctctgagg ttggcgtaga gtag 3564

<210> SEQ ID NO 23
<211> LENGTH: 756
<212> TYPE: DNA
<213> ORGANISM: Bacillus sp.

<400> SEQUENCE: 23
gaaacgcctg agggcccgaa catcggtttg atcaactcat tgtcatcatt tgcgaaagta 60
aaccgctttg gtttcattga gacgccatac cgccgcgttg atcctgaaac aggaaaagta 120
acgcctagaa tcgactacct gactgctgat gaagaggata actatgtcgt agcccaagcg 180
aatgctaagc tgagcgatga cggttctttc ttggatgaca gcatcgtagc gcgtttcaga 240
ggggaaaaca ccgttgtagc ccgcaaccgc gtggattaca tggacgtatc tcctaaacag 300
gttgtatctg ctgcgacagc atgtattccg ttcttggaaa acgatgactc gaaccgcgcc 360
ctcatgggag cgaacatgca gcgtcaggct gtgcctttga tgcagccgga agctccgatc 420
gtcggaacgg gtatggaata cgtatccggt aaagactccg gtgcagccgt tatttgtaaa 480
caccctggta tcgtagaacg ggtggaagcg aaaaacgtat gggtgcgccg ctatgaagaa 540
attgacggcc aaaaagtaaa aggcaacctg gataagtaca gcttgctgaa atttgtccgc 600
tccaaccaag gtacgtgcta caaccagcgt ccgatcgtca gtgtcggcga tgaagtagtc 660
aaaggagaaa tccttgctga cggaccttca atggagcttg gtgaacttgc tctcggccgc 720
aacgtaatgg tcggcttcat gacatgggat ggttac 756

<210> SEQ ID NO 24
<211> LENGTH: 3246
<212> TYPE: DNA
<213> ORGANISM: Bacillus sp.

<400> SEQUENCE: 24
atgggtgatt tccctattat gacagatacc ggtactttta tcatcaacgg tgcagaacgt 60
gttatcgtat ctcagcttgt tcggtctcca agtgtatatt tcagtggtaa agtagacaag 120
aacggtaaaa aaggttttac cgcgactgtc attccaaacc gtggcgcatg gttagaatac 180
gaaactgatg cgaaagatgt tgtgtatgtc cgcattgatc gcacacgtaa gttgccggtt 240
acggttcttt tgcgtgctct cggcttcggt tccgaccaag agattctcga tctcattggt 300
gagaacgaat atctccgcaa tacactggat aaggacaaca ctgaaaacag tgacaaagcg 360
cttcttgaaa tctatgagcg ccttcgtccc ggagagccgc ctacagtaga aaacgcaaaa 420
agcttgctgg attcccgttt cttcgatccg aagcgatacg accttgcgaa tgtaggacgc 480
tataaaatta ataaaaagct tcatatcaag aaccgcctgt ttaaccagcg ccttgcagaa 540
acactggtgg atccggaaac cggtgaaatt ctcgctgaaa aagggcagat tcttgacaga 600
agaacacttg ataaagtact gccatactta gaaaatggaa tcggcttcag aaaactttat 660
cctaacggcg gcgttgtcga ggatgaagtg atgcttcaat ccattaaaat ctatgctcct 720
accgatgcag aaggagagca gacgatcaat gtgatcggca atgcttacat cgaagaggcg 780
attaaaaaca ttacgcctgc tgatattatt tcttctatca gctacttctt caacctcctg 840
cacggagtgg gtgacactga tgatatcgac catctcggaa accgccgtct gcgttctgta 900
ggtgagctcc tgcaaaacca attccgtatc ggtttaagcc ggatggaacg tgtcgttcgt 960

```
gaaagaatgt ctattcaaga cacgaataca attacgccgc agcagctgat taacatcaga   1020
cctgttattg cgtctattaa agagttcttc ggaagctcac agctttctca attcatggat   1080
cagacgaacc cgcttgctga attgacgcac aaacgccgtc tgtcagctct cggaccgggc   1140
ggtttgacac gtgagcgcgc aggtatggaa gtacgtgacg ttcactactc tcactatggc   1200
cgtatgtgtc cgattgaaac gcctgagggc ccgaacatcg gtttgatcaa ctcattgtca   1260
tcatttgcga aagtaaaccg ctttggtttc attgagacgc cataccgccg cgttgatcct   1320
gaaacaggaa aagtaacgcc tagaatcgac tacctgactg ctgatgaaga ggataactat   1380
gtcgtagccc aagcgaatgc taagctgagc gatgacggtt ctttcttgga tgacagcatc   1440
gtagcgcgtt tcagagggga aaacaccgtt gtagcccgca accgagtgga ttacatggac   1500
gtatctccta aacaggttgt atctgctgcg acagcatgta ttccgttctt ggaaaacgat   1560
gactcgaacc gcgccctcat gggagcgaac atgcagcgtc aggctgtgcc tttgatgcag   1620
ccggaagctc cgatcgtcgg aacgggtatg gaatacgtat ccggtaaaga ctccggtgca   1680
gccgttattt gtaaacaccc tggtatcgtt gaacgggtgg aagcgaaaaa cgtatgggtg   1740
cgccgctatg aagaaattga cggtcaaaaa gtaaaaggca acctggataa gtacagcttg   1800
ctgaaatttg tccgctccaa ccaaggtacg tgctacaatc agcgtccgat cgtcagtgtc   1860
ggcgacgaag tagtcaaagg agaaatcctt gctgacggac cttcaatgga gcttggtgaa   1920
cttgctctcg gccgcaacgt aatggtcggc ttcatgacat gggatggtta caactatgag   1980
gatgccatca tcatgagtga acgccttgtg aaagatgatg tatacacatc tattcacatt   2040
gaagaatatg aatcagaagc acgtgataca aagcttgggc cggaagagat cacccgcgat   2100
attccaaacg taggggaaga tgcgcttcgc aatcttgatg accgcggaat tatccgtatc   2160
ggtgcggaag tcaacgacgg agaccttctc gtaggtaaag taacgcctaa aggtgtaact   2220
gagcttacgg ctgaagaacg ccttcttcat gcgatctttg gagaaaaagc gcgtgaagtc   2280
cgtgatactt ctctccgtgt gcctcacggc ggcggcggaa ttatccacga cgtaaaagtc   2340
ttcaaccgtg aagacggcga cgaacttcct ccgggagtga accagcttgt acgcgtatat   2400
atcgttcaga aacgtaagat ttctgaaggt gataaaatgg ccggacgtca cggaaacaaa   2460
ggggttatct cgaagattct tcctgaagaa gatatgcctt accttcctga cggcacgccg   2520
atcgatatca tgcttaaccc gctgggtgta ccatcacgta tgaatatcgg tcaggtatta   2580
gaacttcaca tgggtatggc tgcccgctac ctcggcattc acatcgcgtc acctgtattt   2640
gacggcgcgc gtgaagaaga tgtgtgggaa acacttgaag aagcaggcat gtcaagagac   2700
gctaaaacag ttctttatga cggccgtacg ggagaaccgt tcgacaaccg tgtatctgtc   2760
ggaatcatgt acatgatcaa actggcgcac atggttgatg ataaacttca tgcccgttct   2820
acaggtcctt actcacttgt tacgcagcag cctctcggcg gtaaagccca attcggcgga   2880
cagcgtttcg gtgagatgga ggtttgggcg cttgaagctt acggcgcagc ttacacgctt   2940
caagaaatcc tgactgtgaa gtccgatgac gtggtcggac gtgtgaaaac atatgaagcc   3000
atcgtcaaag gcgacaatgt tccagagcct ggtgttccgg aatcattcaa agtattgatc   3060
aaagagcttc aaagcttagg tatggacgta aaaatccttt caggcgatga agaagaaata   3120
gaaatgagag atctagaaga cgaggaagat gcgaaacaag ctgacggcct tgcattatca   3180
ggtgatgaag cgccggaaga aacagcatct ccagacgttg aacgtgacgc agtaacgaaa   3240
gaatag                                                              3246
```

<210> SEQ ID NO 25
<211> LENGTH: 756
<212> TYPE: DNA
<213> ORGANISM: Bacillus sp.

<400> SEQUENCE: 25

```
gaaacgcctg agggcccgaa catcggtttg atcaactcat tgtcatcatt tgcgaaagta     60
aaccgctttg gtttcattga gacgccatac cgccgcgttg atcctgaaac aggaaaagta    120
acgcctagaa tcgactacct gactgctgat gaagaggata actatgtcgt agcccaagcg    180
aatgctaagc tgagcgatga cggttctttc ttggatgaca gcatcgtagc gcgtttcaga    240
ggggaaaaca ccgttgtagc ccgcaaccgc gtggattaca tggacgtatc tcctaaacag    300
gttgtatctg ctgcgacagc atgtattccg ttcttggaaa acgatgactc gaaccgcgcc    360
ctcatgggag cgaacatgca gcgtcaggct gtgcctttga tgcagccgga agctccgatc    420
gtcggaacgg gtatggaata cgtatccggt aaagactccg gtgcagccgt tatttgtaaa    480
caccctggta tcgtagaacg ggtggaagcg aaaaacgtat gggtgcgccg ctatgaagaa    540
attgacggcc aaaaagtaaa aggcaacctg gataagtaca gcttgctgaa attcgtccgc    600
tccaaccaag gtacgtgcta caaccagcgt ccgatcgtca gtgtcggcga tgaagtagta    660
aaaggagaaa tccttgctga cggaccttca atggagcttg gtgaacttgc tctcggccgc    720
aacgtaatgg tcggcttcat gacatgggat ggttac                              756
```

<210> SEQ ID NO 26
<211> LENGTH: 756
<212> TYPE: DNA
<213> ORGANISM: Bacillus sp.

<400> SEQUENCE: 26

```
gaaacgcctg agggcccgaa catcggtttg atcaactcat tgtcatcatt tgcgaaagta     60
aaccgctttg gtttcattga gacgccatac cgccgcgttg atcctgaaac aggaaaagta    120
acgcctagaa tcgactacct gactgctgat gaagaggata actatgtcgt agcccaagcg    180
aatgctaagc tgagcgatga cggttctttc ttggatgaca gcatcgtagc gcgtttcaga    240
ggggaaaaca ccgttgtagc ccgcaaccgc gtggattaca tggacgtatc tcctaaacag    300
gttgtatctg ctgcgacagc atgtattccg ttcttggaaa acgatgactc gaaccgtgcc    360
ctcatgggag cgaacatgca gcgtcaggct gtgcctttga tgcagccgga agctccgatc    420
gtcggaacgg gtatggaata cgtatccggt aaagactccg gtgcagccgt tatttgtaaa    480
caccctggta tcgttgaacg ggtggaagcg aaaaacgtat gggtgcgccg ctatgaagaa    540
attgacggcc aaaaagtaaa aggcaacctg gataagtaca gcttgctgaa atttgtccgc    600
tccaaccaag gtacgtgcta caaccagcgt ccgatcgtca gtgtcggcga tgaagtagtc    660
aaaggagaaa tccttgctga cggaccttca atggagcttg gtgaacttgc tctcggccgc    720
aacgtaatgg tcggcttcat gacatgggat ggttac                              756
```

<210> SEQ ID NO 27
<211> LENGTH: 756
<212> TYPE: DNA
<213> ORGANISM: Bacillus sp.

<400> SEQUENCE: 27

```
gaaacgcctg agggcccgaa catcggtttg atcaactcat tgtcatcatt tgcgaaagta     60
aaccgctttg gtttcattga gacgccatac cgccgcgttg atcctgaaac aggaaaagta    120
```

```
acgcctagaa tcgactactt gactgctgat gaagaggata actatgtcgt agcccaagcg    180
aatgctaagc tgagcgatga cggttctttc ttggatgaca gcatcgtagc gcgtttcaga    240
ggggaaaaca ccgttgtagc ccgcaaccgc gtggattaca tggacgtttc tcctaaacag    300
gttgtttctg ctgcgacagc atgtattccg ttcttggaaa acgatgactc gaaccgcgcc    360
ctcatgggag cgaacatgca gcgtcaggct gtgcctttga tgcagccgga agctccgatc    420
gtcggaacgg gtatggaata cgtatccggt aaagactccg gtgcagccgt tatttgtaaa    480
caccctggta tcgttgaacg ggtggaagcg aaaaacgtat gggtgcgccg ctatgaagaa    540
attgacggcc aaaaagtaaa aggcaacctg gataagtaca gcttgctgaa atttgtccgc    600
tccaaccaag gtacgtgcta caaccagcgt ccgatcgtca gtgtcggcga tgaagtagtc    660
aaaggagaaa tccttgctga cggaccttca atggagcttg gtgaacttgc tctcggccgc    720
aacgtaatgg tcggcttcat gacatgggat ggttac                              756
```

```
<210> SEQ ID NO 28
<211> LENGTH: 3564
<212> TYPE: DNA
<213> ORGANISM: Paenibacillus sp.

<400> SEQUENCE: 28

atgaggggtg agtttaagtt ggcaggacat cttgttcaat atggtcgacg cactcggcgc     60
agttatgcac gtattaatga ggtactcgag gttccgaacc tgattgagat ccaacaaaaa    120
tcctatgatt ggtttttgga ggaaggatta agggaaatgt ttcgggatat ttctccaatt    180
caggatttca ctggaaatct gattctggag tttatcgact attctctcgg agaacccaaa    240
tataccgttg acgacgcaaa ggaacgcgac gttacgtatg cagcaccgct tcgggtaaaa    300
gtccggctta ttaataaaga aaccggggaa gtgaaagagc aggaagtatt catgggagac    360
ttcccgctga tgactgaaac gggtacgttt attattaacg gtgcggaacg ggttattgtc    420
agccagttgg ttcgctctcc cagcgtctat ttcagcacaa aagtcgacaa gaatgcgaaa    480
acaacataca ccgcaacggt aattcctaac cggggggctt ggctcgaact ggagatggat    540
gcgaaggata ttatctatgt ccggattgac cgtacccgta aaattccggt tacggtgttg    600
ctgcgtgcgc tgggctttgg cactgatgct gagattctgg atttgctcgg caatgacgaa    660
tatatccgca acacacttga taaagacaac acggattcca ccgagaaagc gctgattgaa    720
atttatgagc gtcttcgtcc aggtgagccg cctacactgg ataacgcaaa gagcttgcta    780
gttgctcgct tctttgatcc taaacgttat gatctggcca acgtaggccg ttacaaaatc    840
aataaaaagc ttcacatcaa aaaccgtttg ttcaatcaac gacttgctga gactttgatt    900
gatacaacaa ctggtgaaat catcgctgaa gccggtcaaa tggtagatcg ccgcctgttg    960
gacgagattt tggcccaact ggaggaatca gtaggacatc gtacgtatca tgttgcgagt   1020
ggtgtgctag aaagcaatga tattccactt caaacaatcg atgtattctc accaattgag   1080
gatggcaaag tagtaaaact gattgctaat ggaaatattg ataaatcggt taagaatatt   1140
acgcctgccg atattatttc ctccatcagt tattttatta acttgcttca cggaatcgga   1200
agtacggacg atattgacca tttgggtaac cgtcgtttgc gttctgtagg tgagttgctc   1260
caaaaccagt tccgtatcgg tttatcccgt atggaacgcg tggtgcgtga aagaatgtca   1320
attcaggatg ctaatgtaat tacgccacaa gcgctgatta acatacgtcc agtaattgct   1380
tcgattaaag agttctttgg tagctcgcag ctgtctcagt ttatggatca gacgaacccg   1440
```

```
cttgctgaat taacgcacaa acgtcgtctg tccgcactcg gacccggcgg tttgacgcgc   1500
gaacgcgcgg gcatggaagt gcgtgacgtc catccgagtc actacggccg tatgtgtcct   1560
atcgagacac cagagggacc aaacattggt ttgatcaact ctttgtccac ttttgcacgc   1620
attaacgagt atggatttat cgaagctcct tatcgttggg tagatccaaa aaccggaaaa   1680
gttacagacc agattgatta cctgactgct gatgaagaag ataactacat tgtagctcag   1740
gcgaatgcgg aattgacgga ggaaaacacc tttaaggatg aggttgtcat tgtccgttat   1800
aacaaacagt ctgataacat tattccgatg gctagtagcc gtgtcgatta catggacgta   1860
tcgcctaaac aggtcgtatc ggtcgcgact gcactgattc cgttcttgga gaatgatgac   1920
tctaaccgcg cattgatggg ttccaacatg cagcgtcagg ctgtcccgct tctgattccg   1980
aagtctccat tggtcggaac aggaatggag cacaagtctg caaaagattc cggtgtttgc   2040
gttgtatcca aatacaacgg agttatcgaa cgttcttcgg ctaacgaaat ttggttgcgt   2100
cgtatcgaaa ctgtagatgg cgctgaagtg aagggcgaca ttgttaagta taaattacac   2160
aaatttatgc gatctaacca aggaacttgc atcaaccaac gtccgattgt gaacagagga   2220
gatattgtca aagttggcga tattcttgcg gatggtccat ctacagagat gggtgagttg   2280
gcgttgggac gtaacgttgt cgttgccttc atgacttggg aaggttacaa ctacgaggat   2340
gcgatcttgc tgagtgagaa actggttaag gaagatgtat acacctcaat ccatattgag   2400
gaatacgaat ccgaggctcg tgacacgaag cttggacctg aagaaatcac tcgcgacatt   2460
ccaaatgtcg gtgaagaagc gcttcgcaac ttggatgagc gtggaatcat acgtattggt   2520
gctgaaattg gcgcaggtga cattctcgtt ggtaaagtaa cacctaaagg tgtgactgaa   2580
ttgacagctg aagaacgtct cttacacgca atctttggtg agaaggcacg cgaggttcgc   2640
gatacttctt tgagagttcc tcacggaaca gacgggattg ttgtagatgt aaaggtattt   2700
acacgtgaaa atggcgatga actgccacca ggtgtaaatc agttggttcg agtatatatt   2760
gctcaaaaac gtaaaatctc cgaaggcgat aaaatggctg gacgtcacgg taacaagggt   2820
gtcgttgccc gtattctgcc tgaagaagat atgccgttcc tgccggatgg cacaccagta   2880
caggtcgttc tgaacccgct gggcgtacct tcacggatga acatcggaca ggtgcttgaa   2940
gtccatctgg gtatggctgc aatgcgtctt ggtattcatg tggcaactcc agtattcgat   3000
ggtgccaagg aatatgacgt attcgataca atggaagagg caggcatgca gcgtaatggt   3060
aagactgtgt tgtatgacgg acgtacgggt gatcgttttg aacgtgaagt tactgtcggt   3120
gtcatgcaca tgatcaaact ggcgcacatg gtcgatgata aaatccatgc tcgttctaca   3180
ggtccttact ctctcgttac gcaacaacca ttgggtggta aagctcaatt tggtggacag   3240
cgcttcgggg agatggaagt atgggcattg gaagcctacg gcgcagcgta cacgcttcag   3300
gaaattttga ctgtgaaatc tgatgatgtg gttggacgtg ttaaaactta cgaatccatt   3360
gtcaaaggtg aaaatgtacc tgaaccgggt gttccagaat catttaaggt cttgatcaag   3420
gagctgcaaa gcttgggtat ggacgtgaag attctgtctg aagacgaaca agagatcgaa   3480
atgagagagc ttgatgatga ggatgacaca accggcgata agctgagttt gaatctggaa   3540
ggctctgagg ttggcgtaga gtag                                          3564
```

<210> SEQ ID NO 29
<211> LENGTH: 3564
<212> TYPE: DNA
<213> ORGANISM: Paenibacillus sp.

<400> SEQUENCE: 29

```
atgaggggtg agtttaagtt ggcaggacat cttgttcaat atggtcgacg cactcggcgc     60
agttatgcac gtattaatga ggtactcgag gttcccaacc tgattgagat ccaacaaaaa    120
tcatatgatt ggtttttgga ggaaggatta cgggaaatgt ttcgggatat ttctccaatt    180
caagatttca caggaaatct gattttggag tttatcgatt actctctcgg agaacccaaa    240
tataccgttg acgacgcaaa agaacgcgac gttacgtatg cggcaccgct tcgggtaaaa    300
gtccggctta ttaataagga aaccggggaa gtaaaagagc aggaagtatt catgggagac    360
ttcccgctga tgactgaaac gggtacgttt attattaacg gtgcggaacg ggttattgtc    420
agccagttgg ttcgctctcc cagcgtctat ttcagcacaa aagtcgacaa gaatgcgaaa    480
acaacataca ccgcaacggt aattcctaac cggggggctt ggctcgaact ggagatggat    540
gcgaaggata ttatctatgt ccggattgac cgtacccgta aaattccggt tacggtgttg    600
ctgcgtgcac ttggctttgg cactgatgct gagattctgg atttgctcgg caatgacgaa    660
tatatccgca acacacttga taaagacaac acggattcca cggagaaagc gctgattgaa    720
atttatgagc gtcttcgtcc gggtgagcca cctacattgg ataatgcaaa gagcttgctt    780
gttgcacgct tctttgatcc aaaacgttat gatctggcca acgtaggccg ttacaaaatc    840
aataaaaagc ttcacatcaa aaaccgtctg ttcaatcaac gcctagctga gacactgatt    900
gatacaacaa ctggtgaaat tatcgctgaa gcagggcaaa tggtagaccg ccgcttgttg    960
gacgagattt tggcacaact agaagagtcg gttggacacc gtacgtatca tgttgctagt   1020
ggcgtattgg aaagcaatga tattccgctt caaacgatcg atgtattctc gccaatcgaa   1080
gacggtaaag tagtaaaact gattgccaat ggaaatatcg ataaatcggt taagaacatt   1140
acgcctgccg atattatttc ctccatcagt tattttatta acttgcttca cggaatcgga   1200
agtacggacg acattgacca tttgggtaac cgtcgtttgc gttctgtagg tgagttgctc   1260
caaaatcagt tccgtattgg tctgtcccgt atggaacgcg tggtacgcga aagaatgtca   1320
attcaggatg ctaatgtaat tacgccacaa gcgctgatta acatacgtcc ggtcattgcg   1380
tcgattaaag agttctttgg tagctctcag ctgtctcagt tcatggatca gacaaacccg   1440
cttgctgaac taacacacaa acgtcgtttg tctgcactcg gacccggcgg tttgacgcgc   1500
gaacgcgcgg gcatggaagt acgtgacgtc catccgagtc actacggccg tatgtgtcct   1560
atcgagacac cagagggacc aaacattggt ttgatcaact ctttgtcaac ttttgcacgt   1620
atcaacgaat acggatttat cgaagctcct tatcgctggg tagatccgaa gactggaaaa   1680
gttacagatc agattgatta cctgactgct gatgaagaag ataactacat cgttgctcag   1740
gcaaatgcgg aattgacgga agaaaacacc tttaaggatg aagtcgttat tgttcgctat   1800
aacaagcagt ctgataacat tattccaatg gcaagtagcc gtgtcgatta catggacgta   1860
tcacctaaac aggttgtatc ggtcgcaact gctctgatcc cgttcctgga gaatgatgac   1920
tcgaaccgtg cattgatggg ttccaacatg cagcggcagg ctgtcccatt gctgattccg   1980
aaagcgcctt tggtaggaac agggatggaa cataagtctg caaaagattc cggtgtgtgc   2040
gttgtgtcca agtacaacgg ggtgattgaa cgttcttcgg ctaacgaaat ttggctgcgt   2100
cgtattgaaa cagtagatgg cgctgaagtc aaaggcgata ttgttaagta taaattacac   2160
aaatttatgc gttctaacca aggaacatgc atcaaccagc gtccaatcgt aaacagaggc   2220
gatattgtca aagttggcga tattcttgct gacggtcctt ccaccgagat gggtgagttg   2280
gcactgggac gtaacgttgt cgtagcgttc atgacttggg aaggttacaa ctacgaggat   2340
```

gcgatcttgc tgagcgagaa gctggttaaa gaggatgtat atacctcgat ccatatcgag 2400
gaatacgaat ctgaagcccg tgatacgaaa cttggaccag aagaaatcac tcgtgatatt 2460
ccgaatgtcg gtgaagaagc gcttcgcaat ctagatgagc gcggcatcat tcgcatcggt 2520
gctgaaatcg ccgcaggtga cattcttgtt ggtaaagtaa cacctaaggg tgtaactgag 2580
ttgacagctg aagaacgtct cttgcatgca atcttcggtg agaaggcgcg cgaggttcgt 2640
gatacttcct tgagagttcc tcacggaacc gacggaatcg tcgtagatgt taaagtattt 2700
acacgtgaaa atggcgatga gctgccaccg ggtgtaaacc agttggtacg cgtctatatt 2760
gctcaaaaac gtaaaatttc cgaaggcgat aaaatggccg gacgtcacgg taacaagggt 2820
gtcgttgccc gtattctgcc tgaagaagat atgccgttct tgccagatgg cacgccagta 2880
caagtcgtac tgaatccgct gggcgtacct tcacggatga acatcggaca ggtgcttgaa 2940
gtgcatttgg gtatggctgc aatgcgtctt ggtattcatg tggcaactcc agtattcgat 3000
ggtgccaagg agtatgacgt atttgatacg atggaagaag cgggtatgca acgcaatggt 3060
aagacagtgt tgtatgatgg gcgtacaggt gatcgttttg aacgtgaagt tacggtcggt 3120
gtcatgcaca tgatcaaact ggcgcacatg gtcgacgata agatccatgc tcgttctaca 3180
ggcccttact ctctcgttac gcagcaaccg ttgggtggta aagctcaatt cggtggtcag 3240
cgcttcgggg agatggaagt atgggcactg gaagcctacg gtgcggcgta tacgcttcag 3300
gaaattttga ctgtgaaatc cgatgacgtg gttggacgtg ttaaaactta cgaatccatc 3360
gtcaaaggtg aaaatgtccc agaaccgggt gttcctgaat cattcaaggt cttgatcaaa 3420
gagctgcaaa gcttgggtat ggacgtgaag attctgtctg aagacgaaca agagatcgaa 3480
atgagagagc ttgatgatga ggatgataca actggcgata agctgagttt gaatctggaa 3540
ggctctgagg ttggcgtaga gtag 3564

<210> SEQ ID NO 30
<211> LENGTH: 756
<212> TYPE: DNA
<213> ORGANISM: Bacillus sp.

<400> SEQUENCE: 30
gaaacgcctg agggcccgaa catcggtttg atcaactcat tgtcatcatt tgcgaaagta 60
aaccgctttg gtttcattga gacgccatac cgccgcgttg atcctgaaac aggaaaagta 120
acgcctagaa tcgactacct gactgctgat gaagaggata actatgtcgt agcccaagcg 180
aatgctaagc tgagcgatga cggttctttc ttggatgaca gcatcgtagc gcgtttcaga 240
ggggaaaaca ccgttgtagc ccgcaaccgc gtggattaca tggacgtatc tcctaaacag 300
gttgtatctg ctgcgacagc atgtattccg ttcttggaaa acgatgactc gaaccgcgcc 360
ctcatgggag cgaacatgca gcgtcaggct gtgcctttga tgcagccgga agctccgatc 420
gtcggaacgg gtatggaata cgtatccggt aaagactccg gtgcagccgt tatttgtaaa 480
caccctggta tcgtagaacg ggtggaagcg aaaaacgtat gggtgcgccg ctatgaagaa 540
attgacggcc aaaaagtaaa aggcaacctg gataagtaca gcttgctgaa atttgtccgc 600
tccaaccaag gtacgtgcta caaccagcgt ccgatcgtca gtgtcggcga tgaagtagtc 660
aaaggagaaa tccttgctga cggaccttca atggagcttg gtgaacttgc tctcggccgc 720
aacgtaatgg tcggcttcat gacatgggat ggttac 756

<210> SEQ ID NO 31
<211> LENGTH: 3564

<212> TYPE: DNA
<213> ORGANISM: Paenibacillus sp.

<400> SEQUENCE: 31

```
atgaggggtg agtttaagtt ggcaggacat cttgttcaat atggtcgacg cactcggcgc     60
agttatgcac gtattaatga ggtactcgag gttccgaacc tgattgagat ccaacaaaaa    120
tcctatgatt ggtttttgga ggaaggatta agggaaatgt ttcgggatat ttctccaatt    180
caggatttca ctggaaatct gattctggag tttatcgact attctctcgg agaacccaaa    240
tataccgttg acgacgcaaa ggaacgcgac gttacgtatg cagcaccgct tcgggtaaaa    300
gtccggctta ttaataaaga aaccggggaa gtgaaagagc aggaagtatt catgggagac    360
ttcccgctga tgactgaaac gggtacgttt attattaacg gtgcggaacg ggttattgtc    420
agccagttgg ttcgctctcc cagcgtctat ttcagcacaa aagtcgacaa gaatgcgaaa    480
acaacataca ccgcaacggt aattcctaac cggggggctt ggctcgaact ggagatggat    540
gcgaaggata ttatctatgt ccggattgac cgtacccgta aaattccggt tacggtgttg    600
ctgcgtgcgc tgggctttgg cactgatgct gagattctgg atttgctcgg caatgacgaa    660
tatatccgca acacacttga taaagacaac acggattcca ccgagaaagc gctgattgaa    720
atttatgagc gtcttcgtcc aggtgagccg cctacactgg ataacgcaaa gagcttgcta    780
gttgctcgct tctttgatcc taaacgttat gatctggcca acgtaggccg ttacaaaatc    840
aataaaaagc ttcacatcaa aaaccgtttg ttcaatcaac gacttgctga gactttgatt    900
gatacaacaa ctggtgaaat catcgctgaa gccggtcaaa tggtagatcg ccgcctgttg    960
gacgagattt tggcccaact ggaggaatca gtaggacatc gtacgtatca tgttgcgagt   1020
ggtgtgctag aaagcaatga tattccactt caaacaatcg atgtattctc accaattgag   1080
gatggcaaag tagtaaaact gattgctaat ggaaatattg ataaatcggt taagaatatt   1140
acgcctgccg atattatttc ctccatcagt tattttatta acttgcttca cggaatcgga   1200
agtacggacg atattgacca tttgggtaac cgtcgtttgc gttctgtagg tgagttgctc   1260
caaaaccagt tccgtatcgg tttatcccgt atggaacgcg tggtgcgtga aagaatgtca   1320
attcaggatg ctaatgtaat tacgccacaa gcgctgatta acatacgtcc agtaattgct   1380
tcgattaaag agttctttgg tagctcgcag ctgtctcagt ttatggatca gacgaacccg   1440
cttgctgaat taacgcacaa acgtcgtctg tccgcactcg gacccggcgg tttgacgcgc   1500
gaacgcgcgg gcatggaagt gcgtgacgtc catccgagtc actacggccg tatgtgtcct   1560
atcgagacac cagagggacc aaacattggt ttgatcaact ctttgtccac ttttgcacgc   1620
attaacgagt atggatttat cgaagctcct tatcgttggg tagatccaaa aaccggaaaa   1680
gttacagacc agattgatta cctgactgct gatgaagaag ataactacat tgtagctcag   1740
gcgaatgcgg aattgacgga ggaaaacacc tttaaggatg aggttgtcat tgtccgttat   1800
aacaaacagt ctgataacat tattccgatg gctagtagcc gtgtcgatta catggacgta   1860
tcgcctaaac aggtcgtatc ggtcgcgact gcactgattc cgttcttgga gaatgatgac   1920
tctaaccgcg cattgatggg ttccaacatg cagcgtcagg ctgtcccgct tctgattccg   1980
aagtctccat tggtcggaac aggaatggag cacaagtctg caaaagattc cggtgtttgc   2040
gttgtatcca aatacaacgg agttatcgaa cgttcttcgg ctaacgaaat ttggttgcgt   2100
cgtatcgaaa ctgtagatgg cgctgaagtg aagggcgaca ttgttaagta taaattacac   2160
aaatttatgc gatctaacca aggaacttgc atcaaccaac gtccgattgt gaacagagga   2220
```

```
gatattgtca aagttggcga tattcttgcg gatggtccat ctacagagat gggtgagttg   2280

gcgttgggac gtaacgttgt cgttgccttc atgacttggg aaggttacaa ctacgaggat   2340

gcgatcttgc tgagtgagaa actggttaag gaagatgtat acacctcaat ccatattgag   2400

gaatacgaat ccgaggctcg tgacacgaag cttggacctg aagaaatcac tcgcgacatt   2460

ccaaatgtcg gtgaagaagc gcttcgcaac ttggatgagc gtggaatcat acgtattggt   2520

gctgaaattg gcgcaggtga cattctcgtt ggtaaagtaa cacctaaagg tgtgactgaa   2580

ttgacagctg aagaacgtct cttacacgca atctttggtg agaaggcacg cgaggttcgc   2640

gatacttctt tgagagttcc tcacggaaca gacgggattg ttgtagatgt aaaggtattt   2700

acacgtgaaa atggcgatga actgccacca ggtgtaaatc agttggttcg agtatatatt   2760

gctcaaaaac gtaaaatctc cgaaggcgat aaaatggctg gacgtcacgg taacaagggt   2820

gtcgttgccc gtattctgcc tgaagaagat atgccgttcc tgccggatgg cacaccagta   2880

caggtcgttc tgaacccgct gggcgtacct tcacggatga acatcggaca ggtgcttgaa   2940

gtccatctgg gtatggctgc aatgcgtctt ggtattcatg tggcaactcc agtattcgat   3000

ggtgccaagg aatatgacgt attcgataca atggaagagg caggcatgca gcgtaatggt   3060

aagactgtgt tgtatgacgg acgtacgggt gatcgttttg aacgtgaagt tactgtcggt   3120

gtcatgcaca tgatcaaact ggcgcacatg gtcgatgata aaatccatgc tcgttctaca   3180

ggtccttact ctctcgttac gcaacaacca ttgggtggta aagctcaatt tggtggacag   3240

cgcttcgggg agatggaagt atgggcattg gaagcctacg gcgcagcgta cacgcttcag   3300

gaaattttga ctgtgaaatc tgatgatgtg gttggacgtg ttaaaactta cgaatccatt   3360

gtcaaaggtg aaaatgtacc tgaaccgggt gttccagaat catttaaggt cttgatcaag   3420

gagctgcaaa gcttgggtat ggacgtgaag attctgtctg aagacgaaca agagatcgaa   3480

atgagagagc ttgatgatga ggatgacaca accggcgata agctgagttt gaatctggaa   3540

ggctctgagg ttggcgtaga gtag                                          3564
```

<210> SEQ ID NO 32
<211> LENGTH: 756
<212> TYPE: DNA
<213> ORGANISM: Bacillus sp.

<400> SEQUENCE: 32

```
gaaacgcctg agggcccgaa catcggtttg atcaactcat tgtcatcatt tgcgaaagta     60

aaccgctttg gtttcattga gacgccatac cgccgcgttg atcctgaaac aggaaaagta    120

acgcctagaa tcgactacct gactgctgat gaagaggata actatgtcgt agcccaagcg    180

aatgctaagc tgagcgatga cggttctttc ttggatgaca gcatcgtagc gcgtttcaga    240

ggggaaaaca ccgttgtagc ccgcaaccgc gtggattaca tggacgtatc tcctaaacag    300

gttgtatctg ctgcgacagc atgtattccg ttcttggaaa acgatgactc gaaccgcgcc    360

ctcatgggag cgaacatgca gcgtcaggct gtgcctttga tgcagccgga agctccgatc    420

gtcggaacgg gtatggaata cgtatccggt aaagactccg gtgcagccgt tatttgtaaa    480

caccctggta tcgttgaacg ggtggaagcg aaaaacgtat gggtgcgccg ctatgaagaa    540

attgacggcc aaaaagtaaa aggcaacctg gataagtaca gcttgctgaa atttgtccgc    600

tccaaccaag gtacgtgcta caaccagcgt ccgatcgtca gtgtcggcga tgaagtagtc    660
```

-continued

```
aaaggagaaa tccttgctga cggaccttca atggagcttg gtgaacttgc tctcggccgc    720

aacgtaatgg tcggcttcat gacatgggat ggttac                              756
```

METHODS AND AGRICULTURAL COMPOSITIONS FOR PREVENTING OR CONTROLLING PLANT DISEASES

CROSS-REFERENCE TO RELATED APPLICATION

This application is a national phase application under 35 U.S.C. § 371 of PCT Application No. PCT/US2018/024638, filed on Mar. 27, 2018, which claims priority under 35 U.S.C. § 119(e) to U.S. Provisional Application No. 62/477,297, filed on Mar. 27, 2017, and 62/597,796, filed on Dec. 12, 2017. The content of each of these applications is hereby incorporated by reference in its entirety.

SEQUENCE LISTING

The instant application contains a Sequence Listing which has been submitted via EFS-web in ASCII format and is hereby incorporated by reference in its entirety. The ASCII copy, created on Sep. 25, 2019, is named SL_514145.8_ST25, and is 64,736 bytes in size.

FIELD

The present disclosure relates to novel methods of preventing or controlling plant diseases or pathogens by applying an agricultural composition comprising the bacterial isolates belonging to the genera *Bacillus, Paenibacillus*, or their mutants. The disclosure also relates to a method of enhancing disease resistance of a plant by applying the bacterial isolates to the plant seed. Further provided are methods of using the bacterial isolates, e.g., seed treatment, in-furrow application, foliar application, alone or in combination with other fungicides and bactericides, or in an integrated management program that rotates spray controls. In addition, the present disclosure provides an agricultural composition comprising the bacterial isolates belonging to the genera *Bacillus, Paenibacillus*, or their mutants.

BACKGROUND

Plant diseases significantly reduce agricultural food production. The reduction of food production caused by plant diseases poses serious social and economic challenges and can even be catastrophic to the rapidly increasing global population. Every year, over 10% of global food yield loss is attributed to various plant pathogens, e.g., bacteria, fungi, viruses, and nematodes.

Particularly, soil-borne and foliar pathogens can cause significant threats to the agricultural and food industries. The estimated soybean yield loss in the United States (U.S.) attributed to soil-borne fungi and oomycetes was nearly a half billion bushels during 2006-2009. Soil-borne pathogens may cause root decay, tissue discoloration, crown rot, or wilting of foliage of infected plants. However, the complex soil environment and conditions for soil-borne pathogens make it even more difficult to understand the characteristics of diseases caused by soil-borne pathogens. Soil-borne pathogens are also difficult to control or prevent because they can reside and survive in the soil for many years before infecting the susceptible vegetable crops, e.g., soybeans.

There are many types of soybean pathogens, e.g., *Fusarium virguliforme* (the cause of soybean sudden death syndrome ("SDS")), *Macrophomina phaseolina* (the cause of charcoal rot disease), *Pythium* spp. and *Rhizoctonia solani* (the cause of seedling damping off and root rot diseases). To control soybean pathogens, multiple modes of actions (e.g., disease resistant plant cultivars, effective fungicides, and proven grower management practices) are often needed to prevent the pathogen threat and to manage the potential pathogen resistance to fungicides that are widely used in practice.

However, the current chemical fungicides have not been very effective against soil-borne or foliar pathogens. There has not been a very effective chemical control option for soybean SDS disease. Although partial resistance controlled by quantitative trait loci exists for SDS, the incorporation into soybean cultivars has been slow due to low heritability and weak efficacy in the field. The federal government still considers identifying alternatives to synthetic chemicals for plant pathogen control a national priority to reduce the overuse of fungicidal chemicals, to increase environmental sustainability, and to lower the risk of developing fungicide-resistant pathogens.

Therefore, there remains a need in the art to develop effective agricultural compositions or methods against plant diseases, including fungal diseases and those diseases caused by soil-borne and foliar pathogens.

SUMMARY OF THE DISCLOSURE

The disclosure is directed to a method of controlling plant diseases comprising, or alternatively consisting essentially of, or yet further consisting of applying an effective amount of an agricultural composition to a plant and/or to a seed of the plant, said composition comprising, or alternatively consisting essentially of, or yet further consisting of a bacterial isolate belonging to *Bacillus* or *Paenibacillus* or a mutant thereof. In one embodiment, the mutant has the key characteristics of wild type bacterial isolates. In one aspect, the bacterial isolate belongs to *Bacillus amyloliquefaciens, Paenibacillus* spp., or *Paenibacillus polymyxa*. In one embodiment, the bacterial strain comprises, or alternatively consists essentially of, or yet further consists of MS1479, MS2379, MS2414, MS2820, MS0633, MS2335, MS2652, MS2658, MS2681, MS2697, or MS2712. A sample of each bacterial strain has been deposited with the American Type Culture Collection (ATCC®), Manassas, VA, USA. The bacterial isolates or their mutants of this disclosure may be genetically modified or not genetically modified. Methods for genetic modification for plants are known by one of ordinary skill in the art. Non-limiting genetic modification includes genetic engineering, selection, CRISPR, and natural evolution.

In another embodiment, the agricultural composition comprises, or alternatively consists essentially of, or yet further consists of a culture media selected from the group comprising LB, TSB, BS3, BS3-M2, BS3-M9, BS3-M10, GB6-M, GB6-M3, GB6-M7, GB6-M8, GB6-M9, GB6-M22, GB6-M23, GB6-M10, GB6-M31, GB6-M33, and GB6-M34. In further embodiments, the agricultural composition comprises, or alternatively consists essentially of, or yet further consists of the culture media comprising BS3, BS3-M2, BS3-M9 or BS3-M10. In another embodiment, the agricultural composition comprises, or alternatively consists essentially of, or yet further consists of the culture media comprising GB6-M, GB6-M3, GB6-M7, GB6-M8, GB6-M9, GB6-M22, GB6-M23, GB6-M10, GB6-M31, GB6-M33, or GB6-M34.

In one embodiment, the agricultural composition comprises 5-20 g/L Soy peptone, 2-10 g/L Urea, 1-5 g/L $CaCl_2$, 2-10 g/L $KH_2PO_4$, 2-10 g/L $K_2HPO_4$, and 10-30 g/L Sucrose. In another embodiment, the agricultural composition comprises 5-20 g/L Soy peptone, 2-10 g/L Urea, 0-5 g/L $CaCl_2$, 2-10 g/L $KH_2PO_4$, 2-10 g/L $K_2HPO_4$, and 10-30 g/L Sucrose. In a further embodiment, the agricultural composition comprises 5-20 g/L Soy peptone, 2-10 g/L Urea, 0-5 g/L $CaCl_2$, 2-10 g/L $KH_2PO_4$, 2-10 g/L $K_2HPO_4$, and 10-30 g/L Sucrose. In another embodiment, the agricultural composition comprises 10-30 g/L low fat soy flour, 1-5 g/L $CaCl_2$, 2-10 g/L $KH_2PO_4$, 2-10 g/L $K_2HPO_4$, and 10-30 g/L Sucrose. In one embodiment, the agricultural composition comprises 10-30 g/L Maltrin® (M-250 or M-180), 5-20 g/L Dextrose, 2-10 g/L yeast extract, 2-10 g/L low fat soy flour, and 0.1-5 g/L $CaCO_3$. In one aspect of the disclosure, the agricultural composition comprises 5-30 g/L Maltrin® (M-250 or M-180), 5-25 g/L Dextrose, 1-10 g/L yeast extract, 0.1-5 g/L ammonia sulfate, and 0.2-3 g/L $CaCO_3$. In one embodiment, the agricultural composition comprises 5-40 g/L Maltrin® (M-250 or M-180), 5-20 g/L Dextrose, 2-15 g/L yeast extract, 2-15 g/L low fat soy flour, 0.2-1.5 g/L Ammonia sulfate, and 0.5-3 g/L $CaCO_3$. In another embodiment, the agricultural composition comprises 5-40 g/L Maltrin® (M-250 or M-180), 5-20 g/L Dextrose, 5-20 g/L low fat soy flour, and 0.2-5 g/L $CaCO_3$. In a further embodiment, the agricultural composition comprises 5-40 g/L Maltrin® (M-250 or M-180), 5-25 g/L Dextrose, 1-10 g/L yeast extract, 2-10 g/L low fat soy flour, 0.2-1.5 g/L ammonia sulfate, and 0.2-3 g/L $CaCO_3$. In a yet another embodiment, the agricultural composition comprises 5-20 g/L low fat soy flour, 0.5-5 g/L $CaCl_2$, 2-10 g/L $KH_2PO_4$, 2-10 g/L $K_2HPO_4$, 10-30 g/L Sucrose, and 0.1-5 g/L ammonia sulfate. In a further embodiment, the agricultural composition comprises 30-70 g/L Maltrin® (M-250 or M-180), 5-25 g/L dextrose, 5-15 g/L inactive dry yeast, 2-10 g/L low fat soy flour, 0.5-3 g/L ammonia sulfate, 0.5-3 g/L $CaCO_3$, and 0.2-1.5 ml antifoam. In a further embodiment, the agricultural composition comprises 50-100 g/L Maltrin® (M-250 or M-180), 5-25 g/L dextrose, 10-20 g/L yeast, 2-10 g/L low fat soy flour, 1-4 g/L ammonia sulfate, 1-5 g/L $CaCO_3$, and 0.2-1.5 ml antifoam.

In one aspect, the agricultural composition comprises a fungicide, biocontrol agent, nematicide, bactericide, herbicidal safener, herbicide, insecticide, biostimulant, plant growth regulator, liquid fertilizer, or viral inhibitor. In one embodiment, the fungicide comprises captan, thiram, metalaxyl, fludioxonil, oxadixyl, fusaricidin, or isomers of each of those materials. In another embodiment, the agricultural composition comprises a lytic enzyme.

In another aspect, the plant disease comprises an oomycete disease, a fungal disease, a viral disease, or a bacterial disease. In one embodiment, the plant disease is caused by an oomycete of *Pythium* species or *Phytophthora* species and/or by a fungus of *Rhizoctonia* species, *Fusarium* species, *Alternaria* species, *Verticillium* species, *Macrophomina* species, *Botrytis* species, *Leptosphaeria* species, *Podosphaera* species, or *Sclerotinia* species.

In one embodiment, the agricultural composition comprises, or alternatively consists essentially of, or yet further consists of the bacteria ranging from $1\times10^3$ to $1\times10^9$ colony-forming units (cfu)/seed when the agricultural composition is applied to the seed. In another embodiment, the agricultural composition comprises, or alternatively consists essentially of, or yet further consists of the bacteria ranging from $1\times10^4$ to $1\times10^8$ cfu/seed when the agricultural composition is applied to the seed. In a further embodiment, the agricultural composition comprises, or alternatively consists essentially of, or yet further consists of the bacteria ranging from $1\times10^5$ to $1\times10^7$ cfu/seed when the agricultural composition is applied to the seed. In another embodiment, the agricultural composition comprises, or alternatively consists essentially of, or yet further consists of the bacteria ranging from $1\times10^5$ to $1\times10^6$ cfu/seed when the agricultural composition is applied to the seed. In one aspect, the cfu/seed is assessed by cfu recovery. In another aspect, the seed is coated with a polymer. It is also contemplated that the agricultural composition is adhered to a carrier.

In another aspect, the agricultural composition is applied in-furrow when the agricultural composition is applied to a plant or a seed before or during planting. In another aspect, the agricultural composition is applied in the vicinity of the seed or the plant. In one aspect, the agricultural composition is applied to the plant directly. In another embodiment, the agricultural composition is applied to the stem and leaves of the plant (e.g. foliar application). In a further embodiment, the agricultural composition is applied to a reproductive tissue, including, but not limited to, buds, flowers, and developing structures that contain seeds such as fruit and seed pods.

In another aspect, the disclosure is related to a method of preventing and/or controlling plant diseases, comprising applying an effective amount of an agricultural composition to a seed or above ground parts of the plant, said composition comprising a bacterial isolate belonging to *Bacillus* or *Paenibacillus*. In one aspect, the bacterial isolate belongs to *Bacillus amyloliquefaciens, Paenibacillus* spp., or *Paenibacillus polymyxa*. In one aspect, the agricultural composition comprises, or alternatively consists essentially of, or yet further consists of MS1479, MS2379, MS2414, MS2820, MS0633, MS2335, MS2652, MS2658, MS2681, MS2697, or MS2712. The bacterial isolates can be fermented or grown in a medium known in the art (e.g., LB and TSB) or the special medium of this disclosure. The special medium comprises BS3, BS3-M2, GB6-M3, GB6-M7, GB6-M8, GB6-M9, GB6-M22, GB6-M23, GB6-M10, GB6-M31, GB6-M33, GB6-M34, or combination thereof. Therefore, in a further embodiment, the agricultural composition comprises, or alternatively consists essentially of, or yet further consists of a culture media of LB, TSB, BS3, GB6-M, GB6-M7, GB6-M8, GB6-M9, GB6-M10, GB6-M31, GB6-M33, GB6-M34, or combination thereof.

In one embodiment, the seed is dried before it is planted. In a further embodiment, the seed is stored under stable conditions before it is planted. In one embodiment, the stable condition is at room temperature, ranging from 15° C. to 30° C. In another embodiment, the stable condition comprises a hermetic condition, under which the moisture is not taken up until the seed is planted. The hermetic condition is more desirable for storing a large number of seeds. Exclusion of air and oxygen from the seeds can prevent the oxidation of the seed nutrients. In another aspect, the seed is coated with a culture media and dried before the seed is planted. In one embodiment, the culture media comprise, or alternatively consist essentially of, or yet further consist of LB, TSB, BS3, BS3-M2, GB6-M3, GB6-M7, GB6-M8, GB6-M9, GB6-M22, GB6-M23, GB6-M10, GB6-M31, GB6-M33, GB6-M34, or combination thereof. In another aspect, before a seed is planted, the seed is coated in a culture media comprising, or alternatively consisting essentially of, or yet further consisting of BS3, BS3-M2, GB6-M3, GB6-M7, GB6-M8, GB6-M9, GB6-M22, GB6-M23, GB6-M10, GB6-M31, GB6-M33, GB6-M34, or combination thereof.

fermentations of MS1479, MS2379, MS2414, and MS2820 in either TSB ("Tryptic Soy Broth"-Sigma Aldrich 22092), BS3, BS3-M2, or GB6-M3 medium at various dilutions (undiluted (1×), 10-fold dilution (1/10×), and 50-fold dilution (1/50×)).

FIG. 2 shows the fermentation profiles of MS1479 and MS2414 over the elapsed fermentation time (EFT) of grown in GB6-M3 Medium. The profiles include pH, colony forming units (cfu) per ml, and total carbohydrate (g/L) of MS1479 (FIG. 2A), viscosity (cP), glucose (g/ml), sucrose (g/ml), and $CO_2$ (%) of MS1479 (FIG. 2B), pH, total carbohydrate (g/L), cfu/ml of MS2414 (FIG. 2C), and viscosity (cP), pH, sucrose (g/L), and glucose (g/L) of MS2414 (FIG. 2D).

Figure 3:
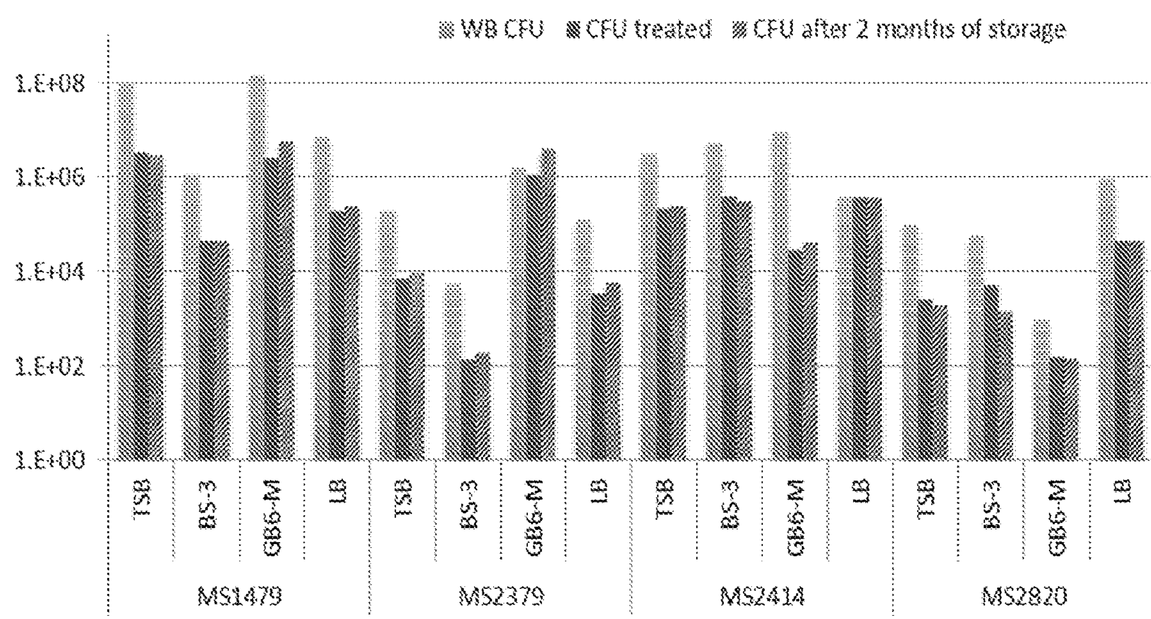

FIG. 3 depicts the comparison of cfu/ml of WB of MS1479, MS2379, MS2414, and MS2820 grown in either TSB, BS3, GB6-M, or LB medium and the recovered cfu/ml from soybean seeds measured immediately after treatment with 0.1 ml of one of the WB samples (cfu Treated) and after two months of storage (cfu after Two Months of Storage).

Figure 4:
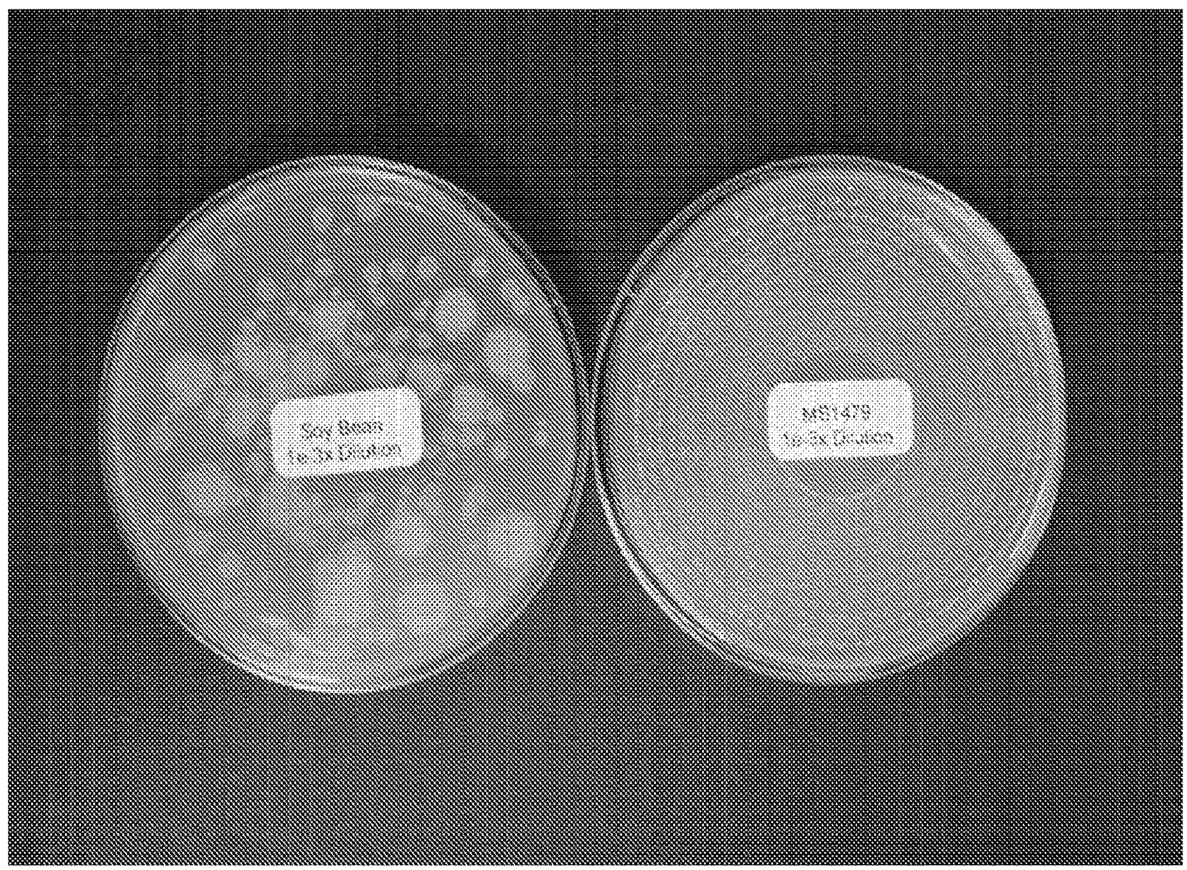

FIG. 4 shows cfu recovery from roots from eight-day-old germinating soybean seeds which were not treated or treated with MS1479. Left plate: from untreated soybean seeds. Right plate: from *Paenibacillus* (MS1479) treated soybean seeds. Numerous, small, and uniform colonies typical of *Paenibacillus* were present on the right plate.

Figure 5:
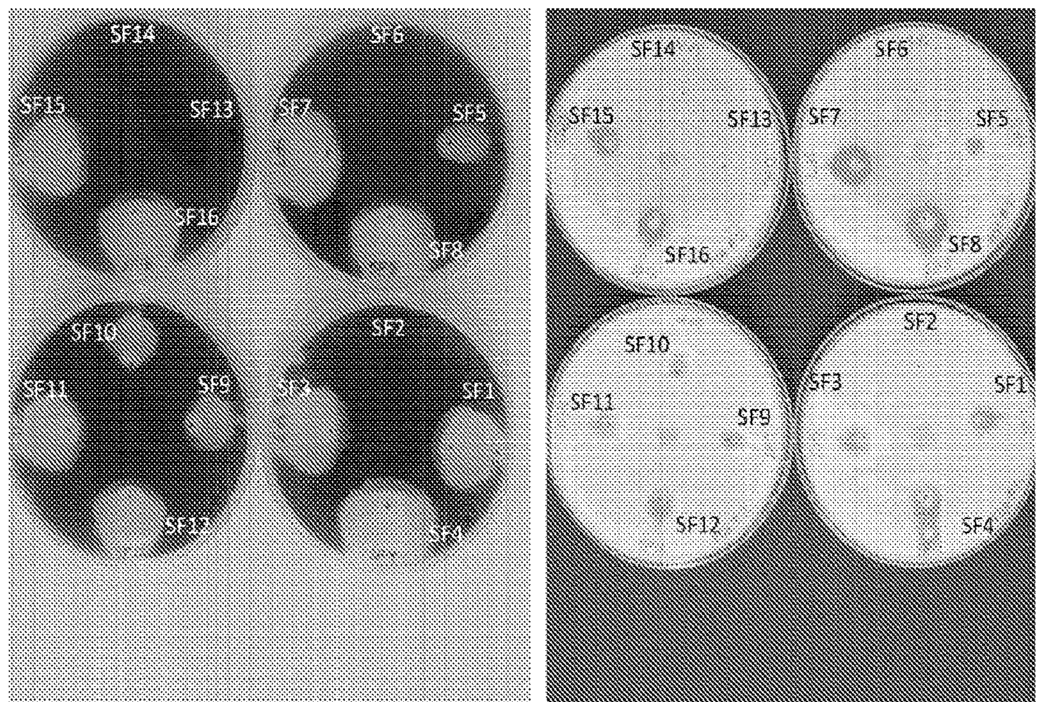
Figure 5:
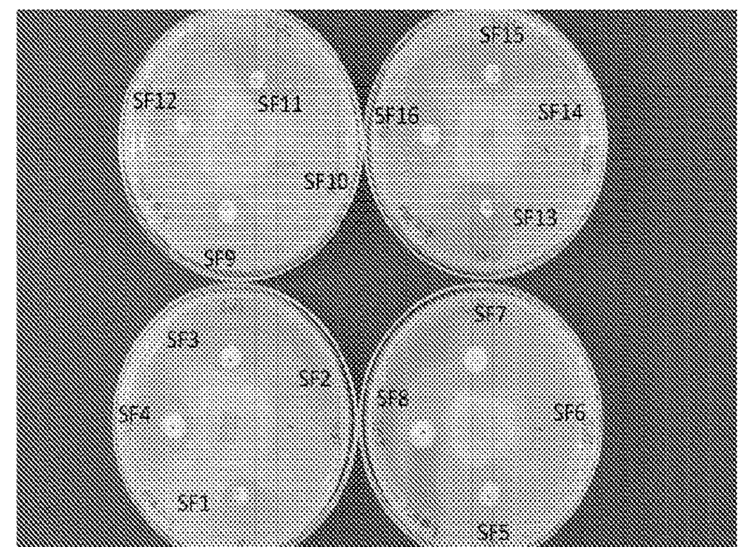
Figure 5:
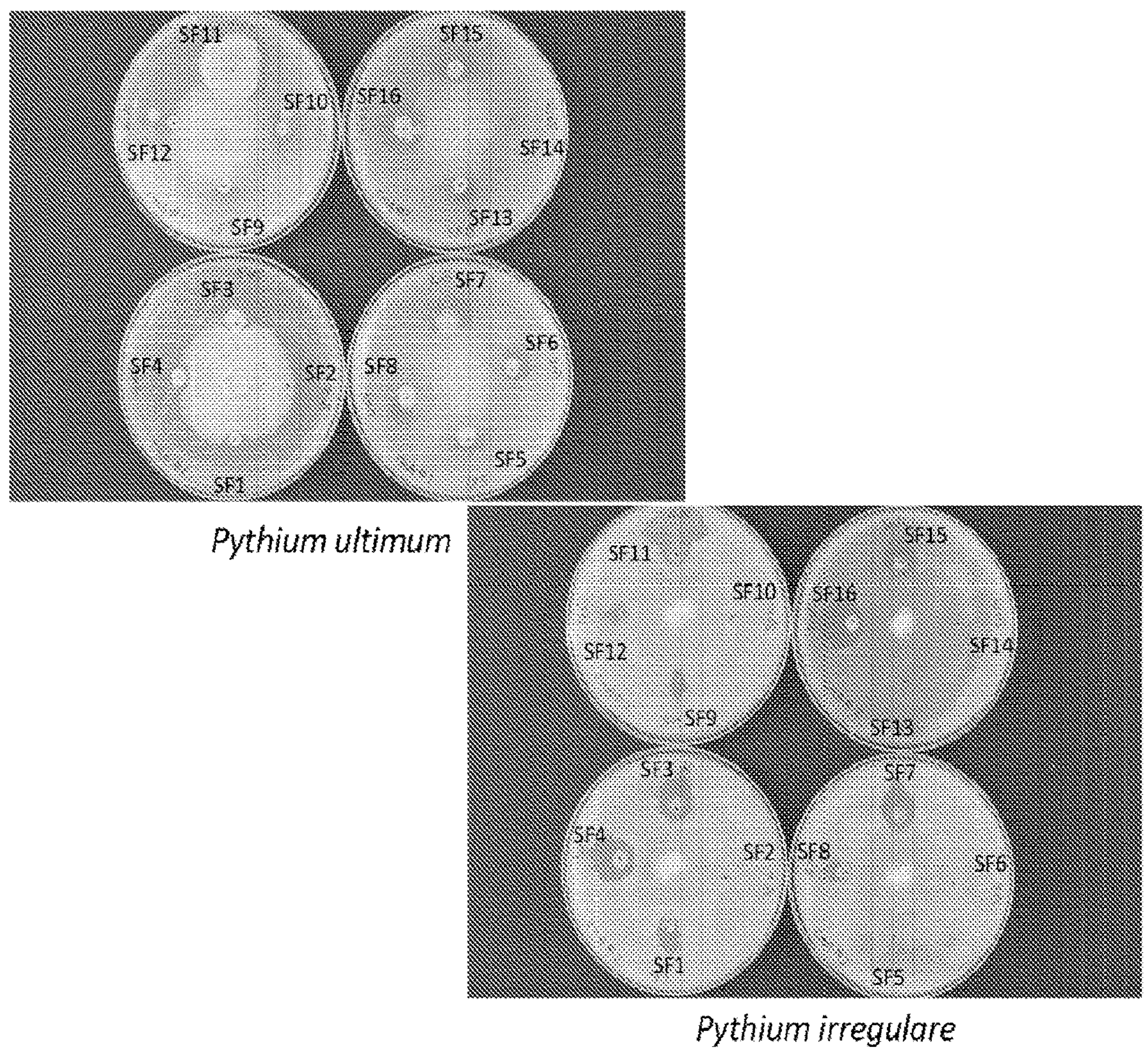

FIG. 5 depicts the in-vitro inhibition (evident as zones of clearing) of *Macrophomina phaseolina, Rhizoctonia solani, Botrytis cinerea, Pythium ultimum*, and *Pythium irregulare* by the different samples shown in the SF sample description table. Each isolate was grown in each of the four media, and the WB from each was spotted per each pathogen plate. The location where each sample is spotted in each plate is labeled with the specific sample number.

Figure 6:
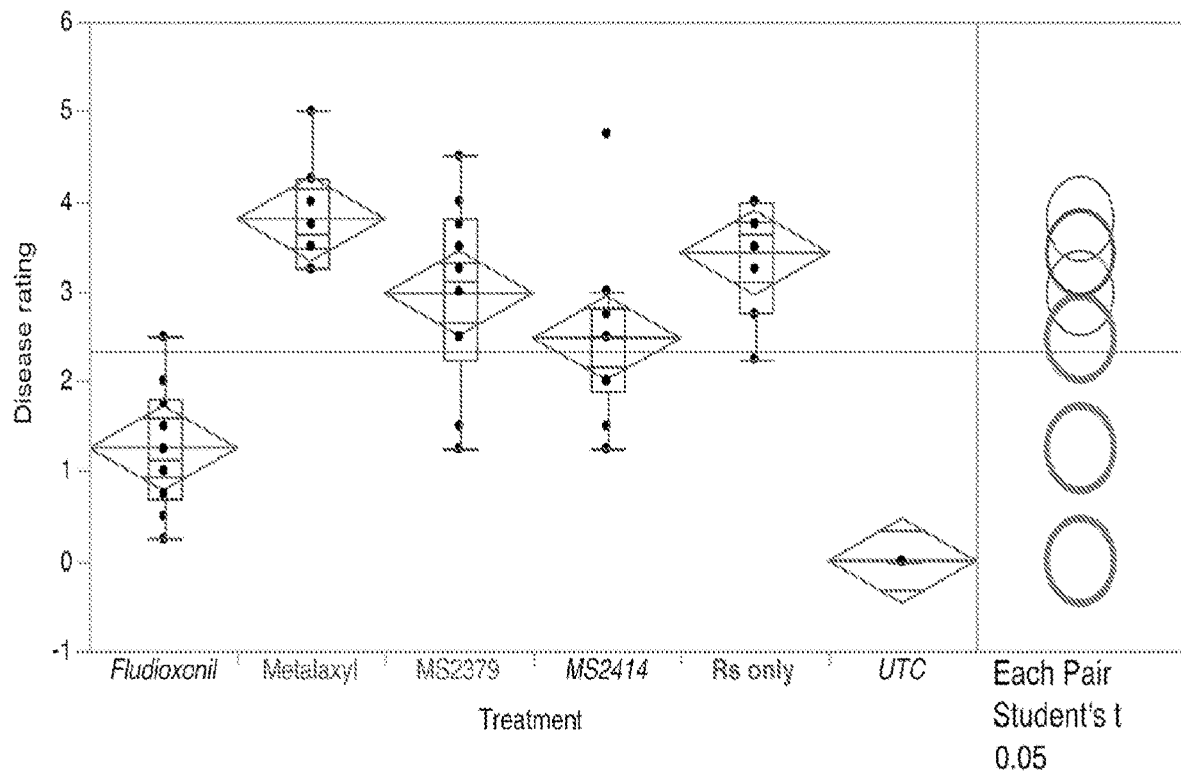

FIG. 6 shows disease ratings (rating scale of 0-5, with 0 being no disease symptoms visible and 5 being a high level of disease symptoms) of germinating soybean seeds treated with fludioxonil (0.02 mg/seed), metalaxyl (0.046 mg/seed), or whole broth of MS2379 or MS2414 grown in GB6-M8 after the seeds were planted into potting mix inoculated with *Rhizoctonia solani.*

Figure 7:
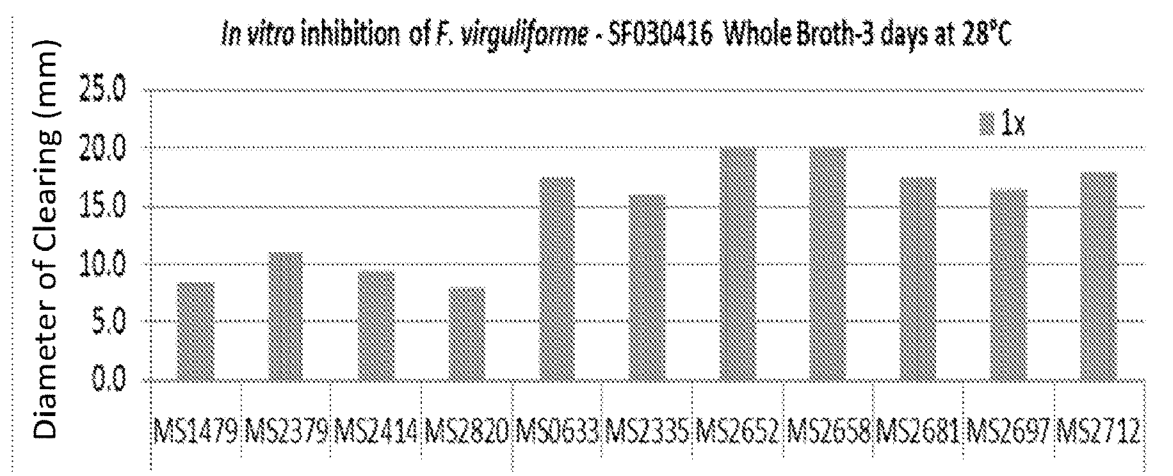

FIG. 7 shows the in-vitro inhibition of *F. virguliforme* by whole broth cultures of MS1479, MS2379, MS2414, MS2820, MS0633, MS2335, MS2652, MS2658, MS2681, MS2697, and MS2712. All were grown in GB6-M8 medium.

Figure 8:
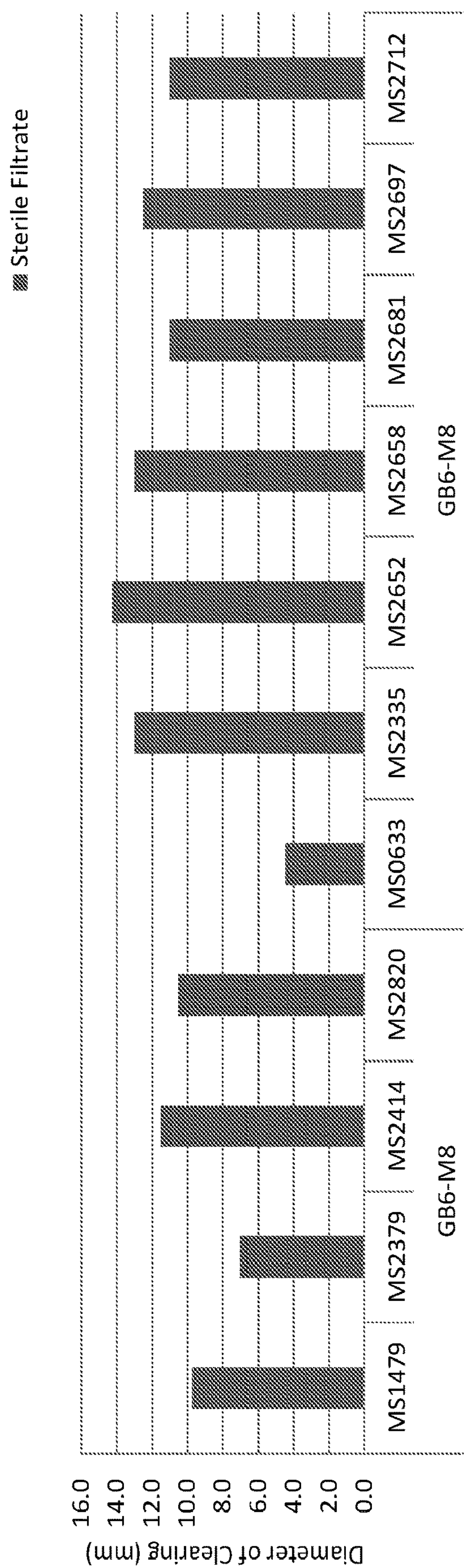

FIG. 8 shows the in-vitro inhibition of *F. virguhforme* by sterile filtrates from the cultures of MS1479, MS2379, MS2414, MS2820, MS0633, MS2335, MS2652, MS2658, MS2681, MS2697, and MS2712. All were grown in GB6-M8 medium.

Figure 9:
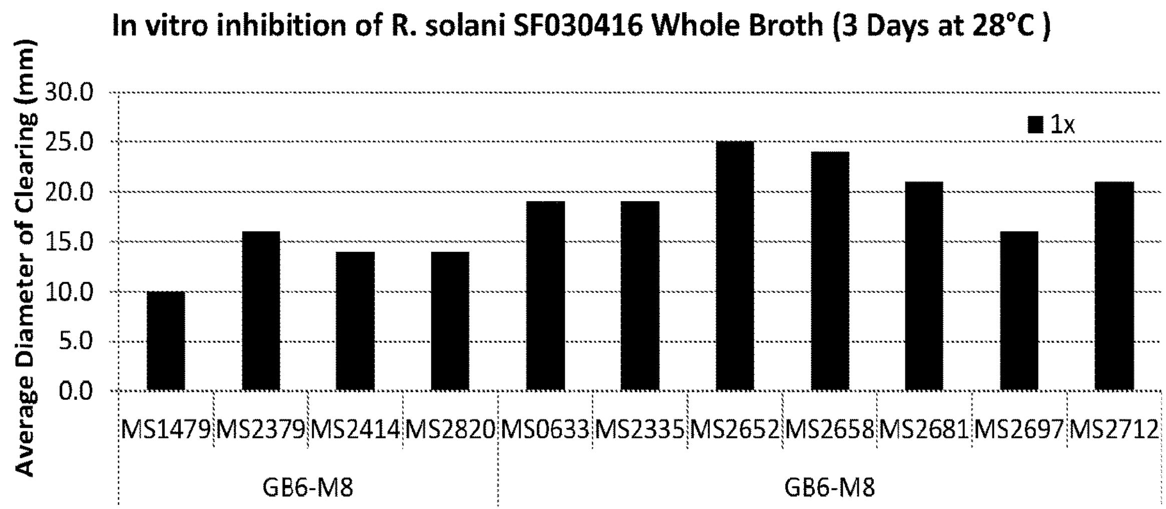

FIG. 9 shows the in-vitro inhibition of *R. solani* by whole broth cultures of MS1479, MS2379, MS2414, MS2820, MS0633, MS2335, MS2652, MS2658, MS2681, MS2697, and MS2712. All were grown in GB6-M8 medium.

Figure 10:
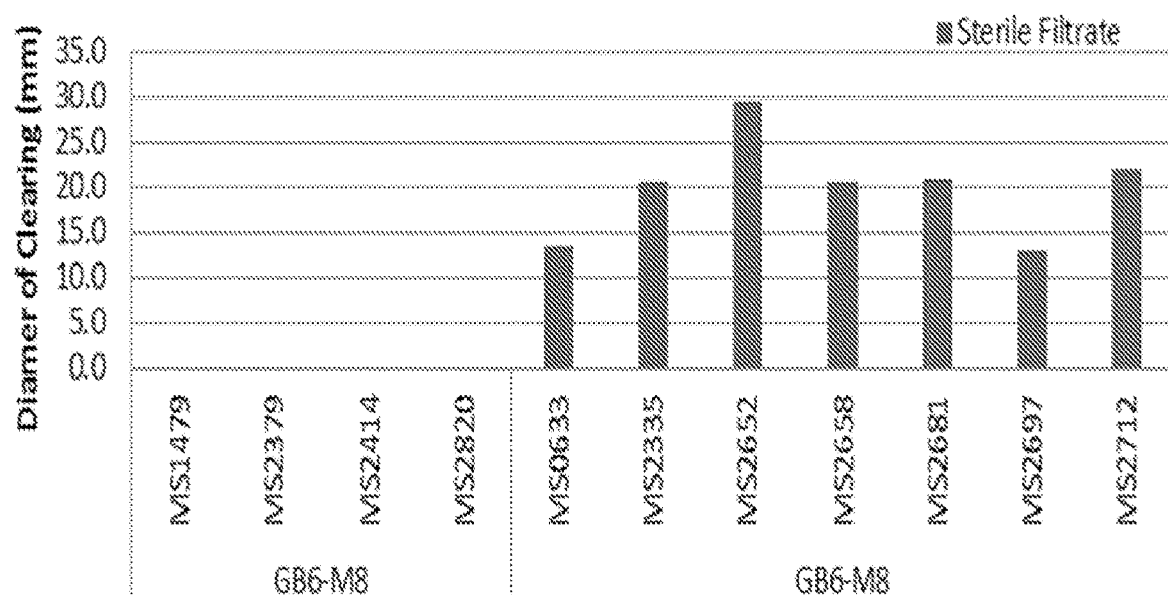

FIG. 10 shows the in-vitro inhibition of *R. solani* by sterile filtrates from the cultures of MS1479, MS2379, MS2414, MS2820, MS0633, MS2335, MS2652, MS2658, MS2681, MS2697, and MS2712. All were grown in GB6-M8 medium.

Figure 11:
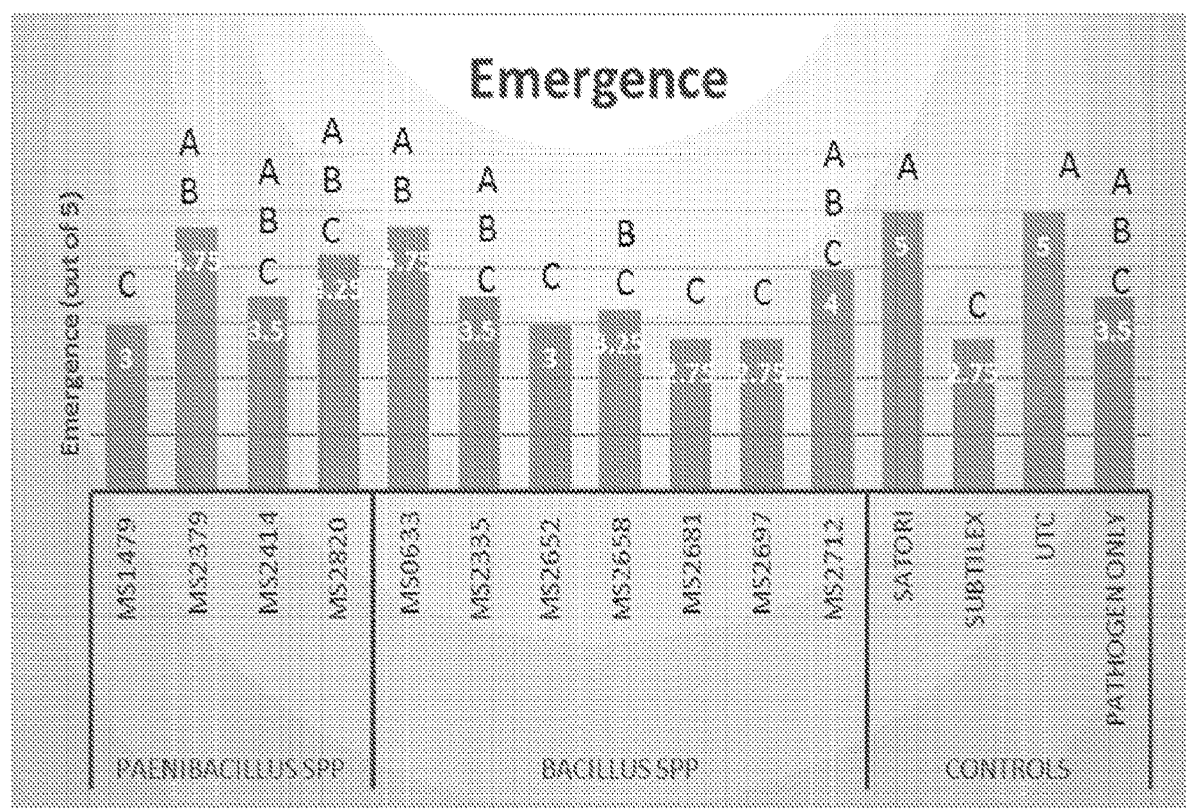

FIG. 11 shows the number of soybean seedlings emerged (out of five) in the presence of *R. solani* in a pot assay.

Figure 12:
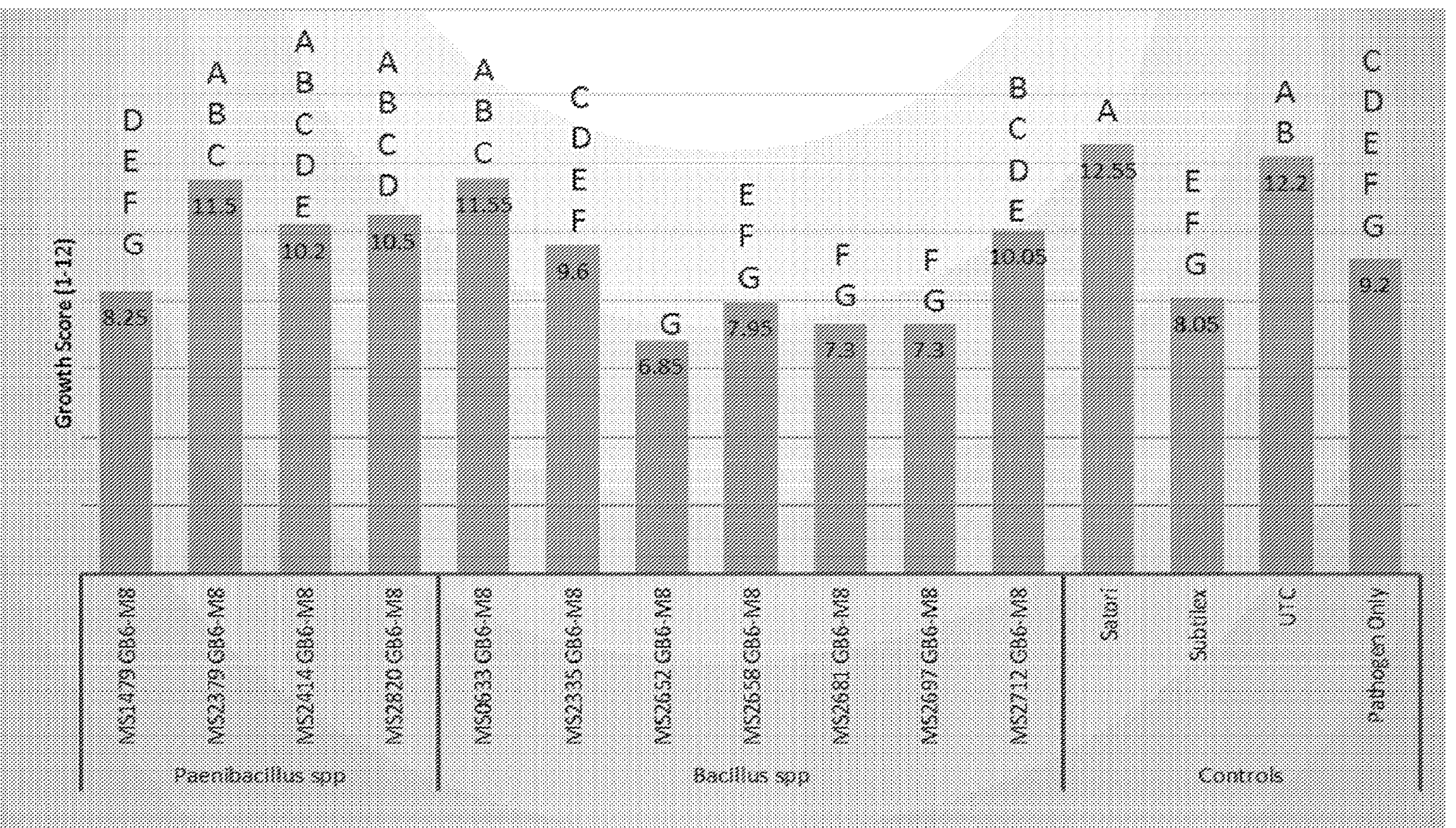

FIG. 12 shows the growth score rating (1-12) of soybean seedlings which germinated in the presence of *R. solani* in a pot assay.

Figure 13:
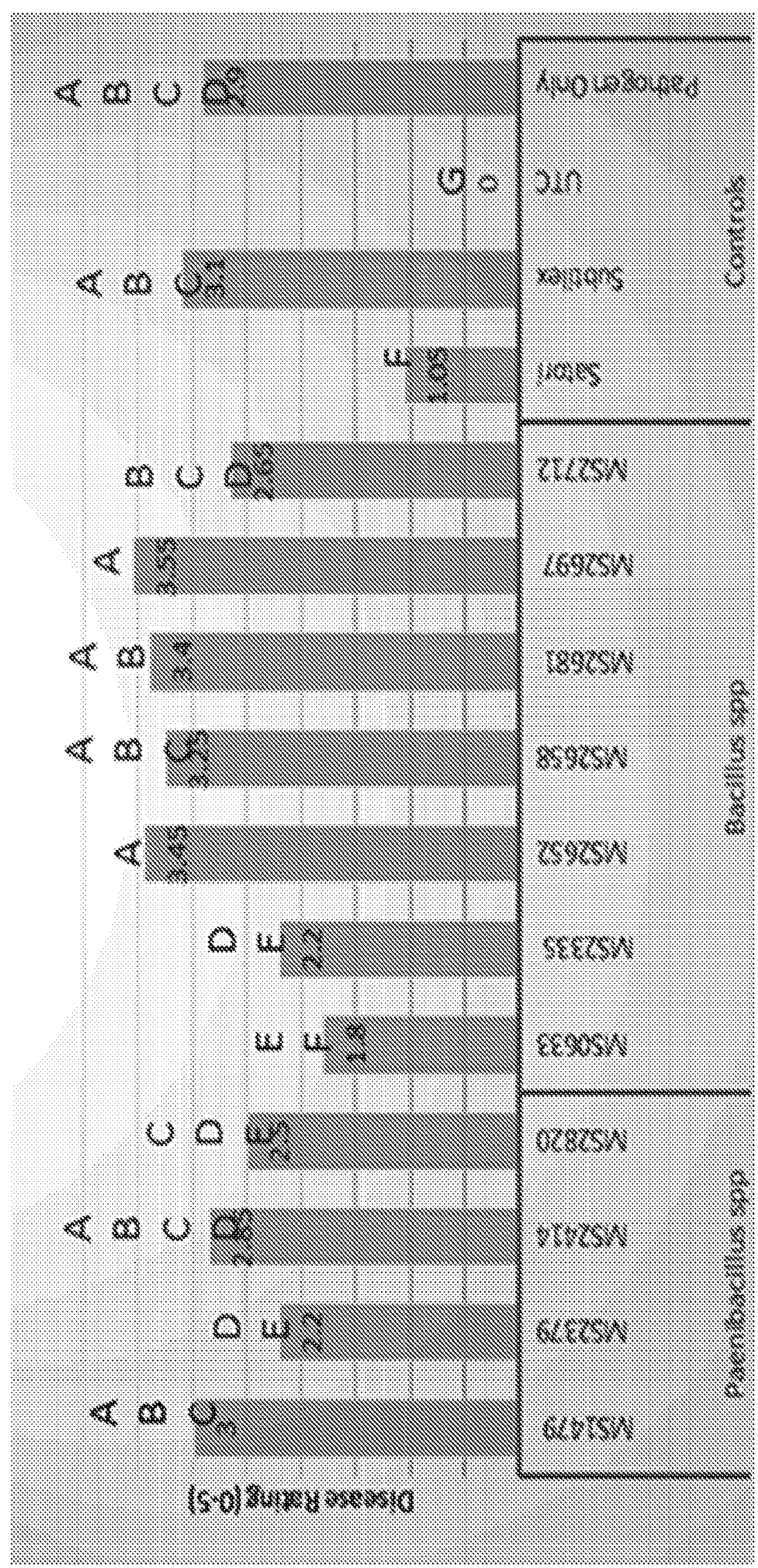

FIG. 13 shows the disease severity rating (0-5) of soybean seedlings which germinated in the presence of *R. solani* in a pot assay.

Figure 14A:
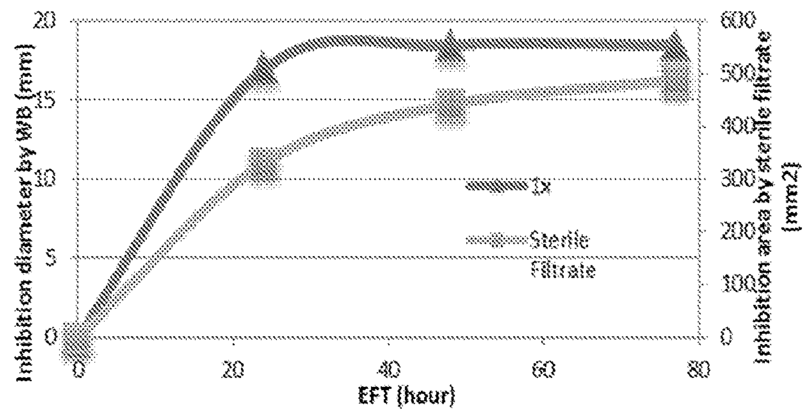
Figure 14B:
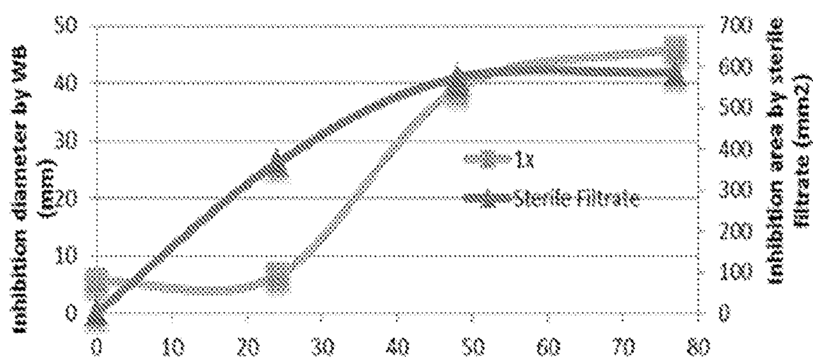
Figure 14C:
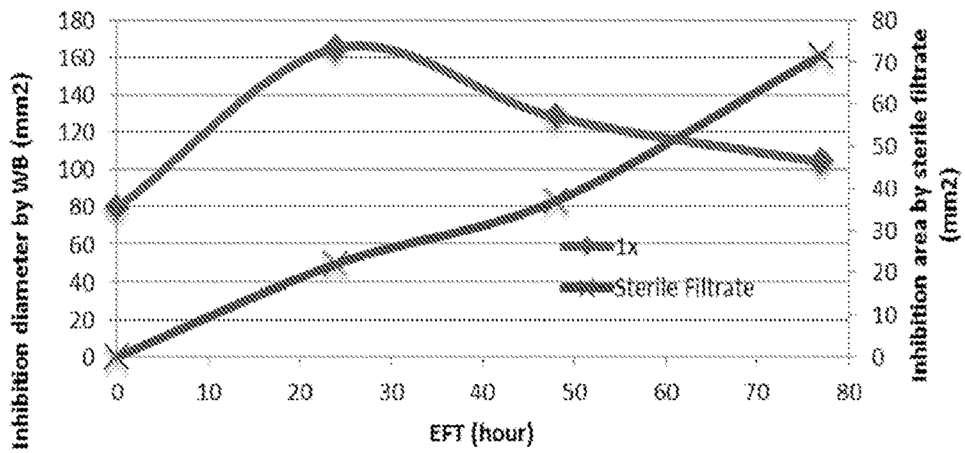
Figure 14D:
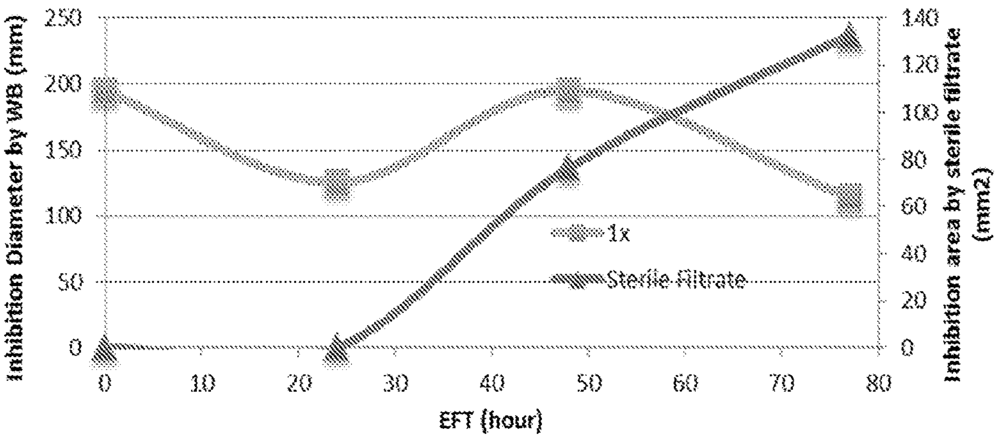
Figure 14E:
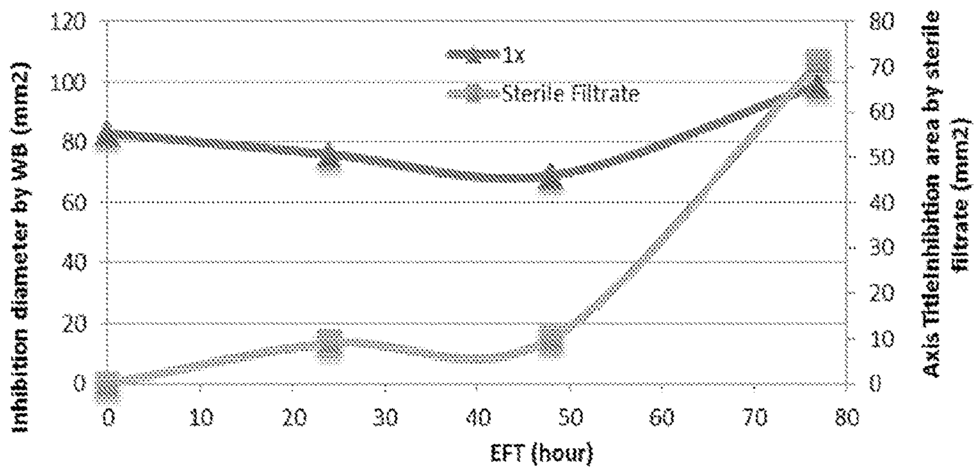
Figure 14F:
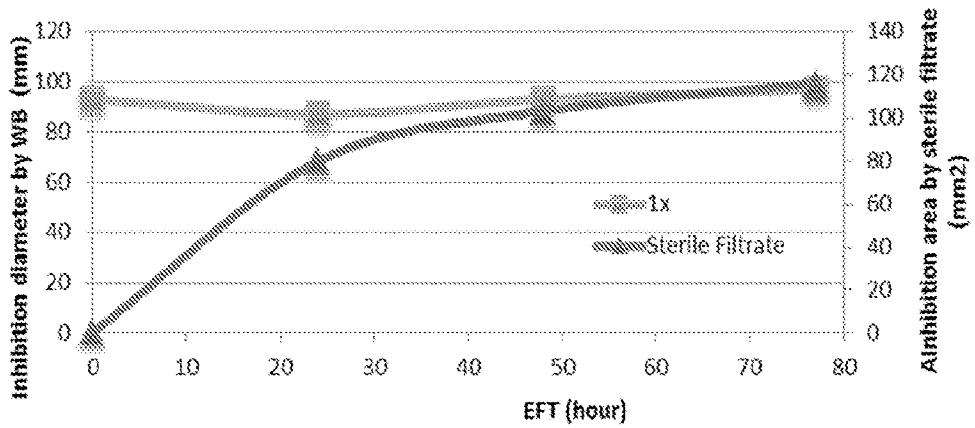
Figure 14G:
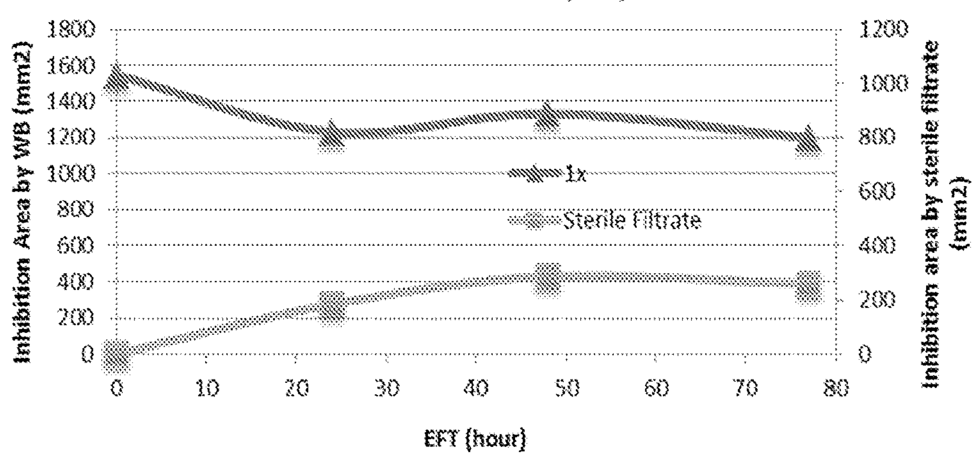
Figure 14H:
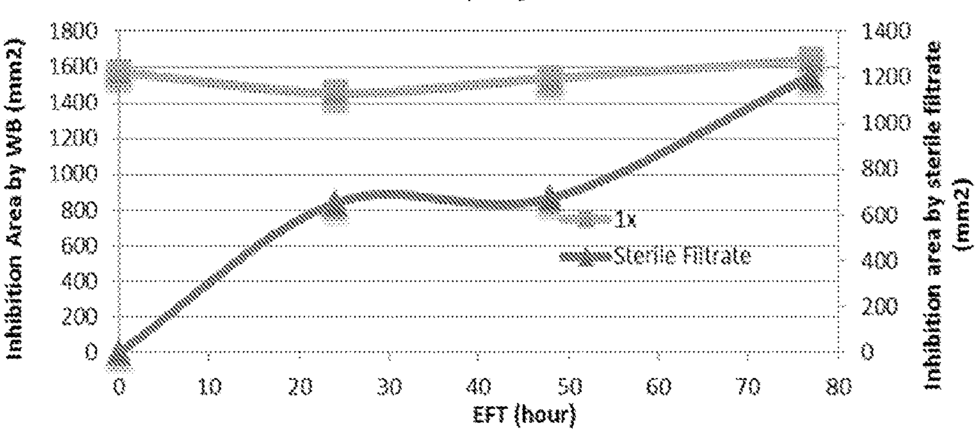

FIG. 14 shows the in-vitro inhibition of fungal species by bacterial isolates grown in GB6-M8 in a 20 L fermenter at different elapsed fermentation times: inhibition diameters of *P. irregulare* colonies by WB (1×) or sterile filtrate of MS2379 (FIG. 14A); inhibition diameters of *P. irregulare* colonies by WB (1×) or sterile filtrate of MS2414 (FIG. 14B); inhibition diameters of *R. solani* colonies by WB (1×) or sterile filtrate of MS2379 (FIG. 14C); inhibition diameters of *R. solani* colonies by WB (1×) or sterile filtrate of MS2414 (FIG. 14D); inhibition diameters of *F. virguhforme* colonies by WB (1×) or sterile filtrate of MS2379 (FIG. 14E); inhibition diameters of *F. virguhforme* colonies by WB (1×) or sterile filtrate of MS2414 (FIG. 14F); inhibition diameters of *B. cinerea* colonies by WB (1×) or sterile filtrate of MS2379 (FIG. 14G); and inhibition diameters of *B. cinerea* colonies by WB (1×) or sterile filtrate of MS2414 (FIG. 14H).

Figure 15:
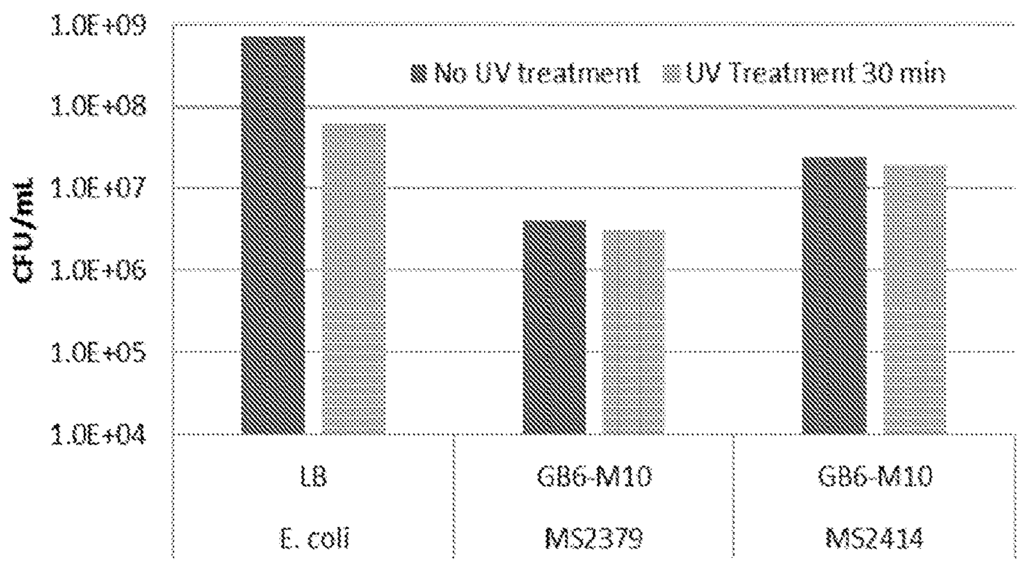
Figure 16A:
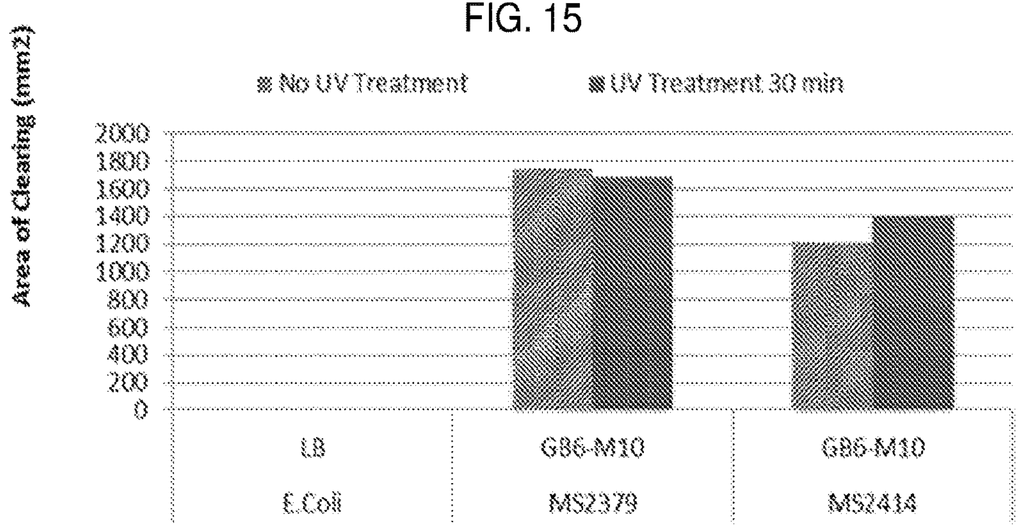
Figure 16B:
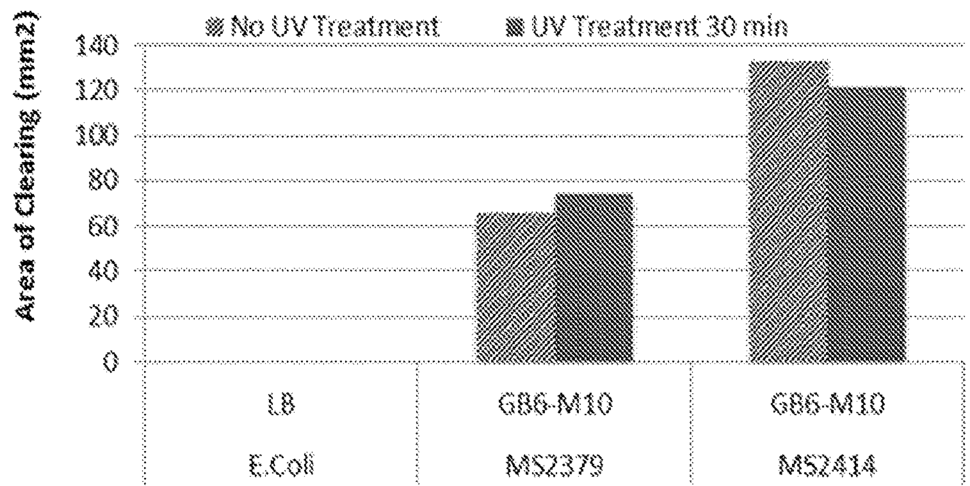
Figure 16C:
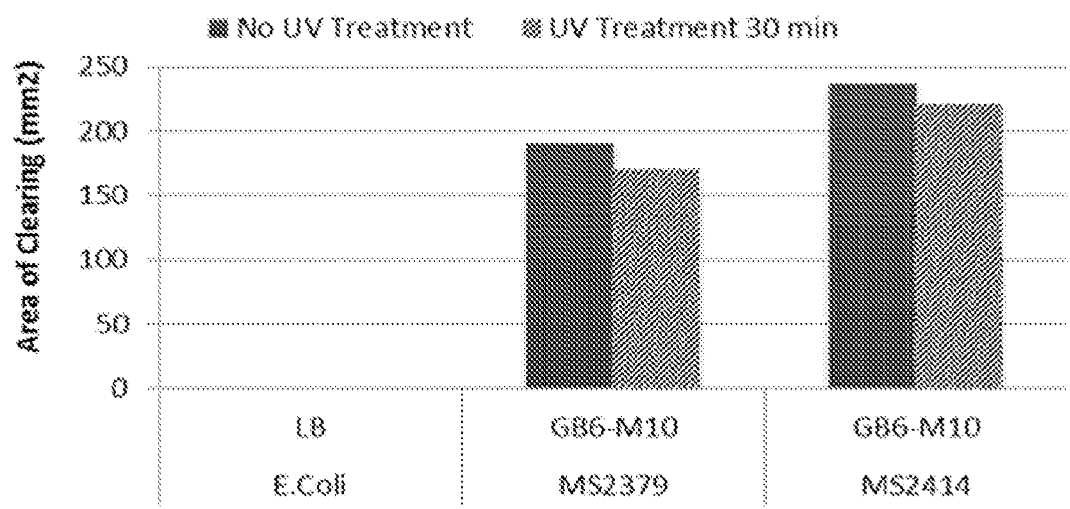
Figure 16D:
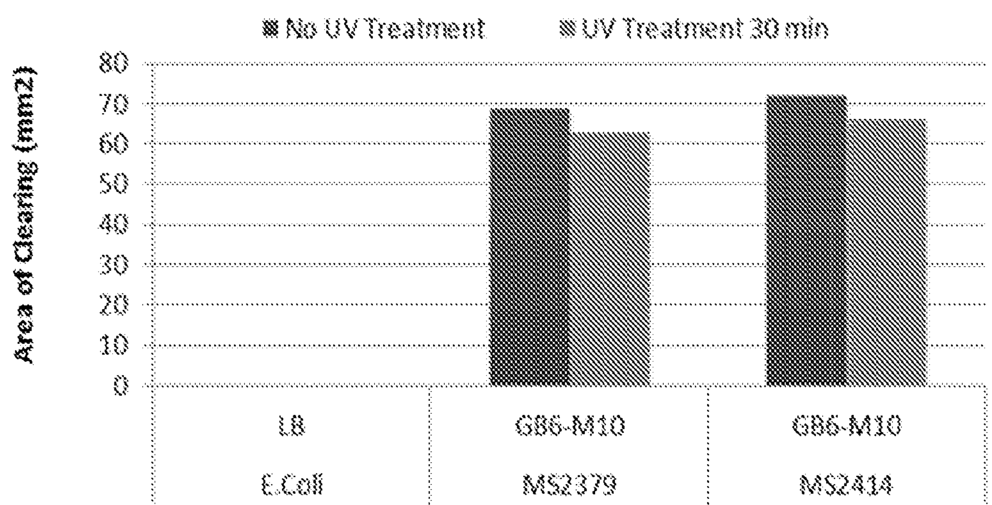

FIG. 15 shows the cfus per ml of *E. coli* grown in LB medium, MS2379 in GB6-M8 medium, and MS2414 grown in GB6-M8 medium before and after 30 minutes of UV irradiation.

FIG. 16 shows the biocontrol activities of non-irradiated and UV-irradiated (30 minutes) whole broth of MS2379 and MS2414 grown in GB6-M10 medium against *B. cinerea* (FIG. 16A), *P. irregulare* (FIG. 16B), *R. solani* (FIG. 16C), and *F. virguhforme* (FIG. 16D) measured by in-vitro assays.

Figure 17A:
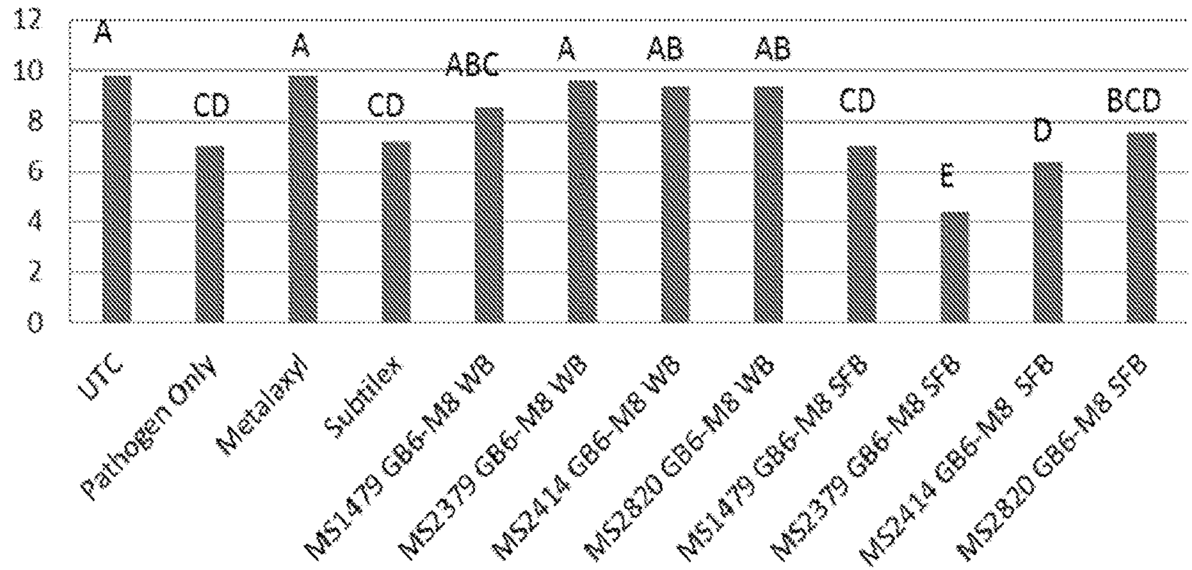
Figure 17B:
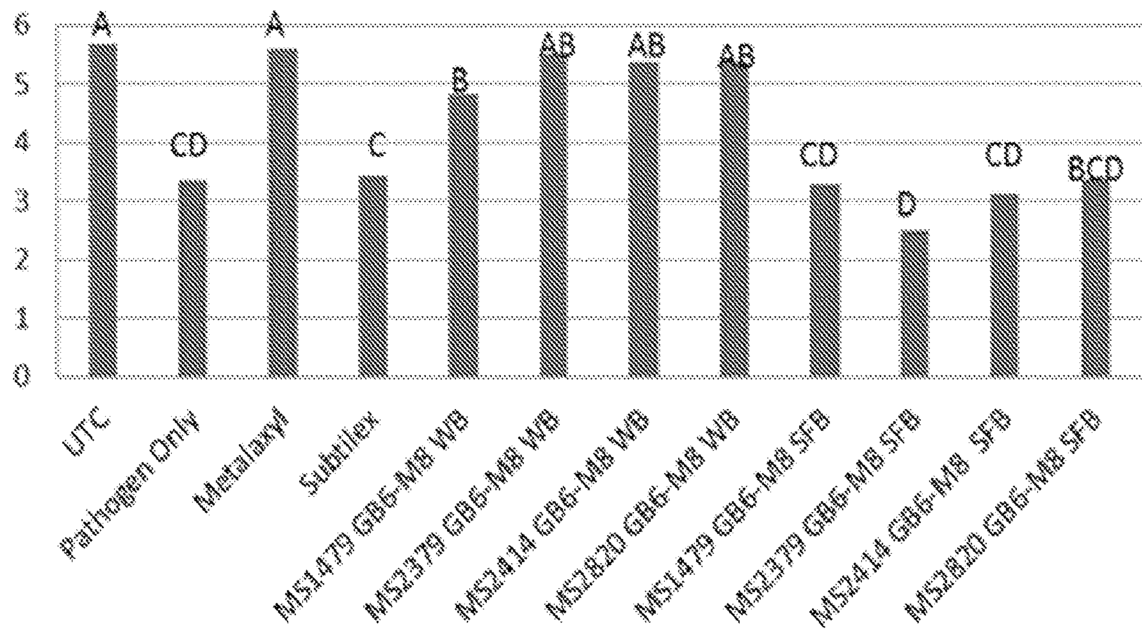

FIG. 17 shows the seedling emergences (FIG. 17A) and growth scores (FIG. 17B) in the presence of *Pythium irregulare*. The seeds were treated with metalaxyl (0.046 mg AI/seed), Subtilex (20 μl/seed of reconstituted powder at 1 g/100 ml), 20 μl of whole broth (WB), and sterile filtrates of MS1479, MS2379, MS2414, and MS2820 grown in GB6-M8 medium.

Figure 18:
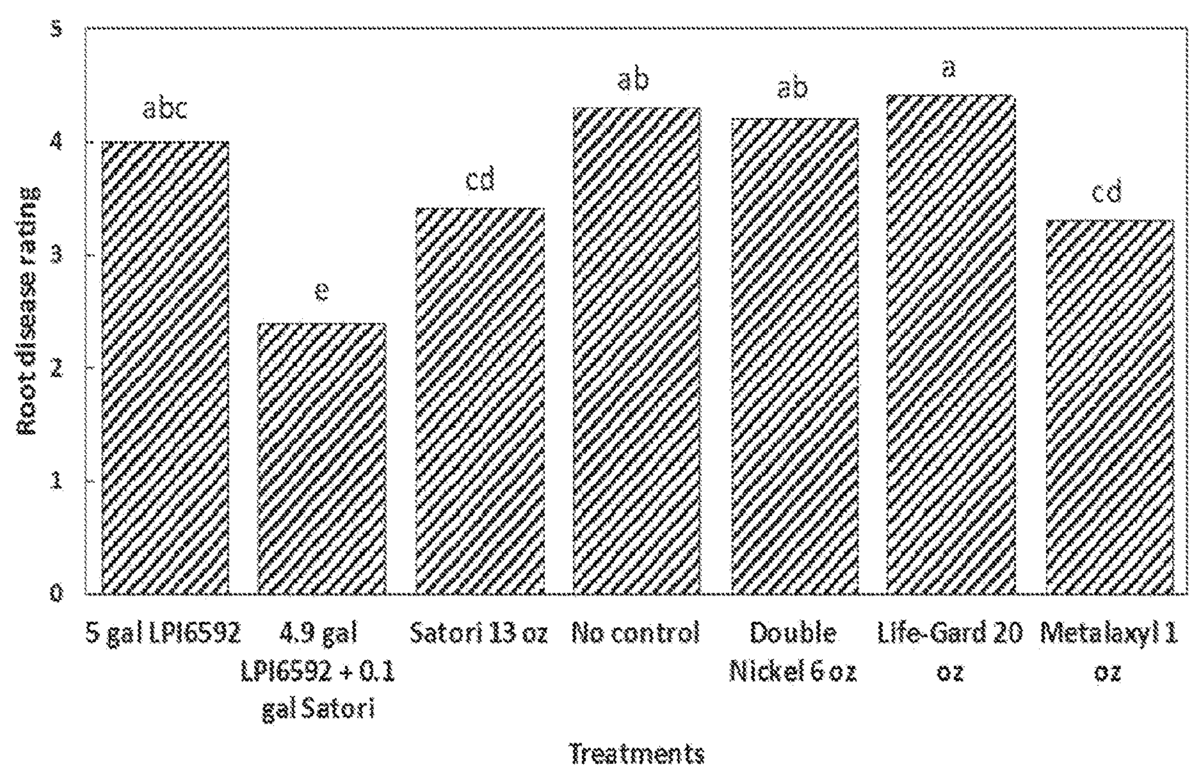

FIG. 18 depicts *Phytophthora sojae* root disease score on soybean plants treated with MS2379 fermented in GB6-M31 with or without the fungicide Satori® in comparison with commercial biocontrol standards Double Nickel™ 55 and LifeGard™ WG and the fungicide Dyna-Shield Metalaxyl 14 d after planting and inoculation. Common letters above the bars indicate no significant difference at P=0.05 using the least significant difference test.

Figure 19:
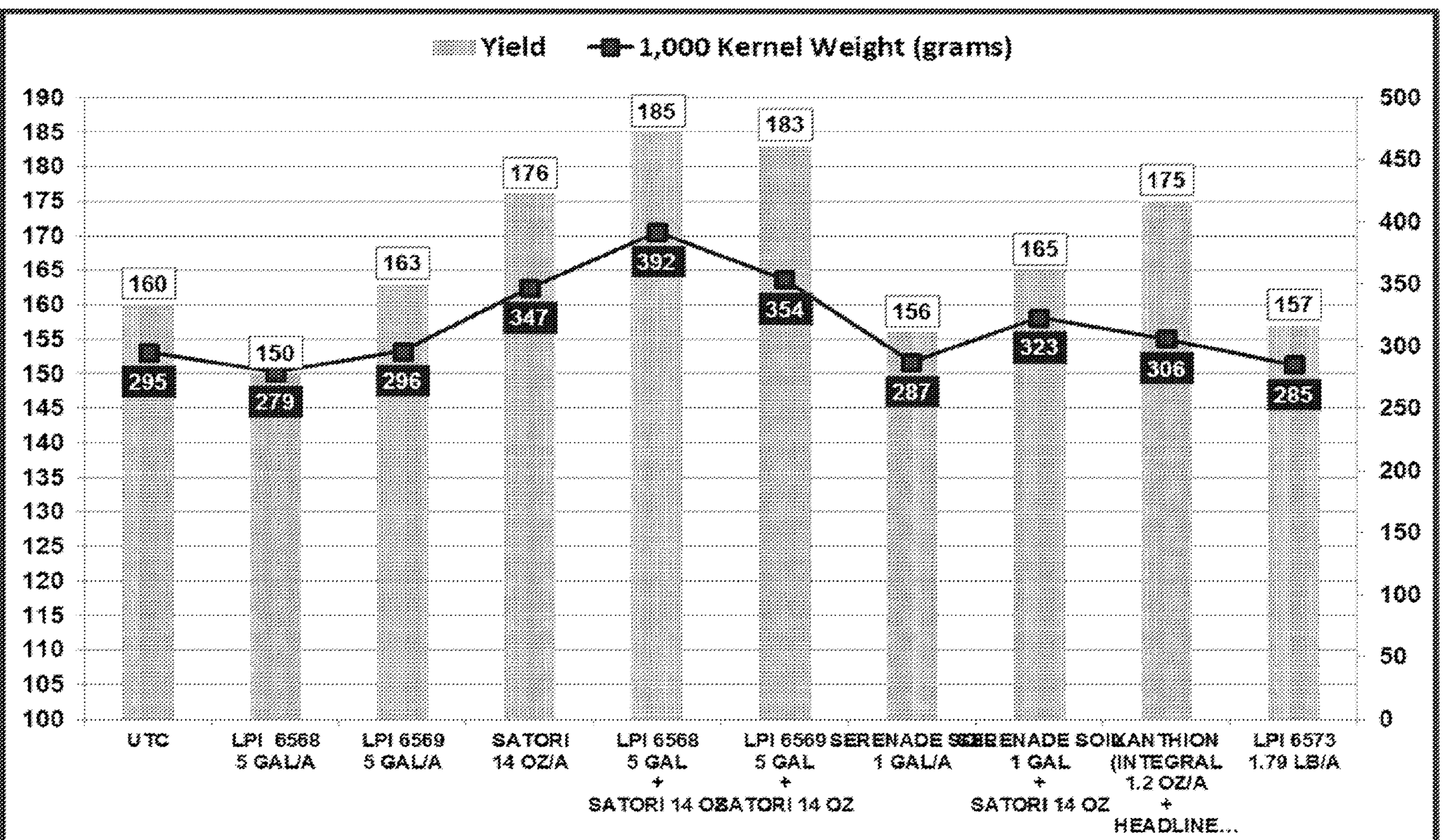

FIG. 19 shows the results of in-furrow application of MS2379 and MS2414 to corn in field study. LPI 6568=MS2379; LPI 6569=MS2414.

Figure 20:
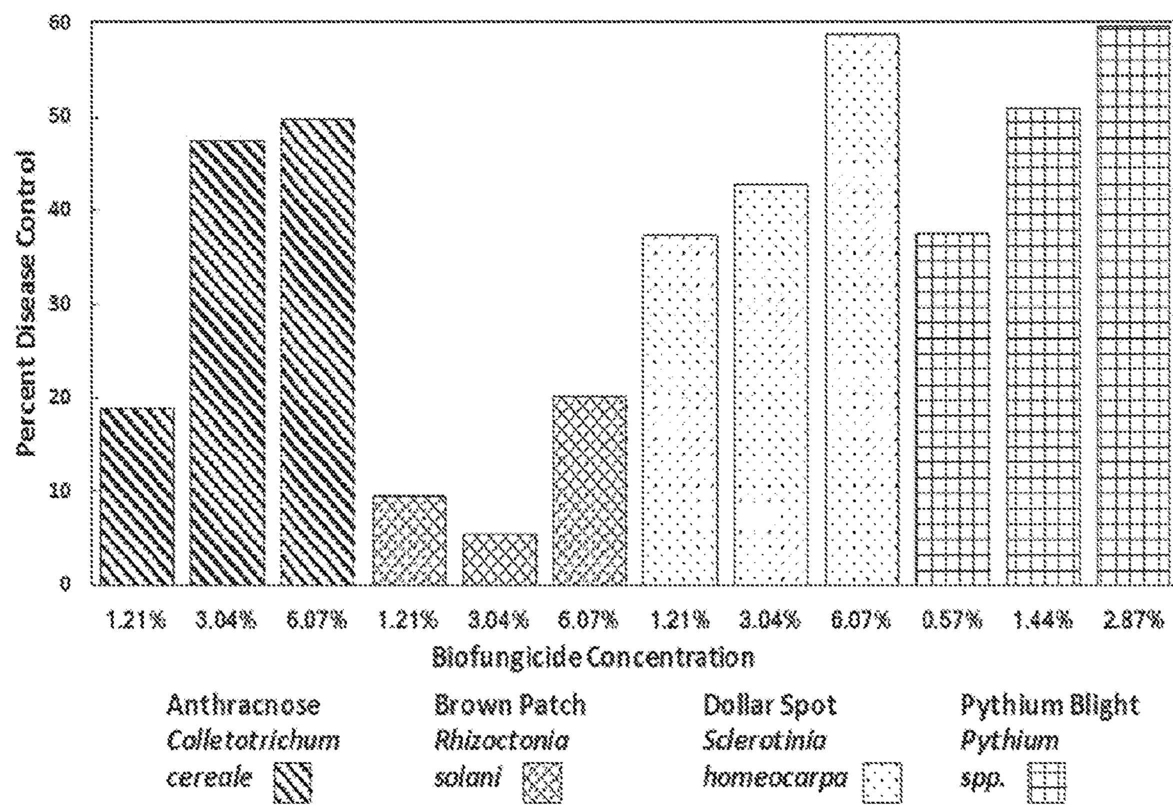

FIG. 20 shows the percentage of disease control relative to the untreated control against four turf diseases by MS2379 fermented in GB6-M31 medium. The fermentations were applied by spraying 1, 2.5, and 5 gal/acre onto established plots infected with turf diseases.

Figure 21:
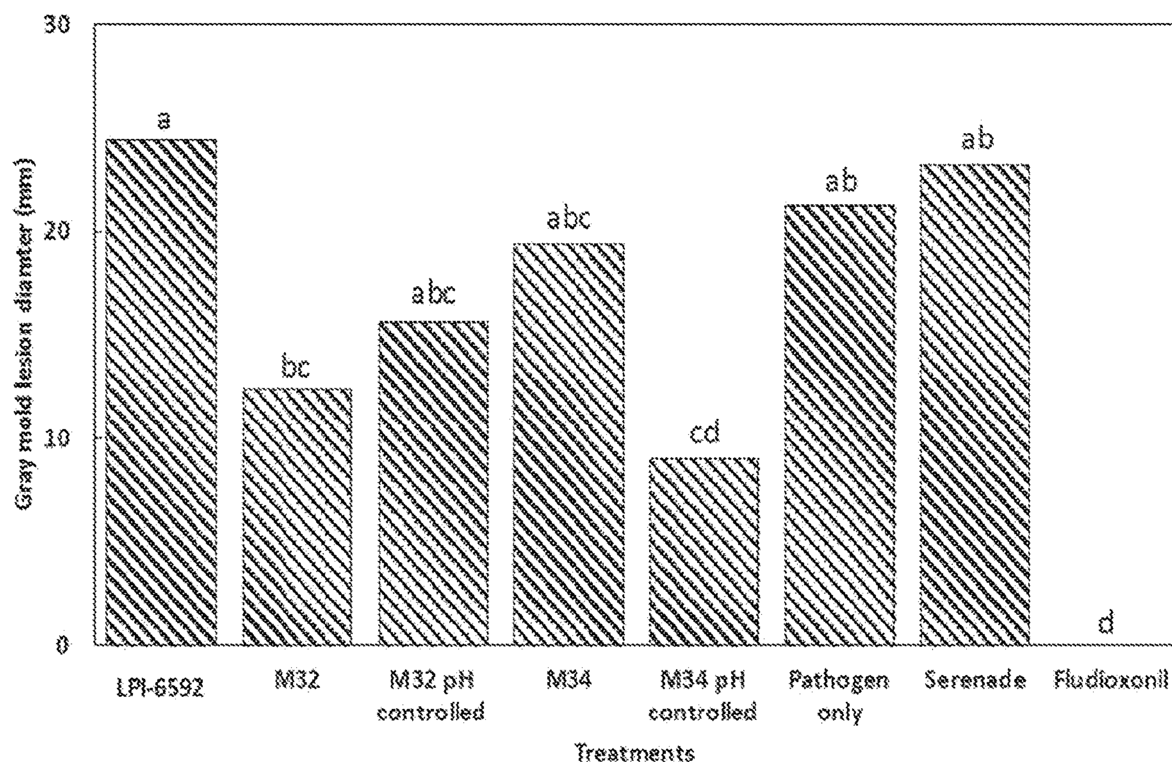

FIG. 21 shows the diameters of gray mold lesions, caused by *Botrytis cinerea*, on detached canola leaves treated with biocontrol samples and controls, seven days after inoculation.

Figure 22A:
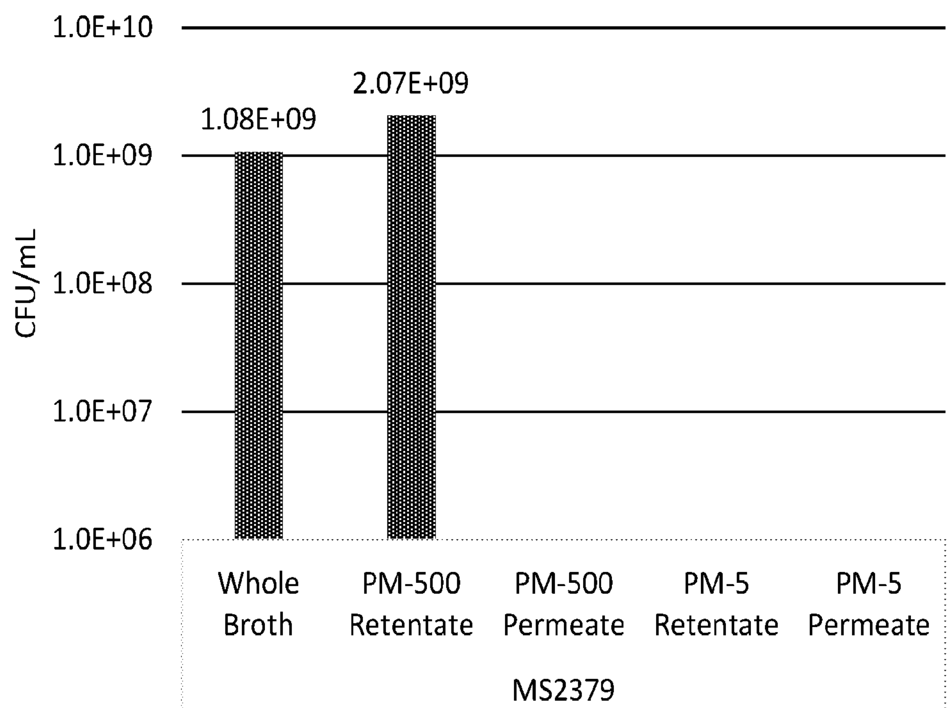
Figure 22B:
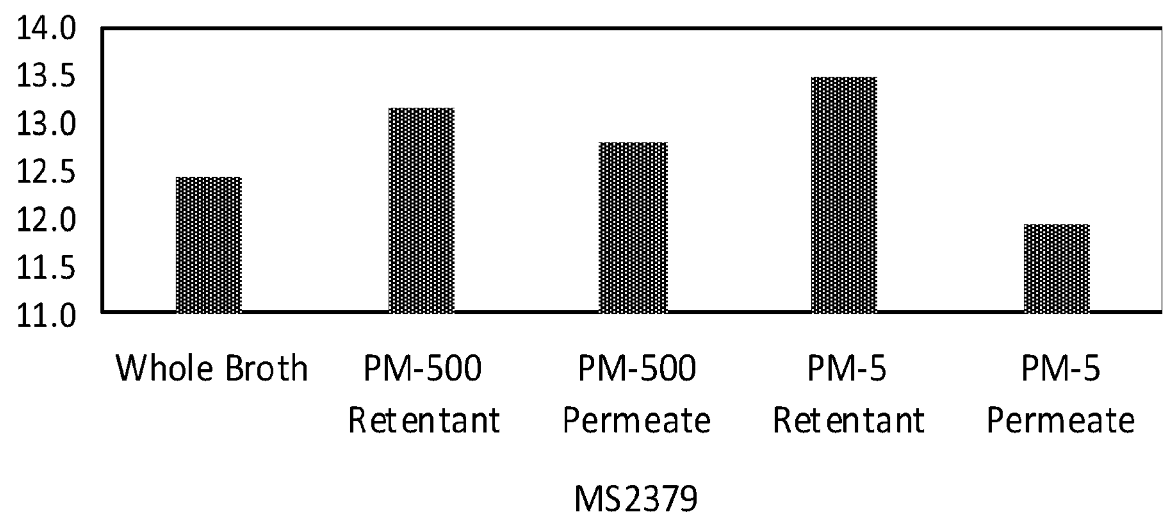

FIG. 22A shows the comparison of cfu concentration in the fermentation whole broth, retentate and permeate after ultrafiltration using hollow fiber filter. FIG. 22B shows comparison of protease activity in the fermentation whole broth, retentate and permeate after ultrafiltration using hollow fiber filter.

Figure 23A:
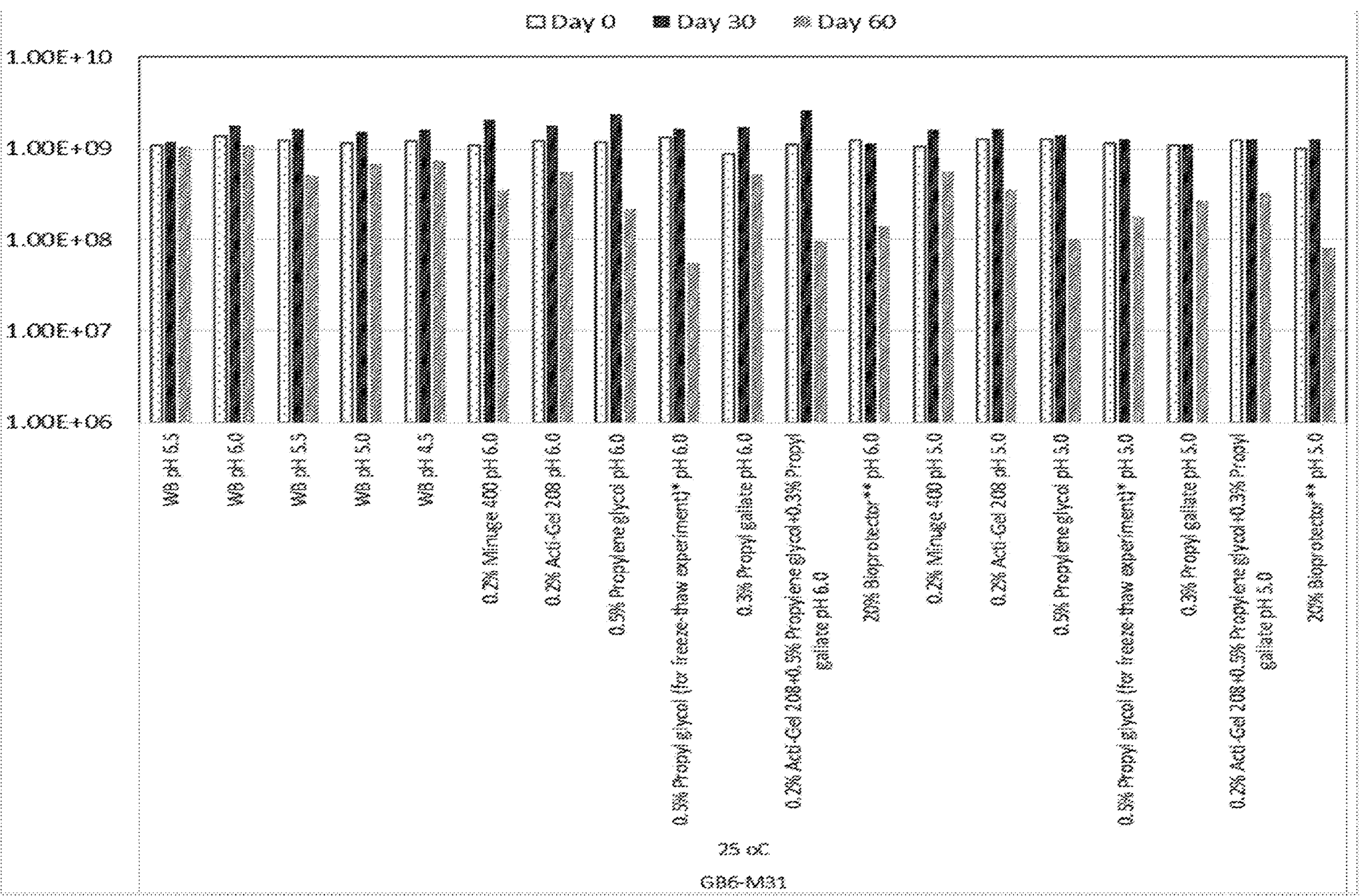
Figure 23B:
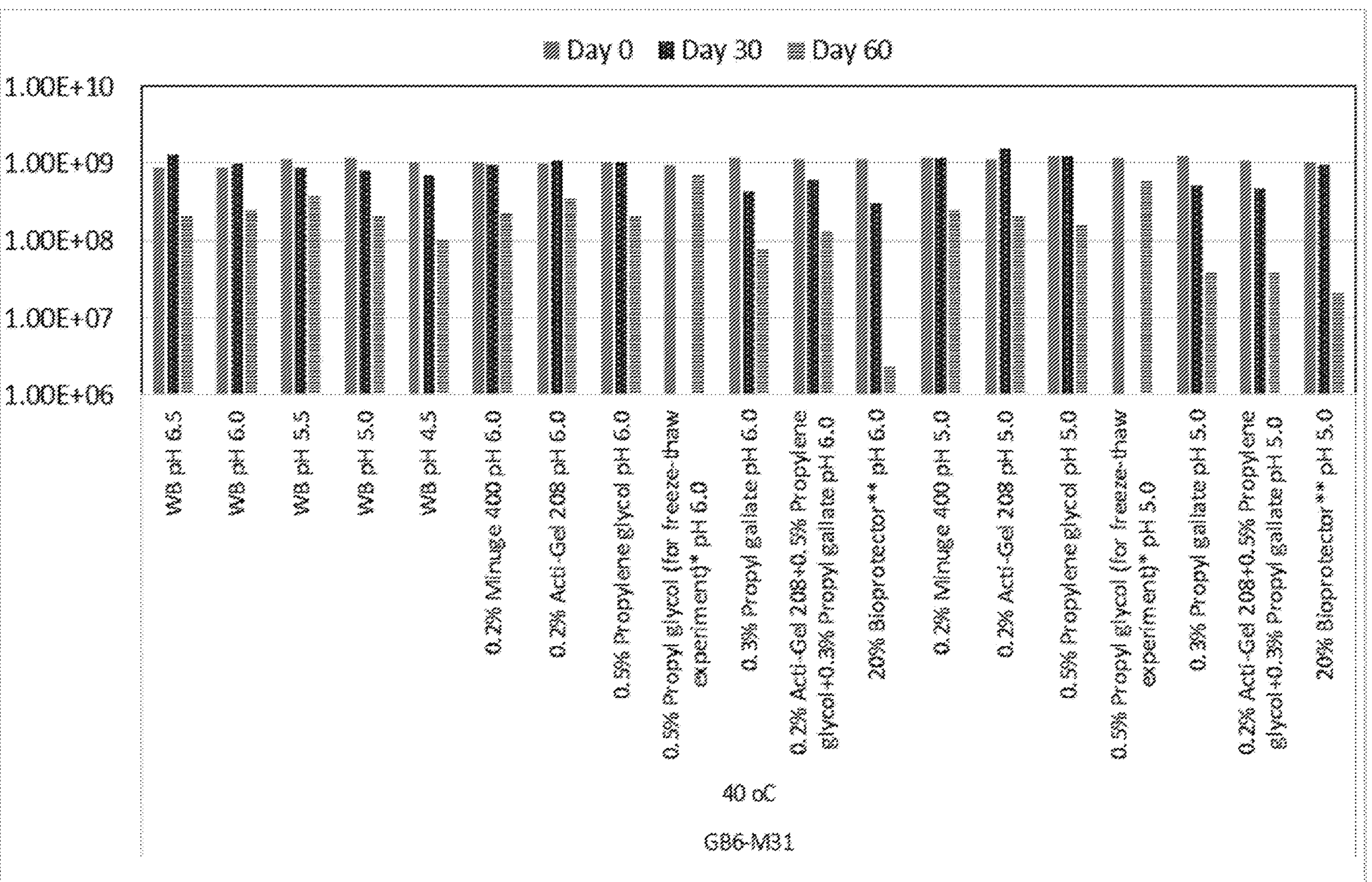
Figure 23C:
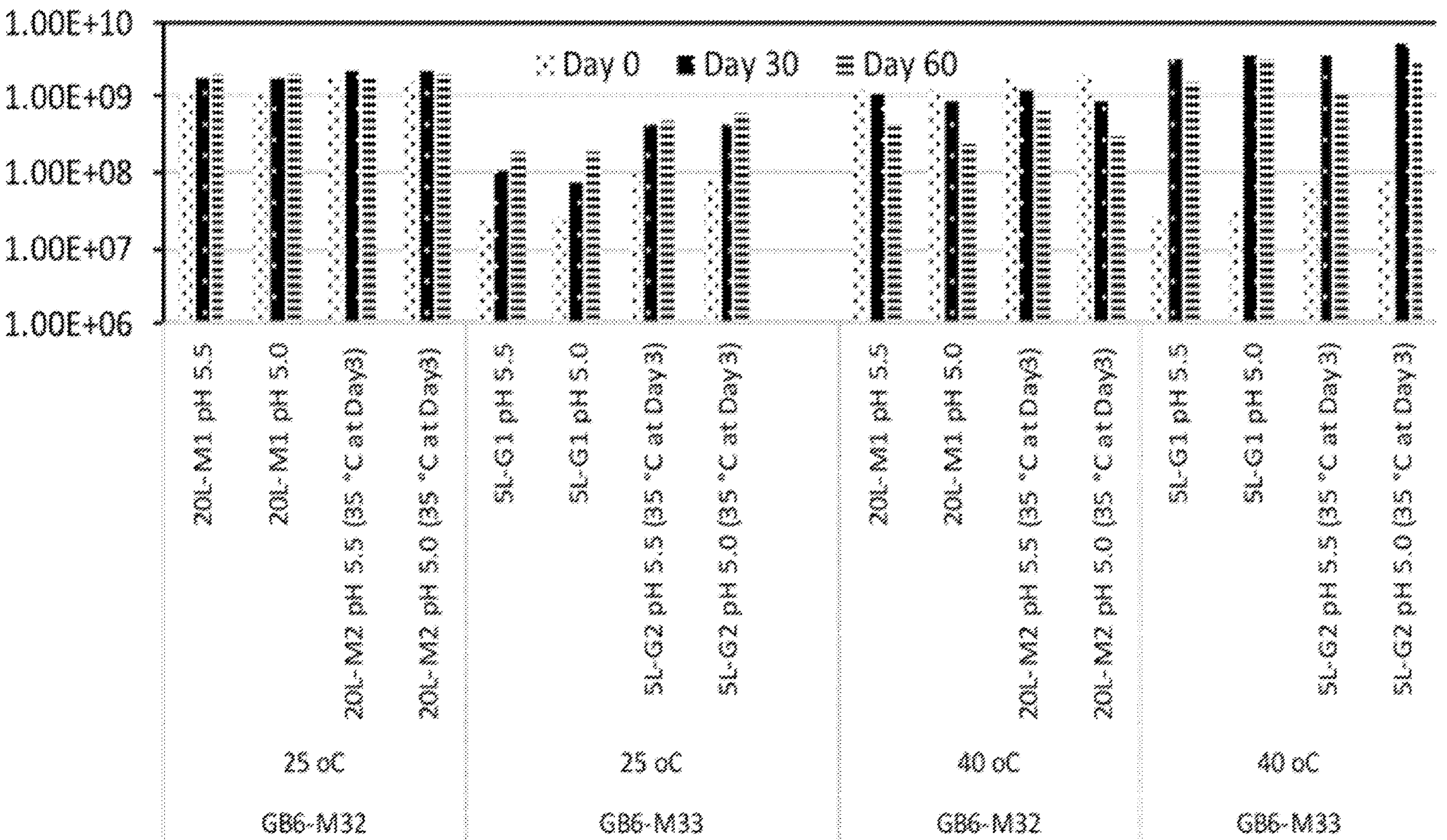

FIG. 23A shows the cfus of MS2379 in GB6-M31 after two months of storage at room temperature (25° C.). FIG. 23B shows the cfus of MS2379 in GB6-M31 after two months of storage at 40° C. FIG. 23C shows comparison of the stability of WBs from fermentation at 26° C. throughout fermentation and fermentation increasing temperature from 26° C. to 35° C. at 48 hours during storage at 25° C. and 40° C.

DETAILED DESCRIPTION

After reading this description, it will become apparent to one skilled in the art how to implement the disclosure in various alternative embodiments and alternative applications. However, not all embodiments of the present disclosure are described herein. It will be understood that the embodiments presented here are presented by way of an example only, and not limitation. As such, this detailed description of various alternative embodiments should not be construed to limit the scope or breadth of the present disclosure as set forth below.

Before the present disclosure is disclosed and described, it is to be understood that the aspects described below are not limited to specific compositions, methods of preparing such compositions, or uses thereof, as such may, of course, vary. It is also to be understood that the terminology used herein is for the purpose of describing particular aspects only and is not intended to be limiting.

Throughout this disclosure, various publications, patents, and published patent specifications are referenced by an identifying citation. The disclosures of these publications, patents, and published patent specifications are hereby incorporated by reference in their entirety into the present disclosure.

Definitions

Unless defined otherwise, all technical and scientific terms used herein have the same meaning as commonly understood by one of ordinary skill in the art to which this disclosure belongs.

In this specification and in the claims that follow, reference will be made to a number of terms that shall be defined to have the following meanings:

The terminology used herein is for the purpose of describing particular embodiments only and is not intended to be limiting of the disclosure. As used herein, the singular forms "a," "an," and "the" are intended to include the plural forms as well, unless the context clearly indicates otherwise.

All numerical designations, e.g., pH, temperature, time, concentration, amounts, and molecular weight, including ranges, are approximations which are varied (+) or (–) by 10%, 1%, or 0.1%, as appropriate. It is to be understood, although not always explicitly stated, that all numerical designations may be preceded by the term "about." It is also to be understood, although not always explicitly stated, that the reagents described herein are merely exemplary and that equivalents of such are known in the art.

The term "about" when used before a numerical designation, e.g., temperature, time, amount, concentration, and such others, including a range, indicates approximations which may vary by (+) or (–) 10%, 5%, 1%, or any subrange or subvalue there between. Preferably, the term "about" when used with regard to a dose amount means that the dose may vary by +/–10%.

The term "comprising" or "comprises" is intended to mean that the agricultural compositions and methods include the recited elements but do not exclude others. "Consisting essentially of," when used to define compositions and methods, shall mean excluding other elements of any essential significance to the combination. For example, an agricultural composition consisting essentially of the elements as defined herein would not exclude other elements that do not materially affect the basic and novel characteristic(s) of the claimed disclosure. "Consisting of" shall mean excluding more than trace amounts of other ingredients and substantial method steps recited. Embodiments defined by each of these transition terms are within the scope of this disclosure.

The term "treating" or "treatment" covers the treatment of a disease described herein, in a plant, and includes: (i) inhibiting a disease, i.e., arresting its development; (ii) relieving a disease; (iii) slowing progression of the disease; (iv) inhibiting, relieving, or slowing progression of one or more symptoms of the disease or disorder; and/or (v) reducing the growth of the disease-causing organism. For example, treatment of a disease associated with soil-borne or foliar pathogens includes, but is not limited to, reduction in root decay, tissue discoloration, crown rot, and/or wilting of foliage, and the like.

The term "administering" or "administration" of a composition, an inhibitory agent, or a drug to a plant includes any route of introducing or delivering to a plant an agricultural composition to perform its intended function. Administration can be carried out by any suitable route, including in-furrow, in vicinity of the plant, to vegetative tissue of plant, including leaves and reproductive tissues, or by pre-treating the plant seed before planting.

It is also to be appreciated that the various modes of treatment or prevention of medical diseases and conditions as described are intended to mean "substantial," which includes total but also less than total treatment or prevention, and wherein some biologically or medically relevant result is achieved.

As used herein, the term "effective amount" refers to an amount of composition which is capable of inhibiting, relieving, and/or suppressing the plant diseases. The precise effective amount will vary based on the type of the plants, the diseases, the level of infections, and/or the types of pathogens that cause the plant diseases.

As used herein, the term "plant" or "plants" means, in a broad sense, to include not only herbaceous varieties, including, but not limited to, crops, vegetables, flowers, foliage plants, turf grasses, fruits, but also trees, shrubs, and the like. The non-limiting examples of crops include corn, rice, wheat, barley, rye, oat, sorghum, cotton, soybean, peanut, buckwheat, beet, rapeseed, sunflower, sugar cane, cannabis, and tobacco. The non-limiting examples of vegetables or fruits include solanaceous vegetables (eggplant, tomato, pimento, pepper, potato, etc.), cucurbitaceous vegetables (cucumber, pumpkin, zucchini, watermelon, melon, squash, etc.), cruciferous vegetables (Japanese radish, white turnip, horseradish, kohlrabi, Chinese cabbage, cabbage, leaf mustard, broccoli, cauliflower, etc.), asteraceous vegetables (burdock, crown daisy, artichoke, lettuce, etc.), liliaceous vegetables (green onion, onion, garlic, and asparagus), apiaceous vegetables (carrot, parsley, celery, parsnip, etc.), chenopodiaceous vegetables (spinach, Swiss chard, etc.), lamiaceous vegetables (*Perilla frutescens*, mint, basil, etc.), strawberry, sweet potato, *Dioscorea japonica*, and *Colocasia*. The non-limiting examples of fruits include pomaceous fruits (apple, pear, Japanese pear, Chinese quince, quince, etc.), stone fleshy fruits (peach, plum, nectarine, *Prunus mume*, cherry fruit, apricot, prune, etc.), citrus fruits (*Citrus unshiu*, orange, lemon, lime, grapefruit, etc.), nuts (chestnuts, walnuts, hazelnuts, almonds, pistachio, cashew nuts, macadamia nuts, etc.), berries (blueberry, cranberry, blackberry, raspberry, etc.), grape, kaki fruit, olive, Japanese plum, banana, coffee, date palm, and coconuts. Non-limiting examples of trees include fruit trees, tea, mulberry, flowering plant, and roadside trees (ash, birch, dogwood, *Eucalyptus, Ginkgo biloba*, lilac, maple, *Quercus*, poplar, Judas tree, *Liquidambar formosana*, plane tree, zelkova, Japanese arborvitae, fir wood, hemlock, juniper, *Pinus, Picea*, and *Taxus cuspidata*). Plant refers to both native and genetically engineered aforementioned varieties.

The term "agricultural composition" refers to a material or a combination of materials that are capable of improving the rate of growth or health of plants, increasing the yields of plants or their fruits, and/or improving or change the environments where the plants grow. In one embodiment, the agricultural composition can prevent, inhibit, or ameliorate a plant disease that affects the health, growth, and/or yield of a plant. In another embodiment, the agriculture composition supplements the soil with various nutrients for plant growth and produces the nutritional response from the plants. In another embodiment, the agricultural composition comprises a microbial species that is capable of inhibiting plant diseases. The microbial species may be fermented or cultured in a culture medium such that the microbial species is rendered significantly different characteristics than its natural counterpart when used in the agricultural composition. For example, the microbial species, when used in the agricultural composition of this disclosure, can become significantly more effective against a particular plant pathogen than the same species directly from nature, even when the same number of colony forming units is used. The distinct attributes are not expected from a natural species of the agricultural composition. Other components in the agricultural composition do not necessarily co-exist with the microbial species in nature. In one embodiment, the agricultural composition comprises at least one or more of other components which include a wetting agent, a binding agent, a filler, a preservative, a mineral, an adjuvant, a thickening agent, a bioprotector, an osmotic protectant, or an organic additive.

As used herein, MS 1479 refers to a bacterial strain deposited as ATCC® Patent Deposit Designation No. PTA-124701, on Feb. 14, 2018.

As used herein, MS2379 refers to a bacterial strain deposited as ATCC® Patent Deposit Designation No. PTA-124703, on Feb. 14, 2018.

As used herein, MS2414 refers to a bacterial strain deposited as ATCC® Patent Deposit Designation No. PTA-124704, on Feb. 14, 2018.

As used herein, MS2820 refers to a bacterial strain deposited as ATCC® Patent Deposit Designation No. PTA-124710, on Feb. 14, 2018.

As used herein, MS0633 refers to a bacterial strain deposited as ATCC® Patent Deposit Designation No. PTA-124700, on Feb. 14, 2018.

As used herein, MS2335 refers to a bacterial strain deposited as ATCC® Patent Deposit Designation No. PTA-124702, on Feb. 14, 2018.

As used herein, MS2652 refers to a bacterial strain deposited as ATCC® Patent Deposit Designation No. PTA-124705, on Feb. 14, 2018.

As used herein, MS2658 refers to a bacterial strain deposited as ATCC® Patent Deposit Designation No. PTA-124706, on Feb. 14, 2018.

As used herein, MS2681 refers to a bacterial strain deposited as ATCC® Patent Deposit Designation No. PTA-124707, on Feb. 14, 2018.

As used herein, MS2697 refers to a bacterial strain deposited as ATCC® Patent Deposit Designation No. PTA-124708, on Feb. 14, 2018.

As used herein, MS2712 refers to a bacterial strain deposited as ATCC® Patent Deposit Designation No. PTA-124709, on Feb. 14, 2018.

Non-limiting examples of wetting agents include phenyl naphthalene sulphonates, alkyl naphthalene sulfonate, sodium alkyl naphthalene sulfonate, sodium salt of sulfonated alkylcarboxylate, polyoxyalkylated ethyl phenols, polyoxyethoylated fatty alcohols, polyoxythoxylated fatty amines, lignin derivatives, alkane sulfonates, alkylbenzene sulfonates, salts of polycarboxylic acids, salts of esters of sulfosuccinic acid, alkylnaphthalenesulphonates, alkylbenzenesulfonates, alkylpolyglycol ether sulfonates, alkyl ether phosphates, alkyl ether sulphates and alkyl sulfosuccinic monoesters.

Non-limiting examples of wetting agents include polyvinyl alcohols, phenyl naphthalene sulphonate, lignin derivatives, polyvinyl pyrrolidone, polyalkylpyrrolidone, carboxymethylcellulose, xanthan gum, polyethoxylated fatty acids, polyethoxylated fatty alcohols, ethylene oxide copolymer, propylene oxide copolymer, polyethylene glycols and polyethylene oxides.

Non-limiting examples of fillers include bentonite, subbentonite, attapulgite, kaolinites, montmorillonite, bauxite, hydrated aluminas, calcined aluminas, diatomaceous earth, chalk, fuller's earth, dolomite, kiesulguhr, loess, prophyllites, talc, vermiculites, limestone, natural and synthetic silicates, silicas and china clay.

Non-limiting examples of wetting agents of additives include macronutrients, micronutrients compost fertilizers, natural elements, natural organisms, *Trichoderma*, humic acid extracts, *Bacillus thuringiensis*, viruses, natural fungi, plant extracts, pyrethrums, biological control products, natural oils, natural extracts, minerals and urea groups.

The term "insecticide," as used herein, is used in its broad sense as meaning not only substances which will kill insects but substances which will be noxious to insects, scale, and mites.

The term "fungicide," as used herein, is used in its broad sense as meaning not only substances which kill fungi and oomycetes (including blight, spores, and the like) but substances that are noxious to fungi and oomycetes.

The term "herbicide" is used herein to mean a compound which controls or modifies the growth of plants. Controlling or modifying effects include all deviations from natural development, for example, killing, retardation, leaf burn, dwarfing, and the like. The non-limiting list of the herbicides includes amide herbicides, aromatic acid herbicides, arsenical herbicides, benzofuranyl alkylsulfonate herbicides, benzothiazole herbicide, benzoylcyclohexanedione herbicide, carbamate herbicides, carbanilate herbicides, cyclohexene oxime herbicides, cyclopropylisoxazole herbicides, dicarboximide herbicides, dinitroaniline herbicides, dinitrophenol herbicides, diphenyl ether herbicides, dithiocarbamate herbicides, halogenated aliphatic herbicides, imidazolinone herbicides, inorganic herbicides, nitrile herbicides, organophosphorus herbicides, oxadiazolone herbicides, oxazole herbicides, phenoxy herbicides, phenylenediamine herbicides, pyrazole herbicides, pyridazine herbicides, pyridazinone herbicides, pyridine herbicides, pyrimidinediamine herbicides, pyrimidinyloxybenzylamine herbicides, quaternary ammonium herbicides, thiocarbamate herbicides, thiocarbonate herbicides, thiourea herbicides, triazine herbicides, triazinone herbicides, triazole herbicides, triazolone herbicides, triazolopyrimidine herbicides, unclassified herbicides, uracil herbicides, and urea herbicides.

The term "herbicide safener," as used herein, refers to a compound or compounds that selectively protect the plants from herbicide damage without significantly reducing activity in target weed species.

The term "nematicide," as used herein, refers to a compound or compounds that can protect the plants from nematodes. A non-limiting list of nematicides includes avermectin nematicides, botanical nematicides, carbamate nematicides, fumigant nematicides, organophosphorus nematicides, the unclassified nematicides, and the like.

As used herein, the term "bactericide" means any agents, compositions, compounds, biologics, and chemicals that can inhibit, suppress, and/or limit the functions, growth, or pathogenic activities of a bacterial species.

As used herein, the terms "isolate" and "strain," used interchangeably in this application, refer to a pure microbial culture separated from its natural origin, such as an isolate obtained by culturing a single microbial colony. In one embodiment, an isolate is a pure culture derived from a heterogeneous, wild population of microorganisms.

As used herein, the term "strain" refers to an isolate or a group of isolates exhibiting phenotypic and/or genotypic traits belonging to the same lineage, distinct from those of other isolates or strains of the same species.

As used herein, the term "viral inhibitor" means any agents, compositions, compounds, biologics, and chemicals that can inhibit, suppress, and/or limit the functions, growth, or pathogenic activities of a virus.

As used herein, the term "culture medium" refers to all kinds of media which are used for culturing the microorganism, including, but not limited to, a liquid broth and the remaining medium when cells grown in the medium are removed, e.g., the supernatant remaining when cells grown in a liquid broth are removed by centrifugation, filtration, sedimentation, or other means well known in the art.

As used herein, the term "whole culture broth," "whole broth," or "WB" refers to a liquid culture of a microorganism in the culture medium.

As used herein, the term "whole broth sterile filtrate," "sterile filtrate," or "SF" refers to liquid which is separated from the whole culture broth by use of a size exclusion filter, such as a 0.22 μm filter, such that any intact bacterial cells are removed.

As used herein, the term "B S3" means a culture medium comprising, or alternatively consisting essentially of, or yet further consisting of 5-20 g/L Soy peptone, 2-10 g/L Urea, 1-5 g/L $CaCl_2$, 2-10 g/L $KH_2PO_4$, 2-10 g/L $K_2HPO_4$, and 10-30 g/L Sucrose.

As used herein, the term "B53-M2" means a culture medium comprising, or alternatively consisting essentially of, or yet further consisting of 5-20 g/L Soy peptone, 2-10 g/L Urea, 1-5 g/L $CaCl_2$, 2-10 g/L $KH_2PO_4$, 2-10 g/L $K_2HPO_4$, and 10-30 g/L Sucrose.

As used herein, the term "BS3-M9" means a culture medium comprising, or alternatively consisting essentially of, or yet further consisting of 5-20 g/L Low fat soy flour, 0.5-5 g/L $CaCl_2$, 4 g/L $KH_2PO_4$, 3.5 g/L $K_2HPO_4$, 10-30 g/L Sucrose, and 0.1-5 g/L ammonia sulfate.

As used herein, the term "BS3-M10" means a culture medium comprising, or alternatively consisting essentially of, or yet further consisting of 5-15 g/L low fat soy flour, 2-10 g/L $KH_2PO_4$, 2-10 g/L $K_2HPO_4$, 10-30 g/L Sucrose, and 0.1-5 g/L ammonia sulfate.

As used herein, the term "GB6-M" means a culture medium comprising, or alternatively consisting essentially of, or yet further consisting of 5-40 g/L Maltrin® (M-180), 5-20 g/L Dextrose, 1-10 g/L yeast extract, 1-10 g/L Casein hydrolysate, and 0-5 g/L $CaCO_3$.

As used herein, the term "GB6-M3" means a culture medium comprising, or alternatively consisting essentially of, or yet further consisting of 10-30 g/L Maltrin® (M-250 or M-180), 5-20 g/L Dextrose, 2-10 g/L yeast extract, 2-10 g/L low fat soy flour, and 0.1-5 g/L $CaCO_3$.

As used herein, the term "GB6-M7" means a culture medium comprising, or alternatively consisting essentially of, or yet further consisting of 10-30 g/L Maltrin® (M-250 or M-180), 5-20 g/L Dextrose, 2-10 g/L yeast extract, 0.1-5 g/L Ammonia sulfate, and 0.2-3 g/L $CaCO_3$.

As used herein, the term "GB6-M8" means a culture medium comprising, or alternatively consisting essentially of, or yet further consisting of 10-30 g/L Maltrin® (M-250 or M-180), 5-20 g/L Dextrose, 2-15 g/L yeast extract, 5-20 g/L low fat soy flour, 0.2-1.5 g/L Ammonia sulfate, and 0.2-3 g/L $CaCO_3$.

As used herein, the term "GB6-M9" means a culture medium comprising, or alternatively consisting essentially of, or yet further consisting of 5-40 g/L Maltrin® (M-250 or M-180), 5-20 g/L Dextrose, 5-20 g/L low fat soy flour, and 0.2-5 g/L $CaCO_3$.

As used herein, the term "GB6-M10" means a culture medium comprising, or alternatively consisting essentially of, or yet further consisting of 5-40 g/L Maltrin® (M-250 or M-180), 5-25 g/L Dextrose, 1-10 g/L yeast extract, 1-10 g/L Low fat soy flour, 0.2-2 g/L ammonia sulfate, and 0-5 g/L $CaCO_3$.

As used herein, the term "GB6-M22" means a culture medium comprising, or alternatively consisting essentially of, or yet further consisting of 50-100 g/L Maltrin® (M-250 or M-180), 5-20 g/L Dextrose, 10-20 g/L yeast extract, 2-10 g/L low fat soy flour, 1-4 g/L ammonia sulfate, 1-4 g/L $CaCO_3$, and 0.1-1.5 ml/L antifoam.

As used herein, the term "GB6-M23" means a culture medium comprising, or alternatively consisting essentially of, or yet further consisting of 50-100 g/L Maltrin® (M-250 or M-180), 5-20 g/L Dextrose, 10-20 g/L yeast extract, 5-15 g/L low fat soy flour, 1-3 g/L ammonia sulfate, 1-4 g/L $CaCO_3$, and 0.1-1.2 ml/L antifoam.

As used herein, the term "GB6-M31" means a culture medium comprising, or alternatively consisting essentially of, or yet further consisting of 30-70 g/L Maltrin® (M-250 or M-180), 5-25 g/L dextrose, 5-15 g/L yeast, 2-10 g/L low fat soy flour, 0.5-3 g/L ammonia sulfate, 0.5-3 g/L $CaCO_3$, and 0.2-1.5 ml/L antifoam.

As used herein, the term "GB6-M33" means a culture medium comprising, or alternatively consisting essentially of, or yet further consisting of 50-100 g/L Maltrin® (M-250 or M-180), 5-25 g/L dextrose, 10-20 g/L yeast, 2-10 g/L low fat soy flour, 1-4 g/L ammonia sulfate, 1-5 g/L $CaCO_3$, and 0.2-1.5 ml/L antifoam.

As used herein, the term "GB6-M34" means a culture medium comprising, or alternatively consisting essentially of, or yet further consisting of 50-100 g/L Maltrin® (M-250 or M-180), 10-25 g/L dextrose, 1-10 g/L yeast, 2-10 g/L low fat soy flour, 1-4 g/L ammonia sulfate, 2-5 g/L $CaCO_3$, and 0.2-1 ml/L antifoam.

The term "carrier," in the present disclosure, means a natural or synthetic organic or inorganic substance with which the agricultural composition is combined to facilitate its application to the plant, seed, or soil. This carrier is therefore generally inert, biodegradable, and should be acceptable for food safety. The carrier may be solid, including, but not limited to, clays, peat, inorganic soils, natural or synthetic silicates, silica, resins, waxes, solid fertilizers, plant waste products (composts, farmyard manure, soybean meal, soybean and peanut oil, wheat bran, spent mushroom compost, bagasse, plant debris, and the like), vermiculite perlite, ground rock phosphate, calcium sulfate, polyacrylamide gels, alginate beads, diatomaceous earth, and the like or liquid (water, alcohols, in particular butanol, carbohydrates, glucose, nutritional additions, and the like).

As used herein, the term "seed treatment," "seed coating," or "seed treatment formulation" refers to applying a material to a seed before or during the seed is planted. In one embodiment, the seed is planted in soil, in liquid, or in a medium suitable for seed germination. The applied material can improve the handling characteristics of the seed, protect the seed prior to and/or during germination, support germination, and/or promote the growth of the resulting plant. In some embodiments, the seed treatment is employed to improve the handling characteristics or other physical characteristics of seeds and to include no other agricultural active ingredients. In another embodiment, the seed treatment applies one or more active ingredients to seeds, where the one or more active ingredients promote the uniform stand establishment by preventing or treating soil-borne (or foliar) diseases and insects.

As used herein, the term "seed medium" refers to a preparation to assist the beginning of the fermentation process. In one embodiment, the seed medium is a microbiological culture that is used to inoculate or cultivate the microbes.

As used herein, the term "production medium" refers to a medium that supplies the nutrients required by organisms or cells. In some embodiments, the production medium comprises a carbon source, a nitrogen source, a growth factor, a micronutrient, or combination thereof.

In a further embodiment, the treatment (e.g., seed or foliar treatment) utilizes a binder formulation of multiple ingredients (interchangeably referred to as "a seed treatment formulation") combined with at least one agricultural active ingredient, often multiple active ingredients, to provide a coating that binds a desired amount of the active ingredient(s) on the seed. The binder formulation is mixed with the active ingredient(s) and water diluent prior to being applied to seeds. For example, polymers are used in seed treatment formulations with beneficial microbes to improve the sticking of microbes to the seed, to reduce dust, to improve seed flow and handling, to improve the longevity of the microbial content on stored seed, and/or to improve rapid activity from the biological component upon seed planting.

one embodiment, control pathogen-infected roots, vegetative tissues, and/or reproductive tissues in more mature plants.

This disclosure provides isolates of *Bacillus* and *Paenibacillus* which may exert multiple modes of actions to control a broad spectrum of soil-borne and foliar plant pathogens. The newly identified strains of *Paenibacillus* are designated as MS1479, MS2379, MS2414, and MS2820. The strains of *Bacillus* are designated as MS0633, MS2335, MS2652, MS2658, MS2681, MS2697, and MS2712. All isolates have been maintained in the proprietary culture collection of Agricen Sciences in Pilot Point, Texas since their original isolation. A sample of each bacterium will be or has been deposited with the American Type Culture Collection (ATCC). The seven *Bacillus* isolates belong to the species of *Bacillus amyloliquefaciens* based on 16S rRNA analysis. 16S rRNA gene sequences of the bacterial isolates are shown in SEQ ID NO. 1-11; gyrB gene sequences are shown in SEQ ID NO. 12-21; and rpoB gene sequences are shown in SEQ ID NO. 22-32.

It is contemplated that the disclosure is related to a method of controlling and/or preventing plant diseases comprising applying an effective amount of an agricultural composition to a plant and/or to a seed of the plant, where the agricultural composition comprises bacterial isolates belonging to *Bacillus* or *Paenibacillus*. In one aspect, the bacterial isolate belongs to *Bacillus amyloliquefaciens, Paenibacillus* spp. or *Paenibacillus polymyxa*. It is further contemplated that the agricultural composition comprises, or alternatively consists essentially of, or yet further consists of MS1479, MS2379, MS2414, MS2820, MS0633, MS2335, MS2652, MS2658, MS2681, MS2697, or MS2712. In one embodiment, the composition comprises a spore of the bacterial strain.

As shown in Table 1, comparing these strains to all of the deposited *P. polymyxa* (and *P. terrae*) genomes in the publically available National Center of Biotechnology Information ("NCBI") database, MS2379 has an ANI (average nucleotide identity) value <95% and is likely to be a novel species of *Paenibacillus*. The general rule for bacterial systematics suggests that strains with greater than 95% ANI are the same species. See Goris et al., IJSEM 57:81-91 (2007). Strains MS2414 (and MS1479 which is highly similar to MS2414) and MS2820 have sufficient overlap with some *Paenibacillus polymyxa* strain genomes to be included in this species.

TABLE 1

Pairwise ANI comparisons between *Paenibacillus* strains and publically available genomes

| *Paenibacillus* strain | *P. polymyxa* M1 | *P. polymyxa* CR1 | *P. polymyxa* E681 | *P. polymyxa* SC2 | *P. polymyxa* SQR-21 | *P. terrae* HPL-003 |
|---|---|---|---|---|---|---|
| MS2379 | 93.4% | 89.8% | 89.8% | 93.4% | 93.0% | 86.5% |
| MS2414 | 90.8% | 96.8% | 96.4% | 90.8% | 90.6% | 88.0% |
| MS2820 | 91.2% | 95.8% | 95.7% | 90.9% | 90.8% | 87.8% |

*Paenibacillus* and *Bacillus* Isolates

*Paenibacillus* species are facultative anaerobic, endospore-forming, gram-positive organisms previously included in the *Bacillus* genus. *Bacillus* is also a gram-positive genus. In this disclosure, the isolates of *Paenibacillus* and *Bacillus* are used to promote plant growth and suppress seedling damping-off caused by fungi and oomycetes, including, but not limited to, *F. oxysporum, R. solani*, or *P. ultimum*. The isolates of *Paenibacillus* and *Bacillus*, in By comparing the whole genome sequences of the *Paenibacillus* isolates, MS1479 and MS2414 are very similar (ANI=99.8%), and are less similar to either MS2379 (89.7%) or MS2820 (ANI=95.7%). MS2414 and MS2820 are the most similar to strain *P. polymyxa* CR1 (96.8% and 95.8% ANI, respectively). The strain that is most closely related to MS2379 is *P. polymyxa* M1, yet it has only 93.4% ANI with MS2379. Of these *Paenibacillus* isolates, MS2379 has lower ANIs with MS1479 (ANI=89.7%), MS2414 (ANI=89.7%) and MS2820 (ANI=89.9%).

To maximize the potential of the isolates, different media were used to determine their effects on sporulation efficiency, cfu counts, and biocontrol activities of the bacterial isolates of this disclosure, e.g., MS1479, MS2379, MS2414, MS2820, MS0633, MS2335, MS2652, MS2658, MS2681, MS2697, or MS2712. As shown in a summary in Table 2, the GB6 and BS3 media improved the cfus, sporulation rates, and bioactivities of the *Paenibacillus* isolates over that of Tryptic Soy Broth ("TSB") medium. Notably, the sterile filtrate broth of MS1479, MS2379, MS2414, and MS2820 had no or minimum inhibition activity against *Pythium* spp. when cultured in TSB medium, but gained such activity when cultured in GB6 and BS3. Thus, an optimized fermentation medium can provide the bacteria distinctive characteristics that are missing in their natural counterparts, e.g., gained anti-pathogenic (e.g., anti-fungal) activities against plant-pathogenic fungal species that are proof against the naturally occurring bacteria before cultured in the media of this disclosure. Moreover, the culture with the medium can also prolong the anti-pathogenic function against targeted plant diseases or pathogens. Therefore, in one aspect, the disclosure provides an agricultural composition comprising a bacterial isolate of *Paenibacillus* or *Bacillus*, or a mutant thereof, wherein the bacterial isolate is fermented and/or cultured in a culture medium comprising LB, TSB, BS3, BS3-M2, BS3-M9, BS3-M10, GB6-M, GB6-M3, GB6-M7, GB6-M8, GB6-M9, GB6-M22, GB6-M23, GB6-M10, GB6-M31, GB6-M33, GB6-M34, or combination thereof. In one embodiment, the bacterial isolate comprises MS1479, MS2379, MS2414, MS2820, MS0633, MS2335, MS2652, MS2658, MS2681, MS2697, MS2712, or combination thereof. In another embodiment, the bacterial isolate comprises MS2379 or MS2414. In one embodiment, the culture medium comprises BS3-M2, BS3-M9, BS3-M10, GB6-M, GB6-M3, GB6-M7, GB6-M8, GB6-M9, GB6-M22, GB6-M23, GB6-M10, GB6-M31, GB6-M33, GB6-M34, or combination thereof. In another embodiment, the culture medium comprises GB6-M10, GB6-M31, GB6-M33, GB6-M34, or combination thereof.

In another embodiment, the bacterial isolate is fermented by a process that comprises: (1) inoculating the bacterial isolate in a seed medium and (2) expanding the culture with a production medium. In one embodiment, the seed medium comprises LB, TSB, BS3, BS3-M2, BS3-M9, BS3-M10, GB6-M, GB6-M3, GB6-M7, GB6-M8, GB6-M9, GB6-M22, GB6-M23, GB6-M10, GB6-M31, GB6-M33, GB6-M34, or combination thereof. In another embodiment, the production medium comprises GB6-M10, GB6-M31, GB6-M33, GB6-M34, or combination thereof.

In another aspect, the disclosure provides optimized fermentation media and process for the bacterial isolates. In one aspect of the disclosure, the agricultural composition comprises, or alternatively consists essentially of, or yet further consists of LB, TSB, BS3, BS3-M2, BS3-M9, BS3-M10, GB6-M3, GB6-M7, GB6-M8, GB6-M9, GB6-M22, GB6-M23, GB6-M10, GB6-M31, GB6-M33, or GB6-M34 culture medium. In another aspect, the agricultural composition comprises BS3, BS3-M2, GB6-M3, GB6-M7, GB6-M8, GB6-M9, GB6-M22, GB6-M23, GB6-M10, GB6-M31, GB6-M33, or GB6-M34 culture medium or the combination thereof.

TABLE 2

In-vitro controls against four target fungal pathogens by either whole broth (WB) or whole broth sterile filtrate broth (SFB) of different strain/medium combinations.

| Isolate | Fermentation Medium | cfu/ml | Sporulation (%) | *Pythium* spp. control[1] WB | *Pythium* spp. control[1] SFB | *R. solani* control[1] WB | *R. solani* control[1] SFB | *F. virguliforme* control WB | *M. phaseolina* control[1] WB |
|---|---|---|---|---|---|---|---|---|---|
| MS1479 | TSB | $8.7 \times 10^7$ | ~80 | ++ | 0 | ++ | 0 | + | +++ |
| | BS3-M | $8.0 \times 10^8$ | ~60 | ++ | +++ | +++ | ++ | ++ | +++ |
| | GB6-M | $1.4 \times 10^8$ | ~80 | ++ | ++ | +++ | + | ++ | +++ |
| MS2379 | TSB | $1.5 \times 10^5$ | <5 | + | 0 | + | 0 | ++ | ++ |
| | BS3-M | $2.3 \times 10^8$ | ~90 | ++ | + | +++ | 0 | + | +++ |
| | GB6-M | $1.5 \times 10^8$ | ~60 | ++ | + | +++ | 0 | + | +++ |
| MS2414 | TSB | $9.2 \times 10^6$ | <5 | + | 0 | ++ | 0 | 0 | ++ |
| | BS3-M | $4.1 \times 10^8$ | ~80 | +++ | ++ | +++ | + | ++ | +++ |
| | GB6-M | $3.9 \times 10^8$ | ~50 | +++ | ++ | +++ | ++ | ++ | +++ |
| MS2820 | TSB | $1.1 \times 10^6$ | <5 | + | 0 | + | 0 | 0 | 0 |
| | BS3-M | $9.0 \times 10^7$ | ~70 | ++ | +++ | +++ | ++ | + | +++ |
| | GB6-M | $8.9 \times 10^7$ | ~50 | ++ | + | +++ | 0 | + | +++ |

[1]in-vitro relative score, based on the size of pathogen-free zones with 0 being no clearing and +++ being clear zones of greater than 1 cm between the pathogen and the isolate or comparable to test strain with known high bioactivity.

The disclosure also provides a method of seed treatment by using the identified *Paenibacillus* and/or *Bacillus* species, which provides broad-spectrum control of various soil-borne or foliar plant pathogens, including fungal and oomycete pathogens. In one embodiment, the pathogen comprises fungi, oomycetes, bacteria, viruses, viroids, virus-like organisms, phytoplasmas, protozoa, nematodes, and parasitic plants. The methods of treating the seeds include, but are not limited to, treating the seeds directly as a seed treatment with the agricultural composition, treating the seeds before or after planting, or treating the seeds in-furrow or in the vicinity of the seed via spray, drench, banded, or broadcast applications. The plant diseases targeted by the methods of this disclosure comprise a fungal disease, a bacterial disease, a viral disease, parasitic disease, or any combination thereof.

In one embodiment, the plant disease is a fungal disease, which includes white blister, downy mildews, powdery mildews, clubroot, *Sclerotinia* rot, *Fusarium* wilts and rots, *Botrytis* rots, anthracnose, *Rhizoctonia* rots, damping-off, cavity spot, tuber diseases, rusts, black root rot, target spot, *Aphanomyces* root rot, *Ascochyta* collar rot, gummy stem blight, *Alternaria* leaf spot, black leg, ring spot, late blight, *cercospora*, leaf blight, *Septoria* spot, leaf blight, or combination thereof. The fungal diseases can be caused by a variety of fungal species. In one embodiment, the methods can treat the fungal disease, which is caused by one or more of fungal species, which comprise *Macrophomina phaseolina, Fusarium virguliforme, Rhizoctonia solani, Botrytis cinerea, Pythium ultimum, Pythium irregulare, Albugo candida, Plasmodiophora brassicae, S. sclerotiorum, S. minor, Sclerotium rolfsii, S. cepivorum, Fusarium solani, F. oxysporum, Colletotrichum* spp., *Microdochium panattonianum, Pythium sulcatum, Uromyces appendiculatus, Puccinia sorghi, Puccinia allii Alternaria solani, Aphanomyces euteiches* pv. *Phaseoli, Didymella bryoniae, Alternaria cucumerina, A. alternate, Leptosphaeria maculans, Mycosphaerella brassicicola, Septoria apiicola, Cercospora beticola, Septoria petroelini, Septoria lactucae, Septoria lactucae, Alternaria dauci*, or combination thereof.

In another embodiment, the fungal disease is caused by one or more of *Macrophomina phaseolina, Fusarium virguliforme, Rhizoctonia solani, Botrytis cinerea, Pythium ultimum*, and *Pythium irregulare*.

The identified isolates of *Paenibacillus* and/or *Bacillus* demonstrate a broad spectrum of activities against pathogens, including but not limited to soil-borne or foliar plant pathogens *Macrophomina phaseolina, Fusarium virguliforme, Botrytis cinerea, Phytophthora* spp., *Pythium* spp., and *Rhizoctonia solani*. In one aspect of the disclosure, with the optimized fermentation medium and process, the isolates of *Paenibacillus* and/or *Bacillus* have shown increased efficacy against pathogens, both in vitro and in vivo, and increased yield of bacterial resting spores.

Methods of Suppressing or Controlling Pathogens and Disease

The disclosure features a method of controlling or suppressing plant diseases which includes applying an agricultural composition comprising, or alternatively consisting essentially of, or yet further consisting of a bacterial isolate belonging to *Bacillus* or *Paenibacillus* to a subject infected with the pathogen. In one aspect, the bacterial isolate belongs to *Bacillus amyloliquefaciens, Paenibacillus polymyxa*, or *Paenibacillus* spp. In another aspect, the agricultural composition comprises, or alternatively consists essentially of, or yet further consists of MS1479, MS2379, MS2414, MS2820, MS0633, MS2335, MS2652, MS2658, MS2681, MS2697, or MS2712. In one embodiment, the agricultural composition is applied to a plant and/or a seed of the plant to prevent or control the pathogens. It is contemplated that when the agricultural composition is applied to the plant, it can be applied including, but not limited to, in-furrow, in the vicinity of roots of the plant, to the plant part(s) (roots, branches, and stems), to the leaves of the plant, a plant seed, an immature seedling, a tissue in the plant, and/or to the area in proximity to the plant. In a further embodiment, the agricultural composition is applied to a reproductive tissue, including, but not limited to, buds, flowers, and developing structures that contain seeds such as fruit and seed pods. In another embodiment, the agricultural composition is administered by seed coating, spraying in the planting furrow with seeds, or foliar spray.

In one embodiment, the agricultural composition is admixed with a soil, and the mixture of soil and composition mixture is applied to the soil, to the plant foliage, and/or to the plant seeds, before or after germination. In one embodiment, the agricultural composition is applied to the soil or the plant within 1, 2, 3, 4, 5, 6, 7, 8, 9, or 10 days after germination. In one embodiment, the agricultural composition is applied to the soil or the plant more than 10 days after germination.

The agricultural composition can be applied within 2 weeks of plant emergence. The agricultural composition may be applied within 10 days of sowing the plant seeds, optionally within 3, 5, or 7 days of sowing the seeds. In another embodiment, the agricultural composition can be applied by foliar feeding, once or on multiple occasions. In foliar feeding, the agricultural composition can be applied during the growing seasons or during reproduction.

The agricultural composition typically is applied in an amount effective to control or suppress fungal growth, e.g., an amount sufficient to control or suppress observable symptoms of a fungal disease on a plant. The rate of application may vary according to the plant species to be protected, the efficacy of the bacterial strain against the pathogen to be controlled, and the severity of the disease pressure. Typically, when the agricultural composition is applied to the plant, the concentration of the bacterial isolate is at least about $1.3\times10^3$ cfu/cm$^2$ to about $1.3\times10^5$ cfu/cm$^2$, $1.3\times10^5$ cfu/cm$^2$ to about $1.3\times10^{10}$ cfu/cm$^2$, about $1.3\times10^6$ cfu/cm$^2$ to about $1.3\times10^9$ cfu/cm$^2$, or about $1.3\times10^7$ cfu/cm$^2$ to about $1.3\times10^8$ cfu/cm$^2$. In some embodiments, the concentration of the bacterial isolate is from $1\times10^5$ cfu/ml to $1\times10^{10}$ cfu/ml, from $1\times10^6$ cfu/ml to $5\times10^9$ cfu/ml, from $1\times10^7$ cfu/ml to $1\times10^9$ cfu/ml, or from $5\times10^7$ cfu/ml to $5\times10^8$ cfu/ml.

Based on the nature of the agricultural composition, a method of application such as spraying, atomizing, dusting, scattering, or pouring is chosen in accordance with the intended objectives and the prevailing circumstances.

Agricultural compositions, whole broth, supernatants, or sterile filtrates within this disclosure may be formulated with components that act as carriers or seed treatment formulations that aid dispersion, provide nutrient additives, and/or improve adhesion. For example, agricultural compositions can be formulated as wettable powders, granules, and the like, or can be microencapsulated in a suitable medium and the like. Examples of other formulations include, but are not limited to, liquid, oil dispersion, spreadable granule, dusts, soluble powders, wettable granules, dry flowables, aqueous flowables, wettable dispersible granules, suspension concentrate, emulsifiable concentrates, and aqueous suspensions. Other suitable formulations include those suitable for foliar application.

In another aspect, the disclosure provides a method to extend or prolong the shelf-life of agricultural compositions. As result of the method, the bacterial isolates in the agricultural composition maintain a high cfu/ml even after a storage period. Factors such as pH values, temperatures, and other agents may affect the stability or shelf-life of the agricultural composition. In some embodiments, the method of extending or prolonging the shelf-life of agricultural composition further comprises adding an agent to the agricultural composition, wherein the agent comprises a preservative, a mineral, a thickening agent, a stabilizing agent, a bioprotector, an adjuvant, or combination thereof. Thus, the formulation of the agricultural composition comprises an agent, wherein the agent comprises a preservative, a mineral, a thickening agent, a stabilizing agent, a bioprotector, an adjuvant, or combination thereof. Non-limiting examples of preservatives include methylparaben, potassium sorbate, BIT (1,2-Benzisothiazolin-3-one), and Proxel GXL (Arch). The Proxel GXL, in one embodiment, contains 18-20% BIT (1,2-Benzisothiazolin-3-on 3). Non-limiting examples of thickening agents include xanthan gum, gum arabic, and alginate. Non-limiting examples of minerals include magnesium aluminum silicate (clay), Kaolin, Acti-gel 208, and Minuge 400. The bioprotector, in some embodiments, refers to an adjuvant used for biological seed treatment. Non-limiting adjuvant include LI-700 (a proprietary mixture containing 350 g/L Soy phospholipids and 350 g/L Propionic acid), Attach (a proprietary mixture containing 100% pine (terpene) polymers, petrolatum, and a-(p-Dodecylphenyl)-Omega-hydroxypoly (oxyethylene)), and Liberate (an emusifiable concentrate of containing 100% Lecithin, methyl esters of fatty acids, and alcohol ethoxylate). Other suitable preservatives, minerals, thickening agents, stabilizing agents, bioprotectors, or adjuvants are also within the scope of this disclosure and are known to those skilled in the art.

The mass ratio of the agent in the agricultural composition, in one embodiment, range from about 0.0001% to about 50%. In one embodiment, the agricultural composition comprises about 0.001% to about 1%, about 0.002% to about 0.5%, about 0.002% to about 0.1%, or about 0.002% to about 0.005% preservative. In another embodiment, the agricultural composition comprises about 0.002% to about 0.005% preservative. In another embodiment, the agricultural composition comprises about 0.003% preservative. In one embodiment, the preservative is BIT.

In one embodiment, the agricultural composition comprises about 0.01% to about 10%, about 0.02% to about 5%, about 0.02% to about 1%, or about 0.2% to about 0.5% propyl gallate. In one embodiment, the agricultural composition comprises about 0.3% propyl gallate.

In one embodiment, the agricultural composition comprises about 0.01% to about 10%, about 0.02% to about 5%, about 0.2% to about 1%, or about 0.3% to about 0.7% propylene glycol. In one embodiment, the agricultural composition comprises about 0.5% propylene glycol.

In one embodiment, the agricultural composition comprises about 0.01% to about 10%, about 0.02% to about 5%, about 0.02% to about 1%, or about 0.2% to about 0.5% mineral. In one embodiment, the agricultural composition comprises about 0.2% mineral. In one embodiment, the mineral is Acti-gel 208.

In one embodiment, the agricultural composition comprises about 0.01% to about 10%, about 0.02% to about 5%, about 0.02% to about 1%, or about 0.2% to about 0.5% Minuge 400. In one embodiment, the agricultural composition comprises about 0.2% minuge 400.

In one embodiment, the agricultural composition comprises about 1% to about 40%, about 5% to about 30%, or about 10% to about 25% adjuvant. In one embodiment, the agricultural composition comprises about 20% adjuvant. In another embodiment, the adjuvant is Bioprotector (from Lallemand).

The advantageous increase in spore viability and stability of agricultural composition after storage are particularly apparent when the pH of the composition is adjusted to a certain range. Thus, the method of extending or prolonging the shelf-life of agricultural composition further comprises adjusting the pH of the agricultural composition. In one embodiment, the adjusted pH ranges from 3.5 to 7.5, from 4.0 to 7.0, from 4.5 to 6.5, from 5.0 to 6.5, or from 6.0 to 6.5. In another embodiment, the adjusted pH ranges from 5.0 to 6.5.

The precise method of formulating the agricultural composition suitable for use in the present disclosure is not critical, and one of ordinary skill in the art of formulating the agricultural composition can appreciate that different organisms have different formulation constraints. Moreover, the storage and use conditions can vary with the particular application. In general, agricultural composition can be prepared through liquid or solid fermentation and can be combined through blending, spraying, mixing, and/or extruding with one or more inert solid carriers that can include, but are not limited to, clay, bran, lactose, cellulose, vermiculite, or sawdust. In some instances, it may be preferable not to dry the biomass and carrier product, but rather to package and store the moist product.

It is contemplated that the agricultural composition may further comprise an agriculturally acceptable carrier or a seed treatment formulation such as a polymer. Adhering the agricultural composition to a carrier or to a seed by a seed treatment formulation polymer, in some embodiments, may increase the efficacy of the agricultural composition against plant diseases. The polymers may also have an effect on the bioavailability of the agricultural composition and thus provide a slow-release effect. This effect may be desirable if it results in a prolonged efficacy of the agricultural composition. Also, slow-release coatings may improve germination of seeds by reducing the release of the agricultural composition in the early stages of plant development. Moreover, the slow-release coatings may also maintain or enhance the cfu of the bacterial isolates in the agricultural composition. Slow-release effects may be modulated by combining film-forming polymers with inert carriers such as clay. These effects may be further fine-tuned by applying a multi-layered coating as disclosed in WO 2004/049778, which is incorporated hereby in its entirety.

It is contemplated that the method of this disclosure can be used for controlling, preventing, and/or treating the diseases, including, but not limited to, rice blast (*Magnaporthe grisea*), spot leaf blight (*Cochliobolus miyabeanus*), sheath blight (*Rhizoctonia solani*), silly seedling (*Gibberella fujikuroi*), powdery mildew (*Erysiphe graminis*), red mold (*Fusarium graminearum, F. avenaceum, F. culmorum, Microdochium nivale*), rust (*Puccinia striiformis, P. graminis, P. recondite, P. hordei*), snow mold (*Typhula* sp., *Micronectriella nivalis*), loose smut (*Ustilago tritici, U. nude*), bunt (*Tilletia caries*), eyespot (*Pseudocercosporella herpotrichoides*), scald disease (*Rhynchosporium secalis*), leaf blight (*Septoria tritici*), spot blight (*Leptosphaeria nodorum*), black leg (*Leptosphaeria maculans*), net blotch (*Pyrenophora teres* Drechsler), black spot disease (*Diaporthe citri*), scab (*Elsinoe fawcetti*), fruit rot (*Penicillium digitatum, P. italicum*), blossom blight (*Monilinia mali*), decomposed disease (*Valsa ceratosperma*), grapevine powdery mildew (*Erysiphe necator*), powdery mildew (*Podosphaera leucotricha*), *Alternaria* blotch (*Alternaria alternate* apple pathotype), scab (*Venturia inaequalis*), anthrax (*Colletotrichum acutatum*), crown rot (*Phytophthora cactorum*), scab (*Venturia nashicola, V. pirina*), purple blotch (*Alternaria alternate* Japanese pear pathotype), frogeye (*Gymnosporangium haraeanum*), fruit rot (*Phytophthora cactorum*), brown rot (*Monilinia fructicola*), black spot disease (*Cladosporium carpophilum*), *Phomopsis* rot (*Phomopsis* sp.), eastern black disease (*Elsinoe ampelina*), nights grapes rot (*Glomerella cingulata*), powdery mildew (*Uncinula necator*), rust (*Phakopsora ampelopsidis*), black rot (*Guignardia bidwellii*), downy mildew (*Plasmopara viticola*), anthracnose (*Gloeosporium kaki*), brown stem rot (*Cercospora kaki, Mycosphaerella nawae*), anthracnose (*Colletotrichum lagenarium*), powdery mildew (*Sphaerotheca fuliginea*), vine blight (*Mycosphaerella melonis*), yellow vine disease (*Fusarium oxysporum*), mildew (*Pseudoperonospora cubensis*), *Phytophthora* rot (*Phytophthora* sp.), seedling damping-off (*Pythium* sp.), ring spot disease (*Alternaria solani*), leaf mold (*Cladosporium fulvum*), late blight (*Phytophthora infestans*), brown spot disease (*Phomopsis vexans*), powdery mildew (*Erysiphe cichoracearum*), black spot disease (*Alternaria japonica*), vitiligo (*Cercosporella brassicae*), clubroot (*Plasmodiophora brassicae*), mildew (*Peronospora parasitica*), leek rust (*Puccinia allii*), soybean purpura (*Cercospora kikuchii*), eastern black disease (*Elsinoe glycines*), black spot disease (*Diaporthe phaseolorum* var. *sojae*), rust (*Phakopsora pachyrhizi*), plaque stalks (*Phytophthora sojae*), bean anthracnose (*Colletotrichum lindemuthianum*), peanut black mildew (*Cercospora personata*), brown spot disease (*Cercospora arachidicola*), blight (*Sclerotium rolfsii*), powdery mildew (*Erysiphe pisi*), early blight (*Alternaria solani*), late blight (*Phytophthora infestans*), powder scab (*Spongospora subterranea* f. sp. *subterranea*), powdery mildew (*Sphaerotheca humuli*), net rice disease (*Exobasidium reticulatum*), disease victory (*Elsinoe leucospila*), ring leaf spot (*Pestalotiopsis* sp.), anthracnose (*Colletotrichum theae-sinensis*), frogeye (*Alternaria longipes*), powdery mildew (*Erysiphe cichoracearum*), anthracnose (*Colletotrichum tabacum*), mildew (*Peronospora tabacina*), black shank (*Phytophthora nicotianae*), brown spot (*Cercospora beticola*), leaf rot (*Thanatephorus cucumeris*), root rot (*Thanatephorus cucumeris*), black root rot (*Aphanidermatum cochlioides*), black spot (*Diplocarpon rosae*), powdery mildew (*Sphaerotheca pannosa*), brown spot (*Septoria chrysanthemi-indici*), white rust (*Puccinia horiana*), diseases caused by the genus *Pythium* of various crops, including, but not limited to *Pythium aphanidermatum, Pythium debaryanum, Pythium graminicola, Pythium irregulare, Pythium ultimum*, gray mold (*Botrytis cinerea*), white mold, *Sclerotinia* rot, stem, rot, crown rot (*Sclerotinia sclerotiorum, Sclerotinia minor*), black spot disease (*Alternaria brassicicola*), dollar spot disease (*Sclerotinia homoeocarpa*), brown patch disease and large patch disease (*Rhizoctonia solani*), charcoal rot (*Macrophomina phaseolina*), SDS (*Fusarium virguliforme*), and Sigatoka disease (*Mycosphaerella fijiensis, Mycosphaerella musicola, Pseudocercospora musae*).

In one aspect, the plant diseases caused by oomycetes that can be controlled, prevented, or treated by the method of this disclosure are caused by the aforementioned organisms, particularly diseases caused by the genus *Pythium*, including, but not limited to, *Pythium aphanidermatum, Pythium debaryanum, Pythium graminicola, Pythium irregulare*, and *Pythium ultimum*; the genus *Phytophthora*, including, but not limited to, *Phytophthora infestans, Phytophthora sojae*, and *Phytophthora capsici*; the Peronosporaceae family (the downy mildew family), including, but not limited to, the genus *Peronospora*, including, but not limited to, *Peronospora parasitica* (renamed *Hyaloperonospora brassicae*) and *Peronospora farinosa*; the *Pseudoperonospora* genus, including, but not limited to, *Pseudoperonospora cubensis* and *Pseduoperonospora cannabina*; and the *Hyaloperonospora* genus, including, but limited to, *Hyaloperonospora brassicae.*

It is also contemplated that the plant diseases that can be controlled, prevented, or treated by the method of this disclosure are caused by the aforementioned bacteria and the following bacteria: *Xanthomonas campestris* pv. *Citri, Ralstonia solanacearum, Xanthomonas campestris* pv. vitians, *Erwinia carotovora* subsp. *Carotovora, Xanthomonas campestris* pv. *Campestris, Pseudomonas syringae* pv. *lachrymans, Pseudomonas fuscovaginae, Agrobacterium tumefaciens, A. rhizogenes, A. radiobacter, Pectobacterium carotovorum, Erwinia amylovora, Pseudomonas savastanoi, Xanthomonas oryzae* pv. *Oryzae, X. axonopodis* pv. *Manihotis, Candidatus Liberibacter asiaticus, Pantoea* spp., *Burkholderia* spp., *Acidovorax* spp., *Clavibacter* spp., *Streptomyces* spp., *Xylella* spp., *Spiroplasma citri, S. phoeniceum, S. kunkelii*, and *Phytoplasma* spp.

It is further contemplated that the plant diseases that can be controlled, prevented, or treated by the method of this disclosure are caused by viruses, including, but not limited to, cucumber mosaics (cucumber mosaic cucumovirus, watermelon mosaic potyvirus 2, zucchini yellow mosaic potyvirus), tomato viral diseases (tobacco necrosis necrovirus), strawberry viral diseases (strawberry crinkle cytorhabdovirus, strawberry latent C virus, soybean dwarf luteovirus, strawberry mottle virus, strawberry pseudo mild-yellow edge carlavirus, strawberry vein banding caulimovirus, tobacco mosaics tobamovirus, tobacco necrosis necrovirus), cabbage mosaic (cauliflower mosaic caulimovirus, cucumber mosaic cucumovirus, turnip mosaic potyvirus), soybean viral diseases (southern bean mosaic sobemovirus, peanut stunt cucumovirus, bean common mosaic potyvirus, broad bean wilt fabavirus), tomato spotted wilt tospovirus (TSWV), tomato leaf curl begomovirus (TYLCV), potato virus Y (PVY), cauliflower mosaic virus (CaMV), African cassava mosaic begomovirus (ACMV), plum pox potyvirus (PPV), brome mosaic virus (BMV), potato virus X (PVX), citrus tristeza virus, barley yellow dwarf virus (BYDV), potato leafroll virus and tomato bushy stunt virus, Soybean vein necrosis tospavirus (SVNV), Bean pod mosaic virus (BPMV), Turnip mosaic virus (TuMV), and potato leaf-roll (potato leafroll luteovirus).

It is further contemplated that the plant diseases that can be controlled, prevented, or treated by the method of this disclosure are caused by parasitic nematodes, including, but not limited to, root-knot nematodes (*Meloidogyne* spp.), cyst nematodes (*Heterodera* and *Globodera* spp.), root lesion nematodes (*Pratylenchus* spp.), the burrowing nematode (*Radopholus similis, Ditylenchus dipsaci*), the pine wilt nematode (*Bursaphelenchus xylophilus*), the reniform nematode (*Rotylenchulus reniformis, Xiphinema*), *Nacobbus aberrans*, and *Aphelenchoides besseyi.*

The method further comprises a fermentation process of a culture comprising the bacterial isolate, wherein the fermentation process comprises: (1) inoculating the bacterial isolate in a seed medium and (2) expanding the culture with a production medium. In one embodiment, the seed medium comprises LB, TSB, BS3, BS3-M2, BS3-M9, BS3-M10, GB6-M, GB6-M3, GB6-M7, GB6-M8, GB6-M9, GB6-M22, GB6-M23, GB6-M10, GB6-M31, GB6-M33, GB6-M34, or combination thereof. In another embodiment, the production medium comprises GB6-M10, GB6-M22 or GB6-M23, GB6-M31, GB6-M33, GB6-M34 and/or combination thereof.

The agricultural composition or the bacterial whole broth can be concentrated before application, e.g., seed treatment or foliar application. Methods of concentrating or enriching the whole broth include but are not limited to suspension, centrifuge, filtration, ultrafiltration, separation, or any mechanical or chemical methods known in the art. In one embodiment, the retenant and/or permeate after filtration or ultrafiltration is used to application in the present disclosure.

Methods of Seed Treatment

When used for treating plant seeds, the bacterial isolates can maintain their biological activities, even after long-term storage. In this regard, the disclosure also provides a method of enhancing the disease resistance of a plant, comprising applying an effective amount of an agricultural composition to a seed of the plant, said composition comprising, or alternatively consisting essentially of, or yet further consisting of applying to a bacterial isolate belonging to *Bacillus* or *Paenibacillus*. In one aspect, the bacterial isolate belongs to *Bacillus amyloliquefaciens, Paenibacillus* spp., or *Paenibacillus polymyxa*. In another aspect, the bacterial strain comprises, or alternatively consists essentially of, or yet further consists of MS1479, MS2379, MS2414, MS2820, MS0633, MS2335, MS2652, MS2658, MS2681, MS2697, MS2712, or the combination thereof. In a further embodiment, the agricultural composition comprises, or alternatively consists essentially of, or yet further consists of LB, TSB, BS3, BS3-M2, BS3-M9, BS3-M10, GB6-M, GB6-M3, GB6-M7, GB6-M8, GB6-M9, GB6-M22, GB6-M23, GB6-M10, GB6-M31, GB6-M33, GB6-M34, or the combination thereof.

The seeds, after treatment, may be dried or stored at a proper condition before seeding. The methods to dry the seed after treatment are well known in the art. For example, seeds can be dried by passing air over them. In one aspect, the seeds are stored at room temperature.

The rate of the seed treatment is based on the colony formation unit ("cfu") of the bacteria within the agricultural composition. The optimum cfu per seed needs to be determined by studying its efficacy from in planta assay. In one aspect, the bacteria range from $1\times10^3$ to $1\times10^9$ cfu/seed when applied to the seed. In another aspect, the bacteria range from $1\times10^4$ to $1\times10^8$ cfu/seed when applied to the seeds. In a further aspect, the bacteria range from $1\times10^5$ to $1\times10^7$ cfu/seed when applied to the seeds. In another aspect, the bacteria range from $1\times10^5$ to $1\times10^6$ cfu/seed when applied to the seeds.

In one aspect, the seeds are treated by incubation with wet broth containing the agricultural composition. The ratio of wet broth to the seeds ranges between 10 ml/seed and 0.0001 ml/seed, 1 ml/seed and 0.001 ml/seed, and/or 0.1 ml/seed and 0.01 ml/seed. The incubation time depends on the types of wet broth, the types of pathogens, and the seeds. It is well known for one of ordinary skill in the art to adjust the incubation time and temperature to optimize the results.

The actual cfu/seed of coated seeds can be assessed by any methods that are well known in the art, e.g., the cfu recovery. In a cfu recovery, 1 mL of phosphate buffer (pH 7.2) is added to one seed in a centrifuge tube. The seed is soaked and then sonicated for five minutes. After vortex, the phosphate buffer turns a slightly different color, which indicates the release of cfu from the surface of the seed. The buffer suspension is then tested for cfu.

In one embodiment, the agricultural composition, whether for seed treatment, foliar application, in-furrow application, or other agricultural applications, may be used in combination with one or more fungicides, biocontrol agents, nematicides, bactericides, herbicidal safeners, herbicides, insecticides, biostimulants, plant growth regulators, liquid fertilizers, and/or viral inhibitors. Suitable fungicides include, but are not limited to, captan, thiram, metalaxyl, fusaricidin, fludioxonil, natamycin, oxadixyl, and isomers of each of those materials, and the like. Suitable herbicides include, but are not limited to, carbamates, thiocarbamates, acetamides, triazines, dinitroanilines, glycerol ethers, pyridazinones, uracils, phenoxys, ureas, and benzoic acids. Suitable herbicidal safeners include, but are not limited to, benzoxazine, benzhydryl derivatives, N, N-diallyl dichloroacetamide, various dihaloacyl, oxazolidinyl and thiazolidinyl compounds, ethanone, naphthalic anhydride compounds, and oxime derivatives. Suitable biocontrol agents include, but are not limited to, naturally-occurring or recombinant bacteria and fungi from the genera *Rhizobium, Bacillus, Pseudomonas, Serratia, Trichoderma, Glomus, Gliocladium*, and mycorrhizal fungi. Suitable bactericides include, but are not limited to, 8-hydroxyquinoline sulfate, bronopol, copper hydroxide, cresol, dichlorophen, dipyrithione, dodicin, fenaminosulf, formaldehyde, hexachlorophene, kasugamycin, nitrapyrin, octhilinone, oxytetracycline, probenazole, streptomycin, tecloftalam, and thiomersal. These ingredients may be added as a separate layer on the seed or alternatively may be added as part of the agricultural composition.

In one embodiment, the agricultural composition is used in conjunction with a commercial agent for plants. The commercial agent includes, but is not limited to, an active agent from Awaken® ST (a nutritional seed treatment containing a complex of zinc ammonium acetate with potash, and the plant micronutrients zinc, boron, copper, iron, manganese, and molybdenum), Satori® (a fungicide containing the active ingredient azoxystrobin), Pristine® (a fungicide containing the active ingredients pyraclostrobin and boscalid), Dyna-Shield® Fludioxonil (a fungicide containing the active ingredient fludioxonil), Dyna-Shield® Metalaxyl (a fungicide containing the active ingredient metalaxyl), Serenade® ASO (a biocontrol product containing the active ingredient *Bacillus subtilis* QST-713 strain), Double Nickel™ 55 (a biofungicide containing the active ingredient *Bacillus amyloliquefaciens* D747 strain), LifeGard™ WG (a biological plant activator containing the active ingredient *Bacillus mycoides* isolate J), Subtilex® NG (a biofungicide containing the active ingredient *Bacillus subtilis* MBI-600 strain), Xanthion® (a fungicide containing the active ingredients *Bacillus subtilis* MBI-600 strain (component A) and pyraclostrobin (component B)). In some embodiments, the agricultural formulation is used in conjunction with one or more active ingredients of the commercial agents, which include but are not limited to zinc ammonium acetate, azoxystrobin, pyraclostrobin, boscalid, metalaxyl, *Bacillus subtilis* QST-713 strain, *Bacillus amyloliquefaciens* D747 strain, *Bacillus mycoides* isolate, *Bacillus subtilis* MBI-600, or pyraclostrobin.

The agricultural composition comprises a bio-control formula that is capable of controlling, preventing, and/or treating plant diseases or pathogens. The bio-control formulas, in some embodiments, comprise an insecticide, a nematicide, an acaricide, a fungicide, a bactericide, an herbicide, a plant growth regulator, a spreader, a fertilizer, a microbial material, or a soil amendment. In one embodiment, the formulas are biologically based and thus comprise a microbe. The biologically based formulas include but are not limited to commercially available bio-control formulas (e.g., Serenade®, Saton®, Double Nickel®, LifeGard®, Xanthion® A, and Subtilex®). The agricultural composition that comprises the bio-control formula with or without the bacterial isolates can also be used in a method of treating plant disease or enhancing disease resistance of a plant.

The method further comprises a fermentation process of a culture comprising the bacterial isolate, wherein the fermentation process comprises: (1) inoculating the bacterial isolate in a seed medium and (2) expanding the culture with a production medium. In one embodiment, the seed medium comprises BS3, BS3-M2, GB6-M3, GB6-M7, GB6-M8, GB6-M9, GB6-M22, GB6-M23, GB6-M10, GB6-M31, GB6-M33, and/or GB6-M34. In another embodiment, the production medium comprises GB6-M10, GB6-M31, GB6-M33, GB6-M34, GB6-M22, or GB6-M23.

In another aspect, the disclosure provides a plant seed coated with an agricultural composition, wherein the composition comprises a bacterial isolate of *Paenibacillus* or *Bacillus*, or a mutant thereof. In one embodiment, the bacterial isolate is within a biological culture. In one embodiment, the mutant has the key characteristics of wild type bacterial isolates. In one embodiment, the bacterial isolate comprises MS1479, MS2379, MS2414, MS2820, MS0633, MS2335, MS2652, MS2658, MS2681, MS2697, or MS2712. In another embodiment, the bacterial isolate comprises MS2379 or MS2414.

In one embodiment, the agricultural composition comprises, or alternatively consists essentially of, or yet further consists of the bacteria in an amount ranging from $1\times10^3$ to $1\times10^9$ colony-forming units (cfu)/seed. In another embodiment, the agricultural composition comprises, or alternatively consists essentially of, or yet further consists of the bacteria ranging from $1\times10^4$ to $1\times10^8$ cfu/seed. In a further embodiment, the agricultural composition comprises, or alternatively consists essentially of, or yet further consists of the bacteria ranging from $1\times10^5$ to $1\times10^7$ cfu/seed. In another embodiment, the agricultural composition comprises, or alternatively consists essentially of, or yet further consists of the bacteria ranging from $1\times10^5$ to $1\times10^6$ cfu/seed. In one aspect, the cfu/seed is assessed by cfu recovery. In another aspect, the seed is coated with a polymer. It is also contemplated that the agricultural composition is adhered to a carrier.

In another embodiment, the agricultural composition comprises fungicides, biocontrol agents, nematicides, bactericides, herbicidal safeners, herbicide, insecticide, biostimulants, plant growth regulators, liquid fertilizers, or viral inhibitors.

Agricultural Composition for Controlling Plant Pathogens

In another aspect, the disclosure provides an agricultural composition comprising a bacterial isolate of *Paenibacillus* or *Bacillus*, or a mutant thereof. In one embodiment, the bacterial isolate is within a biological culture. In one embodiment, the mutant has the key characteristics of wild type bacterial isolates. In one embodiment, the bacterial isolate comprises MS1479, MS2379, MS2414, MS2820, MS0633, MS2335, MS2652, MS2658, MS2681, MS2697, or MS2712. In another embodiment, the bacterial isolate comprises MS2379 or MS2414.

The bacterial isolates of this disclosure may be cultured or expanded in different culture media, like traditional media (e.g., LB or TSB). But as noted above, when the bacterial isolates are cultured in special culture media of this disclosure, the cultures containing the bacterial isolates gain anti-pathogen activity against *Pythium* spp., a function that is not observed from the same bacterial isolates cultured from traditional broths (e.g., TSB). As such, the bacterial cultures in the special media are providing new attributes that are not expected from its natural counterparts or counterparts cultured in traditional broths. Moreover, the special media are designed and man-made and do not exist in nature. Thus, the agricultural composition, which comprises a bacterial isolate of *Paenibacillus* or *Bacillus*, or a mutant thereof cultured in the special broths, can carry out functions significantly different from its natural counterpart. In another embodiment, the agricultural composition further comprises one or more of a wetting agent, a binding agent, a filler, and an organic additive.

In some embodiments, the agricultural composition may further comprise an agriculturally acceptable carrier. Agriculturally acceptable carriers include adjuvants, mixers, enhancers, etc., beneficial for application of the chemical formula. The agriculturally acceptable carrier can be a solid or liquid carrier. Non-limiting examples of liquid carriers include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methanol, ethanol, isopropanol, amyl alcohol, ethylene glycol, propylene glycol, glycerine, and the like. Non-limiting examples of solid carriers include talc, pyrophyllite clay, silica, attapulgus clay, kieselguhr, chalk, diatomaceous earth, lime, calcium carbonate, bentonire clay, Fuller's earth, cotton seed hulls, wheat flour, soybean flour, pumice, wood flour, walnut shell flour, lignin, and the like. When an adjuvant is used in a carrier, non-limiting examples of adjuvant include antifoam agents, compatibilizing agents, sequestering agents, neutralizing agents and buffers, corrosion inhibitors, dyes, odorants, penetrations aids, spreading agents, sticking agents, dispersing agents, thickening agents, freeze point depressants, antimicrobial agents, and the like.

The agricultural composition may also comprise a surface-active agent in either solid or liquid composition. The surface-active agent can be anionic, cationic, or nonionic, which includes but is not limited to salts of alkyl sulfates (e.g., diethanolammonium lauryl sulfate), alkylarylsulfonate salts (e.g., calcium dodecylbenzenesulfonate), alkylphenol-alkylene oxide addition products, alcohol-alkylene oxide addition products, soaps, alkylnaphthalenesulfonate salts, dialkyl esters of sulfosuccinate salts, sorbitol esters, quaternary amines, polyethylene glycol esters of fatty acids, block copolymers of ethylene oxide and propylene oxide, and salts of mono and dialkyl phosphate esters.

In one embodiment, the bacterial isolate is cultured in a medium comprising LB, TSB, BS3, BS3-M2, BS3-M9, BS3-M10, GB6-M, GB6-M3, GB6-M7, GB6-M8, GB6-M9, GB6-M22, GB6-M23, GB6-M31, GB6-M33, GB6-M34, or GB6-M10. The bacterial isolates can also be cultured in a special medium of this disclosure, which comprises BS3-M2, BS3-M9, BS3-M10, GB6-M, GB6-M3, GB6-M7, GB6-M8, GB6-M9, GB6-M10, GB6-M22, GB6-M23, GB6-M31, GB6-M33, GB6-M34 or the combination thereof. In some embodiments, the bacterial isolate is cultured in a medium comprising GB6-M10. In one embodiment, the agricultural composition comprises the culture media for the bacterial isolates, including but not limited to LB, TSB, BS3, BS3-M2, BS3-M9, BS3-M10, GB6-M, GB6-M3, GB6-M7, GB6-M8, GB6-M9, GB6-M22, GB6-M23, GB6-M31, GB6-M33, GB6-M34, and GB6-M10.

In some embodiments, the agricultural composition further comprises a bio-control formula, which comprises an insecticide, a nematicide, an acaricide, a fungicide, a bactericide, an herbicide, a plant growth regulator, a spreader, a fertilizer, a microbial material, or a soil amendment. In one embodiment, the formulas are biologically based and thus comprise a microbe. The biologically based formulas include, but are not limited to, commercially available bio-control formulas (e.g., Serenade®, Satori®, Double Nickel®, LifeGard®, Xanthion® A, and Subtilex®). In the agricultural composition, the colony forming unit (cfu) ratio of the bacterial isolate to the microbes in the bio-control formulation is in a range of from 1,000:1 to 1:1,000, 100:1 to 1:100, 50:1 to 1:50, or 10:1 to 1:10. In one embodiment, the cfu ratio is in a range of from 100:1 to 1:1. In another embodiment, the cfu ratio is in a range of from 50:1 to 10:1. In the agricultural composition, the cfu ratio of the bacterial isolate to the microbes in Satori® is in a range of from 1,000:1 to 1:1,000, 100:1 to 1:100, 50:1 to 1:50, or 10:1 to 1:10.

In one embodiment, the concentration of the bacterial isolate is at least $1.3\times10^5$ cfu/ml, $1.3\times10^6$ cfu/ml, $1.3\times10^7$ cfu/ml, $1.3\times10^8$ cfu/ml, $1.3\times10^9$ cfu/ml, or $1.3\times10^{10}$ cfu/ml. In another embodiment, the concentration of the bacterial isolate is from $1\times10^5$ cfu/ml to $1\times10^{10}$ cfu/ml, from $1\times10^6$ cfu/ml to $5\times10^9$ cfu/ml, from $1\times10^7$ cfu/ml to $1\times10^9$ cfu/ml, or from $5\times10^7$ cfu/ml to $5\times10^8$ cfu/ml.

WORKING EXAMPLES

Example 1 In-Vitro Inhibition of *Rhizoctonia* and *Pythium*

Four isolates MS1479, MS2379, MS2414, and MS2820 were tested against fungal pathogens in four production media—TSB medium (30 g/L Tryptic Soybean Broth (TSB, Sigma-Aldrich 78907)), BS3 medium, BS3-M2, and GB6-M3.

In the experiment, 16 one-litter baffled flasks, each containing 250 ml production medium, were inoculated with 2% (5 ml) seed inoculum from the LB medium and cultivated under 28° C., 200 rpm for 72 hours. The results are shown in Table 3. GB6-M3 led to high cfu (~1E+09) and sporulation (90-100%) for all four isolates. BS3-M2 showed significant improvement over BS3 for supporting growth and sporulation. MS2414 is the only isolate that could grow relatively well in BS3, which may indicate its ability to utilize urea. Generally, the TSB medium led to poor sporulation rates for MS2379, MS2414, and MS2820.

TABLE 3

Analysis of fermentation broth at Day 3

| SF# | Isolate | Media | pH | Glucose (g/L) | Sucrose (g/L) | Total Carb. (g/L) | cfu/mL | Sporulation (%) | Viscosity (cP) |
|---|---|---|---|---|---|---|---|---|---|
| 1 | MS1479 | TSB | 7.69 | 0.0 | 0.1 | 0.2 | 1.59E+08 | 95 | 1.9 |
| 2 | | BS3 | 5.56 | 6.8 | 0.0 | 15.6 | 7.39E+07 | 0 | 2.0 |
| 3 | | BS3-M2 | 5.52 | 0.0 | 0.3 | 2.7 | 7.20E+08 | 60 | 45.5 |
| 4 | | GB6-M3 | 6.39 | 0.0 | 0.4 | 4.4 | 1.02E+09 | 90 | 17.7 |
| 5 | MS2379 | TSB | 8.24 | 0.0 | 0.1 | 0.3 | 1.60E+05 | 0 | 2.0 |
| 6 | | BS3 | 6.43 | 8.5 | 0.0 | 17.6 | 8.90E+04 | 0 | 2.3 |
| 7 | | BS3-M2 | 6.04 | 0.0 | 0.4 | 1.9 | 7.01E+08 | 95 | 12.0 |
| 8 | | GB6-M3 | 6.93 | 0.0 | 0.4 | 2.1 | 1.81E+09 | 100 | 19.6 |
| 9 | MS2414 | TSB | 8.10 | 0.0 | 0.1 | 0.3 | 3.90E+05 | 0 | 2.0 |
| 10 | | BS3 | 6.35 | 3.5 | 0.0 | 7.2 | 6.27E+07 | 0 | 2.6 |
| 11 | | BS3-M2 | 6.05 | 0.0 | 0.4 | 2.1 | 5.71E+08 | 70 | 29.2 |
| 12 | | GB6-M3 | 5.67 | 0.0 | 0.4 | 3.5 | 2.93E+08 | 90 | 18.6 |
| 13 | MS2820 | TSB | 8.10 | 0.0 | 0.1 | 0.3 | 2.03E+06 | 0 | 1.8 |
| 14 | | BS3 | 6.61 | 6.6 | 0.0 | 14.4 | 5.42E+05 | 0 | 1.9 |
| 15 | | BS3-M2 | 5.59 | 0.0 | 0.4 | 1.8 | 3.49E+07 | 95 | 60.0 |
| 16 | | GB6-M3 | 5.86 | 0.0 | 0.4 | 1.4 | 5.49E+08 | 90 | 28.4 |

Figure 1:
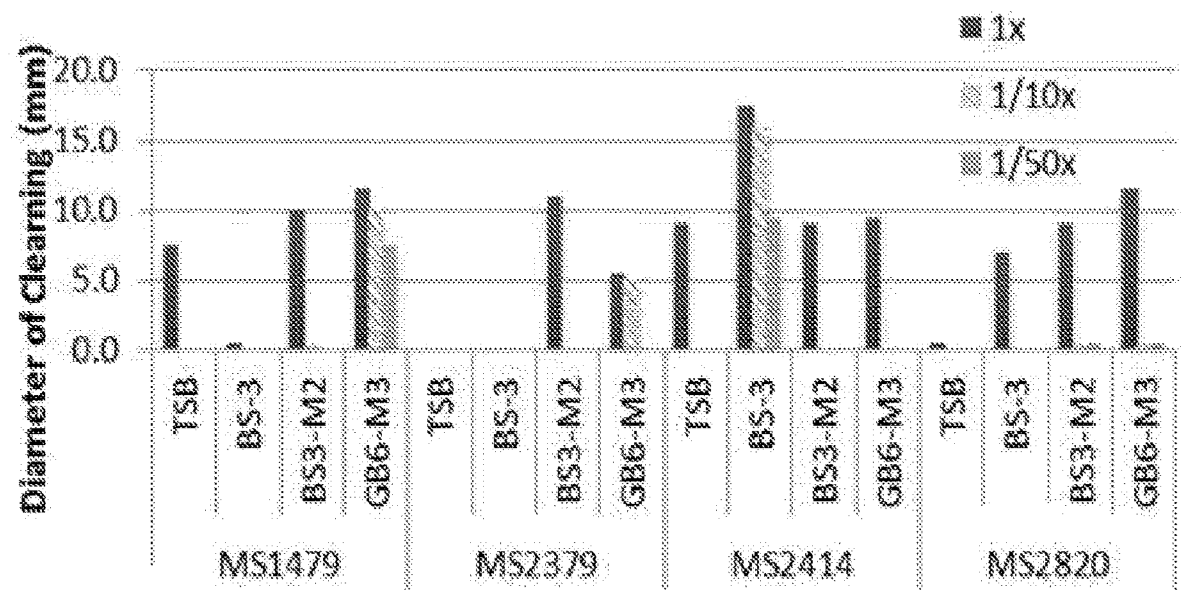
FIG. 1 shows the diameters of clearing (mm) of *Pythium irregulare* in an in-vitro assay testing with whole broth (WB)

All harvested whole broth (WB) samples were tested for in-vitro inhibition of *P. irregulare* at 1×, 10× and 50× dilutions (FIG. 1). As noted above, the bacterial isolates (MS1479, MS2379, MS2414, and MS2820) showed enhanced antibiosis against *P. irregulare* when cultured in special media (i.e., BS3, BS3-M2, and GB6-M3). Similar results of enhanced antibiosis were also observed against *P. ultimum, R. solani*, and *F. virguliforme* in other media (GB6-M7, GB6-M8, and GB6-M9) (data not shown). The inhibitions against those fungal species were dose-dependent for those isolates.

The sterile filtrates from the WB described immediately above were also tested in in-vitro assays. It is contemplated that the methods of obtaining the sterile filtrates are well known in the art. For some bacterial isolates, the sterile filtrates showed different in vitro inhibition profiles from the WB. For example, among the tested bacterial isolates, MS2379 whole broth showed the highest *Rhizoctonia* inhibition activity, while its filtrate had the lowest activity.

Example 2 Fermentation Profiles of Bacterial Isolates

To study the effect of the nitrogen source in GB6 medium on bioactivity of four *Paenibacillus* isolates, the GB6-M based medium was further modified by altering the nitrogen source to increase the antibiotic activity. Sixteen 1 L baffled flasks, each containing 250 ml production medium, were inoculated with 2% (5 ml) seed inoculum from the LB medium. They were cultivated under 26° C., 200 rpm for 72 hours. The four production media include: GB6-M3, GB6-M7, GB6-M8, and GB6-M9.

TABLE 4

Analysis of fermentation broth of Example 2

| SF# | Isolate | Media | pH | Glucose (g/L) | Sucrose (g/L) | Total Carb. (g/L) | cfu/mL | Viscosity (cP) |
|---|---|---|---|---|---|---|---|---|
| 1 | MS1479 | GB6-M3 | 5.50 | 0.01 | 0.35 | 4.5 | 7.96E+08 | 33.3 |
| 2 | | GB6-M7 | 5.65 | 0.01 | 0.28 | 16.7 | 2.70E+08 | 16.7 |
| 3 | | GB6-M8 | 5.09 | 0 | 0.34 | 8.0 | 7.13E+08 | 8.3 |
| 4 | | GB6-M9 | 5.41 | 0 | 0.23 | 9.8 | 1.67E+08 | 1080.0* |
| 5 | MS2379 | GB6-M3 | 5.57 | 0.01 | 0.44 | 3.4 | 7.92E+08 | 37.7 |
| 6 | | GB6-M7 | 6.06 | 0.01 | 0.45 | 4.9 | 7.00E+04 | 19.9 |
| 7 | | GB6-M8 | 5.72 | 0.01 | 0.41 | 4.3 | 8.00E+07 | 19.2 |
| 8 | | GB6-M9 | 6.08 | 0 | 0.28 | 11.8 | 1.85E+08 | 28.6 |
| 9 | MS2414 | GB6-M3 | 5.43 | 0.01 | 0.33 | 9.8 | 1.02E+09 | 504.0* |
| 10 | | GB6-M7 | 5.66 | 0.01 | 0.39 | 7.9 | 2.80E+07 | 4.8 |

TABLE 4-continued

| Analysis of fermentation broth of Example 2 | | | | | | | | |
|---|---|---|---|---|---|---|---|---|
| SF# | Isolate | Media | pH | Glucose (g/L) | Sucrose (g/L) | Total Carb. (g/L) | cfu/mL | Viscosity (cP) |
| 11 | | GB6-M8 | 5.53 | 0.01 | 0.35 | 7.6 | 1.35E+07 | 6.2 |
| 12 | | GB6-M9 | 5.38 | 0 | 0.23 | 9.0 | 1.29E+09 | 967.2* |
| 13 | MS2820 | GB6-M3 | 5.85 | 0.01 | 0.37 | 3.7 | 1.74E+09 | 93.2 |
| 14 | | GB6-M7 | 5.88 | 0.01 | 0.36 | 15.6 | 1.25E+07 | 8.0 |
| 15 | | GB6-M8 | 5.93 | 0.01 | 0.34 | 6.3 | 2.03E+08 | 17.2 |
| 16 | | GB6-M9 | 6.04 | 0.01 | 0.30 | 6.1 | 1.06E+08 | 907.2* |

*Spindle #63 at 50 rpm; All other values are spindle #18 at 50 rpm.

As shown in Table 4, GB6-M9 resulted in high viscosity for MS1479, MS2414, and MS2820, while MS2379 grew relatively poorly in GB6-M7 medium, which contains no soy flour.

MS1479 and MS2414 are very closely related strains of *P. polymyxa* as shown in Table 1. The seed inoculum was prepared by cultivating MS1479 and MS2414 in LB medium at 28° C., 200 rpm overnight. The production media was GB6-M3 (g/L) with 0.5 g/L of Antifoam B. The inoculation rate was 60 ml seed culture for each isolate. Fermentation conditions included: 26° C., no pH control, DO>20%, air flow 1.3 L/min, 48-54 hours of target fermentation time, foam control (10% Antifoam B).

Figure 2A:
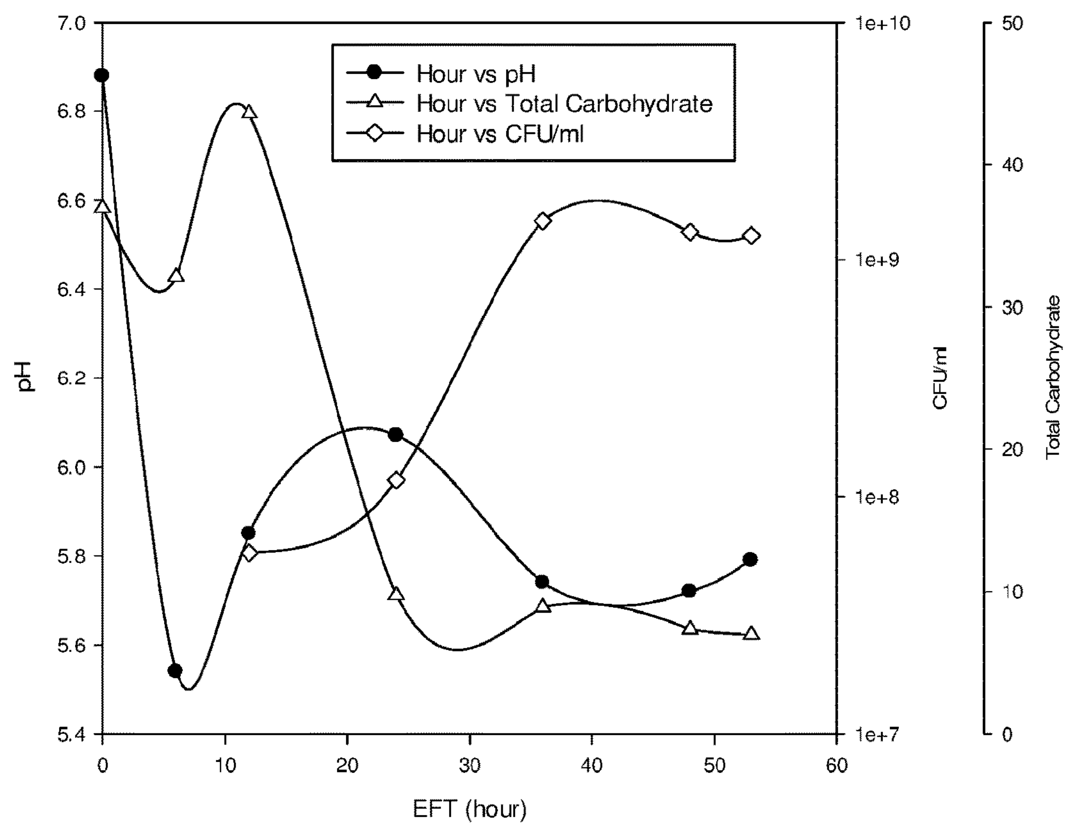
Figure 2B:
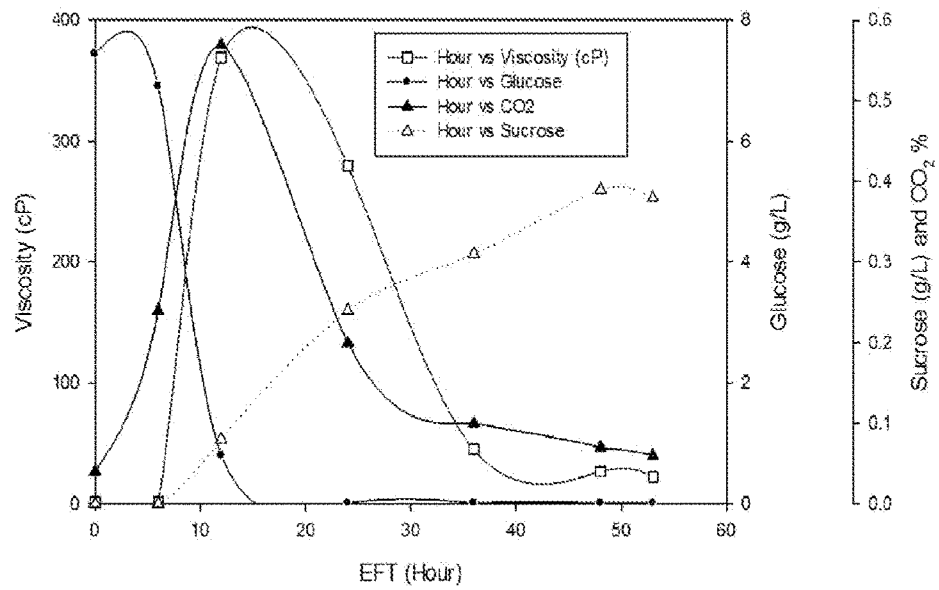
Figure 2C:
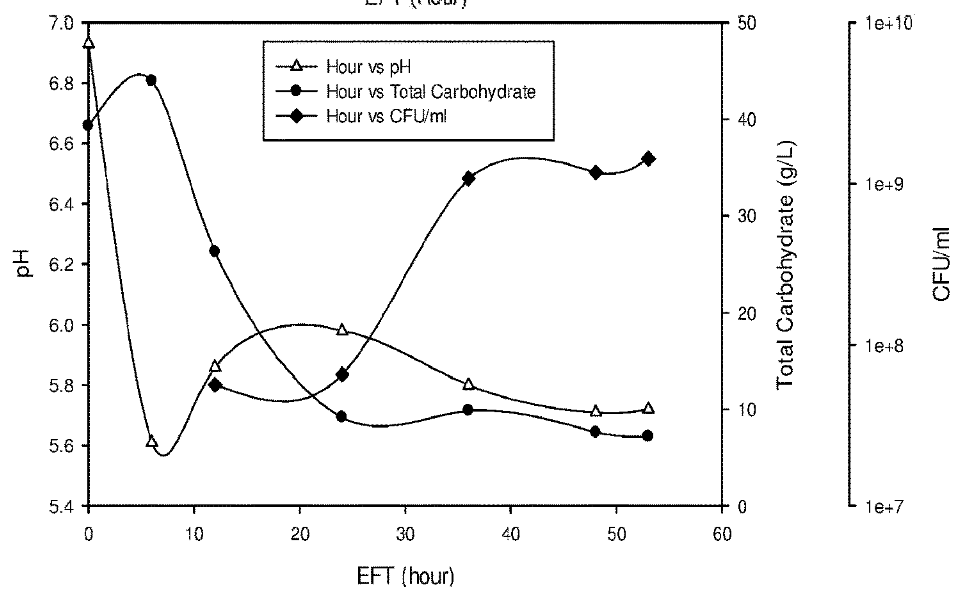

In GB6-M3 medium, MS1479 and MS2414 showed similar fermentation profiles (compare FIG. 2A and FIG. 2C). At the end of fermentation, high cfu ($1\times10^9$) and high sporulation rate (>90%) for both isolates were achieved.

Figure 2D:
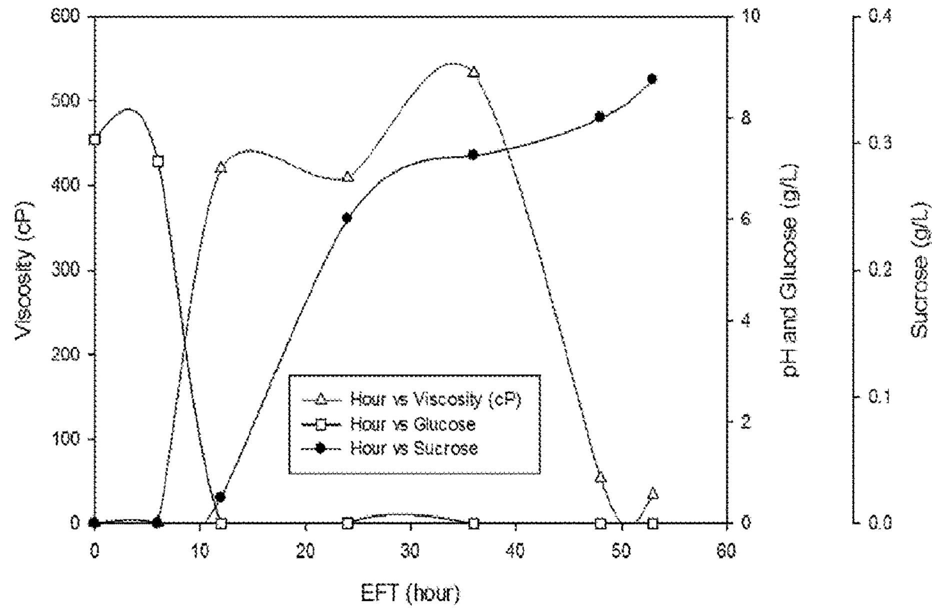

The viscosity of MS1479 decreased quickly after an elapsed fermentation time (ET or EFT) of 24 hours (FIG. 2B), whereas the viscosity of MS2414 was high for a longer time (FIG. 2D). The sucrose concentration increased from ET 12 hours and the increase continued to the end of fermentation for both fermentations. Without being bound by a theory, the sucrose could be a hydrolyzed product of polysaccharide produced by the isolate during fermentation.

Example 3 Seed Treatment

Thirty seeds were treated in a 50 ml centrifuge tube with the 0.1 ml/seed volume of WB. The treated seeds (0.1 ml/seed) were stored at room temperature for two months. Three seeds from each treatment were used for the cfu assay.

The actual cfu/seed of coated seeds was assessed by cfu recovery. 1 mL of phosphate buffer (pH 7.2) was added to one seed in a centrifuge tube. The seed was soaked and then sonicated for 5 minutes. After vortexing, the phosphate buffer turned a slightly different color, which indicated the release of cfu from the surface of the seed. The buffer suspension was then tested for cfu.

Table 5 shows the cfu of the whole broths (WB) used to treat soybean seeds and the initial cfu following seed treatment and a cfu count two months after storage of seed treatment. Each WB was applied to the seed either alone or with the addition of glycerol or sucrose. There was no significant change of cfu after two months of storage. Neither glycerol nor sucrose showed significant effect on the stability.

TABLE 5

Comparison of cfu from WB used in seed treatments from soybean seeds treated with WB samples 1 week after seed treatment and from treated seeds after 2 months storage at room temperature.

| Whole Broth (strain/medium) | Seed Treatment | Initial average cfu per seed 1 week after seed treatment | Average cfu per seed after 2 months of storage |
|---|---|---|---|
| MS1479/BS3-M2 | WB | 6.99E+07 | 7.78E+07 |
| | WB 10% Glycerol | 4.21E+07 | 9.59E+07 |
| | WB 10% Sucrose | 3.41E+07 | 8.12E+07 |
| MS2414/BS3-M2 | WB | 6.83E+07 | 6.90E+07 |
| | WB 10% Glycerol | 4.11E+07 | 9.64E+07 |
| | WB 10% Sucrose | 4.32E+07 | 4.95E+07 |

MS1479 in BS3-M2 medium: 1.22E+09/cfu/ml WB
MS2414 in BS3-M2 medium: 7.62E+08/cfu/ml WB FIG. 3 shows the results of soybean seeds treated with whole broth (WB) of MS1479, MS2379, MS2379, and MS2414 cultivated in TSB, BS3, GB6-M, or LB medium are relatively stable and contain similar cfu/ml even after two months' storage as the initial cfu taken immediately after seed treatment. It is contemplated that the treated seeds can be stored for a reasonable period of time, e.g., at least 2 months, before seeding on the field.

In a separate experiment, biocontrol efficacy of MS2379 was evaluated as a seed treatment in a seed assay using soybean seeds and *Pythium irregulare*, which causes damping off disease affecting a wide range of crops and other plant species. Results showed that as little as 3 fl. oz. per CWT of soybean seed significantly increased seed germination and seedling growth over 40%, compared to the untreated control in the presence of *P. irregulare*. Seed germination after the treatment was comparable to the level produced by the chemical fungicide metalaxyl, a common seed treatment used to control *Pythium* and other oomycete diseases.

Example 4 Root Colonization Assay

*Paenibacillus*-treated and -untreated soybean seeds were germinated in sterilized soil, and eight days later the roots were washed and sonicated at high power for five minutes in sterile water. The water was then plated using a spiral plater. In FIG. 4, the roots from untreated soybean seeds had a low number of bacterial colonies with varied morphologies while the treated seeds produced a large number of colonies of a uniform, predominant colony type of *Paenibacillus*. The results suggested that *Paenibacillus* on the treated seeds persisted and grew on seedling roots in the soil environment.

In another experiment, six seeds from each of the seed treatments were planted in a sterile soil mix (autoclaved for 1.5 hours). The seeds were germinated at room temperature under moderate moisture level. After eight days, three germinated seeds were harvested for seed in-vitro colonization assay. The seed treatment methods and the average total cfu and *Paenibacillus* cfu of roots from three seedlings are shown in Table 6. All samples treated with MS2414 or MS2379 produced bacterial colonies that predominately exhibited *Paenibacillus* morphology.

TABLE 6

Average total cfu and *Paenibacillus* cfu retrieved from roots of three seedlings

| Treatment | Total cfu/ml | *Paenibacillus* cfu/ml |
|---|---|---|
| MS2414 | 1.4E06 | 7.8E05 |
| MS2414 + 10% Glucose | 2.3E06 | 9.1E05 |
| MS2414 + 10% Glycerol | 1.6E06 | 5.7E05 |
| MS2379 | 1.4E06 | 5.6E05 |
| MS2379 + 10% Glucose | 1.5E06 | 5.0E05 |
| MS2379 + 10% Glycerol | 4.2E06 | 4.0E05 |

Example 5 In-Vitro Assay for Plant Pathogen Control

Whole broth was aseptically collected from MS1479, MS2379, MS2414, and MS2820, grown in TSB, BS3, BS3-M2, or GB6-M3 medium, and tested for in-vitro control of nine fungal pathogens. Two (2) μl of whole broth for each isolate was spotted onto the plates with a bacterial or fungal pathogen on the plates or a pathogen-colonized agar cube placed in the center of the plates. All plates were incubated in appropriate conditions: 30° C. incubator (*Xanthomonas perforans* ("Xp") and *Pseudomonas syringae* pathovar tomato ("Ps")); 25° C. incubator (*Macrophomina phaseolina* ("Mp"), *Rhizoctonia solani* ("Rs"), *Botrytis cinerea* ("Bc")); 25° C. growth chamber (*Pseudomonas syringae* ("Ps"), *Pythium ultimum* ("Pu"), *Pythium irregulare* ("Pi"), and *Fusarium virguliforme* ("Fv")). The plates were then measured for the diameter of the clear zone caused by the antibiosis activity. The in-vitro inhibition data is shown in Table 7.

In-vitro antifungal activities against *F. virguliforme, M. phaseolina, R. solani, B. cinerea, P. ultimum* and *P. irregulare* are shown in FIG. 16. It shows that sporulation and biocontrol efficacy of the four isolates were improved when the isolates were grown on the BS3-M or GB6-M medium compared to on the TSB medium. GB6-M medium contains dextrose and maltodextrin as carbon sources, and yeast extract and soy flour as nitrogen sources. BS3-M medium uses sucrose and casein hydrolysate as the carbon and nitrogen sources, respectively.

Microbial isolates grown in LB medium were used as positive and negative standards for the in-vitro inhibition response against each pathogen. These isolates were *E. coli* (ATCC No. 25922); FZB42, *Bacillus amyloliquifaciens* which is marketed as a commercial biofungicide; MS2341, *B. amyloliquifaciens* which was previously tested and demonstrated to have positive *Rhizoctonia* inhibition and negative *Pythium* inhibition; and MS2379 which had, when grown in LB medium, the positive in-vitro inhibition against *Rhizoctonia* and *Pythium*. These isolates grown in LB medium with the in-vitro control activity were scored 0-5 in an in vitro inhibition test against the same nine fungal pathogens (Table 7).

TABLE 7

In-vitro inhibition against fungal and bacterial pathogens by the four *Paenibacillus* isolates grown in four different media.

| SF# | Isolate | Media | cfu/mL | Mp | Rs | Bc | Pu | Pi | Ps | Xp |
|---|---|---|---|---|---|---|---|---|---|---|
| 1 | MS1479 | TSB | 1.59E+08 | 25 | 10 | 14 | 8 | 8 | 0 | 0 |
| 2 | | BS3 | 7.39E+07 | 0 | 0 | 0 | 0 | 0 | 0 | 0 |
| 3 | | BS3-M2 | 7.20E+08 | 26 | 7 | 15 | 13 | 12 | 8 | 6 |
| 4 | | GB6-M3 | 1.02E+09 | 33 | 10 | 20 | 14 | 15 | 7 | 0 |
| 5 | MS2379 | TSB | 1.60E+05 | 11 | 6 | 18 | 13 | 0 | 0 | 0 |
| 6 | | BS3 | 8.90E+04 | 0 | 0 | 0 | 7 | 0 | 0 | 0 |
| 7 | | BS3-M2 | 7.01E+08 | 28 | 15 | 35 | 17 | 12 | 7 | 0 |
| 8 | | GB6-M3 | 1.81E+09 | 28 | 16 | 30 | 13 | 8 | 6 | 0 |
| 9 | MS2414 | TSB | 3.90E+05 | 15 | 7 | 20 | 7 | 5 | 0 | 0 |
| 10 | | BS3 | 6.27E+07 | 14 | 7 | 0 | 11 | 0 | 0 | 0 |
| 11 | | BS3-M2 | 5.71E+08 | 24 | 7 | 20 | 30 | 10 | 6 | 0 |
| 12 | | GB6-M3 | 2.93E+08 | 23 | 9 | 22 | 10 | 5 | 5 | 0 |
| 13 | MS2820 | TSB | 2.03E+06 | 0 | 0 | 8 | 10 | 0 | 4 | 0 |
| 14 | | BS3 | 5.42E+05 | 0 | 0 | 0 | 0 | 0 | 0 | 0 |
| 15 | | BS3-M2 | 3.49E+07 | 25 | 10 | 22 | 15 | 10 | 7 | 5 |
| 16 | | GB6-M3 | 5.49E+08 | 28 | 12 | 18 | 15 | 15 | 0 | 5 |

Mp: *Macrophomina phaseolina* grown on PDA agar
Rs: *Rhizoctonia solani* grown on CMA
Bc: *Botrytis cinerea* grown on PDA.
Pu: *Pythium ultimum* grown on V8 agar
Pi: *Pythium irregulare* grown on V8 plate.
Ps: *Pseudomonas syringae* pathovar tomato (ATCC #BAA-871)
Xp: *Xanthomonas perforans* (ATCC #BAA-983)
PDA: Potato dextrose agar.
CMA: Corn meal agar.
TSA: Tryptic soy agar.

TABLE 8

| Scoring (0-5) of bacterial strains acting as positive (FZB42 MS2341, and MS2379) and negative (*E. coli*) standards for antibiosis activity rating | | | | | | | |
|---|---|---|---|---|---|---|---|
| | Mp - PDA | Rs - PDA | Bc - PDA | Pu - CMA | Pi - CMA | Ps- ¼ TSA | Xp- ¼ TSA |
| *E. coli* | 0 | 0 | 0 | 0 | 0 | 0 | 0 |
| FZB42 | 1 | 2 | 1 | 1 | 0 | 0.5 | 3 |
| MS2341 | 2 | 3 | 3 | 3 | 0 | 1 | 2 |
| MS2379 | 4 | 4 | 5 | 0 | 4 | 2 | 0 |

*E. coli*: Negative control for antibiosis
FZB42: *B. amyloliquifaciens*, Commercial biofungicide standard
MS2341: *B. amyloliquifaciens*, *Rhizoctonia* positive, *Pythium* negative
MS2379: *Paenibacillus* spp., both positive against *Rhizoctonia* and *Pythium*.
Mp: *Macrophomina phaseolina*, grown on PDA
Rs: *Rhizoctonia solani* grown on CMA
Bc: *Botrytis cinerea* grown on PDA.
Pu: *Pythium ultimum* grown on V8 agar
Pi: *Pythium irregulare* grown on V8 agar
Ps: *Pseudomonas syringae* pathovar tomato (ATCC #BAA-871) grown on TSA
XP: *Xanthomonas perforans* (ATCC #BAA-983)
PDA: Potato dextrose agar.
CMA: Corn meal agar.
TSA: Tryptic soy agar.

According to Table 8, all four isolates in BS3-M2 and GB6-M3 showed positive activity against all fungal pathogens where they were tested negative for TSB and BS3 medium against some fungal pathogens. MS2379 in BS3-M2 and GB6-M3 medium showed the highest activity against *Macrophomina* and *Botrytis*.

Example 6 Pot Assay for Controlling *Rhizoctonia*

In pot assays, WB or its dilutions were applied as a seed coating or as a a simulated in-furrow application in pots containing soil inoculated with the pathogen. Measurements of the percent of emergence, plant growth stage, and disease rating were used to assess biocontrol efficacy. Whole broth (WB) or WB dilutions were applied either as a simulated in-furrow treatment or a seed treatment applied to soybean seed. For simulated in-furrow application, 1 ml of biocontrol treatment or negative and positive controls was pipetted over the seed placed in 0.5 cm deep depressions made in peat-lite mix potting medium inoculated with the pathogen and prior to covering with the potting medium. Seed treatments were applied by coating soybean seed with the biocontrol and control treatments prior to planting into an inoculated potting medium. The negative control was reverse osmosis-purified (RO) water applied to seed in inoculated pots. The positive controls were Satori® (azoxystrobin) and Subtilex® (*Bacillus subtilis* strain MBI 600) applied at the labelled rates. In addition, a mock-inoculated treatment without pathogen inoculation was included in each test. Inoculation was done by thoroughly mixing 1 L of a slurry, made by blending two fully *Rhizoctonia solani*-colonized potato dextrose cultures in 200 ml RO water, with 4 L peat-lite mix (e.g., Sunshine LC1 potting mix) using a cement mixer. Experimental units were five seeds per pot and the treatments were arranged in a completely random design with four replicates. The tests were conducted on light carts illuminated with LED lamps (16 hour day/8 hour night) for 7-10 days at 26-28° C. The pots were irrigated as needed with RO water. Measurements of the percent emergence, plant growth stage (Munger, et al., 2008), and disease severity rating (0, no disease, to 5, dead plant) were collected from each plant at the end of each test, and the means of the experimental units were analyzed using JMP version 11 (SAS, Cary, NC).

Example 7 Pot Assay for Controlling *Rhizoctonia* Using Seed Coating

The treated seeds were retained with 100 seeds from each treatment. These seeds were tested by plant testing groups for control of *R. solani*. For a higher precision, each treatment in the assay had 10 replicates (40 plants for each treatment). The statistical analysis of disease rating is shown in FIG. 6. The seeds treated by MS 2414 grown in GB6-M medium showed significant enhanced disease resistance compared to the control.

In a separate pot assay, treatments were applied directly as a drench. The *R. solani* disease ratings in the treatments MS2414 and MS2820 fermented in BS3-M2 medium were not statistically different ($P<0.05$) from the chemical control Fludioxonil (Table 9). This result showed that these isolates were effective in controlling soybean *R. solani* seedling disease. The pot assays to test for biocontrol activity indicates that the four *Paenibacillus* isolates of this disclosure had the ability to limit diseases caused by *R. solani* on germinating soybean seedlings (Table 9).

TABLE 9

| Effects of microbial drench treatments on Ozark soybean seedlings in pots infested with *R. solani* | | | | |
|---|---|---|---|---|
| Treatment | | Evaluation of Seedlings 7 days after sowing | | |
| Isolate | Medium | # Emerged Plants[1] | Plant Growth Stage[2] | Disease Rating[3] |
| MS1479 | BS3 | $0.5^{CDE}$ | $1.1^{EF}$ | $4.5^{BCD}$ |
| | GB6-M | $1.5^{BC}$ | $2.0^{BC}$ | $3.8^{DE}$ |
| | TSB | $0.7^{CDE}$ | $1.3^{DEF}$ | $4.2^{BCDE}$ |

TABLE 9-continued

Effects of microbial drench treatments on Ozark soybean seedlings in pots infested with *R. solani*

| Treatment | | Evaluation of Seedlings 7 days after sowing | | |
|---|---|---|---|---|
| Isolate | Medium | # Emerged Plants[1] | Plant Growth Stage[2] | Disease Rating[3] |
| MS2379 | BS3 | $0.2^{DE}$ | $1.1^{EF}$ | $4.3^{BCDE}$ |
| | GB6-M | $0.5^{CDE}$ | $1.3^{EF}$ | $4.0^{CDE}$ |
| | TSB | $0.2^{DE}$ | $1.1^{EF}$ | $4.6^{BCD}$ |
| MS2414 | BS3 | $0.5^{CDE}$ | $1.2^{EF}$ | $4.1^{BCDE}$ |
| | GB-M3 | $1.5^{BC}$ | $1.5^{CDE}$ | $3.5^{DE}$ |
| | TSB | $0.0^{E}$ | $1.0^{F}$ | $4.7^{B}$ |
| MS2820 | BS3 | $0.0^{E}$ | $1.0^{F}$ | $4.9^{A}$ |
| | GB6-M | $0.5^{CDE}$ | $1.1^{EF}$ | $4.1^{BCDE}$ |
| | TSB | $0.2^{DE}$ | $1.0^{F}$ | $4.6^{BCD}$ |
| Fludioxonil[4] | | $2.0^{B}$ | $2.2^{B}$ | $3.0^{F}$ |
| Mock Inoc.[5] | | $4.0^{A}$ | $4.0^{A}$ | $0.0^{G}$ |
| *R. solani*[6] | | $0.0^{E}$ | $1.0^{E}$ | $4.5^{BCD}$ |

[1]Number of emerged plants of four seeds sown per pot, 10 replicate pots;
[2]1 = un-germinated seed to 4 = plant with > one true leaves;
[3]0 = no disease to 5 = plant dead;
[4]Fludioxonil at 0.06 g/lb of soybean seeds;
[5]Mock-inoculated utilized PDA alone;
[6]*R. solani* inoculation = one and a half homogenized colonized PDA cultures mixed into 4 lb. soil-less peat-lite mix;
Treatments without the same letter were significantly different using LSD (P <0.05).

Example 9 Field Study

Fermentation WBs of MS2379 or MS2414, grown in GB6-M medium, were mixed with Amaranth to generate mixtures that were applied as seed treatments for the field trial study (Table 10). For all treatments, the target concentration is 20 µl water/seed, which corresponds to 60 ml/460 g seeds. Sixty (60) ml liquid was added to every 460 g soybean seeds for a total of six times. Each time, 10 ml of liquid was added to the 460 g seeds and mixed for 15 seconds. Coated seeds were dried for 5-10 minutes under ventilation between the additions. Final coated seeds were dried overnight in a biocontainment hood.

TABLE 10

Seed Treatment for Soybean used for Field Trial

| Treatment | µl WB or Emulsion/seed | active ingredients (% in product) or cfu/ml | mg AI or cfu/Seed | Liquid for seed treatment (60 ml/lb.) |
|---|---|---|---|---|
| Water | 20 µl water/seed | N/A | N/A | Water |
| Metalaxyl | 0.153 µl/seed | 30% | 0.046 mg/Seed | 0.752 ml + 2 ml 10% Amaranth q.s. to 100 ml using water |
| Fludioxonil | 0.017 µl/seed | 40% | 0.007 mg/seed | 0.047 ml + 2 ml 10% Amaranth q.s. to 100 ml using water |
| MS2414 in GB6-M | 20 µl WB/seed | $\sim 3 \times 10^8$ | $\sim 6 \times 10^6$ | 200 ml mixed WB + 4 ml 10% Amaranth |
| MS2379 in GB6-M | 20 µl WB/seed | $\sim 6 \times 10^8$ | $\sim 1.2 \times 10^7$ | 200 ml mixed WB + 4 ml 10% Amaranth |

The results of the field trials for the *Rhizoctonia* and SDS control are summarized in Tables 11 and 12 with the stand data. For the *Rhizoctonia* test, both MS2414 and MS2379 show significant positive effects on stands and disease control compared to the untreated crops and the crops treated with Fludioxonil.

TABLE 11

Means of Rhizoctonia control in field trial conducted in Fisher, Indiana

| Treatment | Application Rate | Stand (No of plants per acre[1]) at 11 DAP | Stand (No of plants per acre[1]) at 16 DAP | Stand (No of plants per acre[1]) at 49 DAP | Vigor Rating (1-5: 1 = worst, 5 = best) | Total # Diseased per plot (187.5 ft$^2$ per plot area) |
|---|---|---|---|---|---|---|
| 1: Untreated | 20 µl Water/Seed | 3049 | 23087 | 12197 | 2.1 | 8.1 |
| 2: MS2414 | 20 µl WB/Seed | 10455 | 28314 | 19167 | 1.5 | 4.1 |
| 3: MS2379 | 20 µl WB/Seed | 6098 | 30492 | 26136 | 2.5 | 6.3 |
| 4: Fludioxonil | 0.02 mg/Seed | 2614 | 20038 | 16939 | 1.8 | 7.3 |

[1]Number of plants per acre calculated on number of plants emerged in a 10 ft. section of each of two rows in a plot.

For the SDS test, soybean seeds were treated with WB at 20 μl/seed by using a Wintersteiger seed treater before the field trial to study the effects of the isolates on the sudden death syndrome ("SDS") of the soybean. The treatments included: (1) MS2414 (GB6-M3) seed treatment, with seed planted above SDS inoculum (*F. virguliforme* at 300 kg per ha infested sorghum grain inoculum was used; Farias Neto et al., Crop Science 46:2547-2554 (2006)); (2) MS2820 (GB6-M3) seed treatment, with seed planted above SDS inoculum; (3) no seed treatment; seed planted above SDS inoculum; and (4) no seed treatment and no SDS inoculum. The results from the test are shown in Table 12.

Soybean Cultivar (2900RR), which was an MG II SDS-susceptible check received from the North Central Soybean Research Program Regional SDS Trial, was used in this study. The Randomized Complete Block Design included five replications. The plot dimensions were two rows spaced 30" apart and 12.5' long but trimmed to 9'. The planting rate was 220 seeds/plot (or 9 seeds per foot). For the SDS treatment, 1.5 ml/ft. SDS inoculum was added to the planting packets. Plots were drip irrigated with 1.5" water each week for 3 weeks.

TABLE 12

Results SDS field trial in Urbana Illinois

| Treatment | Stand count | SDS % (6/30/15) | Disease Progression (AUDPC) (8/20/15-9/08/15) |
|---|---|---|---|
| MS2414 SDS Inoculated | 115.8 | 37% | 15.6 |
| MS2820 SDS Inoculated | 102.2 | 39% | 5.8 |
| Water | 149.4 | 30% | 25.4 |
| No SDS Inoculation | 148.8 | 0% | 8.0 |
| Sig. level | *** | *** | ** |
| LSD (0.05) | 14.05 | 10.2 | 3.2 |

Stand - Number of plants that emerged per 18 ft. of row.

Seedling SDS - Percent of plants with SDS symptoms (chlorosis and or necrosis) on Jun. 30, 2015.

AUDPC - Area of the Disease Progression Curve (cumulative SDS DX scores over observations on 8/20/15, 8/25/15, and 9/3/15.

Disease index (DX) is a combination of disease incidence (DI) and disease severity (DS). It is calculated as DI x DS/9, and has a range of 0 (no disease) to 100 (all plants prematurely dead at or before R6).

Disease Incidence (DI) = % of plants with leaf symptoms, recorded in increments of 5. (http://www.scnresearch.info/462.pdf).

Seed treatment with the bacterial isolates had significant positive effects on SDS control. Stands were reduced in the MS2414 and MS2820, most likely due to the damage that occurred to the seeds in the process of coating the seeds. The results are shown in Table 12.

Over 30% of the plants in treatments with SDS inoculum had SDS symptoms. There was no significant difference in SDS incidence among these treatments. No SDS symptoms were observed in the non-infested treatment. The cumulative disease progression as determined from disease index rating (http://www.scnresearch.info/462.pdf) was significantly lower in plants produced from the seeds treated with MS2820 (5.8) and MS2414 (15.6) as compared to the untreated SDS-inoculated group (25.4). The results showed that that MS2820 and MS2414 reduced the disease incidence and severity of SDS.

Example 10 Biocontrol Activities of *Bacillus* Isolates

Seven *Bacillus* isolates MS0633, MS2335, MS2652, MS2658, MS2681, MS2697, and MS2712 were tested for their biocontrol activities with the four *Paenibacillus* isolates (MS1479, MS2379, MS2414, MS2820). In this experiment, 11 250 ml shake flasks, each containing 50 ml LB medium, were inoculated with 0.1 ml thawed frozen vials or colonies from the plates. The seed inoculum was cultivated at 30° C. and 200 rpm overnight for about 18 hours. Eleven (11) one-liter baffled flasks each containing 250 ml GB6-M8 medium were inoculated with 2% (5 ml) seed inoculum. The cultivation conditions for the *Bacillus* isolates included 28° C. and 200 rpm of shaking speed for 72 hours. The cultivation conditions for four *Paenibacillus* isolates included 26° C. and 200 rpm of shaking speed for 72 hours.

TABLE 13

Analysis of Fermentation Broth

| | Fermentation broth in GB6-M8 | | | | | | Seed inoculum | |
|---|---|---|---|---|---|---|---|---|
| | | Glucose | Sucrose | Total Carb | Protease | | | |
| Isolate | pH | (g/L) | (g/L) | (g/L) | $OD_{440}$ | cfu/mL | pH | $OD_{600}$* |
| MS1479 | 6.09 | 0.0 | 0.2 | 7.5 | 1.08 | 5E+08 | 5.96 | 3.2 |
| MS2379 | 7.00 | 0.0 | 0.3 | 1.4 | 1.46 | 5E+07 | 5.57 | 4.2 |
| MS2414 | 5.98 | 0.0 | 0.2 | 3.6 | 1.14 | 6E+08 | 5.66 | 4.7 |
| MS2820 | 5.88 | 0.0 | 0.2 | 3.7 | 1.19 | 4E+07 | 5.59 | 3.3 |
| MS0633 | 6.01 | 0.1 | 0.1 | 11.9 | 0.97 | 2E+09 | 8.22 | 5.7 |
| MS2335 | 6.19 | 0.2 | 0.1 | 14.1 | 1.38 | 2E+09 | 8.21 | 6.1 |
| MS2652 | 6.06 | 0.0 | 0.1 | 8.5 | 1.44 | 1E+09 | 8.35 | 4.4 |
| MS2658 | 6.15 | 0.1 | 0.1 | 12.3 | 1.34 | 1E+09 | 8.43 | 4.7 |
| MS2681 | 5.60 | 0.1 | 0.1 | 9.0 | 1.43 | 4E+09 | 8.28 | 4.9 |
| MS2697 | 6.18 | 0.6 | 0.1 | 11.9 | 1.31 | 2E+09 | 8.32 | 5.5 |
| MS2712 | 5.82 | 0.1 | 0.1 | 7.9 | 1.50 | 2E+09 | 8.39 | 6.2 |

As shown in Table 13, the spent medium for all *Bacillus* isolates (most are *B. amyloliquefaciens*) contains more carbohydrate residues than the four *Paenibacillus* isolates. Without being bound by a theory, this may indicate that the *Bacillus* isolates may not produce sufficient amylase for utilizing maltodextrin in the medium. The *Bacillus* isolates showed higher cfu/ml in the range of 1-4E09.

The WB of the *Bacillus* isolates showed greater inhibition diameters against *Fusarium* than the four *Paenibacillus* isolates. At the same time, the clearing zones of the *Bacillus* isolates were not as clear as those for the *Paenibacillus*. Without being bound by a theory, this may indicate that *Bacillus* isolates rely on a different mode of action against fungi. MS2652 and MS2658 showed the strongest performance in controlling *Fusarium virguliforme* (FIGS. 7 and 8).

The WB of 4 *Paenibacillus* isolates also showed in-vitro *Pythium* control activities, whereas either WB or sterile filtrate of all *Bacillus* isolates did not show any biocontrol activities against *Pythium* (Table 14). Contrary to their response against *Pythium*, the *Bacillus* isolates showed better control against *Rhizoctonia* (FIGS. 9 and 10).

TABLE 14

In-vitro inhibition of *P. irregulare* by fermentation, whole broth, and sterile filtrate (4 days at 16° C.)

| Isolate | Whole broth (Diameter of inhibition in mm) | Sterile filtrate (Scale 1-4) |
|---|---|---|
| MS1479 | 13.5 | 4 |
| MS2379 | 5.5 | 0 |
| MS2414 | 14.5 | 4 |
| MS2820 | 12.5 | 4 |

Example 11 Pot Test Against *Rhizoctonia solani*

The fermentation whole broth of the 11 isolates (4 *Paenibacilli* and 7 *Bacilli*), grown in GB6-M8 medium, was tested against *R. solani* infection in a pot. The efficacies of the treatment, in terms of plant emergence, plant development, and disease severity, are significantly different. The WB was applied as simulated in-furrow by pipetting 1 ml over each seed after the seeds were placed in a 1 cm deep depression.

The results of a pot assay for *Rhizoctonia* control are shown in FIGS. 11-13. There were significant differences among the treatments for plant emergence, plant development, and disease severity ($\alpha$=0.1) (Table 15). The mean of the negative water control was significantly different from the positive controls—Satori® fungicide and mock-inoculated. The test power was ≥0.95 for all three metrics. MS0633, a *B. amyloliquefaciens* isolate, showed significantly lower disease severity than the water control and showed better biocontrol activities than other isolates in plant emergence and plant development. Overall, MS2379 was the most effective among the tested *Paenibacillus* isolates.

TABLE 15

Plant development, plant emergence, and disease severity of soybean germinating in the presence of *R. solani* in a pot study

| Treatment | | | | | | | | |
|---|---|---|---|---|---|---|---|---|
| | Plant Emergence | | | | | | | |
| Satori ® | 5 | A | | | | | | |
| Mock-inoculated | 5 | A | | | | | | |
| MS0633 GB6-M8 | 4.75 | A | B | | | | | |
| MS2379 GB6-M8 | 4.75 | A | B | | | | | |
| MS2820 GB6-M8 | 4.25 | A | B | C | | | | |
| MS2712 GB6-M8 | 4 | A | B | C | D | | | |
| MS2335 GB6-M8 | 3.5 | | B | C | D | | | |
| MS2414 GB6-M8 | 3.5 | | B | C | D | | | |
| Water | 3.5 | | B | C | D | | | |
| MS2658 GB6-M8 | 3.25 | | | C | D | | | |
| MS1479 GB6-M8 | 3 | | | C | D | | | |
| MS2652 GB6-M8 | 3 | | | C | D | | | |
| MS2681 GB6-M8 | 2.75 | | | | D | | | |
| MS2697 GB6-M8 | 2.75 | | | | D | | | |
| Subtilex ® | 2.75 | | | | D | | | |
| | Plant development | | | | | | | |
| Satori ® | 12.55 | A | | | | | | |
| Mock-inoculated | 12.2 | A | B | | | | | |
| MS0633 GB6-M8 | 11.55 | A | B | C | | | | |
| MS2379 GB6-M8 | 11.5 | A | B | C | | | | |
| MS2820 GB6-M8 | 10.5 | A | B | C | D | | | |
| MS2414 GB6-M8 | 10.2 | A | B | C | D | E | | |
| MS2712 GB6-M8 | 10.05 | | B | C | D | E | | |
| MS2335 GB6-M8 | 9.6 | | | C | D | E | F | |
| Water | 9.2 | | | C | D | E | F | G |
| MS1479 GB6-M8 | 8.25 | | | | D | E | F | G |
| Subtilex ® | 8.05 | | | | | E | F | G |
| MS2658 GB6-M8 | 7.95 | | | | | E | F | G |
| MS2681 GB6-M8 | 7.3 | | | | | | F | G |
| MS2697 GB6-M8 | 7.3 | | | | | | F | G |
| MS2652 GB6-M8 | 6.85 | | | | | | | G |
| | Disease severity | | | | | | | |
| MS2697 GB6-M8 | 3.55 | A | | | | | | |
| MS2652 GB6-M8 | 3.45 | A | | | | | | |
| MS2681 GB6-M8 | 3.4 | A | B | | | | | |
| MS2658 GB6-M8 | 3.25 | A | B | C | | | | |
| Subtilex ® | 3.1 | A | B | C | | | | |
| MS1479 GB6-M8 | 3 | A | B | C | | | | |
| Water | 2.9 | A | B | C | D | | | |
| MS2414 GB6-M8 | 2.85 | A | B | C | D | | | |
| MS2712 GB6-M8 | 2.65 | | B | C | D | | | |
| MS2820 GB6-M8 | 2.5 | | | C | D | E | | |
| MS2335 GB6-M8 | 2.2 | | | | D | E | | |
| MS2379 GB6-M8 | 2.2 | | | | D | E | | |
| MS0633 GB6-M8 | 1.8 | | | | | E | F | |
| Satori ® | 1.05 | | | | | | F | |
| Mock-inoculated | 0 | | | | | | | G |

Test Power

| Metric | $\alpha$ | $\sigma$ | $\delta$ | Number of experimental units | Power |
|---|---|---|---|---|---|
| Emergence | 0.1 | 1.2 | 0.82 | 60 | 0.95 |
| Growth Score | 0.1 | 2.0 | 1.82 | 60 | 0.99 |
| Disease | 0.1 | 0.67 | 0.94 | 60 | 1.00 |

Biocontrol efficacy of MS2379 fermented in GB6-M31 medium against *Rhizoctonia solani* was also evaluated on soybean in a simulated in-furrow application in a plant growth room. Results showed that 1 ml whole broth applied to soybean seed at planting improved plant emergence and development and reduced root infection compared to the untreated control.

Example 12 Pot Assay: Combination of the Fungicide with the Bacterial Isolates in GB6-M8 Medium for Control of *Pythium irregulare*

The effects of bacterial isolates on *Pythium* disease in soybean were tested using a modification of the method of Broders, et al., Plant Dis 91:727-735 (2007)). Soybean seeds were surface sterilized using chlorine gas generated by combining 100 ml of bleach (5.25% NaOCl) with 3.5 ml of HCl (10N). The soybean seeds were then coated with biocontrol or control treatments at approximately 20 µl of treatment per seed and were allowed to dry completely inside a sterile culture hood. The negative control was sterile, distilled water that was applied to the seed. The positive controls were metalaxyl and Subtilex® (*Bacillus subtilis* strain MBI 600) applied at the labelled rates. In addition, a mock-inoculated treatment without pathogen inoculation was included in each test. Water agar (0.8% agar) plates were inoculated in the center with a 10 mm square plug cut from the margin of a 7-day-old *P. irregulare* culture grown on V8 agar. Then, 10 seeds of a single treatment were immediately placed aseptically around the periphery of each inoculated water agar plate on the same day that the pathogen is placed. Experimental units included 10 treated seeds per plate, and there were five replicates per treatment. The plates were arranged in a randomized design and were incubated at 16° C. under fluorescent light (16-hour day, 8-hour night) for 7 days, and then 25° C. under the same lighting regime for another 7 days. The number of germinated seed out of 10 seeds per plate and plant developmental stage (Munger, et al., 2008) of each seed within a plate were recorded and analyzed using MR' version 11 (SAS, Cary, NC).

In order to test the performance of bacterial isolates, with or without the presence of the fungicide Satori® (active ingredient is azoxystrobin), samples were applied as simulated in-furrow by pipetting in 1 ml over each seed after the seeds were placed in a 1 cm deep depression. The combination was prepared by combining each bacterial whole broth (MS1479, MS2379, MS2414, or MS2820) (which was grown in GB6-M8) with an equal volume (1:1) of Satori®. The agar slurry inoculation method was used after blending two agar cultures of *P. irregulare* in 200 ml RO water and then mixed with 4 L of peat-lite mix in a cement mixer. Five soybean seeds (genotype WS2620) were sown in each pot with 1 ml treatment over each seed (in-furrow simulation). Then the pots were incubated at 16° C. for 1 week and then 23° C. for another week before evaluation. The disease severity scale: 1=80-100%, 2=60-79%, 3=40-59%, 4=20-39%, 5=1-19%, and 6=0% damaged roots. (Table 16).

All isolates grown in GB6-M8 medium showed significant control of *Pythium irregulare* as can be seen in plant emergence, plant development, and disease severity (data not shown). Overall, the combined treatments performed similarly to the pure whole broth treatments, with the exception of MS1479, which had lower emergence when combined with Satori® than when not. Overall, MS1479 grown had relatively higher *Pythium* biocontrol activity than the other isolates.

Significant differences among the treatments for plant emergence, plant development, and disease severity were shown in Table 16. The means of the negative water control differed significantly from the metalaxyl positive control with the test power exceeding 0.85 for each of the three metrics. Notably, the biocontrol activity of MS1479 was improved when combined with Satori®. Without being bound by a theory, the active ingredient azoxystrobin in Satori® may control or treat *Pythium* which could explain the improved performance of MS1479. The biocontrol performances of the three other isolates were not improved as significantly as MS1479, when combined with Satori®. In this test, MS2820 had relatively higher *Pythium* biocontrol activity than the other isolates.

TABLE 16

Combination of the fungicide Satori with bacterial isolates for controlling *Pythium irregulare*

| Treatments | | | | | | |
|---|---|---|---|---|---|---|
| | Plant emergence | | | | | |
| Metalaxyl | 5 | A | | | | |
| MS2820 GB6-M8 + 2% Satori ® | 3.75 | A | B | | | |
| MS2379 GB6-M8 + 2% Satori ® | 3.5 | | B | C | | |
| MS2820 GB6-M8 | 3.5 | | B | C | | |
| 2% Satori ® | 3 | | B | C | | |
| MS2414 GB6-M8 | 3 | | B | C | | |
| MS2414 GB6-M8 + 2% Satori ® | 3 | | B | C | | |
| MS1479 GB6-M8 + 2% Satori ® | 2.75 | | B | C | D | |
| Subtilex ® | 2.75 | | B | C | D | |
| Water | 2.75 | | B | C | D | |
| Mock-inoculated (no pathogen) | 2.25 | | | C | D | |
| MS2379 GB6-M8 | 2.25 | | | C | D | |
| MS1479 GB6-M8 | 1.5 | | | | D | |
| | Plant development | | | | | |
| Metalaxyl | 12.55 | A | | | | |
| 2% Satori ® | 10.45 | A | B | | | |
| MS2820 GB6-M8 + 2% Satori ® | 10.25 | A | B | C | | |
| MS2414 GB6-M8 | 9.95 | | B | C | D | |
| MS2414 GB6-M8 + 2% Satori ® | 9.9 | | B | C | D | |
| MS1479 GB6-M8 + 2% Satori ® | 9.65 | | B | C | D | |
| MS2820 GB6-M8 | 9.6 | | B | C | D | |
| MS2379 GB6-M8 + 2% Satori ® | 9.4 | | B | C | D | |
| Mock-inoculated (no pathogen) | 8.8 | | B | C | D | E |
| Water | 8 | | | C | D | E |
| MS2379 GB6-M8 | 8 | | | C | D | E |
| Subtilex ® | 7.6 | | | | D | E |
| MS1479 GB6-M8 | 6.85 | | | | | E |
| | Disease severity | | | | | |
| Metalaxyl | 4.35 | A | | | | |
| MS2820 GB6-M8 + 2% Satori ® | 3.65 | A | B | | | |
| MS2820 GB6-M8 | 3.6 | A | B | | | |
| MS2379 GB6-M8 + 2% Satori ® | 3.4 | | B | | | |
| MS1479 GB6-M8 + 2% Satori ® | 3.35 | | B | | | |
| MS2414 GB6-M8 | 3.05 | | B | C | | |
| Water | 3.05 | | B | C | | |
| MS2414 GB6-M8 + 2% Satori ® | 3 | | B | C | | |
| MS2379 GB6-M8 | 2.95 | | B | C | | |
| Mock-inoculated | 2.9 | | B | C | | |
| Subtilex ® | 2.8 | | B | C | | |
| 2% Satori ® | 2.8 | | B | C | | |
| MS1479 GB6-M8 | 2.25 | | | C | | |

Test power

| Metric | α | σ | δ | Number of experimental units | Power |
|---|---|---|---|---|---|
| Plant emergence | 0.1 | 1.13 | 0.81 | 52 | 0.94 |
| Plant development | 0.1 | 2.04 | 1.42 | 52 | 0.93 |
| Disease severity | 0.1 | 0.79 | 0.49 | 52 | 0.86 |

Example 13 Biocontrol Activities of Bacterial Isolates from 20 L Fermentation Medium The inoculum used to seed the 20 L fermenters was prepared by inoculating two 250 ml LB medium in two 1 L baffled flasks each with 0.5 ml of 1 thawed 1 ml frozen vial and was incubated at 28° C. and 200 rpm of shaking speed for overnight (around 16-18 hours). After incubation, the MS2379 seed inoculum showed pH at 7.43 and $OD_{600}$ 3.24, and the MS2414 seed inoculum showed pH at 7.30 and $OD_{600}$ at 2.83.

The production medium was 15 L GB6-M8. A 300 ml seed culture for each isolate was incubated in the production medium at these fermentation conditions: 26° C., no pH control, DO>30%, 7.5 L/min air flow, 10 psi (0.7 bar) back pressure, and automatic foam control using antifoam B. The results of inhibition assays against the fungal species are shown in FIG. 14.

Example 14 Effect of UV Treatment on the Biocontrol Activity

The experiment was to test the UV stability of foliar treatment for disease control. Whole broth filtrates, the whole broth, and fractions of MS2379 and MS2414 were placed under the UV light. The length of treatment depends on the volume and types of samples to be treated. One skilled in the art can determine the period of times for the UV treatment.

The UV light-treated fermentation whole broth of MS2379 and MS2414 in GB6-M8 did not affect cfu counts of the two isolates as much as it did *E. coli* (FIG. 15). Similar results were also observed when the bacterial isolates were grown in LB. When WB samples of MS2379 and MS2414 in GB6-M10 were tested in vitro against the fungal pathogens, no negative effect of UV exposure on in-vitro inhibition of *B. cinerea, P. irregulare*, and *R. solani* was observed for MS2379 and MS2414 (FIG. 16).

Example 15 Seed Germination after Treatment with WB and Sterile Filtrate

The seed germination assay was used to study the biocontrol activity of whole broth of the isolates grown in GB6-M8 medium against *Pythium irregulare*. As shown in FIG. 17, with several whole broth microbial treatments (MS2379, MS2820, and MS1479), the results for plant development and seed germination were similar to the positive chemical control metalaxyl for both metrics, and even better than Subtilex.

Sterile filtrates from each bacterial culture were less effective against the pathogen compared to the whole broth for both metrics (FIG. 17). Without being bound by a theory, this may indicate that the cells of the isolates may also be used for disease control. The statistical analysis is using JMP with test Power=1 and $\alpha$=0.05. Treatment containing the same letter indicates no statistical difference.

Example 16 Field Trial with MS2379 (LPI-6543) and MS2414 (LPI-6544) in GB6-M8/GB5-M8 Media The protocols for the field study are listed in Table 17.

TABLE 17

Protocols for field study

| Protocol # | Application | State/Location | Crop (s) | Target |
|---|---|---|---|---|
| 6.00 | In-Furrow | Kentucky, Illinois | Soybean | Stand and Yield |
| 6.10 | In-Furrow | Kentucky, Iowa | Corn | Stand and Yield |
| 6.50 | Foliar | California | Grapes | Bunch rot/Botrytis control |

In each field study, the plants are subjected to the following treatments: (1) UTC (untreated control), (2) MS2379, (3) MS2379 with Satori®, (4) MS2414, (5) MS2414 with Satori®, (6) Serenade soil, (7) Serenade with Satori®, and (8) 10× Priaxor™ fungicide. The exact rates of Satori® (e.g., 7 oz/acre which is the same as 0.4 oz/1,000 row feet) can be adjusted based on a number of factors, e.g., the conditions of the field and the plants to be treated.

In a field test, 16 soybean plots were treated in-furrow in two sites with two bacterial isolates with and without Satori® in combination with the bacterial isolates. The control was Serenade with and without Satori®. Another control was Priaxor™, with the active ingredients fluxapyroxad and pyraclostrobin. The treatments were replicated six times in 10 ft. by 40 ft. rows. For each isolate, 16 L WB was needed for the protocol.

Results of a plant growth room bioassay found that the tank-mixed combination of 98% MS2379 whole broth (or LPI 6592) plus 2% Satori that was diluted to 10% provided synergy in control of *Phytophthora* soybean root disease (FIG. 18). Note that the combination treatment was more effective in controlling *Phytophthora* than other commercial fungicides, e.g., LifeGard WG®, metalaxyl, and Double Nickel 55® (FIG. 18). MS2379 was also shown efficacy against other pathogens (e.g., *Pythium irregulare*, and *Rhizoctonia solani*) with or without other fungicides (e.g., Satori or Awaken). The combination with other fungicides showed synergistic effect against pathogens in seed treatment. The synergy is more pronounced when a reduced amount of MS2379 whole broth (e.g., 0.5 ul. whole broth per seed) was used to treat soybean seeds (data not shown).

Moreover, when soybean plants were severely infected with *Pythium* or damping off disease, MS2379, with or without Satori, significantly improved soybean stand when compared to the water control (data not shown). Even when compared with other bio-fungicides (Serenade ASO®, Double Nickel 55®, LifeGard WG®, Xanthion® A, Subtilex®), MS 2379 in GB6-M31 (LPI 6592) was comparative or superior to other bio-fungicides against *Botrytis, Pythium, Phytophthora*, and *Sclerotinia* in various parameters (lesion diameter, germination, root disease rating), when tested at identical cfu concentration (data not shown).

Results of a corn field test showed that in-furrow application of either MS2379 in GB6-M10 (LPI 6568) or MS2414 (LPI 6569), when in combination with Satori, led to much lower infection rates related to the foliar disease southern corn rust (*Puccinia polysora*) and higher grain yields (FIG. 19). Corn plants treated with combination of MS2379 and Satori remained almost devoid of rust pustules and stayed green longer than the positive controls, including treatment with Satori alone (data not shown).

In a vineyard test, grape vines were treated with the following treatments: UTC, MS 2379 in GB6-M31 (LPI 6592) with and without Satori®, Pristine® fungicide and Serenade®. MS2379, with or without Satori®, showed significant biocontrol of powdery mildew on grapes when compared to the water control, Serenade® and combination of Serenade® and Satori® (data not shown).

The fungal control activity of MS 2379 in GB6-M31 (LPI 6592) was also tested on detached canola leaves. At the same $3\times10^8$ cfu concentration, 20% MS 2379 was more effective in inhibiting *Sclerotinia* lesion development on detached canola leaves than the commercially available bio-fungicides (6% Serenade ASO®, 1.5% Double Nickel 55®, 1% LifeGard WG®, 1% Xanthion® A, and 2% Subtilex®) (data not shown).

Example 17 Control of Turf Diseases

Biocontrol efficacy of MS2379 fermented in GB6-M31 medium (LPI-6592) was tested against four turf diseases—anthracnose (*Colletrotrichum cereale*), brown patch (*Rhizoctonia solani*), dollar spot (*Sclerotinia homeocarpa*), and *Pythium* blight (*Phythium* spp.) on established plots with turf diseases. Plots with anthracnose were artificially inoculated, while other plots were infected with natural inoculum.

Biocontrol treatments with MS2379 fermentations were sprayed directly onto established turf plots using rates of 1, 2.5, or 5 gal/acre every 14 days for 10 weeks. The treatments were arranged in a randomized complete block design with four blocks. The percent area with disease was estimated in each test plot four times during the test.

As shown in FIG. 20, MS2379 fermentations at all rates reduced the diseased area affected by the four diseases compared to the untreated control. The 5 gal/acre spray rate provided higher percent disease control than the lower rates (FIG. 20). Among the four diseases, MS2379 fermentations were most effective against dollar spot and *Pythium* blight. Even at a relatively low rate, the fermentation broths were effective against *Pythium* blight.

Example 18 Control of Foliar Diseases

The efficacy of MS2379 fermentations in two new media, GB6-M32 and GB6-M34 against foliar diseases in plants was compared with MS2379 in GB6-M31 medium (LPI-6592). The bacterial isolates were fermented with or without pH controlled (pH 5.8-6.0) during fermentation. For the pH-controlled fermentation, the pH was automatically controlled in the range of 5.6 to 6.0 during fermentation using sterile 1 N NaOH or 10% $H_2SO_4$ in sterile bottles. Samples were applied to detached canola leaves at a concentration of 10% (v/v) active ingredient. Four control treatments were included in the test: untreated control (untreated with pathogen only); the chemical fungicide Dyna-Shield® Fludioxonil (Loveland Products), active ingredient fludioxonil, at 0.06% (v/v); the commercial biological control Serenade ASO® (Bayer Crop Science), active ingredient *Bacillus subtilis* QST 713, at 3% (v/v); and mock-inoculated (without pathogen). The colony-forming-units (CFUs) of the MS2379 and Serenade ASO treatments were normalized at $3\times10^8$ endospores per ml. Treatments were arranged in a completely randomized design with five replicates per treatment. Uniform-sized true leaves from 10-day-old canola plants grown in the greenhouse were excised just prior to using and were thoroughly rinsed in reverse osmosis-purified water for 30 minutes.

In the experiment, a canola leaf was placed with the adaxial side up into 100 mm×15 mm Petri dishes containing 25 ml of water agar amended with 100 ppm benzyl amino purine. The petiole of each leaf was pushed into the agar medium. Each leaf was then uniformly sprayed with 100 µl of each treatment using an airbrush sprayer. The Petri dishes were left open for 1-2 hours until the treatments were completely dried on the leaf surfaces. Then, the center of each leaf was wounded twice using a sterile needle. Immediately after wounding, a 5 mm diameter agar plug, containing mycelia cut with a cork borer from the margins of 3-day-old cultures of *Botrytis cinerea*, was placed over the wounds in the center of each leaf. The plates were covered and placed in an illuminated incubator at 20° C. with 12-hour day/night light cycle for 7 days, when the maximum diameter (mm) of the gray mold lesion that developed on each leaf was measured and recorded. Lesion diameter data of all treatments except the mock-inoculated control was analyzed using AV statistical software.

As shown in FIG. 21, canola leaves treated with MS2379 fermented in GB6-M32 and GB6-M34 media and pH-controlled media had significantly smaller gray mold lesions compared to leaves treated with MS2379 fermented in GB6-M31 (LPI-6592), and Serenade.

MS2379 fermentation in GB6-M31 medium (LPI-6592) was evaluated in pathogen-inoculated greenhouse tests. The protocol included the treatments: LPI-6592 at 1 gal/A, 2.5 gal/A, and 5 gal/A; MS2379 with or without tank-mixing with Satori fungicide (active ingredient azoxystrobin); Satori alone; and a mock-inoculated control. The treatments were applied using a simulated in-furrow application technique if the disease was soil-borne or were sprayed directly on the test plants prior to pathogen inoculation for foliar pathogens.

Results of a greenhouse test using tomato plants inoculated with the soil-borne *Fusarium* wilt pathogen indicated that all levels of MS2379 alone and in combination with Satori significantly increased yield of tomato fruit from 50%-140% higher than the untreated control. The tank-mixed combination of 2.5 gal/acre LPI-6592 with 37 fl. oz./acre Satori produced significantly higher fruit yield (64%) than either 2.5 gal/acre LPI-6592 alone or Satori alone, which was evidence of synergy between the two components in the tank mix.

Efficacy against the foliar disease soybean rust evaluated on juvenile soybean plants in the greenhouse showed that all three levels (1, 2.5, 5 gal/acre) of LPI-6592 applied alone without Satori significantly reduced soybean rust pustule numbers by 88%-93%. Rust pustules were reduced by 97% when MS2379 was tank-mixed with Satori (14 fl. oz./A) or when Satori was used alone.

The efficacies of MS 2379 fermentation against plant diseases were also tested on other plants, e.g., zucchini squash and soybean. In one experiment, MS2379 fermented in GB6-M32 and GB6-M33 media at pH 5.5 and amended with BIT had significantly stronger efficacy than MS2379 in GB6-M31 against cucurbit powdery mildew on zucchini squash plants.

In a separate experiment, MS2379 fermented in GB6-M34 also showed improved efficacy against *Sclerotinia* stem rot of soybean compared to LPI-6592 (MS2379 in GB6-M31).

Table 18 summarized an exemplary and partial list of tests with fungal and oomycete plant diseases that MS 2379 showed efficacy against.

TABLE 18

| Pathogen | Disease | Crop(s) |
|---|---|---|
| *Botrytis cinerea* | Gray mold | strawberry, grape, soybean, canola |
| *Colletotrichum cereale* | Anthracnose | Poa grass |
| *Fusarium graminearum* | Head blight | wheat |
| *Fusarium graminearum* | Stalk rot | corn |
| *Fusarium oxysporum* | Fusarium wilt | tomato |
| *Fusarium virguliforme* | Sudden death syndrome | soybean |
| *Phakopsora pachyrhizi* | Soybean rust | soybean |
| *Phytophthora sojae* | Phytophthora root & stem rot | soybean |
| *Podosphaera xanthii* | Powdery mildew | zucchini squash |
| *Puccinia polysora* | Southern corn rust | corn |
| *Pythium irregulare* | Pythium damping off | soybean, wheat |
| *Pythium spp.* | Pythium blight | Stellar GLR Perennial Ryegrass |
| *Rhizoctonia solani* | Rhizoctonia root rot | soybean, wheat |
| *Rhizoctonia solani* | Brown patch | Alister Colonial Bentgrass |
| *Sclerotinia homeocarpa* | Dollar spot | Crenshaw Creeping Bentgrass |

TABLE 18-continued

| Pathogen | Disease | Crop(s) |
|---|---|---|
| *Sclerotinia sclerotiorum* | Sclerotinia stem rot | soybean, canola |
| *Uncinula necator* | Powdery mildew | grape |
| Various | Seed piece decay | potato |

Example 19 Concentrating the Whole Broth

The bacterial isolates were also concentrated to test efficacy against fungal diseases. Four (4) L of fermentation whole broth of MS2379 grown in GB6-M34 (pH 5.6-6.0 during fermentation) was poured into the container of KOCH demo-filtration unit equipped with PM-500 (Molecular weight cut-off is 500,000 Da) hollow fiber filtration cartridge. The ultrafiltration was carried out by turning on the circulation pump and adjusting the pressure on the permeate site at 1 bar. Filtration was stopped when the volume of permeate reached 2 L and the retentate was then collected. The permeate was further filtered using PM-5 (Molecular weight cut-off is 5,000 Da) hollow fiber filter until retentate was about 10 fold concentrated. All the retentates and permeates from the ultrafiltration were tested for CFU/ml, viscosity (cP) and protease activity. As shown in FIG. 22, the CFU was concentrated about 2 fold in the retentate (FIG. 22A) and PM5-retentate showed the highest protease activity (FIG. 22B).

Example 20 Formulation for Storage

To test the stability of bacterial fermentations after storage, the fermentations (MS2379 in GB6-M31) were added with 0.03% BIT (1,2-Benzisothiazolin-3-one) that was predissolved in propylene glycol. About 8 L preserved WB of MS2379 in GB6-M31 medium were weighed out and adjusted with 50% citric acid or IN NaOH to pH 6.5, 6.0, 5.5, 5.0, 4.5 within target pH+/−0.1. After addition of various formulation ingredients, the pH was readjusted if necessary. 200 ml WB formulation was added to 250 ml bottles in duplicates for each bottle of the same size. One set of sample was placed at 25° C. and another at 40° C. Table 19 summarizes the formulations and pHs for each sample. Two set of samples were with 0.5% propylene glycol with one of them used for freeze and thaw test. Bioprotector (from Lallemand) is an adjuvant which can be used for biological seed treatment or other functions.

TABLE 19

| Treatment # | WB, pH | Formulation |
|---|---|---|
| 1 | pH 6.5 | |
| 2 | pH 6.0 | |
| 3 | pH 5.5 | |
| 4 | pH 5.0 | |
| 5 | pH 4.5 | |
| 6 | pH 6.0 | 0.2% Minuge 400 |
| 7 | | 0.2% Acti-Gel 208 |
| 8 | | 0.5% Propylene glycol |
| 9 | | 0.5% Propyl glycol (for freeze-thaw experiment)* |
| 10 | | 0.3% Propyl gallate |
| 11 | | 0.2% Acti-Gel 208 + 0.5% Propylene glycol + 0.3% Propyl gallate |
| 12 | | 20% Bioprotector** |
| 13 | pH 5.0 | 0.2% Minuge 400 |
| 14 | | 0.2% Acti-Gel 208 |
| 15 | | 0.5% Propylene glycol |
| 16 | | 0.5% Propyl glycol (for freeze-thaw experiment)* |
| 17 | | 0.3% Propyl gallate |
| 18 | | 0.2% Acti-Gel 208 + 0.5% Propylene glycol + 0.3% Propyl gallate |
| 19 | | 20% Bioprotector** |

The CFUs of the formulated samples were measured at Day 0 (immediately after formulation), Day 30, and Day 60 during storage. As shown in FIGS. 23A and 23B, after two months of storage at room temperature, the decrease of CFUs were more significant for formulations at lower pH.

In another experiment, fermentation whole broth was adjusted to pH 5.5 and 5.0 respectively and added 0.03% BIT (1,2-Benzisothiazolin-3-on 3) as preservative. The formulations are shown in Table 20. As shown in FIG. 23C, the whole broth from all fermentations showed good CFU stability with BIT and adjusted pHs.

TABLE 20

| Treatment # | Fermentation WB | Formulation |
|---|---|---|
| 1 | GB6-M32 (26° C. throughout fermentation) | pH 5.5, 0.03% BIT |
| 2 | | pH 5.0, 0.03% BIT |
| 3 | GB6-M32 (Fermentation temperature increased to 35° C. at Day 3) | pH 5.5, 0.03% BIT |
| 4 | | pH 5.0, 0.03% BIT |
| 5 | GB6-M33 (26° C. throughout fermentation) | pH 5.5, 0.03% BIT |
| 6 | | pH 5.0, 0.03% BIT |
| 7 | GB6-M33 Fermentation temperature increased to 35° C. at Day 3) | pH 5.5, 0.03% BIT |
| 8 | | pH 5.0, 0.03% BIT |

EQUIVALENTS

The sample information is shown and it should be understood that although the present disclosure has been specifically disclosed by certain embodiments and optional features, modification, improvement, and variation of the disclosures embodied disclosed herein may be resorted to by those skilled in the art, and that such modifications, improvements, and variations are considered to be within the scope of this disclosure. The materials, methods, and examples provided here are representative of certain embodiments, are exemplary, and are not intended as limitations on the scope of the disclosure.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein.

In addition, where features or aspects of the disclosure are described in terms of Markush groups, those skilled in the art will recognize that the disclosure is also thereby described in terms of any individual member or subgroup of members of the Markush group.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as “have” and “has”), “including” (and any form of including, such as “includes” and “include”), or “containing” (and any form of containing, such as “contains” and “contain”) are inclusive or open-ended and do not exclude additional, unrecited elements or method steps.

Throughout this disclosure, various publications, patents, and published patent specifications are referenced by an identifying citation. All publications, patent applications, patents, and other references mentioned herein are expressly incorporated by reference in their entirety, to the same extent as if each were incorporated by reference individually. In case of conflict, the present specification, including definitions, will control.

Other embodiments are set forth in the following claims.

```
>MS2820_partial_16S_rRNA_gene
                                                                    SEQ ID NO. 1
GAGTTTGATCCTGGCTCAGGACGAACGCTGGCGGCGTGCCTAATACATGCAAGTCGAGCGGGGTTATGTAGA

AGCTTGCTTCTAAATAACCTAGCGGCGGACGGGTGAGTAACACGTAGGCAACCTGCCCACAAGACAGGGATA

ACTACCGGAAACGGTAGCTAATACCCGATACATCCTTTTCCTGCATGGGAGAGGGAGGAAAGACGGAGCAAT

CTGTCACTTGTGGATGGGCCTGCGGCGCATTAGCTAGTTGGTGGGGTAAAGGCCTACCAAGGCGACGATGCG

TAGCCGACCTGAGAGGGTGATCGGCCACACTGGGACTGAGACACGGCCCAGACTCCTACGGGAGGCAGCAG

TAGGGAATCTTCCGCAATGGGCGAAAGCCTGACGGAGCAACGCCGCGTGAGTGATGAAGGTTTTCGGATCG

TAAAGCTCTGTTGCCAGGGAAGAACGTCTTGTAGAGTAACTGCTACAAGAGTGACGGTACCTGAGAAGAAA

GCCCCGGCTAACTACGTGCCAGCAGCCGCGGTAATACGTAGGGGGCAAGCGTTGTCCGGAATTATTGGGCG

TAAAGCGCGCGCAGGCGGCTCTTTAAGTCTGGTGTTTAATCCCGAGGCTCAACTTCGGGTCGCACTGGAAA

CTGGGGAGCTTGAGTGCAGAAGAGGAGAGTGGAATTCCACGTGTAGCGGTGAAATGCGTAGAGATGTGGAG

GAACACCAGTGGCGAAGGCGACTCTCTGGGCTGTAACTGACGCTGAGGCGCGAAAGCGTGGGGAGCAAACA

GGATTAGATACCCTGGTAGTCCACGCCGTAAACGATGAATGCTAGGTGTTAGGGGTTTCGATACCCTTGGT

GCCGAAGTTAACACATTAAGCATTCCGCCTGGGGAGTACGGTCGCAAGACTGAAACTCAAAGGAATTGACG

GGGACCCGCACAAGCAGTGGAGTATGTGGTTTAATTCGAAGCAACGCGAAGAACCTTACCAGGTCTTGACA

TCCCTCTGACCGCTGTAGAGATATGGCTTTCCTTCGGGACAGAGGAGACAGGTGGTGCATGGTTGTCGTCA

GCTCGTGTCGTGAGATGTTGGGTTAAGTCCCGCAACGAGCGCAACCCTTATGCTTAGTTGCCAGCAGGTCA

AGCTGGG

>MS2712_partial_16S_rRNA_gene
                                                                    SEQ ID NO. 2
AGTCGAGCGGACAGATGGGAGCTTGCTCCCTGATGTTAGCGGCGGACGGGTGAGTAACACGTGGGTAACCT

GCCTGTAAGACTGGGATAACTCCGGGAAACCGGGGCTAATACCGGATGGTTGTCTGAACCGCATGGTTCAG

ACATAAAAGGTGGCTTCGGCTACCACTTACAGATGGACCCGCGGCGCATTAGCTAGTTGGTGAGGTAACGG

CTCACCAAGGCGACGATGCGTAGCCGACCTGAGAGGGTGATCGGCCACACTGGGACTGAGACACGGCCCAG

ACTCCTACGGGAGGCAGCAGTAGGGAATCTTCCGCAATGGACGAAAGTCTGACGGAGCAACGCCGCGTGAG

TGATGAAGGTTTTCGGATCGTAAAGCTCTGTTGTTAGGGAAGAACAAGTGCCGTTCAAATAGGGCGGCACC

TTGACGGTACCTAACCAGAAAGCCACGGCTAACTACGTGCCAGCAGCCGCGGTAATACGTAGGTGGCAAGC

GTTGTCCGGAATTATTGGGCGTAAAGGGCTCGCAGGCGGTTTCTTAAGTCTGATGTGAAAGCCCCCGGCTC

AACCGGGGAGGGTCATTGGAAACTGGGGAACTTGAGTGCAGAAGAGGAGAGTGGAATTCCACGTGTAGCGG

TGAAATGCGTAGAGATGTGGAGGAACACCAGTGGCGAAGGCGACTCTCTGGTCTGTAACTGACGCTGAGGA

GCGAAAGCGTGGGGAGCGAACAGGATTAGATACCCTGGTAGTCCACGCCGTAAACGATGAGTGCTAAGTGT

TAGGGGGTTTCCGCCCCTTAGTGCTGCAGCTAACGCATTAAGCACTCCGCCTGGGGAGTACGGTCGCAAGA

CTGAAACTCAAAGGAATTGACGGGGGCCCGCACAAGCGGTGGAGCATGTGGTTTAATTCGAAGCAACGCGA

AGAACCTTACCAGGTCTTGACATCCTCTGACAATCCTAGAGATAGGACGTCCCCTTCGGGGGCAGAGTGAC

AGGTGGTGCATGGTTGTCGTCAGCTCGTGTC
```

-continued

>MS2697_complete_16S_rRNA_gene

SEQ ID NO. 3

TTATCGGAGAGTTTGATCCTGGCTCAGGACGAACGCTGGCGGCGTGCCTAATACATGCAAGTCGAGCGGAC

AGATGGGAGCTTGCTCCCTGATGTTAGCGGCGGACGGGTGAGTAACACGTGGGTAACCTGCCTGTAAGACT

GGGATAACTCGGGAAACCGGGCTAATGATGGTTGTCTGAACCGCATGGTTCAGACATAAAAGGTGGCTTCG

GCTACCACTTACAGATGGACCCGCGGCGCATTAGCTAGTTGGTGAGGTAACGGCTCACCAAGGCGACGATG

CGTAGCCGACCTGAGAGGGTGATCGGCCACACTGGGACTGAGACACGGCCCAGACTCCTACGGGAGGCAGC

AGTAGGGAATCTTCCGCAATGGACGAAAGTCTGACGGAGCAACGCCGCGTGAGTGATGAAGGTTTTCGGAT

CGTAAAGCTCTGTTGTTAGGGAAGAACAAGTGCCGTTCAAATAGGGCGGCACCTTGACGGTACCTAACCAG

AAAGCCACGGCTAACTACGTGCCAGCAGCCGCGGTAATACGTAGGTGGCAAGCGTTGTCCGGAATTATTGG

GCGTAAAGGGCTCGCAGGCGGTTTCTTAAGTCTGATGTGAAAGCCCCCGGCTCAACCGGGGAGGGTCATTG

GAAACTGGGGAACTTGAGTGCAGAAGAGGAGAGTGGAATTCCACGTGTAGCGGTGAAATGCGTAGAGATGT

GGAGGAACACCAGTGGCGAAGGCGACTCTCTGGTCTGTAACTGACGCTGAGGAGCGAAAGCGTGGGGAGCG

AACAGGATTAGATACCCTGGTAGTCCACGCCGTAAACGATGAGTGCTAAGTGTTAGGGGGTTTCCGCCCCT

TAGTGCTGCAGCTAACGCATTAAGCACTCCGCCTGGGGAGTACGGTCGCAAGACTGAAACTCAAAGGAATT

GACGGGGGCCCGCACAAGCGGTGGAGCATGTGGTTTAATTCGAAGCAACGCGAAGAACCTTACCAGGTCTT

GACATCCTCTGACAATCCTAGAGATAGGACGTCCCCTTCGGGGGCAGAGTGACAGGTGGTGCATGGTTGTC

GTCAGCTCGTGTCGTGAGATGTTGGGTTAAGTCCCGCAACGAGCGCAACCCTTGA

TCTTAGTTGCCAGCATTCAGTTGGGCACTCTAAGGTGACTGCCGGTGACAAACCGGAGGAAGGTGGGGATG

ACGTCAAATCATCATGCCCCTTATGACCTGGGCTACACACGTGCTACAATGGACAGAACAAAGGGCAGCGA

AACCGCGAGGTTAAGCCAATCCCACAAATCTGTTCTCAGTTCGGATCGCAGTCTGCAACTCGACTGCGTGA

AGCTGGAATCGCTAGTAATCGCGGATCAGCATGCCGCGGTGAATACGTTCCCGGGCCTTGTACACACCGCC

CGTCACACCACGAGAGTTTGTAACACCCGAAGTCGGTGAGGTAACCTTTATGGAGCCAGCCGCCGAAGGTG

GGACAGATGATTGGGGTGAAGTCGTAACAAGGTAGCCGTATCGGAAGGTGCGGCTGGATCACCTCCTTT

>MS2681_partial_16S_rRNA_gene

SEQ ID NO. 4

AGTCGAGCGGACAGATGGGAGCTTGCTCCCTGATGTTAGCGGCGGACGGGTGAGTAACACGTGGGTAACCT

GCCTGTAAGACTGGGATAACTCCGGGAAACCGGGGCTAATACCGGATGGTTGTCTGAACCGCATGGTTCAG

ACATAAAAGGTGGCTTCGGCTACCACTTACAGATGGACCCGCGGCGCATTAGCTAGTTGGTGAGGTAACGG

CTCACCAAGGCGACGATGCGTAGCCGACCTGAGAGGGTGATCGGCCACACTGGGACTGAGACACGGCCCAG

ACTCCTACGGGAGGCAGCAGTAGGGAATCTTCCGCAATGGACGAAAGTCTGACGGAGCAACGCCGCGTGAG

TGATGAAGGTTTTCGGATCGTAAAGCTCTGTTGTTAGGGAAGAACAAGTGCCGTTCAAATAGGGCGGCACC

TTGACGGTACCTAACCAGAAAGCCACGGCTAACTACGTGCCAGCAGCCGCGGTAATACGTAGGTGGCAAGC

GTTGTCCGGAATTATTGGGCGTAAAGGGCTCGCAGGCGGTTTCTTAAGTCTGATGTGAAAGCCCCCGGCTC

AACCGGGGAGGGTCATTGGAAACTGGGGAACTTGAGTGCAGAAGAGGAGAGTGGAATTCCACGTGTAGCGG

TGAAATGCGTAGAGATGTGGAGGAACACCAGTGGCGAAGGCGACTCTCTGGTCTGTAACTGACGCTGAGGA

GCGAAAGCGTGGGGAGCGAACAGGATTAGATACCCTGGTAGTCCACGCCGTAAACGATGAGTGCTAAGTGT

TAGGGGGTTTCCGCCCCTTAGTGCTGCAGCTAACGCATTAAGCACTCCGCCTGGGGAGTACGGTCGCAAGA

CTGAAACTCAAAGGAATTGACGGGGGCCCGCACAAGCGGTGGAGCATGTGGTTTAATTCGAAGCAACGCGA

AGAACCTTACCAGGTCTTGACATCCTCTGACAATCCTAGAGATAGGACGTCCCCTTCGGGGGCAGAGTGAC

AGGTGGTGCATGGTTGTCGTC

-continued

>MS2658_partial_16S_rRNA_gene

SEQ ID NO. 5

AGTCGAGCGGACAGATGGGAGCTTGCTCCCTGATGTTAGCGGCGGACGGGTGAGTAACACGTGGGTAACCT

GCCTGTAAGACTGGGATAACTCCGGGAAACCGGGGCTAATACCGGATGGTTGTCTGAACCGCATGGTTCAG

ACATAAAAGGTGGCTTCGGCTACCACTTACAGATGGACCCGCGGCGCATTAGCTAGTTGGTGAGGTAACGG

CTCACCAAGGCGACGATGCGTAGCCGACCTGAGAGGGTGATCGGCCACACTGGGACTGAGACACGGCCCAG

ACTCCTACGGGAGGCAGCAGTAGGGAATCTTCCGCAATGGACGAAAGTCTGACGGAGCAACGCCGCGTGAG

TGATGAAGGTTTTCGGATCGTAAAGCTCTGTTGTTAGGGAAGAACAAGTGCCGTTCAAATAGGGCGGCACC

TTGACGGTACCTAACCAGAAAGCCACGGCTAACTACGTGCCAGCAGCCGCGGTAATACGTAGGTGGCAAGC

GTTGTCCGGAATTATTGGGCGTAAAGGGCTCGCAGGCGGTTTCTTAAGTCTGATGTGAAAGCCCCCGGCTC

AACCGGGGAGGGTCATTGGAAACTGGGGAACTTGAGTGCAGAAGAGGAGAGTGGAATTCCACGTGTAGCGG

TGAAATGCGTAGAGATGTGGAGGAACACCAGTGGCGAAGGCGACTCTCTGGTCTGTAACTGACGCTGAGGA

GCGAAAGCGTGGGGAGCGAACAGGATTAGATACCCTGGTAGTCCACGCCGTAAACGATGAGTGCTAAGTGT

TAGGGGGTTTCCGCCCCTTAGTGCTGCAGCTAACGCATTAAGCACTCCGCCTGGGGAGTACGGTCGCAAGA

CTGAAACTCAAAGGAATTGACGGGGGCCCGCACAAGCGGTGGAGCATGTGGTTTAATTCGAAGCAACGCGA

AGAACCTTACCAGGTCTTGACATCCTCTGACAATCCTAGAGATAGGACGTCCCCTTCGGGGGCAGA

>MS2652_partial_16S_rRNA_gene

SEQ ID NO. 6

AGTCGAGCGGACAGATGGGAGCTTGCTCCCTGATGTTAGCGGCGGACGGGTGAGTAACACGTGGGTAACCT

GCCTGTAAGACTGGGATAACTCCGGGAAACCGGGGCTAATACCGGATGGTTGTCTGAACCGCATGGTTCAG

ACATAAAAGGTGGCTTCGGCTACCACTTACAGATGGACCCGCGGCGCATTAGCTAGTTGGTGAGGTAACGG

CTCACCAAGGCGACGATGCGTAGCCGACCTGAGAGGGTGATCGGCCACACTGGGACTGAGACACGGCCCAG

ACTCCTACGGGAGGCAGCAGTAGGGAATCTTCCGCAATGGACGAAAGTCTGACGGAGCAACGCCGCGTGAG

TGATGAAGGTTTTCGGATCGTAAAGCTCTGTTGTTAGGGAAGAACAAGTGCCGTTCAAATAGGGCGGCACC

TTGACGGTACCTAACCAGAAAGCCACGGCTAACTACGTGCCAGCAGCCGCGGTAATACGTAGGTGGCAAGC

GTTGTCCGGAATTATTGGGCGTAAAGGGCTCGCAGGCGGTTTCTTAAGTCTGATGTGAAAGCCCCCGGCTC

AACCGGGGAGGGTCATTGGAAACTGGGGAACTTGAGTGCAGAAGAGGAGAGTGGAATTCCACGTGTAGCGG

TGAAATGCGTAGAGATGTGGAGGAACACCAGTGGCGAAGGCGACTCTCTGGTCTGTAACTGACGCTGAGGA

GCGAAAGCGTGGGGAGCGAACAGGATTAGATACCCTGGTAGTCCACGCCGTAAACGATGAGTGCTAAGTGT

TAGGGGGTTTCCGCCCCTTAGTGCTGCAGCTAACGCATTAAGCACTCCGCCTGGGGAGTACGGTCGCAAGA

CTGAAACTCAAAGGAATTGACGGGGGCCCGCACAAGCGGTGGAGCATGTGGTTTAATTCGAAGCAACGCGA

AGAACCTTACCAGGTCTTGACATCCTCTGACAATCCTAGAGATAGGACGTCCCCTTCGGGGGCAGAGTGAC

AGGTGGTGCATGGTTGTCGTCAGCTCGTGTC

>MS2414_partial_16S_rRNA_gene

SEQ ID NO. 7

ATCCTTTTCCTGCATGGGAGAAGGAGGAAAGACGGAGCAATCTGTCACTTGTGGATGGGCCTGCGGCGCAT

TAGCTAGTTGGTGGGGTAAAGGCCTACCAAGGCGACGATGCGTAGCCGACCTGAGAGGGTGATCGGCCACA

CTGGGACTGAGACACGGCCCAGACTCCTACGGGAGGCAGCAGTAGGGAATCTTCCGCAATGGGCGAAAGCC

TGACGGAGCAACGCCGCGTGAGTGATGAAGGTTTTCGGATCGTAAAGCTCTGTTGCCAGGGAAGAACGTCT

TGTAGAGTAACTGCTACAAGAGTGACGGTACCTGAGAAGAAAGCCCCGGCTAACTACGTGCCAGCAGCCGC

GGTAATACGTAGGGGGCAAGCGTTGTCCGGAATTATTGGGCGTAAAGCGCGCGCAGGCGGCTCTTTAAGTC

TGGTGTTTAATCCCGAGGCTCAACTTCGGGTCGCACTGGAAACTGGGGAGCTTGAGTGCAGAAGAGGAGAG

TGGAATTCCACGTGTAGCGGTGAAATGCGTAGAGATGTGGAGGAACACCAGTGGCGAAGGCGACTCTCTGG

-continued

GCTGTAACTGACGCTGAGGCGCGAAAGCGTGGGGAGCAAACAGGATTAGATACCCTGGTAGTCCACGCCGT

AAACGATGAATGCTAGGTGTTAGGGGTTTCGATACCCTTGGTGCCGAAGTTAACACATTAAGCATTCCGCC

TGGGGAGTACGGTCGCAAGACTGAAACTCAAAGGAATTGACGGGGACCCGCACAAGCAGTGGAGTATGTGG

TTTAATTCGAAGCAACGCGAAGAACCTTACCAGGTCTTGACATCCCTCTGACCGGTCTAGAGATAGACCTT

TCCTTCGGGACAGAGGAGACAGGTGGTGCATGGTTGTCGTCAGCTCGTGTCGTGAGATGTTGGGTTAAGTC

CCGCAACGAGCGCAACCCTTATGCTTAGTTGCCAGCAGGTCAAGCTGGGCACTCTAAGCAGACTGCCGGTG

ACAAACCGGAGGAAGGTGGGGATGACGTCAAATCATCATGCCCCTTATGACCTGGGCTACACACGTACTAC

AATGGCCGGTACAACGGGAAGCGAAATCGCGAGGTGGAGCCAATCCTAGAAAAGCCGGTCTCAGTTCGGAT

TGTAGGCTGCAACTCGCCTACATGAAGTCGGAATTGCTAGTAATCGCGGATCAGCATGCCGCGGTGAATAC

GTTCCCGGGTCTTGTACACACCGCCCGTCACACCACGAGAGTTTACAACACCCGAAGTCGGTGGGGTAACC

CGCAAGGGAGCCAGCCGCCGAAGGTGGGGTAGATGATTGGGGTGAAGTCGTAACAAGGTAGCCGTATCGGA

AGGTGCGGCTGGATCACCTCCTTTC

>MS2379_complete_16S_rRNA_gene

SEQ ID NO. 8

GAGTTTGATCCTGGCTCAGGACGAACGCTGGCGGCGTGCCTAATACATGCAAGTCGAGCGGGGTTATTTAG

AAGCTTGCTTCTAAATAACCTAGCGGCGGACGGGTGAGTAACACGTAGGCAACCTGCCCACAAGACAGGGA

TAACTACCGGAAACGGTAGCTAATACCCGATACATCCTTTTCCTGCATGGGAGAAGGAGGAAAGACGGAGC

AATCTGTCACTTGTGGATGGGCCTGCGGCGCATTAGCTAGTTGGTGGGGTAAAGGCCTACCAAGGCGACGA

TGCGTAGCCGACCTGAGAGGGTGATCGGCCACACTGGGACTGAGACACGGCCCAGACTCCTACGGGAGGCA

GCAGTAGGGAATCTTCCGCAATGGGCGAAAGCCTGACGGAGCAACGCCGCGTGAGTGATGAAGGTTTTCGG

ATCGTAAAGCTCTGTTGCCAGGGAAGAACGTCTTATAGAGTAACTGCTATAAGAGTGACGGTACCTGAGAA

GAAAGCCCCGGCTAACTACGTGCCAGCAGCCGCGGTAATACGTAGGGGGCAAGCGTTGTCCGGAATTATTG

GGCGTAAAGCGCGCGCAGGCGGCTCTTTAAGTCTGGTGTTTAATCCCGAGGCTCAACTTCGGGTCGCACTG

GAAACTGGGGAGCTTGAGTGCAGAAGAGGAGAGTGGAATTCCACGTGTAGCGGTGAAATGCGTAGAGATGT

GGAGGAACACCAGTGGCGAAGGCGACTCTCTGGGCTGTAACTGACGCTGAGGCGCGAAAGCGTGGGGAGCA

AACAGGATTAGATACCCTGGTAGTCCACGCCGTAAACGATGAATGCTAGGTGTTAGGGGTTTCGATACCCT

TGGTGCCGAAGTTAACACATTAAGCATTCCGCCTGGGGAGTACGGTCGCAAGACTGAAACTCAAAGGAATT

GACGGGGACCCGCACAAGCAGTGGAGTATGTGGTTTAATTCGAAGCAACGCGAAGAACCTTACCAGGTCTT

GACATCCCTCTGACCGCTGTAGAGATATGGCTTTCCTTCGGGACAGAGGAGACAGGTGGTGCATGGTTGTC

GTCAGCTCGTGTCGTGAGATGTTGGGTTAAGTCCCGCAACGAGCGCAACCCTTATGCTTAGTTGCCAGCAG

GTCAAGCTGGGCACTCTAAGCAGACTGCCGGTGACAAACCGGAGGAAGGTGGGGATGACGTCAAATCATCA

TGCCCCTTATGACCTGGGCTACACACGTACTACAATGGCCGGTACAACGGGAAGCGAAGCCGCGAGGTGGA

GCCAATCCTAGAAAAGCCGGTCTCAGTTCGGATTGCAGGCTGCAACTCGCCTGCATGAAGTCGGAATTGCT

AGTAATCGCGGATCAGCATGCCGCGGTGAATACGTTCCCGGGTCTTGTACACACCGCCCGTCACACCACGA

GAGTTTACAACACCCGAAGTCGGTGAGGTAACCGCAAGGGGCCAGCCGCCGAAGGTGGGGTAGATGATTGG

GGTGAAGTCGTAACAAGGTAGCCGTATCGGAAGGTGCGGCTGGATCACCTCCTTTC

>MS2335_partial_16S_rRNA_gene

SEQ ID NO. 9

AGTCGAGCGGACAGATGGGAGCTTGCTCCCTGATGTTAGCGGCGGACGGGTGAGTAACACGTGGGTAACCT

GCCTGTAAGACTGGGATAACTCCGGGAAACCGGGGCTAATACCGGATGGTTGTCTGAACCGCATGGTTCAG

ACATAAAAGGTGGCTTCGGCTACCACTTACAGATGGACCCGCGGCGCATTAGCTAGTTGGTGAGGTAACGG

CTCACCAAGGCGACGATGCGTAGCCGACCTGAGAGGGTGATCGGCCACACTGGGACTGAGACACGGCCCAG

ACTCCTACGGGAGGCAGCAGTAGGGAATCTTCCGCAATGGACGAAAGTCTGACGGAGCAACGCCGCGTGAG

-continued

TGATGAAGGTTTTCGGATCGTAAAGCTCTGTTGTTAGGGAAGAACAAGTGCCGTTCAAATAGGGCGGCACC

TTGACGGTACCTAACCAGAAAGCCACGGCTAACTACGTGCCAGCAGCCGCGGTAATACGTAGGTGGCAAGC

GTTGTCCGGAATTATTGGGCGTAAAGGGCTCGCAGGCGGTTTCTTAAGTCTGATGTGAAAGCCCCCGGCTC

AACCGGGGAGGGTCATTGGAAACTGGGGAACTTGAGTGCAGAAGAGGAGAGTGGAATTCCACGTGTAGCGG

TGAAATGCGTAGAGATGTGGAGGAACACCAGTGGCGAAGGCGACTCTCTGGTCTGTAACTGACGCTGAGGA

GCGAAAGCGTGGGGAGCGAACAGGATTAGATACCCTGGTAGTCCACGCCGTAAACGATGAGTGCTAAGTGT

TAGGGGGTTTCCGCCCCTTAGTGCTGCAGCTAACGCATTAAGCACTCCGCCTGGGGAGTACGGTCGCAAGA

CTGAAACTCAAAGGAATTGACGGGGGCCCGCACAAGCGGTGGAGCATGTGGTTTAATTCGAAGCAACGCGA

AGAACCTTACCAGGTCTTGACATCCTCTGACAATCCTAGAGATAGGACGTCCCCTTCGGGGGC

>MS1479_complete_16S_rRNA_gene

SEQ ID NO. 10

GAGTTTGATCCTGGCTCAGGACGAACGCTGGCGGCGTGCCTAATACATGCAAGTCGAGCGGGATTGTTTAG

AAGCTTGCTTCTAAACAATCTAGCGGCGGACGGGTGAGTAACACGTAGGCAACCTGCCCACAAGACAGGGA

TAACTACCGGAAACGGTAGCTAATACCCGATACATCCTTTTCCTGCATGGGAGAAGGAGGAAAGACGGAGC

AATCTGTCACTTGTGGATGGGCCTGCGGCGCATTAGCTAGTTGGTGGGGTAAAGGCCTACCAAGGCGACGA

TGCGTAGCCGACCTGAGAGGGTGATCGGCCACACTGGGACTGAGACACGGCCCAGACTCCTACGGGAGGCA

GCAGTAGGGAATCTTCCGCAATGGGCGAAAGCCTGACGGAGCAACGCCGCGTGAGTGATGAAGGTTTTCGG

ATCGTAAAGCTCTGTTGCCAGGGAAGAACGTCTTGTAGAGTAACTGCTACAAGAGTGACGGTACCTGAGAA

GAAAGCCCCGGCTAACTACGTGCCAGCAGCCGCGGTAATACGTAGGGGGCAAGCGTTGTCCGGAATTATTG

GGCGTAAAGCGCGCGCAGGCGGCTCTTTAAGTCTGGTGTTTAATCCCGAGGCTCAACTTCGGGTCGCACTG

GAAACTGGGGAGCTTGAGTGCAGAAGAGGAGAGTGGAATTCCACGTGTAGCGGTGAAATGCGTAGAGATGT

GGAGGAACACCAGTGGCGAAGGCGACTCTCTGGGCTGTAACTGACGCTGAGGCGCGAAAGCGTGGGGAGCA

AACAGGATTAGATACCCTGGTAGTCCACGCCGTAAACGATGAATGCTAGGTGTTAGGGGTTTCGATACCCT

TGGTGCCGAAGTTAACACATTAAGCATTCCGCCTGGGGAGTACGGTCGCAAGACTGAAACTCAAAGGAATT

GACGGGGACCCGCACAAGCAGTGGAGTATGTGGTTTAATTCGAAGCAACGCGAAGAACCTTACCAGGTCTT

GACATCCCTCTGACCGGTCTAGAGATAGACCTTTCCTTCGGGACAGAGGAGACAGGTGGTGCATGGTTGTC

GTCAGCTCGTGTCGTGAGATGTTGGGTTAAGTCCCGCAACGAGCGCAACCCTTATGCTTAGTTGCCAGCAG

GTCAAGCTGGGCACTCTAAGCAGACTGCCGGTGACAAACCGGAGGAAGGTGGGGATGACGTCAAATCATCA

TGCCCCTTATGACCTGGGCTACACACGTACTACAATGGCCGGTACAACGGGAAGCGAAATCGCGAGGTGGA

GCCAATCCTAGAAAAGCCGGTCTCAGTTCGGATTGTAGGCTGCAACTCGCCTACATGAAGTCGGAATTGCT

AGTAATCGCGGATCAGCATGCCGCGGTGAATACGTTCCCGGGTCTTGTACACACCGCCCGTCACACCACGA

GAGTTTACAACACCCGAAGTCGGTGGGGTAACCCGCAAGGGAGCCAGCCGCCGAAGGTGGGGTAGATGATT

GGGGTGAAGTCGTAACAAGGTAGCCGTATCGGAAGGTGCGGCTGGATCACCTCCTTTC

>MS0633_partial_16S_rRNA_gene

SEQ ID NO. 11

AGTCGAGCGGACAGATGGGAGCTTGCTCCCTGATGTTAGCGGCGGACGGGTGAGTAACACGTGGGTAACCT

GCCTGTAAGACTGGGATAACTCCGGGAAACCGGGGCTAATACCGGATGGTTGTTTGAACCGCATGGTTCAG

ACATAAAAGGTGGCTTCGGCTACCACTTACAGATGGACCCGCGGCGCATTAGCTAGTTGGTGAGGTAACGG

CTCACCAAGGCGACGATGCGTAGCCGACCTGAGAGGGTGATCGGCCACACTGGGACTGAGACACGGCCCAG

ACTCCTACGGGAGGCAGCAGTAGGGAATCTTCCGCAATGGACGAAAGTCTGACGGAGCAACGCCGCGTGAG

TGATGAAGGTTTTCGGATCGTAAAGCTCTGTTGTTAGGGAAGAACAAGTGCCGTTCAAATAGGGCGGCACC

TTGACGGTACCTAACCAGAAAGCCACGGCTAACTACGTGCCAGCAGCCGCGGTAATACGTAGGTGGCAAGC

-continued

GTTGTCCGGAATTATTGGGCGTAAAGGGCTCGCAGGCGGTTTCTTAAGTCTGATGTGAAAGCCCCCGGCTC

AACCGGGGAGGGTCATTGGAAACTGGGGAACTTGAGTGCAGAAGAGGAGAGTGGAATTCCACGTGTAGCGG

TGAAATGCGTAGAGATGTGGAGGAACACCAGTGGCGAAGGCGACTCTCTGGTCTGTAACTGACGCTGAGGA

GCGAAAGCGTGGGGAGCGAACAGGATTAGATACCCTGGTAGTCCACGCCGTAAACGATGAGTGCTAAGTGT

TAGGGGGTTTCCGCCCCTTAGTGCTGCAGCTAACGCATTAAGCACTCCGCCTGGGGAGTACGGTCGCAAGA

CTGAAACTCAAAGGAATTGACGGGGGCCCGCACAAGCGGTGGAGCATGTGGTTTAATTCGAAGCAACGCGA

AGAACCTTACCAGGTCTTGACATCCTCTGACAATCCTAGAGATAGGACGTCCCCTTCGGGGGCAGAGTGAC

AGGTGGTGCAT

>MS2820_complete_gyrB_gene

SEQ ID NO. 12

CTACTCTACGTATTCCGTGAAATCTACGTTTTCCACGATCCAGCGTTTGCGCGGATCCACCTTATCACCCA

TCAAAGTGGACACCCTACGTTCAGCCTTGGCTGCATCCTCTATCTGAACGCGTAACAAGGTGCGTGAATCG

GGATTCATCGTTGTTTCCCATAACTGATCAGGGTTCATTTCCCCAAGTCCTTTATAGCGCTGAAGCTCAAA

ATTCCGTCCAAATTCTTTTAAATAATTATCAAGCTGCTCGTCAGTCCAAGCATAACGCACCGTTTCGAGCT

TACCCGACTTTCGAGTTATTTTATACAATGGCGGTTGAGCAATAAATATGCGTCCTGCATCAATAAGCTCT

TTCATGTACCGATAAAAGAACGTCAACAACAGCACTTGAATGTGCGCACCATCTGTGTCTGCATCGGTCAT

AATGATGATTTTGGAATAATTGCTGTCTTCCAGCGAAAACTCTGTTCCTACCCCCGCACCAATAGCTGCTG

TAATAGCACGGTACTCATCATTCTTCATAATATCCGCCAGTTTGGATTTCTCCGGATTCATCGGCTTACCC

TTTAGCGGTAAGATGGCCTGAATTTTGGAATCCCGTCCCTGCTTGGCTGATCCTCCAGCCGAATCGCCTTC

CACAATAAACAACTCATTACGTGTAAAATCCTTGGACTGCGCAGGCGACAGTTTACCATTCAAATTGGAAC

TTTCACTGCGCTTTTTACCGGAACGCATCTCATCCCGAGCTTTACGTGCAGCTTCACGCGCTCTGGATGCT

TGAACTGCCTTCTTGATCAAAGTTTGTGCTATCTGCGGATTTTCTTCCAAAAAACGCTGCATCTGCTCAGA

TACGATGGCATCCACTGTACTCCGTGCCGAAGCGCTACCCAGTTGATCCTTTGTCTGACCGACAAATTCAA

CCTCAGCCATCTTGACACTGATTACAACCATCATGCCCTCACGTAGATCGTTGCCCTCCAAGTTTTTATCC

TTTTCTTTCAACATCACCGTTTTCCGGGCATAGTCGTTCATGACACGAGTGTAAGCGGTTTTGAATCCCGT

TTCATGCGTACCTCCGCCACGTGTCGGAATGGAGTTAACGAACGAAGCAATCGTCTCTGTATAACCCGCAT

TGTACTGGATGGCAATCTCTACTTCAATGTCTTCTTTCTCGGCATTAAAGTGAATAACGTCATGCAGCACA

TCCTTGCCCTCATTCAGAAAAGCAACAAACTGACTTGCGCCACCCTCATAAAAATACTCATCTGACTTTCC

GCTGCGTTCGTCTTTAAGTTGAATACGAAGGCCCGAATTTAGAAAAGCAATTTCCTGAAGGCGCTCAGCCA

ACGTATCGTAGTTAAAATGAATGCCTGCTTGAAAAACACGAATATCCGGTTTAAATGTAATTTTCGAGCCC

GTCTTGTTAGTATTGCCCAGCACTTCAAGGCCTGTGGTCGGTTCCCCGACATGCTCCACGCCCTTCTTGTC

CTGCCAATATTCAAACCGCTGACGGTGAATCTTGCCGTCCCGGTAAATTTCTACTTCAAGCCATTCCGAAA

GAGCGTTCGTTACAGATGCACCTACACCGTGCAGACCCCCGGACTTTTTATATCCCGAACCGCCAAACTTG

CCTCCGGCGTGCAAAATGGTGAATACAACCTGAGGCGTAGGAATCCCCGTTTTGTGCATTCCTGTAGGAAT

ACCGCGCCCGTTGTCTGATACCGTAATGGAACCGTCCTTATGCATTGTAATATCAATGCGAGAGCAAAACT

TGGCGAGATGTTCATCCACCGCGTTGTCTACAATTTCCCATACCAAATGATGCAGCCCCGAAGAACTGGTG

CTCCCGATGTACATGCCCGGCCGTTTGCGAACTGCCACAAGCCCTTCGAGCACTTGAATGTCGTCCGCGCC

ATATTCTGAAGCTCCGCTTTGTGTGCCGGACGCTCCCGCAGACAAGTCGATTTTGTCGACCAT

>MS2712_partial_gyrB_gene

SEQ ID NO. 13

GACCGGAACGATTACGCACTTCGTTCCGGATCCGGAAATCTTCAAAGAAACAACCGTATACGACTATGATC

TGCTTTCAAACCGTGTCCGGGAATTGGCCTTCCTGACAAAAGGCGTAAACATCACGATTGAAGACAAACGT

GAAGGACAAGAACGGAAAAACGAGTACCACTACGAAGGCGGAATCAAAAGCTATGTTGAGTACTTAAACCG

-continued

TTCCAAAGAAGTCGTTCATGAAGAGCCGATTTATATCGAAGGCGAGAAAGACGGCATAACGGTTGAAGTTG

CATTGCAATACAACGACAGCTATACAAGCAATATTTATTCTTTCACGAATAATATCAACACATACG

>MS2697_complete_gyrB_gene

SEQ ID NO. 14

ATGGAACAGCAGCAAAATAGTTATGATGAGAATCAGATACAGGTATTAGAAGGTTTGGAAGCTGTTCGAAA

GAGACCGGGGATGTACATCGGATCAACTAACAGCAAAGGCCTTCACCACTTGGTGTGGGAAATCGTCGACA

ACAGTATTGACGAAGCCCTGGCCGGTTATTGTACAGATATTAACATCGAGATTGAAAAAGATAACAGCATT

ACCGTTAAGGACAACGGGCGCGGCATTCCGGTCGGTATCCAGGAGAAGATGGGCCGCCCTGCGGTTGAAGT

CATCATGACCGTTCTCCACGCCGGCGGTAAATTTGACGGAAGCGGATATAAAGTATCCGGCGGTCTTCACG

GTGTAGGGGCGTCTGTCGTAAACGCCTTGTCGACCACTCTTGACGTTACGGTTCATCGTGACGGAAAAATC

CACTATCAGGCGTACGAGCGCGGTGTACCTGTGGCCGATCTTGAAGTGATCGGTGATACTGATAAGACCGG

AACGATTACGCACTTCGTTCCGGATCCGGAAATTTTCAAAGAAACAACCGTATACGACTATGATCTGCTTT

CAAACCGTGTCCGGGAATTGGCCTTCCTGACAAAAGGCGTAAACATCACGATTGAAGACAAACGTGAAGGA

CAAGAACGGAAAAACGAGTACCACTACGAAGGCGGAATCAAAAGCTATGTTGAGTACTTAAACCGTTCCAA

AGAAGTCGTTCATGAAGAGCCGATTTATATCGAAGGCGAGAAAGACGGCATAACGGTTGAAGTTGCATTGC

AATACAACGACAGCTATACAAGCAATATTTATTCTTTCACGAATAATATCAACACATACGAAGGCGGCACG

CACGAGGCCGGATTTAAAACCGGTCTGACCCGTGTCATAAACGACTATGCAAGAAGAAAAGGGATTTTCAA

AGAAAATGATCCGAATTTAAGCGGGGATGATGTGAGAGAAGGGCTGACTGCCATTATTTCAATTAAGCACC

CTGATCCGCAATTCGAAGGTCAGACGAAAACGAAGCTCGGCAACTCCGAAGCGAGAACGATCACTGATACG

CTGTTTTCTTCTGCGCTGGAAACATTCCTTCTTGAAAATCCGGACTCAGCCCGCAAAATCGTTGAAAAAGG

TTTAATGGCCGCAAGAGCGCGGATGGCAGCGAAAAAAGCGCGGGAATTGACCCGCCGCAAAAGTGCGCTTG

AGATTTCCAATCTGCCGGGCAAACTGGCGGACTGTTCTTCTAAAGATCCGAGCATTTCCGAGCTGTATATC

GTAGAGGGTGACTCTGCGGGCGGATCAGCGAAACAGGGACGGGACCGTCATTTCCAAGCCATTCTGCCGCT

GCGCGGTAAGATTCTGAACGTTGAGAAAGCCAGACTTGATAAGATTCTCTCAAACAATGAGGTCAGATCAA

TGATCACGGCCCTCGGAACAGGAATCGGAGAAGATTTTAATCTTGAAAAAGCGCGTTATCATAAAGTGGTC

ATCATGACGGATGCCGATGTTGACGGCGCCCACATCAGAACGCTTTTATTAACGTTCTTCTACAGATACAT

GCGGGAAATCATCGAAAACGGCTATGTCTACATTGCCCAGCCGCCGCTTTATAAAGTGCAGCAGGGAAAAC

GGGTGGAATACGCTTATAACGATAAGCAGCTTGATGAGCTGTTAAAAGAGCTTCCGCAATCACCTAAGCCC

GGCCTCCAGCGTTATAAAGGTCTTGGAGAAATGAACGCGACTCAGCTTTGGGAAACGACAATGGACCCTGC

GACCAGAACGCTTCTGCAAGTCAATCTTGAAGATGCAATGGACGCTGACGAGACTTTTGAAATGCTGATGG

GTGACAAAGTAGAACCGCGGAGAAACTTCATAGAAGCAAACGCCAGATACGTGAAAAATCTTGATATTTAA

>MS2681_partial_gyrB_gene

SEQ ID NO. 15

TCCTGACAAAAGGCGTAAACATCACGATTGAAGACAAACGTGAAGGACAAGAACGGAAAAACGAGTACCAC

TACGAAGGCGGAATCAAAAGCTATGTTGAGTACTTAAACCGTTCCAAAGAAGTCGTTCATGAAGAGCCGAT

TTATATCGAAGGCGAGAAAGACGGCATAACGGTTGAAGTTGCATTGCAATACAACGACAGCTATACAAGCA

ATATTTATTCTTTCACGAATAATATCAACACATACGAAGGCG

>MS2658_partial_gyrB_gene

SEQ ID NO. 16

CACGGTGTAGGGGCATCTGTCGTAAACGCCTTGTCGACCACTCTTGACGTTACGGTTCATCGTGACGGAAA

AATCCACTATCAGGCGTACGAGCGCGGTGTACCTGTGGCCGATCTTGAAGTGATCGGTGATACTGATAAGA

CCGGAACGATTACGCACTTCGTTCCGGATCCGGAAATCTTCAAAGAAACAATCGTATACGACTATGATCTG

CTTTCAAACCGTGTCCGGGAATTGGCCTTCCTGACAAAAGGCGTAAACATCACGATTGAAGACAAACGTGA

-continued

AGGACAAGAACGGAAAAACGAGTACCACTACGAAGGCGGAATCAAAAGCTATGTTGAGTACTTAAACCGTT

CCAAAGAAGTCGTTCATGAAGAGCCGATTTATATCGAAGGCGAGAAAGACGGCATAACGGTTGAAGTTGCA

TTGCAATACAACGACAGCTATACAAGCAATATTTATTCTTTCACGAATAATATCAACACATACGAAGGC

>MS2414_complete_gyrB_gene

SEQ ID NO. 17

CTACTCTACGTATTCCGTGAAATCTACGTTTTCCACGATCCAGCGCTTGCGCGGATCCACCTTATCACCCA

TCAAAGTGGACACCCTGCGTTCAGCCTTGGCTGCATCCTCTATCTGAACGCGTAACAAGGTGCGTGAATCG

GGATTCATCGTTGTTTCCCATAACTGATCAGGGTTCATTTCCCCAAGTCCTTTATAGCGCTGAAGCTCAAA

ATTTCGTCCAAATTCTTTTAAATAATTATCAAGCTGCTCGTCAGTCCAAGCATAACGCACCGTTTCGAGCT

TACCCGACTTTCGAGTTATTTTATACAATGGCGGTTGAGCAATAAATATGCGTCCTGCATCAATAAGCTCT

TTCATGTACCGATAAAAGAACGTCAACAACAGCACTTGAATGTGCGCACCATCTGTATCTGCATCGGTCAT

AATGATGATTTTGGAATAATTGCTGTCTTCCAGCGAAAACTCTGTTCCTACTCCCGCACCAATAGCTGCTG

TAATAGCACGGTACTCATCATTCTTCATAATATCCGCCAGTTTGGATTTTTCCGGATTCATCGGCTTGCCC

TTTAGCGGCAATATGGCCTGAATTTTGGAATCCCGTCCCTGCTTGGCTGAACCTCCAGCCGAATCGCCTTC

CACAATAAACAACTCATTACGTGTAAAATCCTTGGACTGCGCAGGCGACAGTTTACCATTCAAATTGGAAC

TTTCACTGCGCTTTTTACCGGAACGCATCTCATCTCGAGCTTTACGTGCAGCTTCACGCGCTCTGGATGCT

TGAACTGCCTTCTTGATCAAAGTTTGTGCTATCTGCGGATTTTCTTCCAAAAAACGCTGCATCTGCTCAGA

TACGATGGCATCCACTGTACTCCGTGCCGAAGCGCTACCCAGCTGATCCTTTGTCTGGCCGACAAATTCAA

CTTCAGCCATTTTGACACTGATTACAGCCATCATGCCCTCACGTAGATCGTTGCCCTCCAAGTTTTTATCC

TTTTCTTTCAACATCACCGTTTTGCGCGCATAGTCGTTCATGACACGAGTGTAAGCGGTTTTGAATCCCGT

TTCATGCGTACCTCCGCCACGTGTCGGAATGGAGTTAACGAACGAAGCAATCGTCTCTGTATAACCAGCAT

TGTACTGGATGGCAATCTCTACTTCAATGTCTTCTTTCTCGGCATTAAAGTGAATAACGTCATGTAGCACA

TCCTTGCCCTCATTCAGAAAAGCAACAAACTGACTTGCGCCACCCTCATAAAAATACTCATCTGACTTTCC

GCTGCGTTCGTCTTTAAGTTGAATACGAAGGCCCGAATTTAGAAAAGCAATTTCCTGAAGGCGCTCAGCCA

ACGTATCGTAGTTAAAATGAATGCCTGCCTGAAAAACACGAATATCCGGTTTAAATGTAATTTTCGAGCCC

GTCTTGTTAGTATTGCCCAGCACTTCAAGGCCTGTGGTCGGTTCTCCGACATGCTCCACGCCCTTCTTGTC

CTGCCAATATTCAAACCGCTGACGGTGAATCTTGCCGTCCCGGTAAATTTCTACTTCAAGCCATTCCGAAA

GAGCGTTCGTTACAGACGCACCTACACCGTGCAGACCCCCGGACTTTTTATATCCCGAACCGCCAAACTTA

CCTCCGGCGTGCAAAATGGTGAATACAACCTGAGGCGTAGGAATTCCCGTTTTGTGCATTCCTGTAGGAAT

ACCGCGCCCGTTGTCTGATACTGTAACGGAACCGTCCTTATGCATTGTAATATCAATGCGAGAGCAAAACT

TGGCGAGATGTTCATCCACCGCGTTGTCTACAATTTCCCATACCAAATGATGCAGTCCCGAAGAACTGGTG

CTCCCGATGTACATGCCCGGCCGTTTGCGAACTGCCACAAGCCCTTCGAGCACTTGAATGTCGTCCGCGCC

ATATTCTGAAGCTCCGCTTTGTGTGCCGGATACTCCCGCAGACAAGTCGATTTTGTCGACCAT

>MS2379_complete_gyrB_gene

SEQ ID NO. 18

CTACTCTACGTATTCCGTGAAATCCACGTTTTCCACGATCCAGCGCTTACGTGGATCTACCTTGTCACCCA

TCAATGTGGACACACGGCGTTCAGCTTTGGCAGCATCCTCAATTTGAACGCGCAACAGGGTGCGTGATTCG

GGATTCATTGTCGTTTCCCATAACTGATCAGGATTCATCTCCCCGAGTCCTTTATAACGTTGAAGCTCAAA

ATTCCGTCCAAATTCTTTTAGGTAATTATCAAGCTGCTCGTCAGTCCAGGCATAACGAACCGTTTCGAGCT

TACCCGACTTGCGGGTTATTTTATACAATGGCGGCTGAGCAATAAATATGCGTCCTGCATCAATGAGTTCT

TTCATGTACCGATAAAAGAACGTCAACAACAGTACTTGAATGTGCGCGCCGTCCGTATCTGCGTCGGTCAT

AATGATGATTTTGGAATAATTGCTGTCTTCCAGCGAGAACTCTGTTCCTACCCCCGCGCCAATCGCTGCCG

TAATAGCACGGTACTCATCATTTTTCATAATATCGGCAAGCTTTGACTTTTCCGGATTCATCGGCTTGCCC

-continued

TTTAACGGTAAAATAGCCTGGATCTTGGAATCTCGACCCTGTTTGGCCGATCCTCCCGCCGAATCGCCTTC

CACGATAAATAATTCATTACGTGTAAAATCTTTAGATTGCGCAGGCGACAGCTTACCATTCAAATTAGAAC

TTTCACTGCGCTTCTTGCCAGAACGCATTTCGTCCCGAGCCTTACGCGCAGCTTCACGTGCTTTGGACGCT

TGAACTGCCTTTTTAATCAAAGTTTGCGCAATCTGTGGATTTTCTTCCAAGAAACGCTGCATCTGTTCAGA

TACGATGGCATCCACTGTACTTCGTGCCGAAGCACTCCCCAGCTGATCTTTTGTCTGACCGACAAATTCAA

CCTCAGCCATCTTGACACTGATTACAGCCATCATGCCCTCACGTAGATCGTTACCCTCCAGGTTTTTATCC

TTTTCCTTCAACAGCGCTGTTTTGCGTGCATAGTCATTCATCACACGAGTGTAAGCGGTTTTGAAGCCTGT

TTCATGCGTTCCCCCGCCACGTGTTGGAATGGAGTTAACGAACGAAGCAATCGTCTCTGTGTAACCAGCAT

TGTATTGGATGGCAATCTCTACTTCAATGTCCTCTTTCTCAGCATTAAAGTGAATAACATCATGCAGTACA

TCCTTGCCCTCATTCAAAAAAGCAACAAACTGACTCGCTCCACCCTCATAATAATATTCATCTGACTTTCC

ACTGCGTTCGTCTTTAAGCTGAATACGAAGGCCGGAATTCAGAAAGGCAATTTCCTGAAGGCGCTCAGCCA

GTGTATCATAGTTAAAATGGATGCCTGACTGAAAAACGCGAATATCCGGTTTAAATGTAACTTTTGAGCCC

GTCTTGTTAGTATTGCCCAGCACTTCAAGGCCTGTGGTCGGTTCACCGACATGCTCCACGCCCTTCTTGTC

CTGCCAATATTCGAACCGCTGACGGTGAATCTTGCCGTCCCGGTAGATTTCCACTTCAAGCCATTCCGAAA

GAGCGTTCGTTACAGACGCACCTACCCCATGCAGACCCCCGGACTTTTTATATCCCGAACCGCCAAACTTA

CCTCCGGCGTGCAAAATGGTGAATACAACTTGAGGCGTAGGAATTCCCATTTTATGCATTCCCGTAGGAAT

ACCGCGCCCGTTGTCTGATACTGTAATAGAGCCGTCCTTATGCATTGTGATATCAATGCGAGAGCAAAACT

TGGCAAGATGTTCATCCACCGCGTTGTCTACAATTTCCCATACCAAATGATGCAGTCCCGAAGAACTGGTG

CTCCCGATGTACATGCCCGGCCGTTTGCGAACTGCCACAAGCCCTTCGAGCACTTGAATGTCGTCCGCGCC

ATATTCTGAAGCTCCGTTCTGTGTACCGGAAGCTCCCGCAGACAAGTCGATTTTGTCGACCAT

>MS2335_partial_gyrB_gene

SEQ ID NO. 19

TCTTCAAAGAAACAATCGTATACGACTATGATCTGCTTTCAAACCGTGTCCGGGAATTGGCCTTCCTGACA

AAAGGCGTAAACATCACGATTGAAGACAAACGTGAAGGACAAGAACGGAAAAACGAGTACCACTACGAAGG

CGGAATCAAAAGCTATGTTGAGTACTTAAACCGTTCCAAAGAAGTCGTTCATGAAGAGCCGATTTATATCG

AAGGCGAGAAAGACGGCATAACGGTTGAAGTTGCATTGCAATACAACGACAGCTATACAAGCAATATTTAT

TCTTTCACGAATAATATCAACACATACG

>MS1479_complete_gyrB_gene

SEQ ID NO. 20

CTACTCTACGTATTCCGTGAAATCTACGTTTTCCACGATCCAGCGCTTGCGCGGATCCACCTTATCACCCA

TCAAAGTGGACACCCTGCGTTCAGCCTTGGCTGCATCCTCTATCTGAACGCGTAACAAGGTGCGTGAATCG

GGATTCATCGTTGTTTCCCATAACTGATCAGGGTTCATTTCCCCAAGTCCTTTATAGCGCTGAAGCTCAAA

ATTTCGTCCAAATTCTTTTAAATAATTATCAAGCTGCTCGTCAGTCCAAGCATAACGCACCGTTTCGAGCT

TACCCGACTTTCGAGTTATTTTATACAATGGCGGTTGAGCAATAAATATGCGTCCTGCATCAATAAGCTCT

TTCATGTACCGATAAAAGAACGTCAACAACAGCACTTGAATGTGCGCACCATCTGTATCTGCATCGGTCAT

AATGATGATTTTGGAATAATTGCTGTCTTCCAGCGAAAACTCTGTTCCTACTCCCGCACCAATAGCTGCTG

TAATAGCACGGTACTCATCATTCTTCATAATATCCGCCAGTTTGGATTTTTCCGGATTCATCGGCTTGCCC

TTTAGCGGCAATATGGCCTGAATTTTGGAATCCCGTCCCTGCTTGGCTGAACCTCCAGCCGAATCGCCTTC

CACAATAAACAACTCATTACGTGTAAAATCCTTGGACTGCGCAGGCGACAGTTTACCATTCAAATTGGAAC

TTTCACTGCGCTTTTTACCGGAACGCATCTCATCTCGAGCTTTACGTGCAGCTTCACGCGCTCTGGATGCT

TGAACTGCCTTCTTGATCAAAGTTTGTGCTATCTGCGGATTTTCTTCCAAAAAACGCTGCATCTGCTCAGA

TACGATGGCATCCACTGTACTCCGTGCCGAAGCGCTACCCAGCTGATCCTTTGTCTGGCCGACAAATTCAA

-continued

CTTCAGCCATTTTGACACTGATTACAGCCATCATGCCCTCACGTAGATCGTTGCCCTCCAAGTTTTTATCC

TTTTCTTTCAACATCACCGTTTTGCGCGCATAGTCGTTCATGACACGAGTGTAAGCGGTTTTGAATCCCGT

TTCATGCGTACCTCCGCCACGTGTCGGAATGGAGTTAACGAACGAAGCAATCGTCTCTGTATAACCAGCAT

TGTACTGGATGGCAATCTCTACTTCAATGTCTTCTTTCTCGGCATTAAAGTGAATAACGTCATGTAGCACA

TCCTTGCCCTCATTCAGAAAAGCAACAAACTGACTTGCGCCACCCTCATAAAAATACTCATCTGACTTTCC

GCTGCGTTCGTCTTTAAGTTGAATACGAAGGCCCGAATTTAGAAAAGCAATTTCCTGAAGGCGCTCAGCCA

ACGTATCGTAGTTAAAATGAATGCCTGCCTGAAAAACACGAATATCCGGTTTAAATGTAATTTTCGAGCCC

GTCTTGTTAGTATTGCCCAGCACTTCAAGGCCTGTGGTCGGTTCTCCGACATGCTCCACGCCCTTCTTGTC

CTGCCAATATTCAAACCGCTGACGGTGAATCTTGCCGTCCCGGTAAATTTCTACTTCAAGCCATTCCGAAA

GAGCGTTCGTTACAGACGCACCTACACCGTGCAGACCCCCGGACTTTTTATATCCCGAACCGCCAAACTTA

CCTCCGGCGTGCAAAATGGTGAATACAACCTGAGGCGTAGGAATTCCCGTTTTGTGCATTCCTGTAGGAAT

ACCGCGCCCGTTGTCTGATACTGTAACGGAACCGTCCTTATGCATTGTAATATCAATGCGAGAGCAAAACT

TGGCGAGATGTTCATCCACCGCGTTGTCTACAATTTCCCATACCAAATGATGCAGTCCCGAAGAACTGGTG

CTCCCGATGTACATGCCCGGCCGTTTGCGAACTGCCACAAGCCCTTCGAGCACTTGAATGTCGTCCGCGCC

ATATTCTGAAGCTCCGCTTTGTGTGCCGGATACTCCCGCAGACAAGTCGATTTTGTCGACCAT

>MS0633_partial_gyrB_gene

SEQ ID NO. 21

GAAATCTTCAAAGAAACAATCGTATACGACTATGATCTGCTTTCAAACCGTGTCCGGGAATTGGCCTTCCT

GACAAAAGGCGTAAACATCACGATTGAAGACAAACGTGAAGGACAAGAACGGAAAAACGAGTACCACTACG

AAGGCGGAATCAAAAGCTATGTTGAGTACTTAAACCGTTCCAAAGAAGTCGTTCATGAAGAGCCGATTTAT

ATCGAAGGCGAGAAAGACGGCATAACGGTTGAAGTTGCGTTGCAATACAACGACAGCTATACAAGCAACAT

TTATTCTTTCACAAATAACATCAACACATACGAAGGC

>MS2820_complete_rpoB_gene

SEQ ID NO. 22

ATGAGGGGTGAGTTTAAGTTGGCAGGACATCTTGTTCAATATGGTCGACGCACTCGGCGCAGTTATGCACG

TATTAATGAGGTACTCGAGGTTCCGAACCTGATTGAGATCCAACAAAAATCCTATGATTGGTTTTTGGAGG

AAGGATTACGGGAAATGTTTCGGGATATTTCACCAATTCAAGATTTCACTGGAAATCTGATTTTGGAGTTT

ATCGACTATTCTCTCGGAGAACCCAAATATACCGTTGACGACGCAAAGGAACGCGACGTTACGTATGCAGC

ACCGCTTCGGGTAAAAGTCCGGCTTATTAATAAAGAGACCGGGGAAGTGAAAGAGCAGGAAGTATTCATGG

GAGACTTCCCGCTGATGACTGAAACGGGTACGTTTATTATTAACGGTGCGGAACGGGTTATTGTCAGCCAG

TTGGTTCGCTCTCCCAGCGTCTATTTCAGCACAAAAGTCGACAAGAATGCGAAAACAACATACACCGCAAC

GGTAATTCCTAACCGGGGGGCTTGGCTCGAACTGGAGATGGATGCGAAGGATATTATCTATGTCCGGATTG

ACCGTACCCGTAAAATTCCGGTTACGGTGTTGCTGCGTGCACTTGGCTTTGGCACTGATGCTGAGATTCTG

GATTTGCTCGGCAATGACGAATATATCCGCAACACACTTGATAAAGACAATACGGATTCCACGGAGAAAGC

GCTGATTGAAATTTATGAGCGTCTTCGCCCGGGTGAGCCACCTACACTGGATAACGCAAAGAGCTTGCTTG

TTGCACGCTTCTTTGATCCAAAACGTTATGATCTGGCCAACGTAGGCCGTTACAAAATCAATAAAAAGCTT

CACATCAAAAACCGTCTGTTCAATCAACGTCTTGCTGAGACATTGATTGATACAACAACTGGTGAAATTAT

CGCTGAAGCAGGACAAATGGTGGATCGTCGCCTGTTGGACGAGATTCTGGCCCAACTGGAGGAATCAGTAG

GACACCGCACGTATCATGTTGCTAGCGGCGTGCTGGAAAGCAATGATATTCCACTTCAAACGATTGATGTG

TTCTCGCCAATCGAGGACGGTAAAGTAGTAAAACTGATTGCTAACGGAAATATTGATAAATCGGTTAAGAA

TATTACGCCTGCCGATATTATTTCCTCCATCAGTTATTTTATTAACTTGCTTCACGGTATCGGAAGTACGG

ACGATATTGACCATTTGGGTAACCGTCGTTTACGTTCTGTAGGTGAGTTGCTCCAAAACCAGTTCCGTATC

GGTTTATCCCGTATGGAACGCGTGGTGCGTGAAAGAATGTCGATTCAGGATGCTAATGTAATTACGCCACA

-continued

AGCGTTGATTAACATACGTCCAGTAATTGCTTCGATTAAAGAGTTCTTTGGTAGCTCGCAGCTGTCACAGT

TTATGGATCAGACAAACCCGCTTGCTGAATTAACGCACAAACGTCGTCTGTCCGCACTCGGACCCGGCGGT

TTGACGCGTGAACGCGCAGGCATGGAAGTGCGTGACGTCCATCCAAGTCACTACGGCCGTATGTGTCCTAT

CGAGACACCAGAGGGACCAAACATTGGTTTGATCAACTCTTTGTCCACATTTGCACGTATCAACGAGTACG

GATTTATCGAAGCTCCTTATCGTTGGGTAGATCCGAAAACCGGAAAAGTTACAGACCAGATTGATTACCTG

ACTGCTGATGAAGAAGATAACTACATCGTAGCTCAGGCGAACGCGGAATTGACGGAGGAAAACACCTTTAA

GGATGAGGTCGTCATTGTCCGTTATAACAAACAGTCTGATAACATTATTCCAATGGCTAGTAGCCGTGTTG

ATTACATGGACGTATCACCTAAACAGGTCGTATCAGTTGCGACAGCACTGATTCCGTTTCTGGAGAATGAT

GACTCTAACCGCGCATTGATGGGTTCCAATATGCAACGTCAGGCTGTCCCACTATTGATTCCGAAGTCTCC

ATTGGTCGGAACAGGAATGGAGCACAAGTCTGCAAAAGATTCTGGTGTTTGCATTGTATCCAAATACAACG

GAGTTATCGAACGCTCTTCGGCTAACGAAATTTGGTTGCGTCGTATCGAAACTGTAGATGGTGCTGAAGTG

AAGGGCGACATTGTTAAGTATAAATTACACAAATTTATGCGATCTAACCAAGGAACTTGCATTAACCAACG

TCCGATTGTGAACAGAGGAGATATTGTCAAAGTTGGCGATATTCTTGCAGATGGTCCATCTACGGAGATGG

GTGAGTTGGCGTTGGGACGTAACGTTGTCGTTGCCTTCATGACTTGGGAAGGTTACAACTACGAGGATGCG

ATCCTGCTGAGTGAGAAACTGGTCAAGGAGGATGTATACACCTCGATCCATATTGAGGAATACGAATCCGA

GGCTCGTGACACGAAACTTGGACCTGAAGAAATCACTCGTGACATTCCAAATGTCGGTGAAGAGGCGCTTC

GCAACTTGGATGAGCGTGGAATCATTCGTATTGGTGCCGAAATCGGTGCAGGTGACATTCTTGTTGGTAAA

GTTACACCTAAAGGTGTGACTGAATTGACAGCTGAGGAACGTCTCTTACACGCAATCTTTGGTGAGAAGGC

ACGCGAGGTTCGCGATACTTCTTTGAGAGTTCCTCACGGAACAGATGGGATTGTTGTAGATGTAAAGGTGT

TTACACGTGAAAATGGTGATGAACTGCCACCAGGTGTAAATCAGTTGGTTCGTGTATATATTGCTCAAAAA

CGTAAAATCTCCGAAGGCGATAAAATGGCTGGACGTCACGGTAACAAGGGTGTCGTTGCCCGTATTTTGCC

TGAAGAAGATATGCCGTTCCTGCCGGATGGCACACCAGTACAGGTCGTTCTGAACCCGCTGGGGGTACCTT

CACGGATGAACATCGGACAGGTGCTTGAAGTCCATCTGGGTATGGCTGCAATGCGTCTTGGTATTCATGTG

GCAACTCCAGTATTCGATGGTGCCAAGGAGTATGACGTGTTCGATACAATGGAAGAGGCAGGCATGCAGCG

TAATGGTAAGACTGTGTTGTATGACGGACGTACGGGTGATCGTTTTGAACGTGAAGTTACTGTCGGTGTCA

TGCACATGATCAAACTGGCGCACATGGTCGATGATAAAATCCATGCTCGTTCTACAGGTCCTTACTCTCTC

GTTACGCAGCAACCATTGGGTGGTAAAGCTCAATTCGGTGGACAGCGCTTCGGGGAGATGGAAGTATGGGC

ATTGGAAGCCTACGGCGCGGCGTACACGCTTCAGGAAATTTTGACTGTGAAATCCGATGATGTGGTTGGAC

GTGTTAAAACTTACGAATCCATTGTCAAAGGTGAAAATGTACCTGAACCGGGTGTTCCAGAATCATTTAAG

GTCTTGATCAAAGAGCTGCAAAGCTTGGGTATGGACGTGAAGATTCTGTCTGAAGACGAACAAGAGATTGA

AATGAGAGAGCTTGATGATGAGGATGACACAAGCGGCGATAAGCTGAGTTTGAATCTGGAAGGCTCTGAGG

TTGGCGTAGAGTAG

>MS2712_partial_rpoB_gene

SEQ ID NO. 23

GAAACGCCTGAGGGCCCGAACATCGGTTTGATCAACTCATTGTCATCATTTGCGAAAGTAAACCGCTTTGG

TTTCATTGAGACGCCATACCGCCGCGTTGATCCTGAAACAGGAAAAGTAACGCCTAGAATCGACTACCTGA

CTGCTGATGAAGAGGATAACTATGTCGTAGCCCAAGCGAATGCTAAGCTGAGCGATGACGGTTCTTTCTTG

GATGACAGCATCGTAGCGCGTTTCAGAGGGGAAAACACCGTTGTAGCCCGCAACCGCGTGGATTACATGGA

CGTATCTCCTAAACAGGTTGTATCTGCTGCGACAGCATGTATTCCGTTCTTGGAAAACGATGACTCGAACC

GCGCCCTCATGGGAGCGAACATGCAGCGTCAGGCTGTGCCTTTGATGCAGCCGGAAGCTCCGATCGTCGGA

ACGGGTATGGAATACGTATCCGGTAAAGACTCCGGTGCAGCCGTTATTTGTAAACACCCTGGTATCGTAGA

-continued

ACGGGTGGAAGCGAAAAACGTATGGGTGCGCCGCTATGAAGAAATTGACGGCCAAAAAGTAAAAGGCAACC

TGGATAAGTACAGCTTGCTGAAATTTGTCCGCTCCAACCAAGGTACGTGCTACAACCAGCGTCCGATCGTC

AGTGTCGGCGATGAAGTAGTCAAAGGAGAAATCCTTGCTGACGGACCTTCAATGGAGCTTGGTGAACTTGC

TCTCGGCCGCAACGTAATGGTCGGCTTCATGACATGGGATGGTTAC

>MS2697_complete_rpoB_gene

SEQ ID NO. 24

ATGGGTGATTTCCCTATTATGACAGATACCGGTACTTTTATCATCAACGGTGCAGAACGTGTTATCGTATC

TCAGCTTGTTCGGTCTCCAAGTGTATATTTCAGTGGTAAAGTAGACAAGAACGGTAAAAAAGGTTTTACCG

CGACTGTCATTCCAAACCGTGGCGCATGGTTAGAATACGAAACTGATGCGAAAGATGTTGTGTATGTCCGC

ATTGATCGCACACGTAAGTTGCCGGTTACGGTTCTTTTGCGTGCTCTCGGCTTCGGTTCCGACCAAGAGAT

TCTCGATCTCATTGGTGAGAACGAATATCTCCGCAATACACTGGATAAGGACAACACTGAAAACAGTGACA

AAGCGCTTCTTGAAATCTATGAGCGCCTTCGTCCCGGAGAGCCGCCTACAGTAGAAAACGCAAAAAGCTTG

CTGGATTCCCGTTTCTTCGATCCGAAGCGATACGACCTTGCGAATGTAGGACGCTATAAAATTAATAAAAA

GCTTCATATCAAGAACCGCCTGTTTAACCAGCGCCTTGCAGAAACACTGGTGGATCCGGAAACCGGTGAAA

TTCTCGCTGAAAAAGGGCAGATTCTTGACAGAAGAACACTTGATAAAGTACTGCCATACTTAGAAAATGGA

ATCGGCTTCAGAAAACTTTATCCTAACGGCGGCGTTGTCGAGGATGAAGTGATGCTTCAATCCATTAAAAT

CTATGCTCCTACCGATGCAGAAGGAGAGCAGACGATCAATGTGATCGGCAATGCTTACATCGAAGAGGCGA

TTAAAAACATTACGCCTGCTGATATTATTTCTTCTATCAGCTACTTCTTCAACCTCCTGCACGGAGTGGGT

GACACTGATGATATCGACCATCTCGGAAACCGCCGTCTGCGTTCTGTAGGTGAGCTCCTGCAAAACCAATT

CCGTATCGGTTTAAGCCGGATGGAACGTGTCGTTCGTGAAAGAATGTCTATTCAAGACACGAATACAATTA

CGCCGCAGCAGCTGATTAACATCAGACCTGTTATTGCGTCTATTAAAGAGTTCTTCGGAAGCTCACAGCTT

TCTCAATTCATGGATCAGACGAACCCGCTTGCTGAATTGACGCACAAACGCCGTCTGTCAGCTCTCGGACC

GGGCGGTTTGACACGTGAGCGCGCAGGTATGGAAGTACGTGACGTTCACTACTCTCACTATGGCCGTATGT

GTCCGATTGAAACGCCTGAGGGCCCGAACATCGGTTTGATCAACTCATTGTCATCATTTGCGAAAGTAAAC

CGCTTTGGTTTCATTGAGACGCCATACCGCCGCGTTGATCCTGAAACAGGAAAAGTAACGCCTAGAATCGA

CTACCTGACTGCTGATGAAGAGGATAACTATGTCGTAGCCCAAGCGAATGCTAAGCTGAGCGATGACGGTT

CTTTCTTGGATGACAGCATCGTAGCGCGTTTCAGAGGGGAAAACACCGTTGTAGCCCGCAACCGAGTGGAT

TACATGGACGTATCTCCTAAACAGGTTGTATCTGCTGCGACAGCATGTATTCCGTTCTTGGAAAACGATGA

CTCGAACCGCGCCCTCATGGGAGCGAACATGCAGCGTCAGGCTGTGCCTTTGATGCAGCCGGAAGCTCCGA

TCGTCGGAACGGGTATGGAATACGTATCCGGTAAAGACTCCGGTGCAGCCGTTATTTGTAAACACCCTGGT

ATCGTTGAACGGGTGGAAGCGAAAAACGTATGGGTGCGCCGCTATGAAGAAATTGACGGTCAAAAAGTAAA

AGGCAACCTGGATAAGTACAGCTTGCTGAAATTTGTCCGCTCCAACCAAGGTACGTGCTACAATCAGCGTC

CGATCGTCAGTGTCGGCGACGAAGTAGTCAAAGGAGAAATCCTTGCTGACGGACCTTCAATGGAGCTTGGT

GAACTTGCTCTCGGCCGCAACGTAATGGTCGGCTTCATGACATGGGATGGTTACAACTATGAGGATGCCAT

CATCATGAGTGAACGCCTTGTGAAAGATGATGTATACACATCTATTCACATTGAAGAATATGAATCAGAAG

CACGTGATACAAAGCTTGGGCCGGAAGAGATCACCCGCGATATTCCAAACGTAGGGGAAGATGCGCTTCGC

AATCTTGATGACCGCGGAATTATCCGTATCGGTGCGGAAGTCAACGACGGAGACCTTCTCGTAGGTAAAGT

AACGCCTAAAGGTGTAACTGAGCTTACGGCTGAAGAACGCCTTCTTCATGCGATCTTTGGAGAAAAAGCGC

GTGAAGTCCGTGATACTTCTCTCCGTGTGCCTCACGGCGGCGGCGGAATTATCCACGACGTAAAAGTCTTC

AACCGTGAAGACGGCGACGAACTTCCTCCGGGAGTGAACCAGCTTGTACGCGTATATATCGTTCAGAAACG

TAAGATTTCTGAAGGTGATAAAATGGCCGGACGTCACGGAAACAAAGGGGTTATCTCGAAGATTCTTCCTG

AAGAAGATATGCCTTACCTTCCTGACGGCACGCCGATCGATATCATGCTTAACCCGCTGGGTGTACCATCA

-continued

CGTATGAATATCGGTCAGGTATTAGAACTTCACATGGGTATGGCTGCCCGCTACCTCGGCATTCACATCGC

GTCACCTGTATTTGACGGCGCGCGTGAAGAAGATGTGTGGGAAACACTTGAAGAAGCAGGCATGTCAAGAG

ACGCTAAAACAGTTCTTTATGACGGCCGTACGGGAGAACCGTTCGACAACCGTGTATCTGTCGGAATCATG

TACATGATCAAACTGGCGCACATGGTTGATGATAAACTTCATGCCCGTTCTACAGGTCCTTACTCACTTGT

TACGCAGCAGCCTCTCGGCGGTAAAGCCCAATTCGGCGGACAGCGTTTCGGTGAGATGGAGGTTTGGGCGC

TTGAAGCTTACGGCGCAGCTTACACGCTTCAAGAAATCCTGACTGTGAAGTCCGATGACGTGGTCGGACGT

GTGAAAACATATGAAGCCATCGTCAAAGGCGACAATGTTCCAGAGCCTGGTGTTCCGGAATCATTCAAAGT

ATTGATCAAAGAGCTTCAAAGCTTAGGTATGGACGTAAAAATCCTTTCAGGCGATGAAGAAGAAATAGAAA

TGAGAGATCTAGAAGACGAGGAAGATGCGAAACAAGCTGACGGCCTTGCATTATCAGGTGATGAAGCGCCG

GAAGAAACAGCATCTCCAGACGTTGAACGTGACGCAGTAACGAAAGAATAG

>MS2681_partial_rpoB_gene

SEQ ID NO. 25

GAAACGCCTGAGGGCCCGAACATCGGTTTGATCAACTCATTGTCATCATTTGCGAAAGTAAACCGCTTTGG

TTTCATTGAGACGCCATACCGCCGCGTTGATCCTGAAACAGGAAAAGTAACGCCTAGAATCGACTACCTGA

CTGCTGATGAAGAGGATAACTATGTCGTAGCCCAAGCGAATGCTAAGCTGAGCGATGACGGTTCTTTCTTG

GATGACAGCATCGTAGCGCGTTTCAGAGGGGAAAACACCGTTGTAGCCCGCAACCGCGTGGATTACATGGA

CGTATCTCCTAAACAGGTTGTATCTGCTGCGACAGCATGTATTCCGTTCTTGGAAAACGATGACTCGAACC

GCGCCCTCATGGGAGCGAACATGCAGCGTCAGGCTGTGCCTTTGATGCAGCCGGAAGCTCCGATCGTCGGA

ACGGGTATGGAATACGTATCCGGTAAAGACTCCGGTGCAGCCGTTATTTGTAAACACCCTGGTATCGTAGA

ACGGGTGGAAGCGAAAAACGTATGGGTGCGCCGCTATGAAGAAATTGACGGCCAAAAAGTAAAAGGCAACC

TGGATAAGTACAGCTTGCTGAAATTCGTCCGCTCCAACCAAGGTACGTGCTACAACCAGCGTCCGATCGTC

AGTGTCGGCGATGAAGTAGTAAAAGGAGAAATCCTTGCTGACGGACCTTCAATGGAGCTTGGTGAACTTGC

TCTCGGCCGCAACGTAATGGTCGGCTTCATGACATGGGATGGTTAC

>MS2658_partial_rpoB_gene

SEQ ID NO. 26

GAAACGCCTGAGGGCCCGAACATCGGTTTGATCAACTCATTGTCATCATTTGCGAAAGTAAACCGCTTTGG

TTTCATTGAGACGCCATACCGCCGCGTTGATCCTGAAACAGGAAAAGTAACGCCTAGAATCGACTACCTGA

CTGCTGATGAAGAGGATAACTATGTCGTAGCCCAAGCGAATGCTAAGCTGAGCGATGACGGTTCTTTCTTG

GATGACAGCATCGTAGCGCGTTTCAGAGGGGAAAACACCGTTGTAGCCCGCAACCGCGTGGATTACATGGA

CGTATCTCCTAAACAGGTTGTATCTGCTGCGACAGCATGTATTCCGTTCTTGGAAAACGATGACTCGAACC

GTGCCCTCATGGGAGCGAACATGCAGCGTCAGGCTGTGCCTTTGATGCAGCCGGAAGCTCCGATCGTCGGA

ACGGGTATGGAATACGTATCCGGTAAAGACTCCGGTGCAGCCGTTATTTGTAAACACCCTGGTATCGTTGA

ACGGGTGGAAGCGAAAAACGTATGGGTGCGCCGCTATGAAGAAATTGACGGCCAAAAAGTAAAAGGCAACC

TGGATAAGTACAGCTTGCTGAAATTTGTCCGCTCCAACCAAGGTACGTGCTACAACCAGCGTCCGATCGTC

AGTGTCGGCGATGAAGTAGTCAAAGGAGAAATCCTTGCTGACGGACCTTCAATGGAGCTTGGTGAACTTGC

TCTCGGCCGCAACGTAATGGTCGGCTTCATGACATGGGATGGTTAC

>MS2652_partial_rpoB_gene

SEQ ID NO. 27

GAAACGCCTGAGGGCCCGAACATCGGTTTGATCAACTCATTGTCATCATTTGCGAAAGTAAACCGCTTTGG

TTTCATTGAGACGCCATACCGCCGCGTTGATCCTGAAACAGGAAAAGTAACGCCTAGAATCGACTACTTGA

CTGCTGATGAAGAGGATAACTATGTCGTAGCCCAAGCGAATGCTAAGCTGAGCGATGACGGTTCTTTCTTG

GATGACAGCATCGTAGCGCGTTTCAGAGGGGAAAACACCGTTGTAGCCCGCAACCGCGTGGATTACATGGA

CGTTTCTCCTAAACAGGTTGTTTCTGCTGCGACAGCATGTATTCCGTTCTTGGAAAACGATGACTCGAACC

-continued

GCGCCCTCATGGGAGCGAACATGCAGCGTCAGGCTGTGCCTTTGATGCAGCCGGAAGCTCCGATCGTCGGA

ACGGGTATGGAATACGTATCCGGTAAAGACTCCGGTGCAGCCGTTATTTGTAAACACCCTGGTATCGTTGA

ACGGGTGGAAGCGAAAAACGTATGGGTGCGCCGCTATGAAGAAATTGACGGCCAAAAAGTAAAAGGCAACC

TGGATAAGTACAGCTTGCTGAAATTTGTCCGCTCCAACCAAGGTACGTGCTACAACCAGCGTCCGATCGTC

AGTGTCGGCGATGAAGTAGTCAAAGGAGAAATCCTTGCTGACGGACCTTCAATGGAGCTTGGTGAACTTGC

TCTCGGCCGCAACGTAATGGTCGGCTTCATGACATGGGATGGTTAC

>MS2414_complete_rpoB_gene

SEQ ID NO. 28

ATGAGGGGTGAGTTTAAGTTGGCAGGACATCTTGTTCAATATGGTCGACGCACTCGGCGCAGTTATGCACG

TATTAATGAGGTACTCGAGGTTCCGAACCTGATTGAGATCCAACAAAAATCCTATGATTGGTTTTTGGAGG

AAGGATTAAGGGAAATGTTTCGGGATATTTCTCCAATTCAGGATTTCACTGGAAATCTGATTCTGGAGTTT

ATCGACTATTCTCTCGGAGAACCCAAATATACCGTTGACGACGCAAAGGAACGCGACGTTACGTATGCAGC

ACCGCTTCGGGTAAAAGTCCGGCTTATTAATAAAGAAACCGGGGAAGTGAAAGAGCAGGAAGTATTCATGG

GAGACTTCCCGCTGATGACTGAAACGGGTACGTTTATTATTAACGGTGCGGAACGGGTTATTGTCAGCCAG

TTGGTTCGCTCTCCCAGCGTCTATTTCAGCACAAAAGTCGACAAGAATGCGAAAACAACATACACCGCAAC

GGTAATTCCTAACCGGGGGGCTTGGCTCGAACTGGAGATGGATGCGAAGGATATTATCTATGTCCGGATTG

ACCGTACCCGTAAAATTCCGGTTACGGTGTTGCTGCGTGCGCTGGGCTTTGGCACTGATGCTGAGATTCTG

GATTTGCTCGGCAATGACGAATATATCCGCAACACACTTGATAAAGACAACACGGATTCCACCGAGAAAGC

GCTGATTGAAATTTATGAGCGTCTTCGTCCAGGTGAGCCGCCTACACTGGATAACGCAAAGAGCTTGCTAG

TTGCTCGCTTCTTTGATCCTAAACGTTATGATCTGGCCAACGTAGGCCGTTACAAAATCAATAAAAAGCTT

CACATCAAAAACCGTTTGTTCAATCAACGACTTGCTGAGACTTTGATTGATACAACAACTGGTGAAATCAT

CGCTGAAGCCGGTCAAATGGTAGATCGCCGCCTGTTGGACGAGATTTTGGCCCAACTGGAGGAATCAGTAG

GACATCGTACGTATCATGTTGCGAGTGGTGTGCTAGAAAGCAATGATATTCCACTTCAAACAATCGATGTA

TTCTCACCAATTGAGGATGGCAAAGTAGTAAAACTGATTGCTAATGGAAATATTGATAAATCGGTTAAGAA

TATTACGCCTGCCGATATTATTTCCTCCATCAGTTATTTTATTAACTTGCTTCACGGAATCGGAAGTACGG

ACGATATTGACCATTTGGGTAACCGTCGTTTGCGTTCTGTAGGTGAGTTGCTCCAAAACCAGTTCCGTATC

GGTTTATCCCGTATGGAACGCGTGGTGCGTGAAAGAATGTCAATTCAGGATGCTAATGTAATTACGCCACA

AGCGCTGATTAACATACGTCCAGTAATTGCTTCGATTAAAGAGTTCTTTGGTAGCTCGCAGCTGTCTCAGT

TTATGGATCAGACGAACCCGCTTGCTGAATTAACGCACAAACGTCGTCTGTCCGCACTCGGACCCGGCGGT

TTGACGCGCGAACGCGCGGGCATGGAAGTGCGTGACGTCCATCCGAGTCACTACGGCCGTATGTGTCCTAT

CGAGACACCAGAGGGACCAAACATTGGTTTGATCAACTCTTTGTCCACTTTTGCACGCATTAACGAGTATG

GATTTATCGAAGCTCCTTATCGTTGGGTAGATCCAAAAACCGGAAAAGTTACAGACCAGATTGATTACCTG

ACTGCTGATGAAGAAGATAACTACATTGTAGCTCAGGCGAATGCGGAATTGACGGAGGAAAACACCTTTAA

GGATGAGGTTGTCATTGTCCGTTATAACAAACAGTCTGATAACATTATTCCGATGGCTAGTAGCCGTGTCG

ATTACATGGACGTATCGCCTAAACAGGTCGTATCGGTCGCGACTGCACTGATTCCGTTCTTGGAGAATGAT

GACTCTAACCGCGCATTGATGGGTTCCAACATGCAGCGTCAGGCTGTCCCGCTTCTGATTCCGAAGTCTCC

ATTGGTCGGAACAGGAATGGAGCACAAGTCTGCAAAAGATTCCGGTGTTTGCGTTGTATCCAAATACAACG

GAGTTATCGAACGTTCTTCGGCTAACGAAATTTGGTTGCGTCGTATCGAAACTGTAGATGGCGCTGAAGTG

AAGGGCGACATTGTTAAGTATAAATTACACAAATTTATGCGATCTAACCAAGGAACTTGCATCAACCAACG

TCCGATTGTGAACAGAGGAGATATTGTCAAAGTTGGCGATATTCTTGCGGATGGTCCATCTACAGAGATGG

GTGAGTTGGCGTTGGGACGTAACGTTGTCGTTGCCTTCATGACTTGGGAAGGTTACAACTACGAGGATGCG

ATCTTGCTGAGTGAGAAACTGGTTAAGGAAGATGTATACACCTCAATCCATATTGAGGAATACGAATCCGA

-continued

GGCTCGTGACACGAAGCTTGGACCTGAAGAAATCACTCGCGACATTCCAAATGTCGGTGAAGAAGCGCTTC

GCAACTTGGATGAGCGTGGAATCATACGTATTGGTGCTGAAATTGGCGCAGGTGACATTCTCGTTGGTAAA

GTAACACCTAAAGGTGTGACTGAATTGACAGCTGAAGAACGTCTCTTACACGCAATCTTTGGTGAGAAGGC

ACGCGAGGTTCGCGATACTTCTTTGAGAGTTCCTCACGGAACAGACGGGATTGTTGTAGATGTAAAGGTAT

TTACACGTGAAAATGGCGATGAACTGCCACCAGGTGTAAATCAGTTGGTTCGAGTATATATTGCTCAAAAA

CGTAAAATCTCCGAAGGCGATAAAATGGCTGGACGTCACGGTAACAAGGGTGTCGTTGCCCGTATTCTGCC

TGAAGAAGATATGCCGTTCCTGCCGGATGGCACACCAGTACAGGTCGTTCTGAACCCGCTGGGCGTACCTT

CACGGATGAACATCGGACAGGTGCTTGAAGTCCATCTGGGTATGGCTGCAATGCGTCTTGGTATTCATGTG

GCAACTCCAGTATTCGATGGTGCCAAGGAATATGACGTATTCGATACAATGGAAGAGGCAGGCATGCAGCG

TAATGGTAAGACTGTGTTGTATGACGGACGTACGGGTGATCGTTTTGAACGTGAAGTTACTGTCGGTGTCA

TGCACATGATCAAACTGGCGCACATGGTCGATGATAAAATCCATGCTCGTTCTACAGGTCCTTACTCTCTC

GTTACGCAACAACCATTGGGTGGTAAAGCTCAATTTGGTGGACAGCGCTTCGGGGAGATGGAAGTATGGGC

ATTGGAAGCCTACGGCGCAGCGTACACGCTTCAGGAAATTTTGACTGTGAAATCTGATGATGTGGTTGGAC

GTGTTAAAACTTACGAATCCATTGTCAAAGGTGAAAATGTACCTGAACCGGGTGTTCCAGAATCATTTAAG

GTCTTGATCAAGGAGCTGCAAAGCTTGGGTATGGACGTGAAGATTCTGTCTGAAGACGAACAAGAGATCGA

AATGAGAGAGCTTGATGATGAGGATGACACAACCGGCGATAAGCTGAGTTTGAATCTGGAAGGCTCTGAGG

TTGGCGTAGAGTAG

>MS2379_complete_rpoB_gene

SEQ ID NO. 29

ATGAGGGGTGAGTTTAAGTTGGCAGGACATCTTGTTCAATATGGTCGACGCACTCGGCGCAGTTATGCACG

TATTAATGAGGTACTCGAGGTTCCCAACCTGATTGAGATCCAACAAAAATCATATGATTGGTTTTTGGAGG

AAGGATTACGGGAAATGTTTCGGGATATTTCTCCAATTCAAGATTTCACAGGAAATCTGATTTTGGAGTTT

ATCGATTACTCTCTCGGAGAACCCAAATATACCGTTGACGACGCAAAAGAACGCGACGTTACGTATGCGGC

ACCGCTTCGGGTAAAAGTCCGGCTTATTAATAAGGAAACCGGGGAAGTAAAAGAGCAGGAAGTATTCATGG

GAGACTTCCCGCTGATGACTGAAACGGGTACGTTTATTATTAACGGTGCGGAACGGGTTATTGTCAGCCAG

TTGGTTCGCTCTCCCAGCGTCTATTTCAGCACAAAAGTCGACAAGAATGCGAAAACAACATACACCGCAAC

GGTAATTCCTAACCGGGGGGCTTGGCTCGAACTGGAGATGGATGCGAAGGATATTATCTATGTCCGGATTG

ACCGTACCCGTAAAATTCCGGTTACGGTGTTGCTGCGTGCACTTGGCTTTGGCACTGATGCTGAGATTCTG

GATTTGCTCGGCAATGACGAATATATCCGCAACACACTTGATAAAGACAACACGGATTCCACGGAGAAAGC

GCTGATTGAAATTTATGAGCGTCTTCGTCCGGGTGAGCCACCTACATTGGATAATGCAAAGAGCTTGCTTG

TTGCACGCTTCTTTGATCCAAAACGTTATGATCTGGCCAACGTAGGCCGTTACAAAATCAATAAAAAGCTT

CACATCAAAAACCGTCTGTTCAATCAACGCCTAGCTGAGACACTGATTGATACAACAACTGGTGAAATTAT

CGCTGAAGCAGGGCAAATGGTAGACCGCCGCTTGTTGGACGAGATTTTGGCACAACTAGAAGAGTCGGTTG

GACACCGTACGTATCATGTTGCTAGTGGCGTATTGGAAAGCAATGATATTCCGCTTCAAACGATCGATGTA

TTCTCGCCAATCGAAGACGGTAAAGTAGTAAAACTGATTGCCAATGGAAATATCGATAAATCGGTTAAGAA

CATTACGCCTGCCGATATTATTTCCTCCATCAGTTATTTTATTAACTTGCTTCACGGAATCGGAAGTACGG

ACGACATTGACCATTTGGGTAACCGTCGTTTGCGTTCTGTAGGTGAGTTGCTCCAAAATCAGTTCCGTATT

GGTCTGTCCCGTATGGAACGCGTGGTACGCGAAAGAATGTCAATTCAGGATGCTAATGTAATTACGCCACA

AGCGCTGATTAACATACGTCCGGTCATTGCGTCGATTAAAGAGTTCTTTGGTAGCTCTCAGCTGTCTCAGT

TCATGGATCAGACAAACCCGCTTGCTGAACTAACACACAAACGTCGTTTGTCTGCACTCGGACCCGGCGGT

TTGACGCGCGAACGCGCGGGCATGGAAGTACGTGACGTCCATCCGAGTCACTACGGCCGTATGTGTCCTAT

-continued

CGAGACACCAGAGGGACCAAACATTGGTTTGATCAACTCTTTGTCAACTTTTGCACGTATCAACGAATACG

GATTTATCGAAGCTCCTTATCGCTGGGTAGATCCGAAGACTGGAAAAGTTACAGATCAGATTGATTACCTG

ACTGCTGATGAAGAAGATAACTACATCGTTGCTCAGGCAAATGCGGAATTGACGGAAGAAAACACCTTTAA

GGATGAAGTCGTTATTGTTCGCTATAACAAGCAGTCTGATAACATTATTCCAATGGCAAGTAGCCGTGTCG

ATTACATGGACGTATCACCTAAACAGGTTGTATCGGTCGCAACTGCTCTGATCCCGTTCCTGGAGAATGAT

GACTCGAACCGTGCATTGATGGGTTCCAACATGCAGCGGCAGGCTGTCCCATTGCTGATTCCGAAAGCGCC

TTTGGTAGGAACAGGGATGGAACATAAGTCTGCAAAAGATTCCGGTGTGTGCGTTGTGTCCAAGTACAACG

GGGTGATTGAACGTTCTTCGGCTAACGAAATTTGGCTGCGTCGTATTGAAACAGTAGATGGCGCTGAAGTC

AAAGGCGATATTGTTAAGTATAAATTACACAAATTTATGCGTTCTAACCAAGGAACATGCATCAACCAGCG

TCCAATCGTAAACAGAGGCGATATTGTCAAAGTTGGCGATATTCTTGCTGACGGTCCTTCCACCGAGATGG

GTGAGTTGGCACTGGGACGTAACGTTGTCGTAGCGTTCATGACTTGGGAAGGTTACAACTACGAGGATGCG

ATCTTGCTGAGCGAGAAGCTGGTTAAAGAGGATGTATATACCTCGATCCATATCGAGGAATACGAATCTGA

AGCCCGTGATACGAAACTTGGACCAGAAGAAATCACTCGTGATATTCCGAATGTCGGTGAAGAAGCGCTTC

GCAATCTAGATGAGCGCGGCATCATTCGCATCGGTGCTGAAATCGCCGCAGGTGACATTCTTGTTGGTAAA

GTAACACCTAAGGGTGTAACTGAGTTGACAGCTGAAGAACGTCTCTTGCATGCAATCTTCGGTGAGAAGGC

GCGCGAGGTTCGTGATACTTCCTTGAGAGTTCCTCACGGAACCGACGGAATCGTCGTAGATGTTAAAGTAT

TTACACGTGAAAATGGCGATGAGCTGCCACCGGGTGTAAACCAGTTGGTACGCGTCTATATTGCTCAAAAA

CGTAAAATTTCCGAAGGCGATAAAATGGCCGGACGTCACGGTAACAAGGGTGTCGTTGCCCGTATTCTGCC

TGAAGAAGATATGCCGTTCTTGCCAGATGGCACGCCAGTACAAGTCGTACTGAATCCGCTGGGCGTACCTT

CACGGATGAACATCGGACAGGTGCTTGAAGTGCATTTGGGTATGGCTGCAATGCGTCTTGGTATTCATGTG

GCAACTCCAGTATTCGATGGTGCCAAGGAGTATGACGTATTTGATACGATGGAAGAAGCGGGTATGCAACG

CAATGGTAAGACAGTGTTGTATGATGGGCGTACAGGTGATCGTTTTGAACGTGAAGTTACGGTCGGTGTCA

TGCACATGATCAAACTGGCGCACATGGTCGACGATAAGATCCATGCTCGTTCTACAGGCCCTTACTCTCTC

GTTACGCAGCAACCGTTGGGTGGTAAAGCTCAATTCGGTGGTCAGCGCTTCGGGGAGATGGAAGTATGGGC

ACTGGAAGCCTACGGTGCGGCGTATACGCTTCAGGAAATTTTGACTGTGAAATCCGATGACGTGGTTGGAC

GTGTTAAAACTTACGAATCCATCGTCAAAGGTGAAAATGTCCCAGAACCGGGTGTTCCTGAATCATTCAAG

GTCTTGATCAAAGAGCTGCAAAGCTTGGGTATGGACGTGAAGATTCTGTCTGAAGACGAACAAGAGATCGA

AATGAGAGAGCTTGATGATGAGGATGATACAACTGGCGATAAGCTGAGTTTGAATCTGGAAGGCTCTGAGG

TTGGCGTAGAGTAG

>MS2335_partial_rpoB_gene

SEQ ID NO. 30

GAAACGCCTGAGGGCCCGAACATCGGTTTGATCAACTCATTGTCATCATTTGCGAAAGTAAACCGCTTTGG

TTTCATTGAGACGCCATACCGCCGCGTTGATCCTGAAACAGGAAAAGTAACGCCTAGAATCGACTACCTGA

CTGCTGATGAAGAGGATAACTATGTCGTAGCCCAAGCGAATGCTAAGCTGAGCGATGACGGTTCTTTCTTG

GATGACAGCATCGTAGCGCGTTTCAGAGGGGAAAACACCGTTGTAGCCCGCAACCGCGTGGATTACATGGA

CGTATCTCCTAAACAGGTTGTATCTGCTGCGACAGCATGTATTCCGTTCTTGGAAAACGATGACTCGAACC

GCGCCCTCATGGGAGCGAACATGCAGCGTCAGGCTGTGCCTTTGATGCAGCCGGAAGCTCCGATCGTCGGA

ACGGGTATGGAATACGTATCCGGTAAAGACTCCGGTGCAGCCGTTATTTGTAAACACCCTGGTATCGTAGA

ACGGGTGGAAGCGAAAAACGTATGGGTGCGCCGCTATGAAGAAATTGACGGCCAAAAAGTAAAAGGCAACC

TGGATAAGTACAGCTTGCTGAAATTTGTCCGCTCCAACCAAGGTACGTGCTACAACCAGCGTCCGATCGTC

AGTGTCGGCGATGAAGTAGTCAAAGGAGAAATCCTTGCTGACGGACCTTCAATGGAGCTTGGTGAACTTGC

TCTCGGCCGCAACGTAATGGTCGGCTTCATGACATGGGATGGTTAC

-continued

>MS1479_complete_rpoB_gene

SEQ ID NO. 31

ATGAGGGGTGAGTTTAAGTTGGCAGGACATCTTGTTCAATATGGTCGACGCACTCGGCGCAGTTATGCACG

TATTAATGAGGTACTCGAGGTTCCGAACCTGATTGAGATCCAACAAAAATCCTATGATTGGTTTTTGGAGG

AAGGATTAAGGGAAATGTTTCGGGATATTTCTCCAATTCAGGATTTCACTGGAAATCTGATTCTGGAGTTT

ATCGACTATTCTCTCGGAGAACCCAAATATACCGTTGACGACGCAAAGGAACGCGACGTTACGTATGCAGC

ACCGCTTCGGGTAAAAGTCCGGCTTATTAATAAAGAAACCGGGGAAGTGAAAGAGCAGGAAGTATTCATGG

GAGACTTCCCGCTGATGACTGAAACGGGTACGTTTATTATTAACGGTGCGGAACGGGTTATTGTCAGCCAG

TTGGTTCGCTCTCCCAGCGTCTATTTCAGCACAAAAGTCGACAAGAATGCGAAAACAACATACACCGCAAC

GGTAATTCCTAACCGGGGGGCTTGGCTCGAACTGGAGATGGATGCGAAGGATATTATCTATGTCCGGATTG

ACCGTACCCGTAAAATTCCGGTTACGGTGTTGCTGCGTGCGCTGGGCTTTGGCACTGATGCTGAGATTCTG

GATTTGCTCGGCAATGACGAATATATCCGCAACACACTTGATAAAGACAACACGGATTCCACCGAGAAAGC

GCTGATTGAAATTTATGAGCGTCTTCGTCCAGGTGAGCCGCCTACACTGGATAACGCAAAGAGCTTGCTAG

TTGCTCGCTTCTTTGATCCTAAACGTTATGATCTGGCCAACGTAGGCCGTTACAAAATCAATAAAAAGCTT

CACATCAAAAACCGTTTGTTCAATCAACGACTTGCTGAGACTTTGATTGATACAACAACTGGTGAAATCAT

CGCTGAAGCCGGTCAAATGGTAGATCGCCGCCTGTTGGACGAGATTTTGGCCCAACTGGAGGAATCAGTAG

GACATCGTACGTATCATGTTGCGAGTGGTGTGCTAGAAAGCAATGATATTCCACTTCAAACAATCGATGTA

TTCTCACCAATTGAGGATGGCAAAGTAGTAAAACTGATTGCTAATGGAAATATTGATAAATCGGTTAAGAA

TATTACGCCTGCCGATATTATTTCCTCCATCAGTTATTTTATTAACTTGCTTCACGGAATCGGAAGTACGG

ACGATATTGACCATTTGGGTAACCGTCGTTTGCGTTCTGTAGGTGAGTTGCTCCAAAACCAGTTCCGTATC

GGTTTATCCCGTATGGAACGCGTGGTGCGTGAAAGAATGTCAATTCAGGATGCTAATGTAATTACGCCACA

AGCGCTGATTAACATACGTCCAGTAATTGCTTCGATTAAAGAGTTCTTTGGTAGCTCGCAGCTGTCTCAGT

TTATGGATCAGACGAACCCGCTTGCTGAATTAACGCACAAACGTCGTCTGTCCGCACTCGGACCCGGCGGT

TTGACGCGCGAACGCGCGGGCATGGAAGTGCGTGACGTCCATCCGAGTCACTACGGCCGTATGTGTCCTAT

CGAGACACCAGAGGGACCAAACATTGGTTTGATCAACTCTTTGTCCACTTTTGCACGCATTAACGAGTATG

GATTTATCGAAGCTCCTTATCGTTGGGTAGATCCAAAAACCGGAAAAGTTACAGACCAGATTGATTACCTG

ACTGCTGATGAAGAAGATAACTACATTGTAGCTCAGGCGAATGCGGAATTGACGGAGGAAAACACCTTTAA

GGATGAGGTTGTCATTGTCCGTTATAACAAACAGTCTGATAACATTATTCCGATGGCTAGTAGCCGTGTCG

ATTACATGGACGTATCGCCTAAACAGGTCGTATCGGTCGCGACTGCACTGATTCCGTTCTTGGAGAATGAT

GACTCTAACCGCGCATTGATGGGTTCCAACATGCAGCGTCAGGCTGTCCCGCTTCTGATTCCGAAGTCTCC

ATTGGTCGGAACAGGAATGGAGCACAAGTCTGCAAAAGATTCCGGTGTTTGCGTTGTATCCAAATACAACG

GAGTTATCGAACGTTCTTCGGCTAACGAAATTTGGTTGCGTCGTATCGAAACTGTAGATGGCGCTGAAGTG

AAGGGCGACATTGTTAAGTATAAATTACACAAATTTATGCGATCTAACCAAGGAACTTGCATCAACCAACG

TCCGATTGTGAACAGAGGAGATATTGTCAAAGTTGGCGATATTCTTGCGGATGGTCCATCTACAGAGATGG

GTGAGTTGGCGTTGGGACGTAACGTTGTCGTTGCCTTCATGACTTGGGAAGGTTACAACTACGAGGATGCG

ATCTTGCTGAGTGAGAAACTGGTTAAGGAAGATGTATACACCTCAATCCATATTGAGGAATACGAATCCGA

GGCTCGTGACACGAAGCTTGGACCTGAAGAAATCACTCGCGACATTCCAAATGTCGGTGAAGAAGCGCTTC

GCAACTTGGATGAGCGTGGAATCATACGTATTGGTGCTGAAATTGGCGCAGGTGACATTCTCGTTGGTAAA

GTAACACCTAAAGGTGTGACTGAATTGACAGCTGAAGAACGTCTCTTACACGCAATCTTTGGTGAGAAGGC

ACGCGAGGTTCGCGATACTTCTTTGAGAGTTCCTCACGGAACAGACGGGATTGTTGTAGATGTAAAGGTAT

TTACACGTGAAAATGGCGATGAACTGCCACCAGGTGTAAATCAGTTGGTTCGAGTATATATTGCTCAAAAA

-continued

CGTAAAATCTCCGAAGGCGATAAAATGGCTGGACGTCACGGTAACAAGGGTGTCGTTGCCCGTATTCTGCC

TGAAGAAGATATGCCGTTCCTGCCGGATGGCACACCAGTACAGGTCGTTCTGAACCCGCTGGGCGTACCTT

CACGGATGAACATCGGACAGGTGCTTGAAGTCCATCTGGGTATGGCTGCAATGCGTCTTGGTATTCATGTG

GCAACTCCAGTATTCGATGGTGCCAAGGAATATGACGTATTCGATACAATGGAAGAGGCAGGCATGCAGCG

TAATGGTAAGACTGTGTTGTATGACGGACGTACGGGTGATCGTTTTGAACGTGAAGTTACTGTCGGTGTCA

TGCACATGATCAAACTGGCGCACATGGTCGATGATAAAATCCATGCTCGTTCTACAGGTCCTTACTCTCTC

GTTACGCAACAACCATTGGGTGGTAAAGCTCAATTTGGTGGACAGCGCTTCGGGGAGATGGAAGTATGGGC

ATTGGAAGCCTACGGCGCAGCGTACACGCTTCAGGAAATTTTGACTGTGAAATCTGATGATGTGGTTGGAC

GTGTTAAAACTTACGAATCCATTGTCAAAGGTGAAAATGTACCTGAACCGGGTGTTCCAGAATCATTTAAG

GTCTTGATCAAGGAGCTGCAAAGCTTGGGTATGGACGTGAAGATTCTGTCTGAAGACGAACAAGAGATCGA

AATGAGAGAGCTTGATGATGAGGATGACACAACCGGCGATAAGCTGAGTTTGAATCTGGAAGGCTCTGAGG

TTGGCGTAGAGTAG

>MS063_partial_rpoB_gene

SEQ ID NO. 32

GAAACGCCTGAGGGCCCGAACATCGGTTTGATCAACTCATTGTCATCATTTGCGAAAGTAAACCGCTTTGG

TTTCATTGAGACGCCATACCGCCGCGTTGATCCTGAAACAGGAAAAGTAACGCCTAGAATCGACTACCTGA

CTGCTGATGAAGAGGATAACTATGTCGTAGCCCAAGCGAATGCTAAGCTGAGCGATGACGGTTCTTTCTTG

GATGACAGCATCGTAGCGCGTTTCAGAGGGGAAAACACCGTTGTAGCCCGCAACCGCGTGGATTACATGGA

CGTATCTCCTAAACAGGTTGTATCTGCTGCGACAGCATGTATTCCGTTCTTGGAAAACGATGACTCGAACC

GCGCCCTCATGGGAGCGAACATGCAGCGTCAGGCTGTGCCTTTGATGCAGCCGGAAGCTCCGATCGTCGGA

ACGGGTATGGAATACGTATCCGGTAAAGACTCCGGTGCAGCCGTTATTTGTAAACACCCTGGTATCGTTGA

ACGGGTGGAAGCGAAAAACGTATGGGTGCGCCGCTATGAAGAAATTGACGGCCAAAAAGTAAAAGGCAACC

TGGATAAGTACAGCTTGCTGAAATTTGTCCGCTCCAACCAAGGTACGTGCTACAACCAGCGTCCGATCGTC

AGTGTCGGCGATGAAGTAGTCAAAGGAGAAATCCTTGCTGACGGACCTTCAATGGAGCTTGGTGAACTTGC

TCTCGGCCGCAACGTAATGGTCGGCTTCATGACATGGGATGGTTAC

---

What is claimed is:

1. A method of controlling a plant disease, enhancing disease resistance of a plant, or both controlling a plant disease and enhancing disease resistance of a plant, the method comprising administering an effective amount of an agricultural composition to a plant seed, an immature seedling, and/or a tissue of a plant, the agricultural composition comprising:

(i) a bacterial isolate of *Paenibacillus* or *Bacillus*, or (ii) a filtrate of the bacterial isolate, wherein the bacterial isolate comprises MS1479 (ATCC Accession No. PTA-124701), MS2379 (ATCC Accession No. PTA-124703), MS2414 (ATCC Accession No. PTA-124704), MS2820 (ATCC Accession No. PTA-124710), MS0633 (ATCC Accession No. PTA-124700), MS2335 (ATCC Accession No. PTA-124702), MS2652 (ATCC Accession No. PTA-124705), MS2658 (ATCC Accession No. PTA-124706), MS2681 (ATCC Accession No. PTA-124707), MS2697 (ATCC Accession No. PTA-124708), or MS2712 (ATCC Accession No. PTA-124709) or combinations thereof.

2. The method of claim 1, wherein the bacterial isolate is MS2379, MS2414, or a combination of MS2379 and MS2414.

3. The method of claim 1, wherein the plant disease comprises a fungal disease, a bacterial disease, a viral disease, or a parasitic disease.

4. The method of claim 3, wherein the fungal disease comprises white blister, downy mildews, powdery mildews, clubroot, sclerotinia rot, fusarium wilts and rots, botrytis rots, anthracnose, rhizoctonia rots, damping-off, cavity spot, tuber diseases, rusts, black root rot, target spot, aphanomyces root rot, ascochyta collar rot, gummy stem blight, alternaria leaf spot, black leg, ring spot, late blight, cercospora, leaf blight, septoria spot, or a combination thereof.

5. The method of claim 1, wherein the agricultural composition further comprises a bio-control formulation, wherein the bio-control formulation comprises a microbe; an insecticide; a nematicide; an acaricide; a fungicide; a bactericide; an herbicide; a plant growth regulator; a spreader; a fertilizer; a microbial material; a soil amendment; an agriculturally acceptable carrier; a wetting agent; a binding agent; a filler; an organic additive; a surface-active agent; or an agent, wherein the agent comprises a preservative, a mineral, a thickening agent, a stabilizing agent, a bioprotector, an adjuvant, or a combination thereof.

6. The method of claim 5, wherein the bio-control formulation comprises a microbe, and wherein a colony forming unit (cfu) ratio of the bacterial isolate to the microbe in the bio-control formulation is in a range of from 1,000:1 to 1:1,000, 100:1 to 1:100, 100:1 to 1:1, 50:1 to 1:50, 50:1 to 10:1, or 10:1 to 1:10.

7. The method of claim 1, wherein a concentration of the bacterial isolate in the agricultural composition is at least $1.3\times10^5$ cfu/ml, $1.3\times10^6$ cfu/ml, $1.3\times10^7$ cfu/ml, $1.3\times10^8$ cfu/ml, $1.3\times10^9$ cfu/ml, or $1.3\times10^{10}$ cfu/ml.

8. The method of claim 1, wherein the bacterial isolate is subjected to a fermentation process prior to the administering step, wherein the fermentation process comprises:

(1) inoculating the bacterial isolate in a seed medium to start a culture, and (2) expanding the culture with a production medium.

9. The method of claim 1, wherein the plant disease is caused by *Macrophomina phaseolina, Fusarium virguliforme, Rhizoctonia solani, Botrytis cinerea, Pythium ultimum*, or *Pythium irregulare*.

10. The method of claim 5, wherein the agricultural composition comprises a fungicide as the bio-control formulation, and wherein the fungicide comprises *Bacillus subtilis* QST-713 strain, azoxystrobin, *Bacillus amyloliquefaciens* D747 strain, *Bacillus mycoides* isolate J, *Bacillus subtilis* MBI-600 strain combined with pyraclostrobin, or *Bacillus subtilis* MBI-600 strain.

11. The method of claim 5, wherein the agricultural composition comprises a fungicide as the bio-control formulation, and wherein the fungicide comprises at least one of *Bacillus subtilis* QST-713 strain, azoxystrobin, *Bacillus amyloliquefaciens* D747 strain, *Bacillus mycoides* isolate J, *Bacillus subtilis* MBI-600 strain, and pyraclostrobin.

* * * * *